US012552805B2

(12) United States Patent
Nakano et al.

(10) Patent No.: US 12,552,805 B2
(45) Date of Patent: Feb. 17, 2026

(54) COMPOUND AND ORGANIC ELECTROLUMINESCENT ELEMENT

(71) Applicant: IDEMITSU KOSAN CO., LTD., Tokyo (JP)

(72) Inventors: Yuki Nakano, Sodegaura (JP); Ryota Takahashi, Sodegaura (JP); Yoshinao Shirasaki, Sodegaura (JP); Yu Kudo, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 850 days.

(21) Appl. No.: 17/800,221

(22) PCT Filed: Feb. 19, 2021

(86) PCT No.: PCT/JP2021/006235
§ 371 (c)(1),
(2) Date: Aug. 16, 2022

(87) PCT Pub. No.: WO2021/167038
PCT Pub. Date: Aug. 26, 2021

(65) Prior Publication Data

US 2023/0145611 A1 May 11, 2023

(30) Foreign Application Priority Data

Feb. 21, 2020 (JP) ................................ 2020-028481

(51) Int. Cl.

| | |
|---|---|
| ***C07D 487/22*** | (2006.01) |
| ***H01L 51/54*** | (2006.01) |
| ***H10K 85/60*** | (2023.01) |
| *H10K 50/11* | (2023.01) |

(52) U.S. Cl.
CPC ......... *C07D 487/22* (2013.01); *H10K 85/631* (2023.02); *H10K 85/636* (2023.02); *H10K 85/6572* (2023.02); *H10K 50/11* (2023.02)

(58) Field of Classification Search
None
See application file for complete search history.

(56) References Cited

FOREIGN PATENT DOCUMENTS

| | | |
|---|---|---|
| WO | WO-2019/111971 A1 | 6/2019 |
| WO | WO-2019/240251 A1 | 12/2019 |
| WO | WO-2020/209292 A1 | 10/2020 |
| WO | WO-2020/209299 A1 | 10/2020 |
| WO | WO-2020/250961 A1 | 12/2020 |

OTHER PUBLICATIONS

International Preliminary Report on Patentability, dated Sep. 1, 2022, which includes an English- language Translation of the Written Opinion issued in the corresponding International Patent Application No. PCT/JP2021/006235, dated Apr. 20, 2021.
International Searching Authority, "International Search Report," issued in connection with International Patent Application No. PCT/JP2021/006235, dated Apr. 20, 2021.

*Primary Examiner* — Andrew K Bohaty
(74) *Attorney, Agent, or Firm* — Foley & Lardner LLP

(57) ABSTRACT

A compound represented by the following formula (1), wherein at least one of $R_a$ to $R_d$ is a substituted or unsubstituted biphenyl-2-yl group; and at least one of $R_a$ to $R_d$ has a specific substituent.

(1)

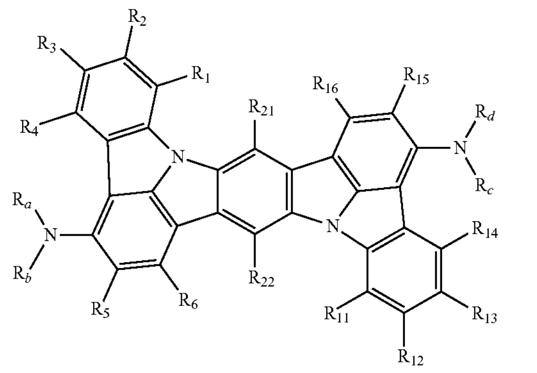

25 Claims, 1 Drawing Sheet

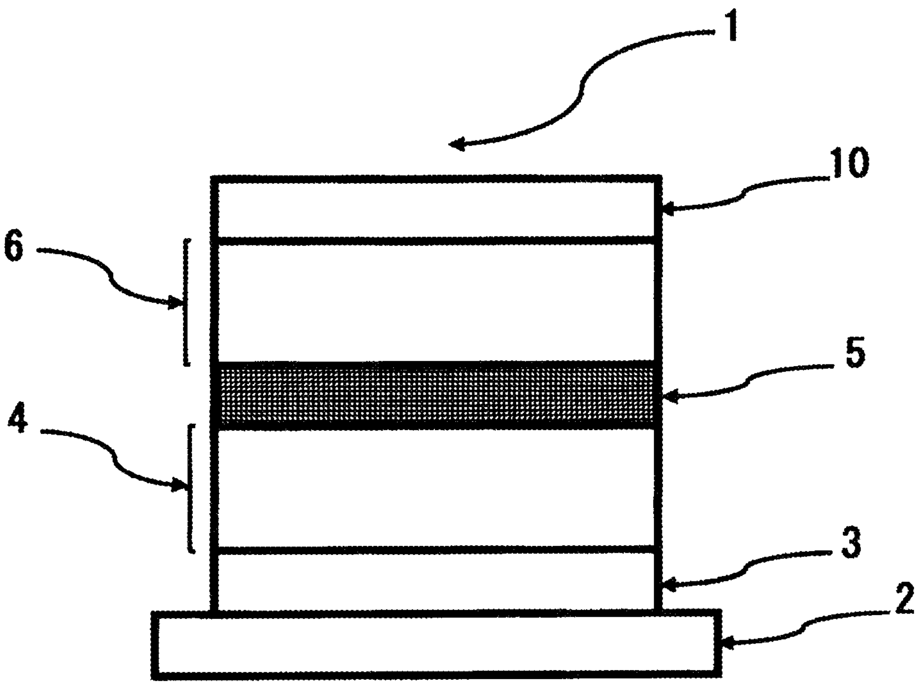
1
10
6
5
4
3
2

COMPOUND AND ORGANIC ELECTROLUMINESCENT ELEMENT

CROSS-REFERENCE TO RELATED APPLICATIONS

The present application claims priority under 37 U.S.C. § 371 to International Patent Application No. PCT/JP2021/006235, filed Feb. 19, 2021, which claims priority to and the benefit of Japanese Patent Application No. 2020-028481, filed on Feb. 21, 2020. The contents of these applications are hereby incorporated by reference in their entireties.

TECHNICAL FIELD

The invention relates to a novel compound and an organic electroluminescence device.

BACKGROUND ART

When voltage is applied to an organic electroluminescence device (hereinafter, referred to as an organic EL device in several cases), holes and electrons are injected into an emitting layer from an anode and a cathode, respectively. Then, thus injected holes and electrons are recombined in the emitting layer, and excitons are formed therein.

Conventional organic EL devices have not yet sufficient device performance. Although the improvement of materials used for organic EL devices is progressing gradually in order to raise the device performance, there is a need for even higher performance. In particular, since the improvement of the lifetime of the organic EL device is a critical challenge leading to the lifetime of the commercialized product, a material capable of realizing an organic EL device having a long lifetime is required.

Patent Document 1 discloses use of a compound having a specific structure in an emitting layer of an organic EL device.

RELATED ART DOCUMENTS

Patent Documents

[Patent Document 1] WO 2019/111971 A1

SUMMARY OF THE INVENTION

It is an object of the invention to provide a compound able to fabricate an organic EL device having a long lifetime As a result of extensive studies to achieve the above object, the inventors have found that use of a compound having a specific structure can give an organic EL device having a long lifetime, and have completed the invention. According to the invention, the following compound and so on are provided.

A compound represented by the following formula (1):

(1)

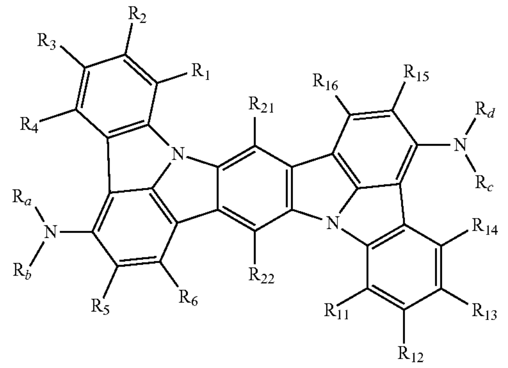

wherein in the formula (1), $R_a$ to $R_d$ are independently a substituted or unsubstituted aryl group including 6 to 50 ring carbon atoms, and at least one of $R_a$ to $R_d$ is a substituted or unsubstituted biphenyl-2-yl group;

at least one of $R_a$ to $R_d$ has a substituent A; the substituent A is one or more selected from the group consisting of a substituted or unsubstituted alkyl group including 1 to 50 carbon atoms, a substituted or unsubstituted cycloalkyl group including 3 to 50 ring carbon atoms, and —$Si(R_{31})(R_{32})(R_{33})$;

one or more sets of adjacent two or more of $R_1$ to $R_6$ and $R_{11}$ to $R_{16}$ form a substituted or unsubstituted, saturated or unsaturated ring, or do not form the substituted or unsubstituted, saturated or unsaturated ring;

$R_{21}$ and $R_{22}$, and $R_1$ to $R_6$ and $R_{11}$ to $R_{16}$ which do not form the substituted or unsubstituted, saturated or unsaturated ring are independently a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —$Si(R_{31})(R_{32})(R_{33})$, —$C(=O)R_{34}$, —$COOR_{35}$, —$N(R_{36})(R_{37})$, a halogen atom, a cyano group, a nitro group, a substituted or unsubstituted aryl group including 6 to 50 ring carbon atoms, or a substituted or unsubstituted monovalent heterocyclic group including 5 to 50 ring atoms;

$R_{31}$ to $R_{37}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms;

when a plurality of each of $R_{31}$ to $R_{37}$ is present, the plurality of each of $R_{31}$ to $R_{37}$ may be the same as or different from each other.

According to the invention, a compound able to fabricate an organic EL device having a long lifetime can be provided.

BRIEF DESCRIPTION OF THE DRAWINGS

The FIGURE is a diagram showing a schematic configuration of an organic EL device according to an aspect of the invention.

MODE FOR CARRYING OUT THE INVENTION

Definition

In this specification, a hydrogen atom includes its isotopes different in the number of neutrons, namely, a protium, a deuterium and a tritium.

In this specification, at a bondable position in a chemical formula where a symbol such as "R", or "D" representing a deuterium atom is not indicated, a hydrogen atom, that is, a protium atom, a deuterium atom or a tritium atom is bonded.

In this specification, the number of ring carbon atoms represents the number of carbon atoms forming a subject ring itself among the carbon atoms of a compound having a structure in which atoms are bonded in a ring form (for example, a monocyclic compound, a fused ring compound, a cross-linked compound, a carbocyclic compound, or a heterocyclic compound). When the subject ring is substituted by a substituent, the carbon contained in the substituent is not included in the number of ring carbon atoms. The same shall apply to "the number of ring carbon atoms" described below, unless otherwise specified. For example, a benzene ring has 6 ring carbon atoms, a naphthalene ring includes 10 ring carbon atoms, a pyridine ring includes 5 ring carbon atoms, and a furan ring includes 4 ring carbon atoms. Further, for example, a 9,9-diphenylfluorenyl group includes 13 ring carbon atoms, and a 9,9'-spirobifluorenyl group includes 25 ring carbon atoms.

When a benzene ring is substituted by, for example, an alkyl group as a substituent, the number of carbon atoms of the alkyl group is not included in the number of ring carbon atoms of the benzene ring. Therefore, the number of ring carbon atoms of the benzene ring substituted by the alkyl group is 6. When a naphthalene ring is substituted by, for example, an alkyl group as a substituent, the number of carbon atoms of the alkyl group is not included in the number of ring carbon atoms of the naphthalene ring. Therefore, the number of ring carbon atoms of the naphthalene ring substituted by the alkyl group is 10.

In this specification, the number of ring atoms represents the number of atoms forming a subject ring itself among the atoms of a compound having a structure in which atoms are bonded in a ring form (for example, the structure includes a monocyclic ring, a fused ring and a ring assembly) (for example, a monocyclic compound, a fused ring compound, a cross-linked compound, a carbocyclic compound and a heterocyclic compound). The number of ring atoms does not include atoms which do not form the ring (for example, a hydrogen atom which terminates a bond of the atoms forming the ring), or atoms contained in a substituent when the ring is substituted by the substituent. The same shall apply to "the number of ring atoms" described below, unless otherwise specified. For example, the number of atoms of a pyridine ring is 6, the number of atoms of a quinazoline ring is 10, and the number of a furan ring is 5. For example, hydrogen atoms bonded to a pyridine ring and atoms constituting a substituent substituted on the pyridine ring are not included in the number of ring atoms of the pyridine ring. Therefore, the number of ring atoms of a pyridine ring with which a hydrogen atom or a substituent is bonded is 6. For example, hydrogen atoms and atoms constituting a substituent which are bonded with a quinazoline ring is not included in the number of ring atoms of the quinazoline ring. Therefore, the number of ring atoms of a quinazoline ring with which a hydrogen atom or a substituent is bonded is 10.

In this specification, "XX to YY carbon atoms" in the expression "a substituted or unsubstituted ZZ group including XX to YY carbon atoms" represents the number of carbon atoms in the case where the ZZ group is unsubstituted by a substituent, and does not include the number of carbon atoms of a substituent in the case where the ZZ group is substituted by the substituent. Here, "YY" is larger than "XX", and "XX" means an integer of 1 or more and "YY" means an integer of 2 or more.

In this specification, "XX to YY atoms" in the expression "a substituted or unsubstituted ZZ group including XX to YY atoms" represents the number of atoms in the case where the ZZ group is unsubstituted by a substituent, and does not include the number of atoms of a substituent in the case where the ZZ group is substituted by the substituent. Here, "YY" is larger than "XX", and "XX" means an integer of 1 or more and "YY" means an integer of 2 or more.

In this specification, the unsubstituted ZZ group represents the case where the "substituted or unsubstituted ZZ group" is a "ZZ group unsubstituted by a substituent", and the substituted ZZ group represents the case where the "substituted or unsubstituted ZZ group" is a "ZZ group substituted by a substituent".

In this specification, a term "unsubstituted" in the case of "a substituted or unsubstituted ZZ group" means that hydrogen atoms in the ZZ group are not substituted by a substituent. Hydrogen atoms in a term "unsubstituted ZZ group" are a protium atom, a deuterium atom, or a tritium atom.

In this specification, a term "substituted" in the case of "a substituted or unsubstituted ZZ group" means that one or more hydrogen atoms in the ZZ group are substituted by a substituent. Similarly, a term "substituted" in the case of "a BB group substituted by an AA group" means that one or more hydrogen atoms in the BB group are substituted by the AA group.

"Substituent as Described in this Specification"

Hereinafter, the substituent described in this specification will be explained.

The number of ring carbon atoms of the "unsubstituted aryl group" described in this specification is 6 to 50, preferably 6 to 30, and more preferably 6 to 18, unless otherwise specified.

The number of ring atoms of the "unsubstituted heterocyclic group" described in this specification is 5 to 50, preferably 5 to 30, and more preferably 5 to 18, unless otherwise specified.

The number of carbon atoms of the "unsubstituted alkyl group" described in this specification is 1 to 50, preferably 1 to 20, and more preferably 1 to 6, unless otherwise specified.

The number of carbon atoms of the "unsubstituted alkenyl group" described in this specification is 2 to 50, preferably 2 to 20, and more preferably 2 to 6, unless otherwise specified.

The number of carbon atoms of the "unsubstituted alkynyl group" described in this specification is 2 to 50, preferably 2 to 20, and more preferably 2 to 6, unless otherwise specified.

The number of ring carbon atoms of the "unsubstituted cycloalkyl group" described in this specification is 3 to 50, preferably 3 to 20, and more preferably 3 to 6, unless otherwise specified.

The number of ring carbon atoms of the "unsubstituted arylene group" described in this specification is 6 to 50, preferably 6 to 30, and more preferably 6 to 18, unless otherwise specified.

The number of ring atoms of the "unsubstituted divalent heterocyclic group" described in this specification is 5 to 50, preferably 5 to 30, and more preferably 5 to 18, unless otherwise specified.

The number of carbon atoms of the "unsubstituted alkylene group" described in this specification is 1 to 50, preferably 1 to 20, and more preferably 1 to 6, unless otherwise specified.

"Substituted or Unsubstituted Aryl Group"

Specific examples of the "substituted or unsubstituted aryl group" described in this specification (specific example group G1) include the following unsubstituted aryl groups (specific example group G1A), substituted aryl groups (specific example group G1B), and the like. (Here, the unsubstituted aryl group refers to the case where the "substituted or unsubstituted aryl group" is an "aryl group unsubstituted by a substituent", and the substituted aryl group refers to the case where the "substituted or unsubstituted aryl group" is an "aryl group substituted by a substituent"). In this specification, in the case where simply referred as an "aryl group", it includes both a "unsubstituted aryl group" and a "substituted aryl group."

The "substituted aryl group" means a group in which one or more hydrogen atoms of the "unsubstituted aryl group" are substituted by a substituent. Specific examples of the "substituted aryl group" include, for example, groups in which one or more hydrogen atoms of the "unsubstituted aryl group" of the following specific example group G1A are substituted by a substituent, the substituted aryl groups of the following specific example group G1B, and the like. It should be noted that the examples of the "unsubstituted aryl group" and the examples of the "substituted aryl group" enumerated in this specification are mere examples, and the "substituted aryl group" described in this specification also includes a group in which a hydrogen atom bonded with a carbon atom of the aryl group itself in the "substituted aryl group" of the following specific group G1B is further substituted by a substituent, and a group in which a hydrogen atom of a substituent in the "substituted aryl group" of the following specific group G1B is further substituted by a substituent.

Unsubstituted Aryl Group (Specific Example Group G1A):

a phenyl group,
a p-biphenyl group,
a m-biphenyl group,
an o-biphenyl group,
a p-terphenyl-4-yl group,
a p-terphenyl-3-yl group,
a p-terphenyl-2-yl group,
a m-terphenyl-4-yl group,
a m-terphenyl-3-yl group,
a m-terphenyl-2-yl group,
an o-terphenyl-4-yl group,
an o-terphenyl-3-yl group,
an o-terphenyl-2-yl group,
a 1-naphthyl group,
a 2-naphthyl group,
an anthryl group,
a benzanthryl group,
a phenanthryl group,
a benzophenanthryl group,
a phenalenyl group,
a pyrenyl group,
a chrysenyl group,
a benzochrysenyl group,
a triphenylenyl group,
a benzotriphenylenyl group,
a tetracenyl group,
a pentacenyl group,
a fluorenyl group,
a 9,9'-spirobifluorenyl group,
a benzofluorenyl group,
a dibenzofluorenyl group,
a fluoranthenyl group,
a benzofluoranthenyl group,
a perylenyl group, and
a monovalent aryl groups derived by removing one hydrogen atom from the ring structures represented by each of the following general formulas (TEMP-1) to (TEMP-15).

(TEMP-1)

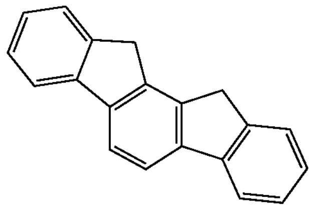

(TEMP-2)

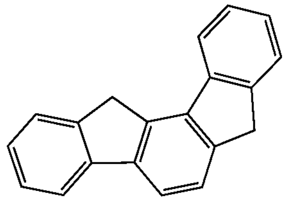

(TEMP-3)

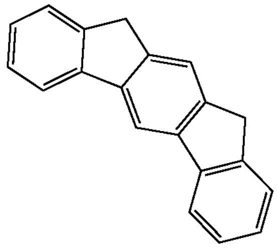

(TEMP-4)

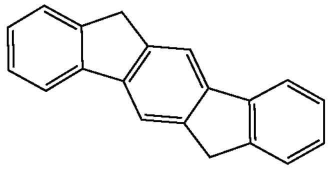

-continued (TEMP-5)

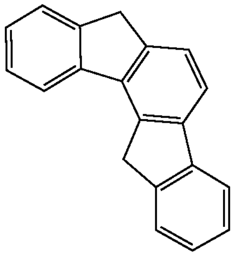

(TEMP-6)

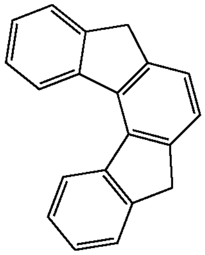

(TEMP-7)

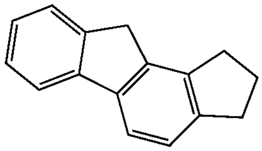

(TEMP-8)

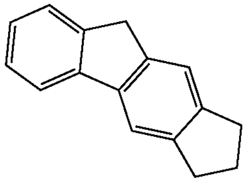

(TEMP-9)

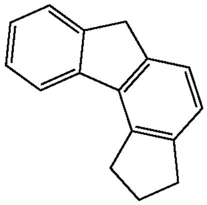

(TEMP-10)

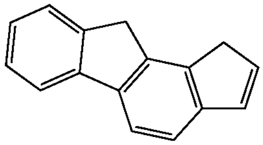

(TEMP-11)

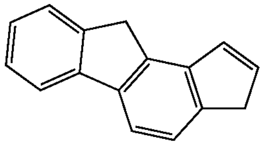

(TEMP-12)

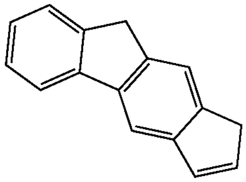

-continued (TEMP-13)

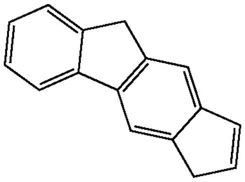

(TEMP-14)

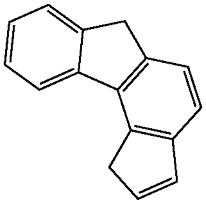

(TEMP-15)

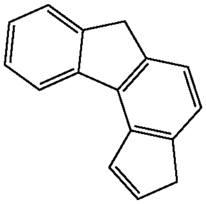

Substituted Aryl Group (Specific Example Group G1B):
- an o-tolyl group,
- a m-tolyl group,
- a p-tolyl group,
- a p-xylyl group,
- a m-xylyl group,
- an o-xylyl group,
- a p-isopropylphenyl group,
- a m-isopropylphenyl group,
- an o-isopropylphenyl group,
- a p-t-butylphenyl group,
- a m-t-butylphenyl group,
- an o-t-butylphenyl group,
- a 3,4,5-trimethylphenyl group,
- a 9,9-dimethylfluorenyl group,
- a 9,9-diphenylfluorenyl group,
- a 9,9-bis(4-methylphenyl)fluorenyl group,
- a 9,9-bis(4-isopropylphenyl)fluorenyl group,
- a 9,9-bis(4-t-butylphenyl)fluorenyl group,
- a cyanophenyl group,
- a triphenylsilylphenyl group,
- a trimethylsilylphenyl group,
- a phenylnaphthyl group,
- a naphthylphenyl group, and
- a group in which one or more hydrogen atoms of a monovalent group derived from the ring structures represented by each of the general formulas (TEMP-1) to (TEMP-15) are substituted by a substituent.

"Substituted or Unsubstituted Heterocyclic Group"

The "heterocyclic group" described in this specification is a ring group having at least one hetero atom in the ring atom. Specific examples of the hetero atom include a nitrogen atom, an oxygen atom, a sulfur atom, a silicon atom, a phosphorus atom, and a boron atom.

The "heterocyclic group" in this specification is a monocyclic group or a fused ring group.

The "heterocyclic group" in this specification is an aromatic heterocyclic group or a non-aromatic heterocyclic group.

Specific examples of the "substituted or unsubstituted heterocyclic group" (specific example group G2) described in this specification include the following unsubstituted heterocyclic group (specific example group G2A), the following substituted heterocyclic group (specific example group G2B), and the like. (Here, the unsubstituted heterocyclic group refers to the case where the "substituted or unsubstituted heterocyclic group" is a "heterocyclic group unsubstituted by a substituent", and the substituted heterocyclic group refers to the case where the "substituted or unsubstituted heterocyclic group" is a "heterocyclic group substituted by a substituent".). In this specification, in the case where simply referred as a "heterocyclic group", it includes both the "unsubstituted heterocyclic group" and the "substituted heterocyclic group."

The "substituted heterocyclic group" means a group in which one or more hydrogen atom of the "unsubstituted heterocyclic group" are substituted by a substituent. Specific examples of the "substituted heterocyclic group" include a group in which a hydrogen atom of "unsubstituted heterocyclic group" of the following specific example group G2A is substituted by a substituent, the substituted heterocyclic groups of the following specific example group G2B, and the like. It should be noted that the examples of the "unsubstituted heterocyclic group" and the examples of the "substituted heterocyclic group" enumerated in this specification are mere examples, and the "substituted heterocyclic group" described in this specification includes groups in which hydrogen atom bonded with a ring atom of the heterocyclic group itself in the "substituted heterocyclic group" of the specific example group G2B is further substituted by a substituent, and a group in which hydrogen atom of a substituent in the "substituted heterocyclic group" of the specific example group G2B is further substituted by a substituent.

Specific example group G2A includes, for example, the following unsubstituted heterocyclic group containing a nitrogen atom (specific example group G2A1), the following unsubstituted heterocyclic group containing an oxygen atom (specific example group G2A2), the following unsubstituted heterocyclic group containing a sulfur atom (specific example group G2A3), and the monovalent heterocyclic group derived by removing one hydrogen atom from the ring structures represented by each of the following general formulas (TEMP-16) to (TEMP-33) (specific example group G2A4).

Specific example group G2B includes, for example, the following substituted heterocyclic group containing a nitrogen atom (specific example group G2B1), the following substituted heterocyclic group containing an oxygen atom (specific example group G2B2), the following substituted heterocyclic group containing a sulfur atom (specific example group G2B3), and the following group in which one or more hydrogen atoms of the monovalent heterocyclic group derived from the ring structures represented by each of the following general formulas (TEMP-16) to (TEMP-33) are substituted by a substituent (specific example group G2B4).

Unsubstituted Heterocyclic Group Containing a Nitrogen Atom (Specific Example Group G2A1):

a pyrrolyl group,
an imidazolyl group,
a pyrazolyl group,
a triazolyl group,
a tetrazolyl group,
an oxazolyl group,
an isoxazolyl group,
an oxadiazolyl group,
a thiazolyl group,
an isothiazolyl group,
a thiadiazolyl group,
a pyridyl group,
a pyridazinyl group,
a pyrimidinyl group,
a pyrazinyl group,
a triazinyl group,
an indolyl group,
an isoindolyl group,
an indolizinyl group,
a quinolizinyl group,
a quinolyl group,
an isoquinolyl group,
a cinnolyl group,
a phthalazinyl group,
a quinazolinyl group,
a quinoxalinyl group,
a benzimidazolyl group,
an indazolyl group,
a phenanthrolinyl group,
a phenanthridinyl group,
an acridinyl group,
a phenazinyl group,
a carbazolyl group,
a benzocarbazolyl group,
a morpholino group,
a phenoxazinyl group,
a phenothiazinyl group,
an azacarbazolyl group, and
a diazacarbazolyl group.

Unsubstituted Heterocyclic Group Containing an Oxygen Atom (Specific Example Group G2A2):

a furyl group,
an oxazolyl group,
an isoxazolyl group,
an oxadiazolyl group,
a xanthenyl group,
a benzofuranyl group,
an isobenzofuranyl group,
a dibenzofuranyl group,
a naphthobenzofuranyl group,
a benzoxazolyl group,
a benzisoxazolyl group,
a phenoxazinyl group,
a morpholino group,
a dinaphthofuranyl group,
an azadibenzofuranyl group,
a diazadibenzofuranyl group,
an azanaphthobenzofuranyl group, and
a diazanaphthobenzofuranyl group.

Unsubstituted Heterocyclic Group Containing a Sulfur Atom (Specific Example Group G2A3):

a thienyl group,
a thiazolyl group,
an isothiazolyl group,
a thiadiazolyl group,
a benzothiophenyl group (benzothienyl group),
an isobenzothiophenyl group (isobenzothienyl group),
a dibenzothiophenyl group (dibenzothienyl group),
a naphthobenzothiophenyl group (naphthobenzothienyl group),
a benzothiazolyl group,
a benzisothiazolyl group,
a phenothiazinyl group,
a dinaphthothiophenyl group (dinaphthothienyl group), an azadibenzothiophenyl group (azadibenzothienyl group), a diazadibenzothiophenyl group (diazadibenzothienyl group), an azanaphthobenzothiophenyl group (azanaphthobenzothienyl group), and a diazanaphthobenzothiophenyl group (diazanaphthobenzothienyl group).

Monovalent Heterocyclic Groups Derived by Removing One Hydrogen Atom from the Ring Structures Represented by Each of the Following General Formulas (TEMP-16) to (TEMP-33) (Specific Example Group G2A4):

(TEMP-16)

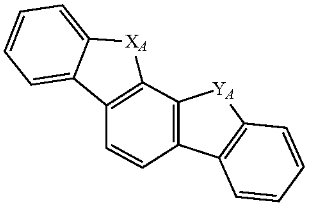

(TEMP-17)

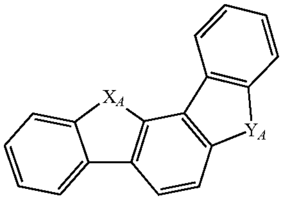

(TEMP-18)

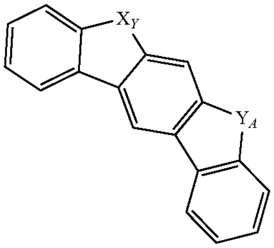

(TEMP-19)

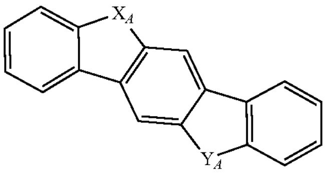

(TEMP-20)

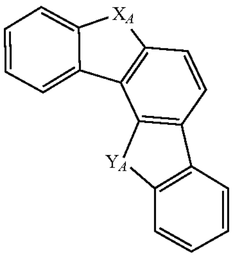

-continued (TEMP-21)

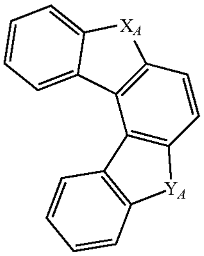

(TEMP-22)

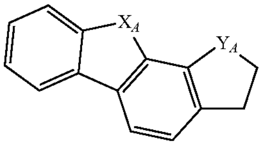

(TEMP-23)

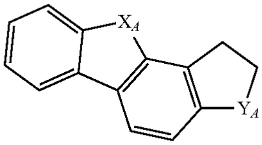

(TEMP-24)

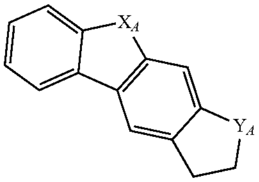

(TEMP-25)

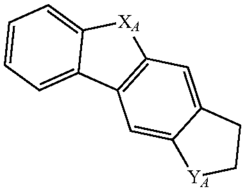

(TEMP-26)

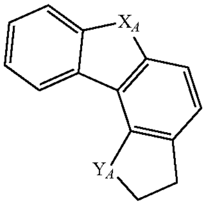

(TEMP-27)

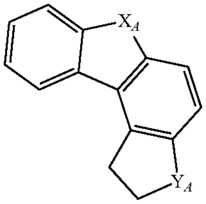

(TEMP-28)

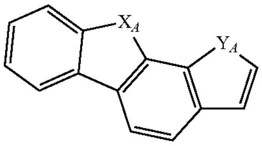

-continued (TEMP-29)

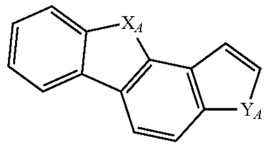

(TEMP-30)

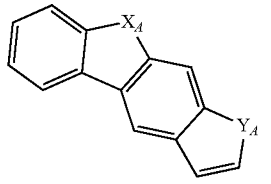

(TEMP-31)

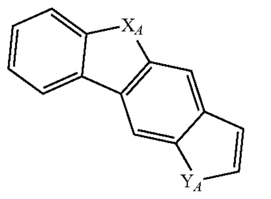

(TEMP-32)

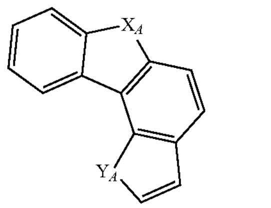

(TEMP-33)

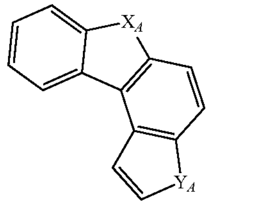

In the general formulas (TEMP-16) to (TEMP-33), $X_A$ and $Y_A$ are independently an oxygen atom, a sulfur atom, NH, or $CH_2$. Provided that at least one of $X_A$ and $Y_A$ is an oxygen atom, a sulfur atom, or NH.

In the general formulas (TEMP-16) to (TEMP-33), when at least one of $X_A$ and $Y_A$ is NH or $CH_2$, the monovalent heterocyclic groups derived from the ring structures represented by each of the general formulas (TEMP-16) to (TEMP-33) includes a monovalent group derived by removing one hydrogen atom from these NH or $CH_2$.

Substituted Heterocyclic Group Containing a Nitrogen Atom (Specific Example Group G2B1):

a (9-phenyl)carbazolyl group,
a (9-biphenylyl)carbazolyl group,
a (9-phenyl)phenylcarbazolyl group,
a (9-naphthyl)carbazolyl group,
a diphenylcarbazol-9-yl group,
a phenylcarbazol-9-yl group,
a methylbenzimidazolyl group,
an ethylbenzimidazolyl group,
a phenyltriazinyl group,
a biphenylyltriazinyl group,
a diphenyltriazinyl group,
a phenylquinazolinyl group, and
a biphenylylquinazolinyl group.

Substituted Heterocyclic Group Containing an Oxygen Atom (Specific Example Group G2B2):

a phenyldibenzofuranyl group,
a methyldibenzofuranyl group,
a t-butyldibenzofuranyl group, and
a monovalent residue of spiro[9H-xanthene-9,9'-[9H]fluorene].

Substituted Heterocyclic Group Containing a Sulfur Atom (Specific Example Group G2B3):

a phenyldibenzothiophenyl group,
a methyldibenzothiophenyl group,
a t-butyldibenzothiophenyl group, and
a monovalent residue of spiro[9H-thioxanthene-9,9'-[9H]fluorene].

Group in which One or More Hydrogen Atoms of the Monovalent Heterocyclic Groups Derived from the Ring Structures Represented by Each of the Following General Formulas (TEMP-16) to (TEMP-33) are Substituted by a Substituent (Specific Example Group G2B4):

The "one or more hydrogen atoms of the monovalent heterocyclic group" means one or more hydrogen atoms selected from hydrogen atoms bonded with ring carbon atoms of the monovalent heterocyclic group, a hydrogen atom bonded with a nitrogen atom when at least one of $X_A$ and $Y_A$ is NH, and hydrogen atoms of a methylene group when one of $X_A$ and $Y_A$ is $CH_2$.

"Substituted or Unsubstituted Alkyl Group"

Specific examples of the "substituted or unsubstituted alkyl group" (specific example group G3) described in this specification include the following unsubstituted alkyl groups (specific example group G3A) and the following substituted alkyl groups (specific example group G3B). (Here, the unsubstituted alkyl group refers to the case where the "substituted or unsubstituted alkyl group" is an "alkyl group unsubstituted by a substituent", and the substituted alkyl group refers to the case where the "substituted or unsubstituted alkyl group" is an "alkyl group substituted by a substituent".). In this specification, in the case where simply referred as an "alkyl group" includes both the "unsubstituted alkyl group" and the "substituted alkyl group."

The "substituted alkyl group" means a group in which one or more hydrogen atoms in the "unsubstituted alkyl group" are substituted by a substituent. Specific examples of the "substituted alkyl group" include groups in which one or more hydrogen atoms in the following "unsubstituted alkyl group" (specific example group G3A) are substituted by a substituent, the following substituted alkyl group (specific example group G3B), and the like. In this specification, the alkyl group in the "unsubstituted alkyl group" means a linear alkyl group. Thus, the "unsubstituted alkyl group" includes a straight-chain "unsubstituted alkyl group" and a branched-chain "unsubstituted alkyl group". It should be noted that the examples of the "unsubstituted alkyl group" and the examples of the "substituted alkyl group" enumerated in this specification are mere examples, and the "substituted alkyl group" described in this specification includes a group in which hydrogen atom of the alkyl group itself in the "substituted alkyl group" of the specific example group G3B is further substituted by a substituent, and a group in which hydrogen atom of a substituent in the "substituted alkyl group" of the specific example group G3B is further substituted by a substituent.

Unsubstituted Alkyl Group (Specific Example Group G3A):

a methyl group,
an ethyl group,
a n-propyl group, an isopropyl group,
a n-butyl group,
an isobutyl group,
a s-butyl group, and
a t-butyl group.

Substituted Alkyl Group (Specific Example Group G3B):
a heptafluoropropyl group (including isomers),
a pentafluoroethyl group,
a 2,2,2-trifluoroethyl group, and
a trifluoromethyl group.

"Substituted or Unsubstituted Alkenyl Group"

Specific examples of the "substituted or unsubstituted alkenyl group" described in this specification (specific example group G4) include the following unsubstituted alkenyl group (specific example group G4A), the following substituted alkenyl group (specific example group G4B), and the like. (Here, the unsubstituted alkenyl group refers to the case where the "substituted or unsubstituted alkenyl group" is a "alkenyl group unsubstituted by a substituent", and the "substituted alkenyl group" refers to the case where the "substituted or unsubstituted alkenyl group" is a "alkenyl group substituted by a substituent."). In this specification, in the case where simply referred as an "alkenyl group" includes both the "unsubstituted alkenyl group" and the "substituted alkenyl group."

The "substituted alkenyl group" means a group in which one or more hydrogen atoms in the "unsubstituted alkenyl group" are substituted by a substituent. Specific examples of the "substituted alkenyl group" include a group in which the following "unsubstituted alkenyl group" (specific example group G4A) has a substituent, the following substituted alkenyl group (specific example group G4B), and the like. It should be noted that the examples of the "unsubstituted alkenyl group" and the examples of the "substituted alkenyl group" enumerated in this specification are mere examples, and the "substituted alkenyl group" described in this specification includes a group in which a hydrogen atom of the alkenyl group itself in the "substituted alkenyl group" of the specific example group G4B is further substituted by a substituent, and a group in which a hydrogen atom of a substituent in the "substituted alkenyl group" of the specific example group G4B is further substituted by a substituent.

Unsubstituted Alkenyl Group (Specific Example Group G4A):
a vinyl group,
an allyl group,
a 1-butenyl group,
a 2-butenyl group, and
a 3-butenyl group.

Substituted Alkenyl Group (Specific Example Group G4B):
a 1,3-butanedienyl group,
a 1-methylvinyl group,
a 1-methylallyl group,
a 1,1-dimethylallyl group,
a 2-methylally group, and
a 1,2-dimethylallylgroup.

"Substituted or Unsubstituted Alkynyl Group"

Specific examples of the "substituted or unsubstituted alkynyl group" described in this specification (specific example group G5) include the following unsubstituted alkynyl group (specific example group G5A) and the like. (Here, the unsubstituted alkynyl group refers to the case where the "substituted or unsubstituted alkynyl group" is an "alkynyl group unsubstituted by a substituent".). In this specification, in the case where simply referred as an "alkynyl group" includes both the "unsubstituted alkynyl group" and the "substituted alkynyl group."

The "substituted alkynyl group" means a group in which one or more hydrogen atoms in the "unsubstituted alkynyl group" are substituted by a substituent. Specific examples of the "substituted alkynyl group" include a group in which one or more hydrogen atoms in the following "unsubstituted alkynyl group" (specific example group G5A) are substituted by a substituent, and the like.

Unsubstituted Alkynyl Group (Specific Example Group G5A):
an ethynyl group.

"Substituted or Unsubstituted Cycloalkyl Group"

Specific examples of the "substituted or unsubstituted cycloalkyl group" described in this specification (specific example group G6) include the following unsubstituted cycloalkyl group (specific example group G6A), the following substituted cycloalkyl group (specific example group G6B), and the like. (Here, the unsubstituted cycloalkyl group refers to the case where the "substituted or unsubstituted cycloalkyl group" is a "cycloalkyl group unsubstituted by a substituent", and the substituted cycloalkyl group refers to the case where the "substituted or unsubstituted cycloalkyl group" is a "cycloalkyl group substituted by a substituent".). In this specification, in the case where simply referred as a "cycloalkyl group" includes both the "unsubstituted cycloalkyl group" and the "substituted cycloalkyl group."

The "substituted cycloalkyl group" means a group in which one or more hydrogen atoms in the "unsubstituted cycloalkyl group" are substituted by a substituent. Specific examples of the "substituted cycloalkyl group" include a group in which one or more hydrogen atoms in the following "unsubstituted cycloalkyl group" (specific example group G6A) are substituted by a substituent, and examples of the following substituted cycloalkyl group (specific example group G6B), and the like. It should be noted that the examples of the "unsubstituted cycloalkyl group" and the examples of the "substituted cycloalkyl group" enumerated in this specification are mere examples, and the "substituted cycloalkyl group" in this specification includes a group in which one or more hydrogen atoms bonded with the carbon atom of the cycloalkyl group itself in the "substituted cycloalkyl group" of the specific example group G6B are substituted by a substituent, and a group in which a hydrogen atom of a substituent in the "substituted cycloalkyl group" of specific example group G6B is further substituted by a substituent.

Unsubstituted Cycloalkyl Group (Specific Example Group G6A):
a cyclopropyl group,
a cyclobutyl group,
a cyclopentyl group,
a cyclohexyl group,
a 1-adamantyl group,
a 2-adamantyl group,
a 1-norbornyl group, and
a 2-norbornyl group.

Substituted Cycloalkyl Group (Specific Example Group G6B):
a 4-methylcyclohexyl group.

"Group Represented by —Si($R_{901}$)($R_{902}$)($R_{903}$)"

Specific examples of the group represented by —Si($R_{901}$)($R_{902}$)($R_{903}$) described in this specification (specific example group G7) include:
—Si(G1)(G1)(G1),
—Si(G1)(G2)(G2),
—Si(G1)(G1)(G2),
—Si(G2)(G2)(G2),
—Si(G3)(G3)(G3), and
—Si(G6)(G6)(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

A plurality of G1's in —Si(G1)(G1)(G1) are the same as or different from each other.

A plurality of G2's in —Si(G1)(G2)(G2) are the same as or different from each other.

A plurality of G1's in —Si(G1)(G1)(G2) are the same as or different from each other.

A plurality of G2's in —Si(G2)(G2)(G2) are be the same as or different from each other.

A plurality of G3's in —Si(G3)(G3)(G3) are the same as or different from each other.

A plurality of G6's in —Si(G6)(G6)(G6) are be the same as or different from each other.

"Group Represented by —O—($R_{904}$)"

Specific examples of the group represented by —O—($R_{904}$) in this specification (specific example group G8) include:

—O(G1),

—O(G2),

—O(G3), and

—O(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

"Group Represented by —S—($R_{905}$)"

Specific examples of the group represented by —S—($R_{905}$) in this specification (specific example group G9) include:

—S(G1),

—S(G2),

—S(G3), and

—S(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

"Group Represented by —N($R_{906}$)($R_{907}$)"

Specific examples of the group represented by —N($R_{906}$)($R_{907}$) in this specification (specific example group G10) include:

—N(G1)(G1),

—N(G2)(G2),

—N(G1)(G2),

—N(G3)(G3), and

—N(G6)(G6).

G1 is the "substituted or unsubstituted aryl group" described in the specific example group G1.

G2 is the "substituted or unsubstituted heterocyclic group" described in the specific example group G2.

G3 is the "substituted or unsubstituted alkyl group" described in the specific example group G3.

G6 is the "substituted or unsubstituted cycloalkyl group" described in the specific example group G6.

A plurality of G1's in —N(G1)(G1) are the same as or different from each other.

A plurality of G2's in —N(G2)(G2) are the same as or different from each other.

A plurality of G3's in —N(G3)(G3) are the same as or different from each other.

A plurality of G6's in —N(G6)(G6) are the same as or different from each other.

"Halogen Atom"

Specific examples of the "halogen atom" described in this specification (specific example group G11) include a fluorine atom, a chlorine atom, a bromine atom, an iodine atom, and the like.

"Substituted or Unsubstituted Fluoroalkyl Group"

The "substituted or unsubstituted fluoroalkyl group" described in this specification is a group in which at least one hydrogen atom bonded with a carbon atom constituting the alkyl group in the "substituted or unsubstituted alkyl group" is substituted by a fluorine atom, and includes a group in which all hydrogen atoms bonded with a carbon atom constituting the alkyl group in the "substituted or unsubstituted alkyl group" are substituted by a fluorine atom (a perfluoro group). The number of carbon atoms of the "unsubstituted fluoroalkyl group" is 1 to 50, preferably 1 to 30, more preferably 1 to 18, unless otherwise specified in this specification. The "substituted fluoroalkyl group" means a group in which one or more hydrogen atoms of the "fluoroalkyl group" are substituted by a substituent. The "substituted fluoroalkyl group" described in this specification also includes a group in which one or more hydrogen atoms bonded with a carbon atom of the alkyl chains in the "substituted fluoroalkyl group" are further substituted by a substituent, and a group in which one or more hydrogen atom of a substituent in the "substituted fluoroalkyl group" are further substituted by a substituent. Specific examples of the "unsubstituted fluoroalkyl group" include a group in which one or more hydrogen atoms in the "alkyl group" (specific group G3) are substituted by a fluorine atom, and the like.

"Substituted or Unsubstituted Haloalkyl Group"

The "substituted or unsubstituted haloalkyl group" described in this specification is a group in which at least one hydrogen atom bonded with a carbon atom constituting the alkyl group in the "substituted or unsubstituted alkyl group" is substituted by a halogen atom, and also includes a group in which all hydrogen atoms bonded with a carbon atom constituting the alkyl group in the "substituted or unsubstituted alkyl group" are substituted by a halogen atom. The number of carbon atoms of the "unsubstituted haloalkyl group" is 1 to 50, preferably 1 to 30, more preferably 1 to 18, unless otherwise specified in this specification. The "substituted haloalkyl group" means a group in which one or more hydrogen atoms of the "haloalkyl group" are substituted by a substituent. The "substituted haloalkyl group" described in this specification also includes a group in which one or more hydrogen atoms bonded with a carbon atom of the alkyl chain in the "substituted haloalkyl group" are further substituted by a substituent, and a group in which one or more hydrogen atoms of a substituent in the "substituted haloalkyl group" are further substituted by a substituent. Specific examples of the "unsubstituted haloalkyl group" include a group in which one or more hydrogen atoms in the "alkyl group" (specific example group G3) are substituted by a halogen atom, and the like. A haloalkyl group is sometimes referred to as an alkyl halide group.

"Substituted or Unsubstituted Alkoxy Group"

Specific examples of the "substituted or unsubstituted alkoxy group" described in this specification include a group represented by —O(G3), wherein G3 is the "substituted or unsubstituted alkyl group" described in the specific example group G3. The number of carbon atoms of the "unsubstituted alkoxy group" is 1 to 50, preferably 1 to 30, more preferably 1 to 18, unless otherwise specified in this specification.

"Substituted or Unsubstituted Alkylthio Group"

Specific examples of the "substituted or unsubstituted alkylthio group" described in this specification include a group represented by —S(G3), wherein G3 is the "substituted or unsubstituted alkyl group" described in the specific example group G3. The number of carbon atoms of the "unsubstituted alkylthio group" is 1 to 50, preferably 1 to 30, more preferably 1 to 18, unless otherwise specified in this specification.

"Substituted or Unsubstituted Aryloxy Group"

Specific examples of the "substituted or unsubstituted aryloxy group" described in this specification include a group represented by —O(G1), wherein G1 is the "substituted or unsubstituted aryl group" described in the specific example group G1. The number of ring carbon atoms of the "unsubstituted aryloxy group" is 6 to 50, preferably 6 to 30, more preferably 6 to 18, unless otherwise specified in this specification.

"Substituted or Unsubstituted Arylthio Group"

Specific examples of the "substituted or unsubstituted arylthio group" described in this specification include a group represented by —S(G1), wherein G1 is a "substituted or unsubstituted aryl group" described in the specific example group G1. The number of ring carbon atoms of the "unsubstituted arylthio group" is 6 to 50, preferably 6 to 30, more preferably 6 to 18, unless otherwise specified in this specification.

"Substituted or Unsubstituted Trialkylsilyl Group"

Specific examples of the "trialkylsilyl group" described in this specification include a group represented by —Si(G3)(G3)(G3), where G3 is the "substituted or unsubstituted alkyl group" described in the specific example group G3. A plurality of G3's in —Si(G3)(G3)(G3) are the same as or different from each other. The number of carbon atoms in each alkyl group of the "trialkylsilyl group" is 1 to 50, preferably 1 to 20, more preferably 1 to 6, unless otherwise specified in this specification.

"Substituted or Unsubstituted Aralkyl Group"

Specific examples of the "substituted or unsubstituted aralkyl group" described in this specification is a group represented by -(G3)-(G1), wherein G3 is the "substituted or unsubstituted alkyl group" described in the specific example group G3, and G1 is the "substituted or unsubstituted aryl group" described in the specific example group G1. Therefore, the "aralkyl group" is a group in which a hydrogen atom of the "alkyl group" is substituted by an "aryl group" as a substituent, and is one form of the "substituted alkyl group." The "unsubstituted aralkyl group" is the "unsubstituted alkyl group" substituted by the "unsubstituted aryl group", and the number of carbon atoms of the "unsubstituted aralkyl group" is 7 to 50, preferably 7 to 30, more preferably 7 to 18, unless otherwise specified in this specification.

Specific examples of the "substituted or unsubstituted aralkyl group" include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, a 2-β-naphthylisopropyl group, and the like.

Unless otherwise specified in this specification, examples of the substituted or unsubstituted aryl group described in this specification preferably include a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a 1-naphthyl group, a 2-naphthyl group, an anthryl group, a phenanthryl group, a pyrenyl group, a chrysenyl group, a triphenylenyl group, a fluorenyl group, a 9,9'-spirobifluorenyl group, 9,9-dimethylfluorenyl group, 9,9-diphenylfluorenyl group, and the like.

Unless otherwise specified in this specification, examples of the substituted or unsubstituted heterocyclic groups described in this specification preferably include a pyridyl group, a pyrimidinyl group, a triazinyl group, a quinolyl group, an isoquinolyl group, a quinazolinyl group, a benzimidazolyl group, a phenanthrolinyl group, a carbazolyl group (a 1-carbazolyl group, a 2-carbazolyl group, a 3-carbazolyl group, a 4-carbazolyl group, or a 9-carbazolyl group), a benzocarbazolyl group, an azacarbazolyl group, a diazacarbazolyl group, a dibenzofuranyl group, a naphthobenzofuranyl group, an azadibenzofuranyl group, a diazadibenzofuranyl group, a dibenzothiophenyl group, a naphthobenzothiophenyl group, an azadibenzothiophenyl group, a diazadibenzothiophenyl group, a (9-phenyl)carbazolyl group (a (9-phenyl)carbazol-1-yl group, a (9-phenyl)carbazol-2-yl group, a (9-phenyl)carbazol-3-yl group, or a (9-phenyl)carbazol-4-yl group), a (9-biphenylyl)carbazolyl group, a (9-phenyl)phenylcarbazolyl group, a diphenylcarbazol-9-yl group, a phenylcarbazol-9-yl group, a phenyltriazinyl group, a biphenylyltriazinyl group, a diphenyltriazinyl group, a phenyldibenzofuranyl group, a phenyldibenzothiophenyl group, and the like.

In this specification, the carbazolyl group is specifically any of the following groups, unless otherwise specified in this specification.

(TEMP-Cz1)

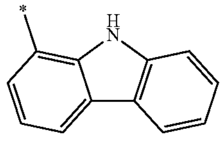

(TEMP-Cz2)

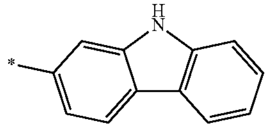

(TEMP-Cz3)

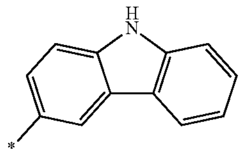

-continued (TEMP-Cz4)

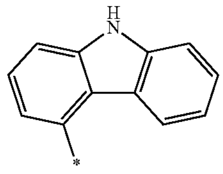

(TEMP-Cz5)

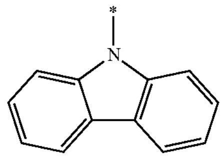

In this specification, the (9-phenyl)carbazolyl group is specifically any of the following groups, unless otherwise specified in this specification.

(TEMP-Cz6)

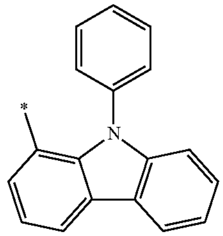

(TEMP-Cz7)

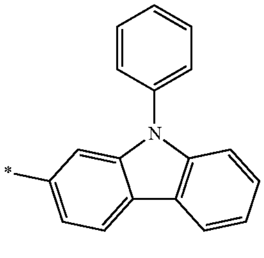

(TEMP-Cz8)

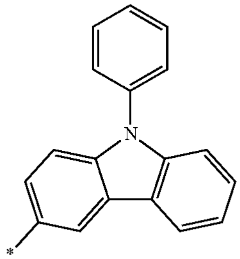

(TEMP-Cz9)

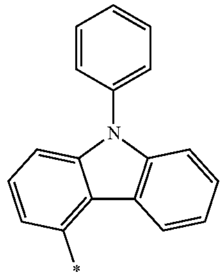

In the general formulas (TEMP-Cz1) to (TEMP-Cz9), * represents a bonding position.

In this specification, the dibenzofuranyl group and the dibenzothiophenyl group are specifically any of the following groups, unless otherwise specified in this specification.

(TEMP-34)

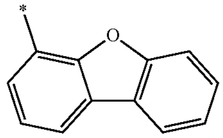

(TEMP-35)

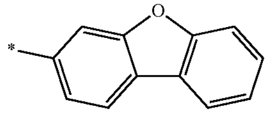

(TEMP-36)

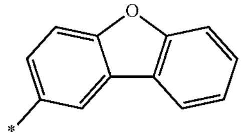

(TEMP-37)

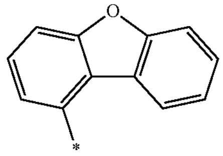

(TEMP-38)

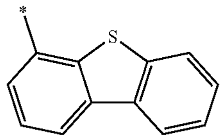

(TEMP-39)

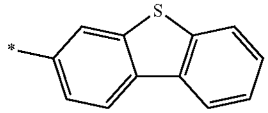

(TEMP-40)

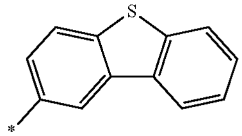

(TEMP-41)

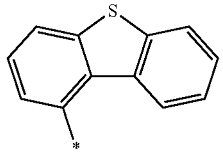

In the general formulas (TEMP-34) to (TEMP-41), * represents a bonding position.

The substituted or unsubstituted alkyl group described in this specification is preferably a methyl group, an ethyl group, a propyl group, an isopropyl group, a n-butyl group, an isobutyl group, a t-butyl group, or the like, unless otherwise specified in this specification.

"Substituted or Unsubstituted Arylene Group"

The "substituted or unsubstituted arylene group" described in this specification is a divalent group derived by removing one hydrogen atom on the aryl ring of the "substituted or unsubstituted aryl group", unless otherwise specified. Specific examples of the "substituted or unsubstituted arylene group" (specific example group G12) include a divalent group derived by removing one hydrogen atom on the aryl ring of the "substituted or unsubstituted aryl group" described in the specific example group G1, and the like.

"Substituted or Unsubstituted Divalent Heterocyclic Group"

The "substituted or unsubstituted divalent heterocyclic group" described in this specification is a divalent group derived by removing one hydrogen atom on the heterocyclic ring of the "substituted or unsubstituted heterocyclic group", unless otherwise specified. Specific examples of the "substituted or unsubstituted divalent heterocyclic group" (specific example group G13) include a divalent group derived by removing one hydrogen atom on the heterocyclic ring of the "substituted or unsubstituted heterocyclic group" described in the specific example group G2, and the like.

"Substituted or Unsubstituted Alkylene Group"

The "substituted or unsubstituted alkylene group" described in this specification is a divalent group derived by removing one hydrogen atom on the alkyl chain of the "substituted or unsubstituted alkyl group", unless otherwise specified. Specific examples of the "substituted or unsubstituted alkylene group" (specific example group G14) include a divalent group derived by removing one hydrogen atom on the alkyl chain of the "substituted or unsubstituted alkyl group" described in the specific example group G3, and the like.

The substituted or unsubstituted arylene group described in this specification is preferably any group of the following general formulas (TEMP-42) to (TEMP-68), unless otherwise specified in this specification.

(TEMP-42)

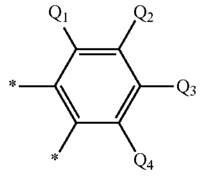

(TEMP-43)

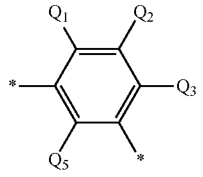

(TEMP-44)

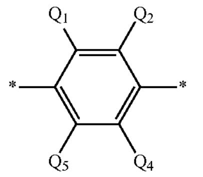

(TEMP-45)

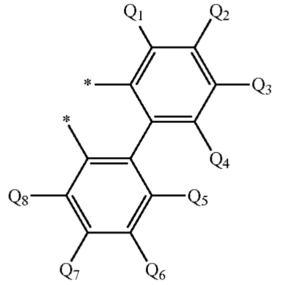

-continued (TEMP-46)

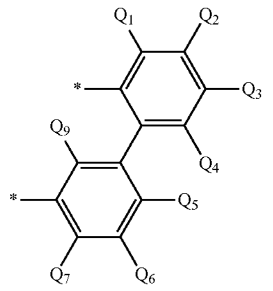

(TEMP-47)

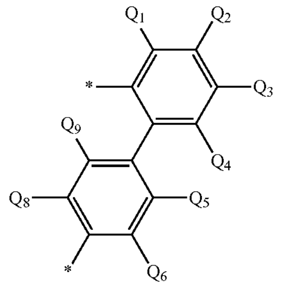

(TEMP-48)

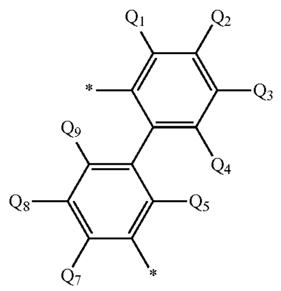

(TEMP-49)

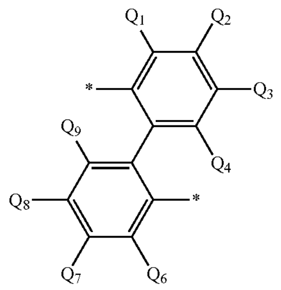

(TEMP-50)

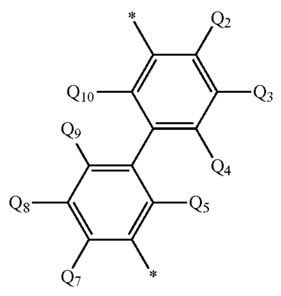

-continued (TEMP-51)

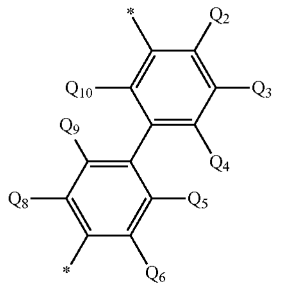

(TEMP-52)

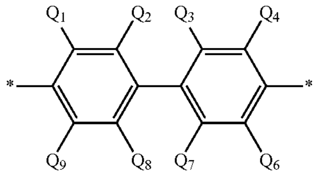

In the general formulas (TEMP-42) to (TEMP-52), $Q_1$ to $Q_{10}$ are independently a hydrogen atom or a substituent.

In the general formulas (TEMP-42) to (TEMP-52), * represents a bonding position.

(TEMP-53)

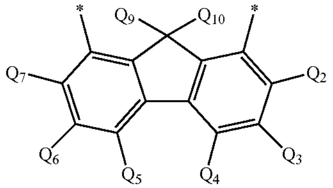

(TEMP-54)

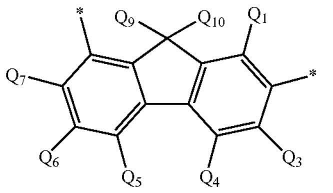

(TEMP-55)

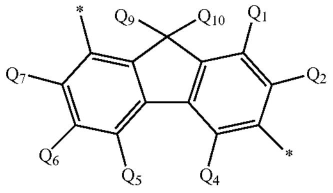

(TEMP-56)

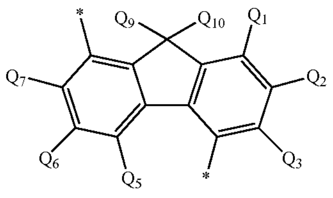

-continued (TEMP-57)

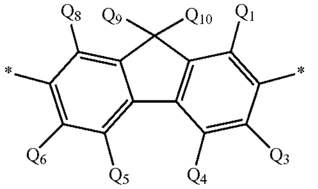

(TEMP-58)

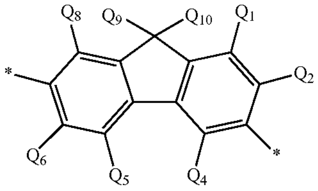

(TEMP-59)

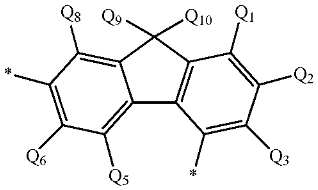

(TEMP-60)

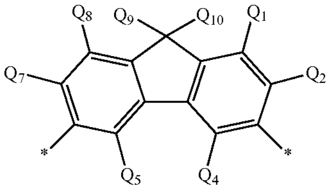

(TEMP-61)

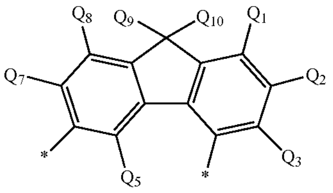

(TEMP-62)

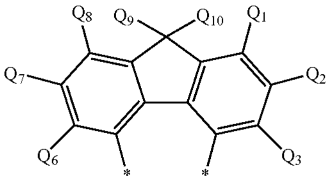

In the general formulas (TEMP-53) to (TEMP-62), $Q_1$ to $Q_{10}$ are independently a hydrogen atom or a substituent.

$Q_9$ and $Q_{10}$ may be bonded with each other via a single bond to form a ring.

In the general formulas (TEMP-53) to (TEMP-62), * represents a bonding position.

(TEMP-63)

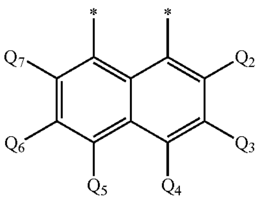

-continued (TEMP-64)

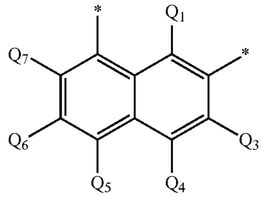

(TEMP-65)

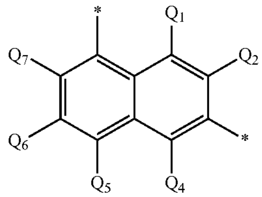

(TEMP-66)

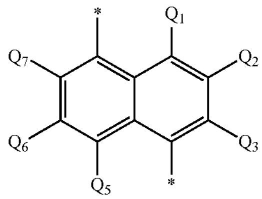

(TEMP-67)

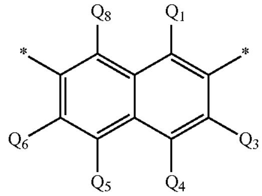

(TEMP-68)

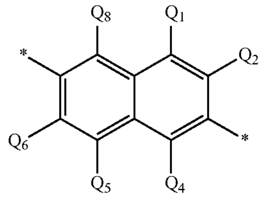

In the general formulas (TEMP-63) to (TEMP-68), $Q_1$ to $Q_8$ are independently a hydrogen atom or a substituent.

In the general formulas (TEMP-63) to (TEMP-68), * represents a bonding position.

The substituted or unsubstituted divalent heterocyclic group described in this specification is preferably any group of the following general formulas (TEMP-69) to (TEMP-102), unless otherwise specified in this specification.

(TEMP-69)

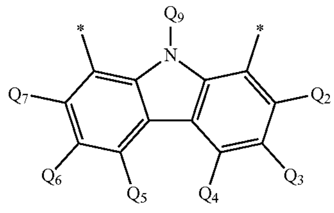

-continued (TEMP-70)

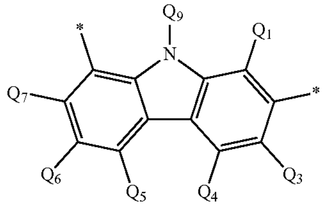

(TEMP-71)

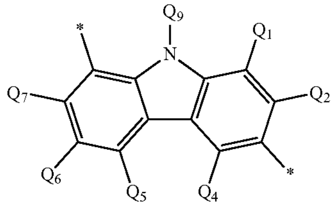

(TEMP-72)

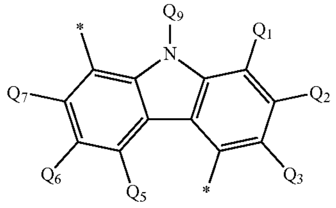

(TEMP-73)

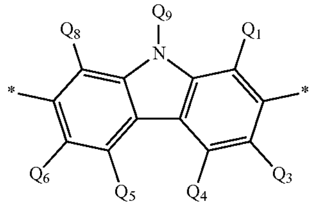

(TEMP-74)

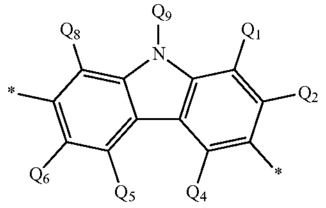

(TEMP-75)

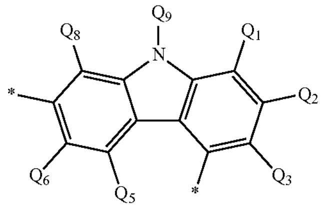

(TEMP-76)

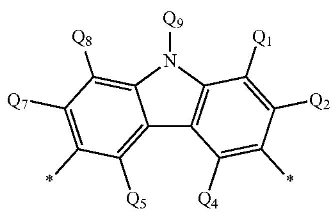

-continued
(TEMP-77)
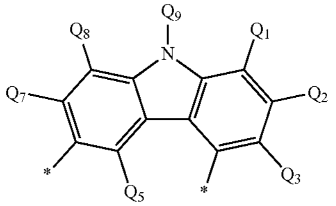
(TEMP-78)
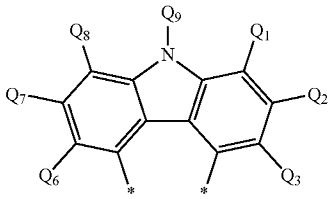
(TEMP-79)
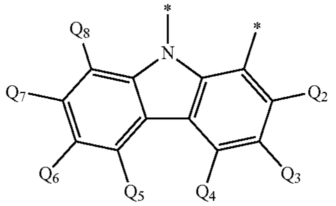
(TEMP-80)
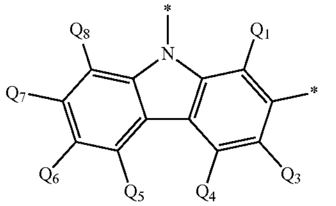
(TEMP-81)
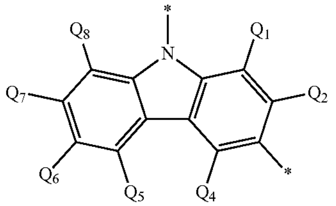
(TEMP-82)
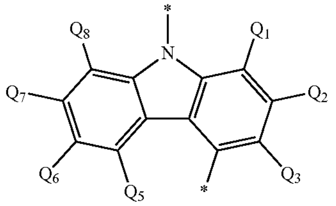
In the general formulas (TEMP-69) to (TEMP-82), $Q_1$ to $Q_8$ are independently a hydrogen atom or a substituent.
(TEMP-83)
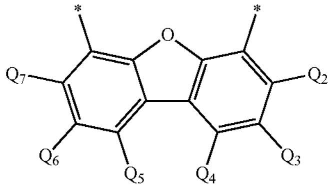
-continued
(TEMP-84)
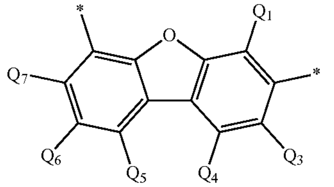
(TEMP-85)
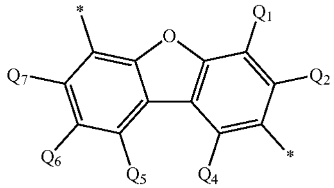
(TEMP-86)
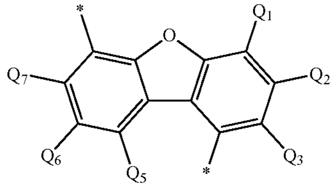
(TEMP-87)
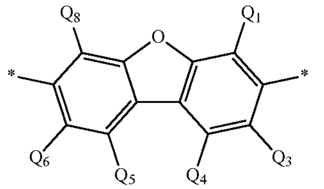
(TEMP-88)
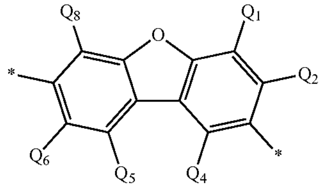
(TEMP-89)
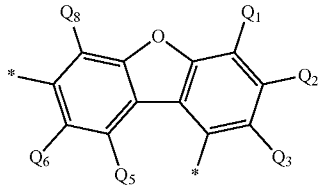
(TEMP-90)
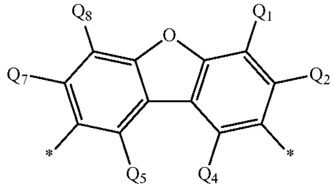
(TEMP-91)
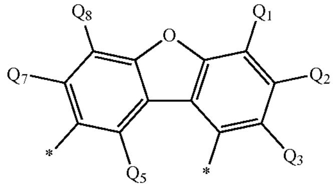

-continued (TEMP-92)

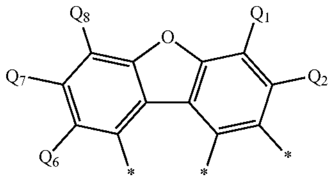

(TEMP-93)

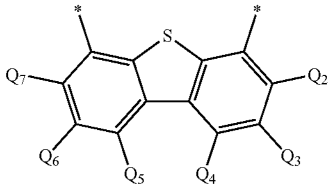

(TEMP-94)

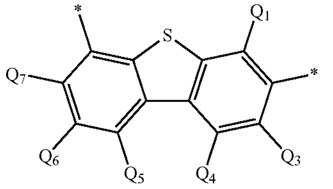

(TEMP-95)

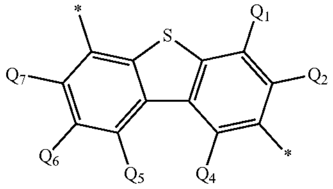

(TEMP-96)

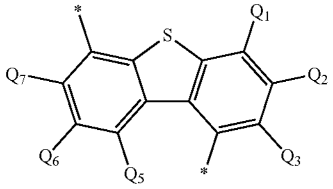

(TEMP-97)

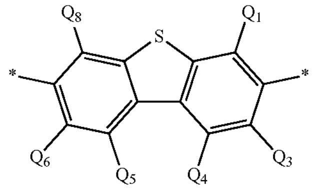

(TEMP-98)

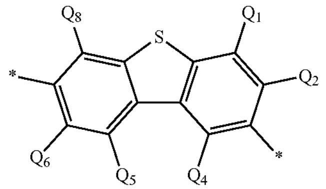

(TEMP-99)

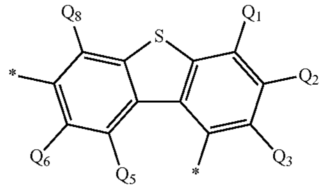

-continued (TEMP-100)

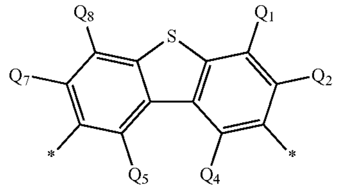

(TEMP-101)

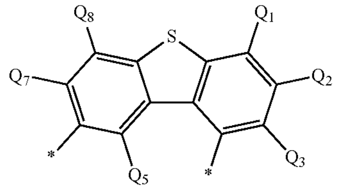

(TEMP-102)

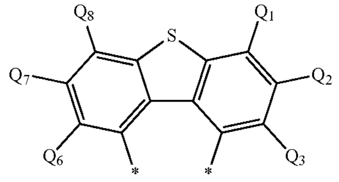

In the general formulas (TEMP-83) to (TEMP-102), $Q_1$ to $Q_8$ are independently a hydrogen atom or a substituent.

The above is the explanation of the "Substituent described in this specification."

"The Case where Bonded with Each Other to Form a Ring"

In this specification, the case where "one or more sets of adjacent two or more form a substituted or unsubstituted monocycle by bonding with each other, form a substituted or unsubstituted fused ring by bonding with each other, or do not bond with each other" means the case where "one or more sets of adjacent two or more form a substituted or unsubstituted monocycle by bonding with each other"; the case where "one or more sets of adjacent two or more form a substituted or unsubstituted fused ring by bonding with each other"; and the case where "one or more sets of adjacent two or more do not bond with each other."

The case where "one or more sets of adjacent two or more form a substituted or unsubstituted monocycle by bonding with each other" and the case where "one or more sets of adjacent two or more form a substituted or unsubstituted fused ring by bonding with each other" in this specification (these cases may be collectively referred to as "the case where forming a ring by bonding with each other") will be described below. The case of an anthracene compound represented by the following general formula (TEMP-103) in which the mother skeleton is an anthracene ring will be described as an example.

(TEMP-103)

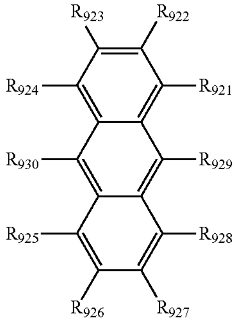

For example, in the case where "one or more sets of adjacent two or more among $R_{921}$ to $R_{930}$ form a ring by bonding with each other", the one set of adjacent two includes a pair of $R_{921}$ and $R_{922}$, a pair of $R_{922}$ and $R_{923}$, a pair of $R_{923}$ and $R_{924}$, a pair of $R_{924}$ and $R_{930}$, a pair of $R_{930}$ and $R_{925}$, a pair of $R_{925}$ and $R_{926}$, a pair of $R_{926}$ and $R_{927}$, a pair of $R_{927}$ and $R_{928}$, a pair of $R_{928}$ and $R_{929}$, and a pair of $R_{929}$ and $R_{921}$.

The "one or more sets" means that two or more sets of the adjacent two or more sets may form a ring at the same time. For example, $R_{921}$ and $R_{922}$ form a ring $Q_A$ by bonding with each other, and at the same, time $R_{925}$ and $R_{926}$ form a ring $Q_B$ by bonding with each other, the anthracene compound represented by the general formula (TEMP-103) is represented by the following general formula (TEMP-104).

(TEMP-104)

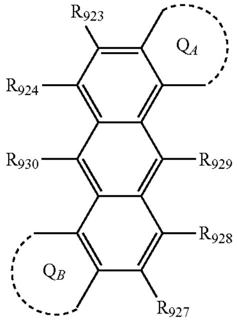

The case where the "set of adjacent two or more" form a ring includes not only the case where the set (pair) of adjacent "two" is bonded with as in the above-mentioned examples, but also the case where the set of adjacent "three or more" are bonded with each other. For example, it means the case where $R_{921}$ and $R_{922}$ form a ring $Q_A$ by bonding with each other, and $R_{922}$ and $R_{923}$ form a ring $Q_C$ by bonding with each other, and adjacent three ($R_{921}$, $R_{922}$ and $R_{923}$) form rings by bonding with each other and together fused to the anthracene mother skeleton. In this case, the anthracene compound represented by the general formula (TEMP-103) is represented by the following general formula (TEMP-105). In the following general formula (TEMP-105), the ring $Q_A$ and the ring $Q_C$ share $R_{922}$.

(TEMP-105)

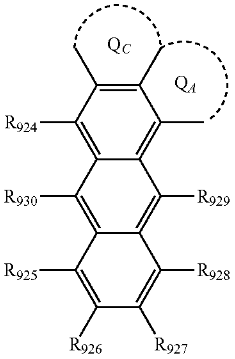

The "monocycle" or "fused ring" formed may be a saturated ring or an unsaturated ring, as a structure of the formed ring alone. Even when the "one pair of adjacent two" forms a "monocycle" or a "fused ring", the "monocycle" or the "fused ring" may form a saturated ring or an unsaturated ring. For example, the ring $Q_A$ and the ring $Q_B$ formed in the general formula (TEMP-104) are independently a "monocycle" or a "fused ring." The ring $Q_A$ and the ring $Q_C$ formed in the general formula (TEMP-105) are "fused ring." The ring $Q_A$ and ring $Q_C$ of the general formula (TEMP-105) are fused ring by fusing the ring $Q_A$ and the ring $Q_C$ together. When the ring $Q_A$ of the general formula (TMEP-104) is a benzene ring, the ring $Q_A$ is a monocycle. When the ring $Q_A$ of the general formula (TMEP-104) is a naphthalene ring, the ring $Q_A$ is a fused ring.

The "unsaturated ring" means an aromatic hydrocarbon ring or an aromatic heterocyclic ring. The "saturated ring" means an aliphatic hydrocarbon ring, or a non-aromatic heterocyclic ring.

Specific examples of the aromatic hydrocarbon ring include a structure in which the group listed as a specific example in the specific example group G1 is terminated by a hydrogen atom.

Specific examples of the aromatic heterocyclic ring include a structure in which the aromatic heterocyclic group listed as a specific example in the example group G2 is terminated by a hydrogen atom.

Specific examples of the aliphatic hydrocarbon ring include a structure in which the group listed as a specific example in the specific example group G6 is terminated by a hydrogen atom.

The term "to form a ring" means forming a ring only with a plurality of atoms of the mother skeleton, or with a plurality of atoms of the mother skeleton and one or more arbitrary elements in addition. For example, the ring $Q_A$ shown in the general formula (TEMP-104), which is formed by bonding $R_{921}$ and $R_{922}$ with each other, is a ring formed from the carbon atom of the anthracene skeleton with which $R_{921}$ is bonded, the carbon atom of the anthracene skeleton with which $R_{922}$ is bonded, and one or more arbitrary elements. For example, in the case where the ring $Q_A$ is formed with $R_{921}$ and $R_{922}$, when a monocyclic unsaturated ring is formed with the carbon atom of the anthracene skeleton with which $R_{921}$ is bonded, the carbon atom of the anthracene skeleton with which $R_{922}$ is bonded, and four carbon atoms, the ring formed with $R_{921}$ and $R_{922}$ is a benzene ring.

Here, the "arbitrary element" is preferably at least one element selected from the group consisting of a carbon element, a nitrogen element, an oxygen element, and a sulfur element, unless otherwise specified in this specification. In the arbitrary element (for example, a carbon element or a nitrogen element), a bond which does not form a ring may be terminated with a hydrogen atom or the like, or may be substituted with "arbitrary substituent" described below. When an arbitrary element other than a carbon element is contained, the ring formed is a heterocyclic ring.

The number of "one or more arbitrary element(s)" constituting a monocycle or a fused ring is preferably 2 or more and 15 or less, more preferably 3 or more and 12 or less, and still more preferably 3 or more and 5 or less, unless otherwise specified in this specification.

The "monocycle" is preferable among the "monocycle" and the "fused ring", unless otherwise specified in this specification.

The "unsaturated ring" is preferable among the "saturated ring" and the "unsaturated ring", unless otherwise specified in this specification.

Unless otherwise specified in this specification, the "monocycle" is preferably a benzene ring.

Unless otherwise specified in this specification, the "unsaturated ring" is preferably a benzene ring.

Unless otherwise specified in this specification, when "one or more sets of adjacent two or more" are "bonded with each other to form a substituted or unsubstituted monocycle" or "bonded with each other to form a substituted or unsubstituted fused ring", this specification, one or more sets of adjacent two or more are preferably bonded with each other to form a substituted or unsubstituted "unsaturated ring" from a plurality of atoms of the mother skeleton and one or more and 15 or less elements which is at least one kind selected from a carbon elements, a nitrogen element, an oxygen element, and a sulfur element.

The substituent in the case where the above-mentioned "monocycle" or "fused ring" has a substituent is, for example, an "arbitrary substituent" described below. Specific examples of the substituent which the above-mentioned "monocycle" or "fused ring" has include the substituent described above in the "Substituent described in this specification" section.

The substituent in the case where the above-mentioned "saturated ring" or "unsaturated ring" has a substituent is, for example, an "arbitrary substituent" described below. Specific examples of the substituent which the above-mentioned "monocycle" or "fused ring" has include the substituent described above in the "Substituent described in this specification" section.

The foregoing describes the case where "one or more sets of adjacent two or more form a substituted or unsubstituted monocycle by bonding with each other" and the case where "one or more sets of adjacent two or more form a substituted or unsubstituted fused ring by bonding with each other" (the case where "forming a ring by bonding with each other").

Substituent in the Case of "Substituted or Unsubstituted"

In one embodiment in this specification, the substituent (in this specification, sometimes referred to as an "arbitrary substituent") in the case of "substituted or unsubstituted" is, for example, a group selected from the group consisting of:

an unsubstituted alkyl group including 1 to 50 carbon atoms, an unsubstituted alkenyl group including 2 to 50 carbon atoms, an unsubstituted alkynyl group including 2 to 50 carbon atoms, an unsubstituted cycloalkyl group including 3 to 50 ring carbon atoms, —$Si(R_{901})(R_{902})(R_{903})$,

—O—$(R_{904})$,

—S—$(R_{905})$,

—$N(R_{906})(R_{907})$, a halogen atom, a cyano group, a nitro group, an unsubstituted aryl group including 6 to 50 ring carbon atoms, and an unsubstituted heterocyclic group including 5 to 50 ring atoms, wherein, $R_{901}$ to $R_{907}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted heterocyclic group including 5 to 50 ring atoms.

When two or more $R_{901}$'s are present, the two or more $R_{901}$'s may be the same as or different from each other.

When two or more $R_{902}$'s are present, the two or more $R_{902}$'s may be the same as or different from each other.

When two or more $R_{903}$'s are present, the two or more $R_{903}$'s may be the same as or different from each other.

When two or more $R_{904}$'s are present, the two or more $R_{904}$'s may be the same as or different from each other.

When two or more $R_{905}$'s are present, the two or more $R_{905}$'s may be the same as or different from each other.

When two or more $R_{906}$'s are present, the two or more $R_{906}$'s may be the same as or different from each other.

When two or more $R_{907}$'s are present, the two or more $R_{907}$'s may be the same as or different from each other.

In one embodiment, the substituent in the case of "substituted or unsubstituted" is a group selected from the group consisting of:

an alkyl group including 1 to 50 carbon atoms, an aryl group including 6 to 50 ring carbon atoms, and a heterocyclic group including 5 to 50 ring atoms.

In one embodiment, the substituent in the case of "substituted or unsubstituted" is a group selected from the group consisting of:

an alkyl group including 1 to 18 carbon atoms, an aryl group including 6 to 18 ring carbon atoms, and a heterocyclic group including 5 to 18 ring atoms.

Specific examples of each of the arbitrary substituents include specific examples of substituent described in the section "Substituent described in this specification" above.

Unless otherwise specified in this specification, adjacent arbitrary substituents may form a "saturated ring" or an "unsaturated ring", preferably form a substituted or unsubstituted saturated 5-membered ring, a substituted or unsubstituted saturated 6-membered ring, a substituted or unsubstituted unsaturated 5-membered ring, or a substituted or unsubstituted unsaturated 6-membered ring, more preferably form a benzene ring.

Unless otherwise specified in this specification, the arbitrary substituent may further have a substituent. The substituent which the arbitrary substituent further has is the same as that of the above-mentioned arbitrary substituent.

In this specification, the numerical range represented by "AA to BB" means the range including the numerical value AA described on the front side of "AA to BB" as the lower limit and the numerical value BB described on the rear side of "AA to BB" as the upper limit.

[Novel Compound]

A compound according to an aspect of the invention is represented by the following formula (1)

(1)

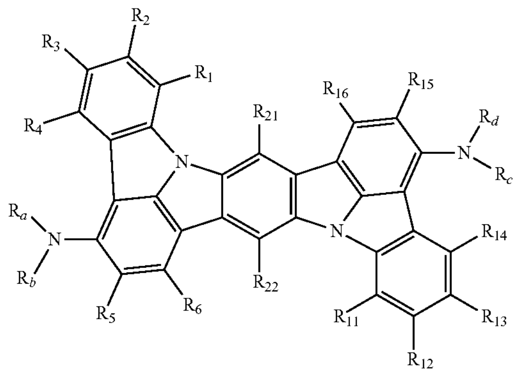

wherein in the formula (1), $R_a$ to $R_d$ are independently a substituted or unsubstituted aryl group including 6 to 50 ring carbon atoms, and at least one of $R_a$ to $R_d$ is a substituted or unsubstituted biphenyl-2-yl group;

at least one of $R_a$ to $R_d$ has a substituent A; the substituent A is one or more selected from the group consisting of a substituted or unsubstituted alkyl group including 1 to 50 carbon atoms, a substituted or unsubstituted cycloalkyl group including 3 to 50 ring carbon atoms, and —$Si(R_{31})(R_{32})(R_{33})$;

one or more sets of adjacent two or more of $R_1$ to $R_6$ and $R_{11}$ to $R_{16}$ form a substituted or unsubstituted, saturated or unsaturated ring, or do not form the substituted or unsubstituted, saturated or unsaturated ring;

$R_{21}$ and $R_{22}$, and $R_1$ to $R_6$ and $R_{11}$ to $R_{16}$ which do not form the substituted or unsubstituted, saturated or unsaturated ring are independently a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —$Si(R_{31})(R_{32})(R_{33})$, —C(═O)$R_{34}$, —$COOR_{35}$, —$N(R_{36})(R_{37})$, a halogen atom, a cyano group, a nitro group, a substituted or unsubstituted aryl group including 6 to 50 ring carbon atoms, or a substituted or unsubstituted monovalent heterocyclic group including 5 to 50 ring atoms;

$R_{31}$ to $R_{37}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms;

when a plurality of each of $R_{31}$ to $R_{37}$ is present, the plurality of each of $R_{31}$ to $R_{37}$ may be the same as or different from each other.

By the use of the compound according to an aspect of the invention, an organic EL device having a long lifetime can be fabricated. Hereinafter, the compound represented by the formula (1) will be described.

In the compound represented by the formula (1), at least one of $R_a$ to $R_d$ is a substituted or unsubstituted biphenyl-2-yl group.

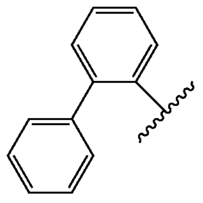

biphenyl-2-yl group

The compound represented by the formula (1) has a structure in which a particular substituent (substituent A) is substituted to at least one of $R_a$ to $R_d$. Namely, the substituent A is substituted to at least one of the aryl group including 6 to 50 ring carbon atoms for $R_a$ to $R_d$. The substituent A may be substituted to the biphenyl-2-yl group described above. In addition, when the aryl group including 6 to 50 ring carbon atoms has another substituent, the substituent A may be substituted to the another substituent.

The substituent A is one or more selected from the group consisting of a substituted or unsubstituted alkyl group including 1 to 50 carbon atoms, a substituted or unsubstituted cycloalkyl group including 3 to 50 ring carbon atoms, and —$Si(R_{31})(R_{32})(R_{33})$. When a plurality of the substituent A's is present in the compound represented by the formula (1), the plurality of the substituent A's may be the same as or different from each other.

In one embodiment, at least two (e.g., two, three, or four) of $R_a$ to $R_d$ are substituted or unsubstituted biphenyl-2-yl groups.

In one embodiment, at least one of $R_a$ and $R_b$ is a substituted or unsubstituted biphenyl-2-yl group and at least one of $R_c$ and $R_d$ is a substituted or unsubstituted biphenyl-2-yl group.

In one embodiment, $R_a$ and $R_c$ are substituted or unsubstituted biphenyl-2-yl groups and $R_b$ and $R_d$ are substituted or unsubstituted aryl groups including 6 to 50 ring carbon atoms other than the substituted or unsubstituted biphenyl-2-yl group.

In one embodiment, all or some of hydrogen atoms contained in $R_a$ to $R_d$ may be deuterium atoms. In addition, all or some of hydrogen atoms contained in the substituted or unsubstituted biphenyl-2-yl group may be deuterium atoms, and all or some of hydrogen atoms contained in the substituted or unsubstituted aryl group including 6 to 50 ring carbon atoms other than the substituted or unsubstituted biphenyl-2-yl group may be deuterium atoms.

In one embodiment, the substituent A is one or more selected from the group consisting of a substituted or unsubstituted alkyl group including 1 to 20 carbon atoms, a substituted or unsubstituted cycloalkyl group including 3 to 20 ring carbon atoms, and —$Si(R_{31})(R_{32})(R_{33})$.

In one embodiment, the substituent A is one or more selected from the group consisting of a substituted or unsubstituted alkyl group including 1 to 20 carbon atoms, and —$Si(R_{31})(R_{32})(R_{33})$.

In the above embodiments, it is preferred that $R_{31}$ to $R_{33}$ are independently a substituted or unsubstituted alkyl group including 1 to 50 carbon atoms, or a substituted or unsubstituted aryl group including 6 to 50 ring carbon atoms.

In one embodiment, the substituent A is a substituted or unsubstituted alkyl group including 1 to 20 carbon atoms.

In one embodiment, the compound represented by the formula (1) is a compound represented by the following formula (1-1).

(1-1)

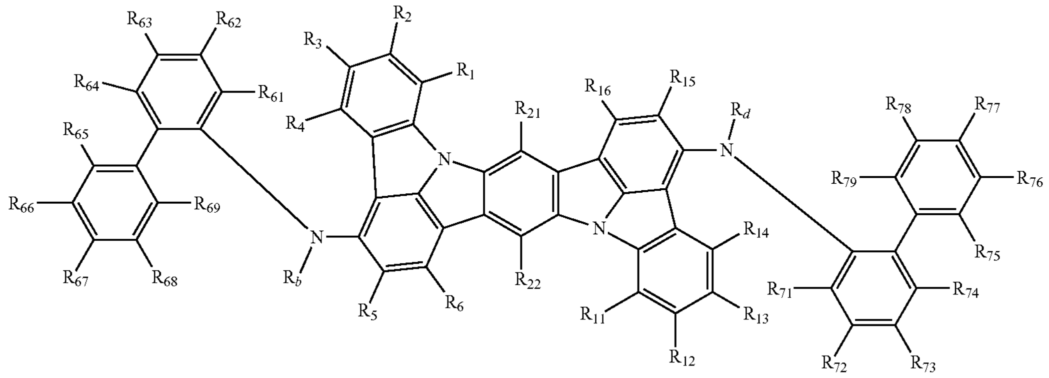

wherein in the formula (1-1), $R_1$ to $R_6$, $R_{11}$ to $R_{16}$, $R_{21}$, $R_{22}$, $R_b$, and $R_d$ are as defined in the formula (1);

$R_{61}$ to $R_{69}$ and $R_{71}$ to $R_{79}$ are independently a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, $-Si(R_{31})(R_{32})(R_{33})$, $-C(=O)R_{34}$, $-COOR_{35}$, $-N(R_{36})(R_{37})$, a halogen atom, a cyano group, a nitro group, a substituted or unsubstituted aryl group including 6 to 50 ring carbon atoms, or a substituted or unsubstituted monovalent heterocyclic group including 5 to 50 ring atoms; and at least one of $R_{61}$ to $R_{69}$, $R_{71}$ to $R_{79}$, the substituent by which $R_b$ is substituted, and the substituent by which $R_d$ is substituted is the substituent A.

In one embodiment, $R_b$ and $R_d$ are substituted or unsubstituted aryl groups including 6 to 30 ring carbon atoms.

In one embodiment, the compound represented by the formula (1) is a compound represented by the following formula (1-2).

(1-2)

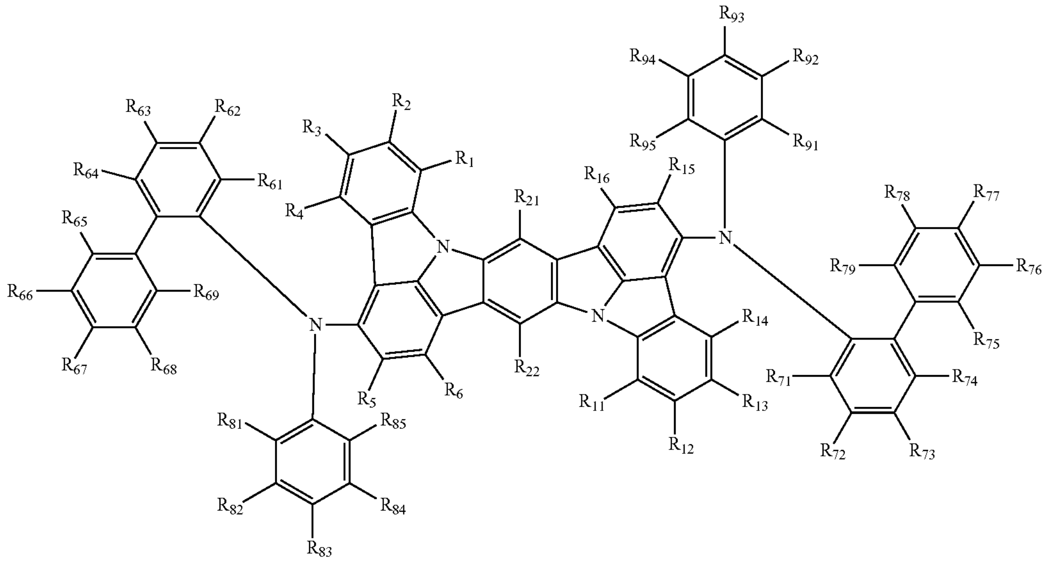

wherein in the formula (1-2), $R_1$ to $R_6$, $R_{11}$ to $R_{16}$, $R_{21}$, and $R_{22}$ are as defined in the formula (1);

$R_{61}$ to $R_{69}$, $R_{71}$ to $R_{79}$, $R_{81}$ to $R_{85}$, and $R_{91}$ to $R_{95}$ are independently a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si($R_{31}$)($R_{32}$)($R_{33}$), —C(=O)$R_{34}$, —COO$R_{35}$, —N($R_{36}$)($R_{37}$), a halogen atom, a cyano group, a nitro group, a substituted or unsubstituted aryl group including 6 to 50 ring carbon atoms, or a substituted or unsubstituted monovalent heterocyclic group including 5 to 50 ring atoms; and at least one of $R_{61}$ to $R_{69}$, $R_{71}$ to $R_{79}$, Rai to $R_{85}$, and $R_{91}$ to $R_{95}$ is the substituent A.

In one embodiment, at least one of $R_{61}$ to $R_{69}$ and $R_{71}$ to $R_{79}$ is the substituent A.

In one embodiment, at least one of $R_{61}$ to $R_{69}$ and at least one of $R_{71}$ to $R_{79}$ are independently the substituent A.

In one embodiment, at least one of Rai to $R_{85}$ and $R_{91}$ to $R_{95}$ is the substituent A.

In one embodiment, at least one of Rai to $R_{85}$ and at least one of $R_{91}$ to $R_{95}$ are independently the substituent A.

In one embodiment, at least one of Rei to $R_{69}$ and $R_{71}$ to $R_{79}$ and at least one of Rai to $R_{85}$ and $R_{91}$ to $R_{95}$ are independently the substituent A.

In one embodiment, $R_{63}$ and $R_{73}$ are independently the substituent A.

In one embodiment, $R_{67}$ and $R_{77}$ are independently the substituent A.

The expression of "one or more sets of adjacent two or more of $R_1$ to $R_6$ and $R_{11}$ to $R_{16}$ form a substituted or unsubstituted, saturated or unsaturated ring or do not form the substituted or unsubstituted, saturated or unsaturated ring" is described below.

"One set of adjacent two or more of $R_1$ to $R_6$ and $R_{11}$ to $R_{16}$" is, for example, a combination of $R_1$ and $R_2$, $R_2$ and $R_3$, $R_3$ and $R_a$, $R_5$ and $R_6$, $R_{11}$ and Rig, $R_1$ and $R_2$ and $R_3$, or the like.

The substituent in the case of "substituted" of the "substituted or unsubstituted" for the saturated or unsaturated ring is the same as the substituent in the case of the "substituted or unsubstituted" described later.

The expression of the "saturated or unsaturated ring" means, for example, when $R_1$ and $R_2$ form a ring, a ring formed by the carbon atom to which $R_1$ is bonded, the carbon atom to which $R_2$ is bonded, and one or more arbitrary atoms. Specifically, in the case when $R_1$ and $R_2$ form a ring, and the carbon atom to which $R_1$ is bonded, the carbon atom to which $R_2$ is bonded, and four carbon atoms form an unsaturated ring, the ring formed by $R_1$ and $R_2$ is a benzene ring.

The "arbitrary atom" is preferably a C atom, an N atom, an O atom, or an S atom. In arbitrary atoms (e.g., in the case where it is a C atom or an N atom), a bond that does not involved in formation of a ring may be terminated with a hydrogen atom or the like.

The "one or more arbitrary atoms" is preferably 2 or more and 15 or less, more preferably 3 or more and 12 or less, and still more preferably 3 or more and 5 or less arbitrary atoms.

Hereinafter, the expression of the "one or more sets of adjacent two or more of X to Y form a substituted or unsubstituted, saturated or unsaturated ring, or do not form the substituted or unsubstituted, saturated or unsaturated ring" means the same as when X is replaced by the above-mentioned $R_1$ and Y is replaced by the above-mentioned $R_6$.

In one embodiment, at least one of $R_1$ to $R_6$, and $R_{11}$ to $R_{16}$ is a substituted or unsubstituted alkyl group including 1 to 50 carbon atoms, and $R_{21}$ and $R_{22}$ are hydrogen atoms.

In one embodiment, at least one of $R_1$ to $R_6$ and at least one of $R_{11}$ to $R_{16}$ are independently a substituted or unsubstituted alkyl group including 1 to 50 carbon atoms, and $R_{21}$ and $R_{22}$ are hydrogen atoms.

In one embodiment, $R_1$ to $R_6$, $R_{11}$ to $R_{16}$, $R_{21}$, and $R_{22}$ are hydrogen atoms.

In one embodiment, $R_{61}$ to $R_{69}$ and $R_{61}$ to $R_{79}$ are hydrogen atoms. In this embodiment, all or some of $R_{61}$ to $R_{69}$ and $R_{71}$ to $R_{79}$, which are hydrogen atoms, may be deuterium atoms.

In one embodiment, $R_{61}$ to $R_{69}$ and $R_{71}$ to $R_{79}$ are hydrogen atoms. In this embodiment, all or some of $R_{61}$ to $R_{69}$ and $R_{71}$ to $R_{79}$, which are hydrogen atoms, may be deuterium atoms. For example, $R_{61}$ to $R_{64}$ and $R_{71}$ to $R_{74}$, which are hydrogen atoms, may be protium atoms, and $R_{65}$ to $R_{69}$ and $R_{75}$ to $R_{79}$, which are hydrogen atoms, may be deuterium atoms.

In one embodiment, the compound represented by the formula (1) is a compound represented by the following formula (1-3).

(1-3)

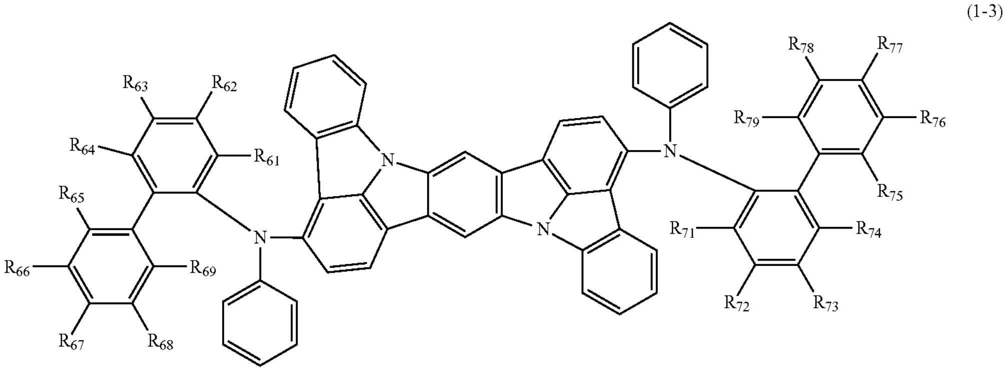

wherein in the formula (1-3), $R_{61}$ to $R_{69}$ and $R_{71}$ to $R_{79}$ are independently a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si($R_{31}$)($R_{32}$)($R_{33}$), —C(═O)$R_{34}$, —COOR$_{35}$, —N($R_{36}$)($R_{37}$), a halogen atom, a cyano group, a nitro group, a substituted or unsubstituted aryl group including 6 to 50 ring carbon atoms, or a substituted or unsubstituted monovalent heterocyclic group including 5 to 50 ring atoms; and at least one of $R_{61}$ to $R_{69}$ and $R_{71}$ to $R_{79}$ is the substituent A.

In one embodiment, the compound represented by the formula (1) is a compound represented by the following formula (1-4).

(1-4)

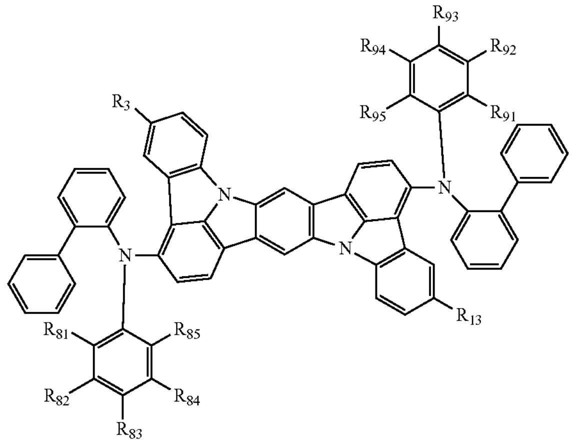

wherein in the formula (1-4), $R_3$ and $R_{13}$ are as defined in the formula (1);

$R_{81}$ to $R_{85}$ and $R_{91}$ to $R_{95}$ are independently a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si($R_{31}$)($R_{32}$)($R_{33}$), —C(═O)$R_{34}$, —COOR$_{35}$, —N($R_{36}$)($R_{37}$), a halogen atom, a cyano group, a nitro group, a substituted or unsubstituted aryl group including 6 to 50 ring carbon atoms, or a substituted or unsubstituted monovalent heterocyclic group including 5 to 50 ring atoms; and at least one of Rai to $R_{85}$ and $R_{91}$ to $R_{95}$ is the substituent A.

In one embodiment, $R_3$ and $R_{13}$ are hydrogen atoms.

In one embodiment, $R_3$ and $R_{13}$ are substituted or unsubstituted alkyl groups including 1 to 50 carbon atoms.

In one embodiment, $R_{82}$ and $R_{92}$ are independently the substituent A.

In one embodiment, $R_{83}$ and $R_{93}$ are independently the substituent A.

In one embodiment, the compound represented by the formula (1) is a compound represented by the following formula (1-5).

(1-5)

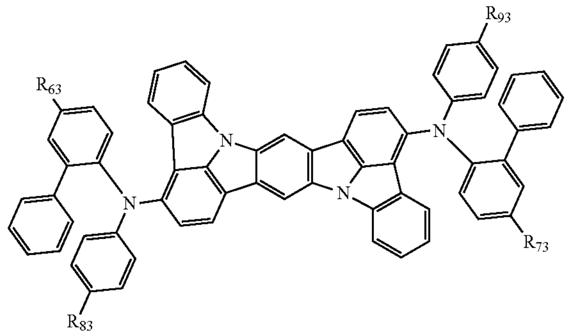

wherein in the formula (1-5), $R_{63}$, $R_{73}$, $R_{83}$, and $R_{93}$ are independently a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —Si($R_{31}$)($R_{32}$)($R_{33}$), —C(═O)$R_{34}$, —COOR$_{35}$, —N($R_{36}$)($R_{37}$), a halogen atom, a cyano group, a nitro group, a substituted or unsubstituted aryl group including 6 to 50 ring carbon atoms, or a substituted or unsubstituted monovalent heterocyclic group including 5 to 50 ring atoms; and at least one of $R_{63}$ and $R_{73}$ is the substituent A.

In one embodiment, $R_{83}$ and $R_{93}$ are independently a substituted or unsubstituted alkyl group including 1 to 50 carbon atoms.

The substituent in the case of the "substituted or unsubstituted" in the compound represented by the formula (1) is selected from the group consisting of an alkyl group including 1 to 50 carbon atoms, a haloalkyl group including 1 to 50 carbon atoms, an alkenyl group including 2 to 50 carbon atoms, an alkynyl group including 2 to 50 carbon atoms, a cycloalkyl group including 3 to 50 ring carbon atoms, an alkoxy group including 1 to 50 carbon atoms, an alkylthio group including 1 to 50 carbon atoms, an aryloxy group including 6 to 50 ring carbon atoms, an arylthio group including 6 to 50 ring carbon atoms, an aralkyl group including 7 to 50 carbon atoms, —$Si(R_{41})(R_{42})(R_{43})$, —$C(=O)R_{44}$, —$COOR_{45}$, —$S(=O)_2R_{46}$, —$P(=O)(R_{47})(R_{48})$, —$Ge(R_{49})(R_{50})(R_{51})$, —$N(R_{52})(R_{53})$ (wherein $R_{41}$ to $R_{53}$ are independently a hydrogen atom, an alkyl group including 1 to 50 carbon atoms, an aryl group including 6 to 50 ring carbon atoms, or a monovalent heterocyclic group including 5 to 50 ring atoms; and when two or more of each of $R_{41}$ to $R_{53}$ are present, the two or more of each of $R_{41}$ to $R_{53}$ may be the same as or different from each other), hydroxy group, a halogen atom, a cyano group, a nitro group, a substituted or unsubstituted aryl group including 6 to 50 ring carbon atoms, and a substituted or unsubstituted monovalent heterocyclic group including 5 to 50 ring atoms.

In one embodiment, the substituent in the case of the “substituted or unsubstituted” in the compound represented by the formula (1) is an alkyl group including 1 to 50 carbon atoms, an aryl group including 6 to 50 ring carbon atoms, and a monovalent heterocyclic group including 5 to 50 ring atoms.

In one embodiment, the substituent in the case of the “substituted or unsubstituted” in the compound represented by the formula (1) is selected from the group consisting of an alkyl group including 1 to 30 carbon atoms, an aryl group including 6 to 30 ring carbon atoms, and a monovalent heterocyclic group including 5 to 30 ring atoms.

In one embodiment, the substituent in the case of the “substituted or unsubstituted” in the compound represented by the formula (1) is selected from the group consisting of an alkyl group including 1 to 18 carbon atoms, an aryl group including 6 to 18 ring carbon atoms, and a monovalent heterocyclic group including 5 to 18 ring atoms.

Specific examples of each substituent in the compound represented by the formula (1), a substituent in the case of the “substituted or unsubstituted,” and a halogen atom are the same as those described above, respectively.

The compound represented by the formula (1) can be synthesized in accordance with Examples by using known alternative reactions or raw materials tailored to the target product.

Specific examples of the compound represented by the formula (1) will be described below, but these are merely examples, and the compound represented by the formula (1) is not limited to the following specific examples.

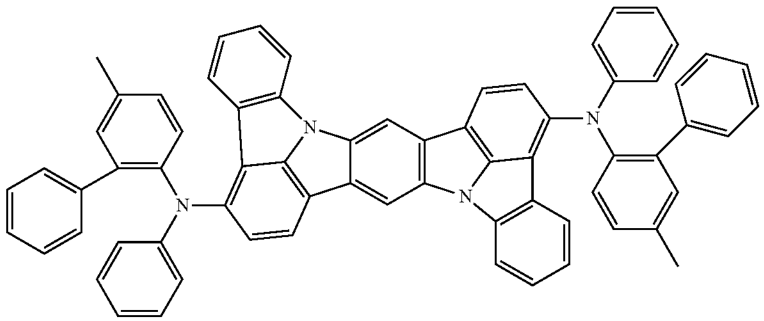

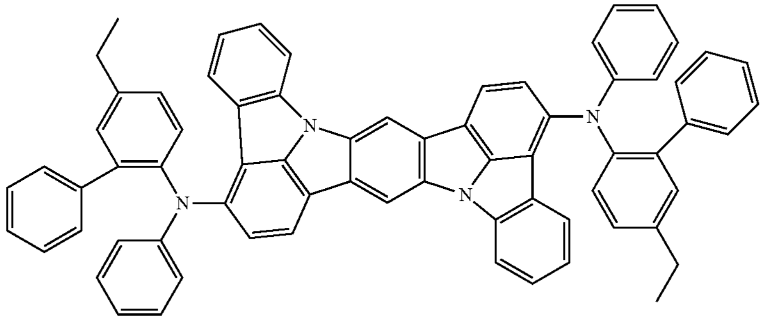

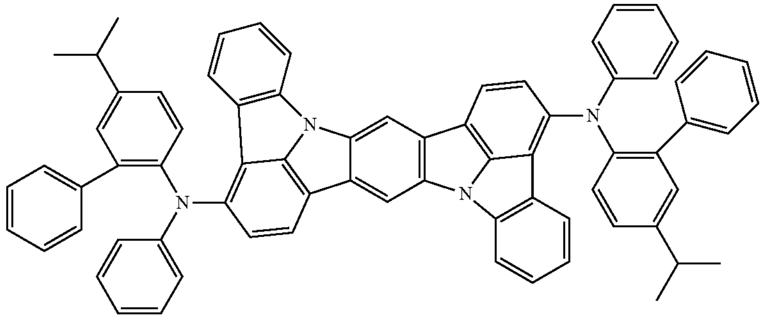

-continued
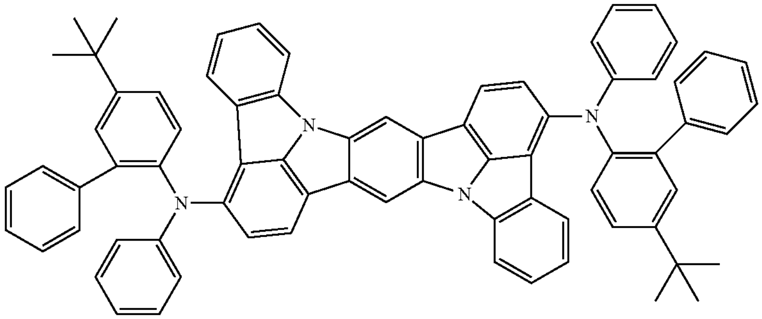
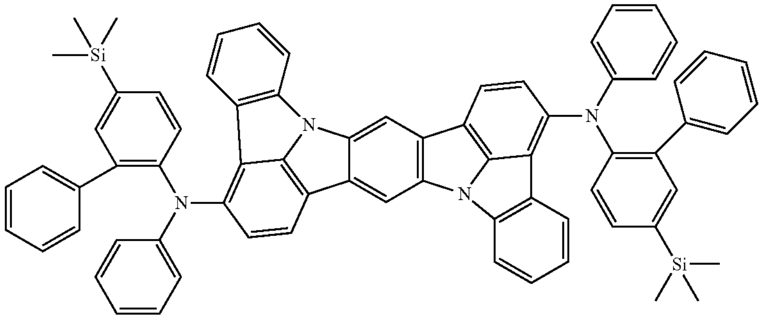
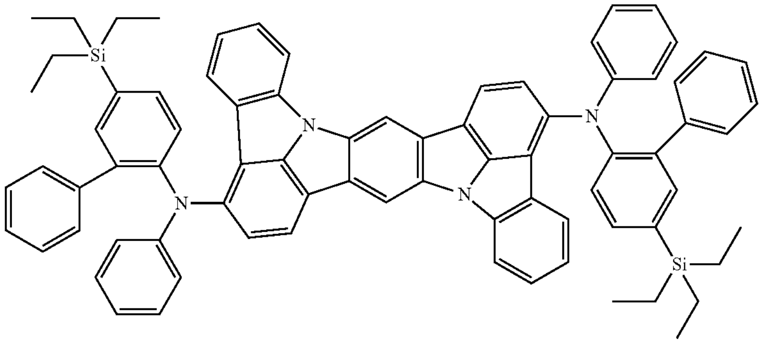
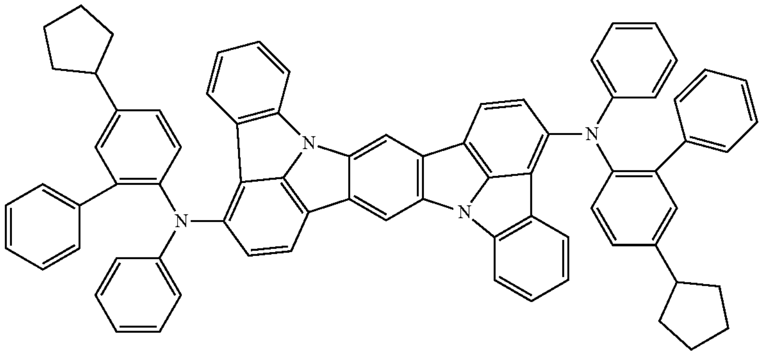
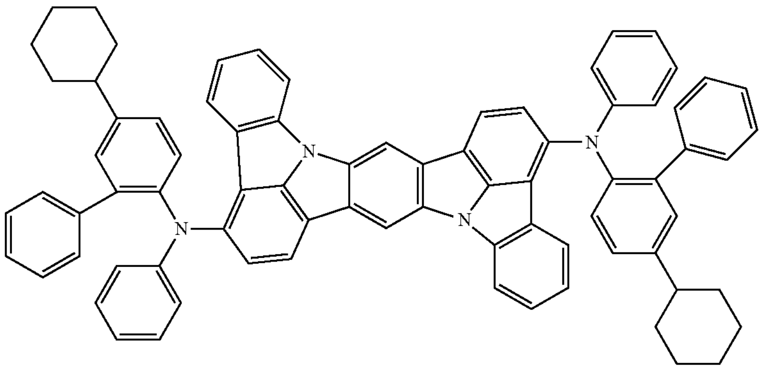

-continued
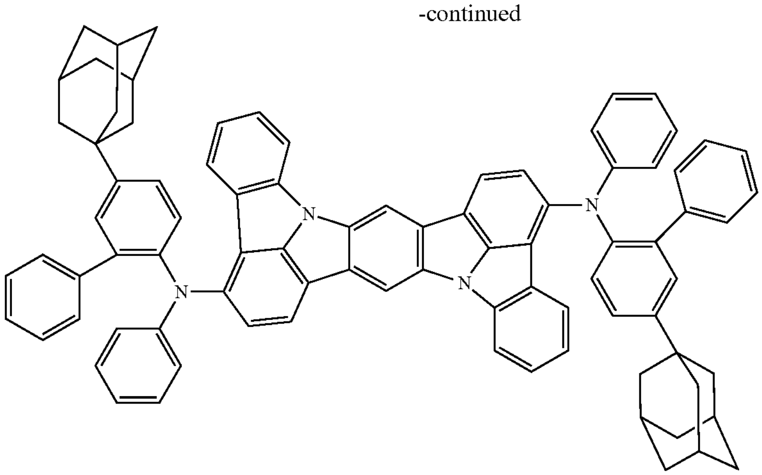
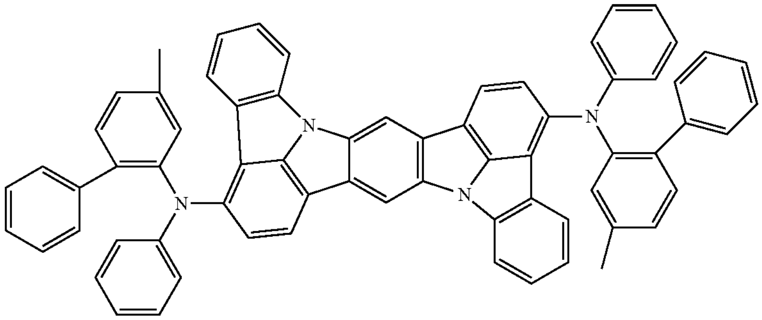
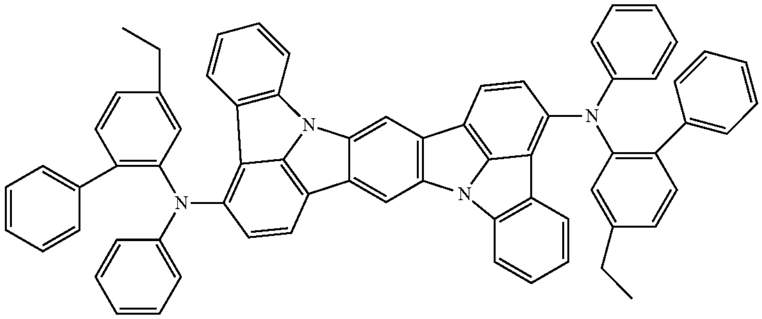
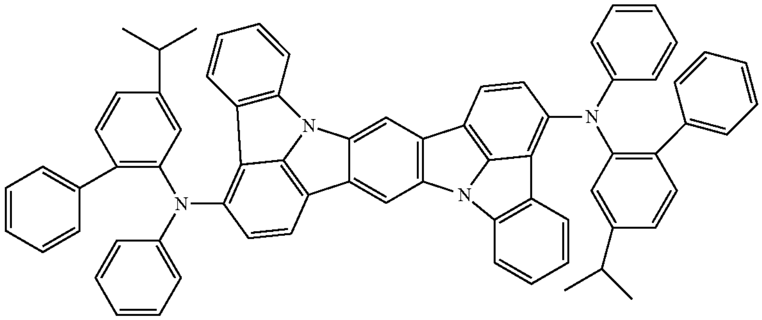
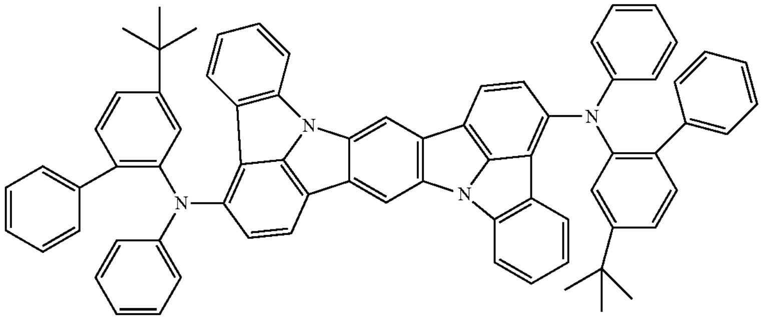

-continued
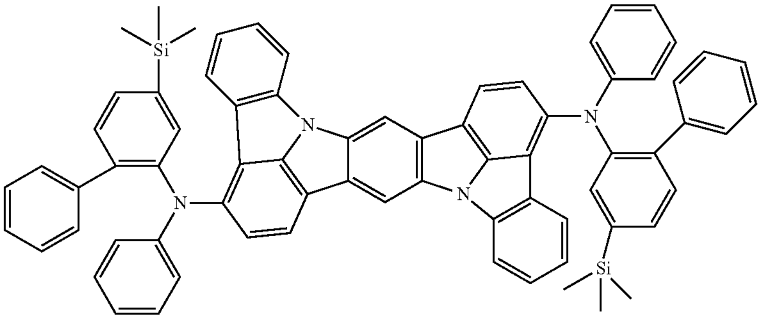
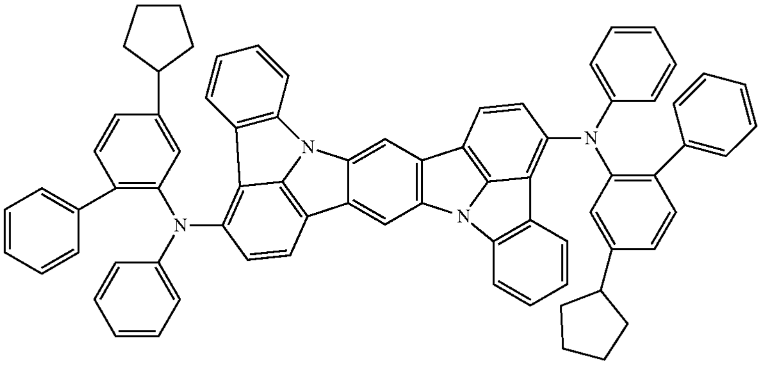
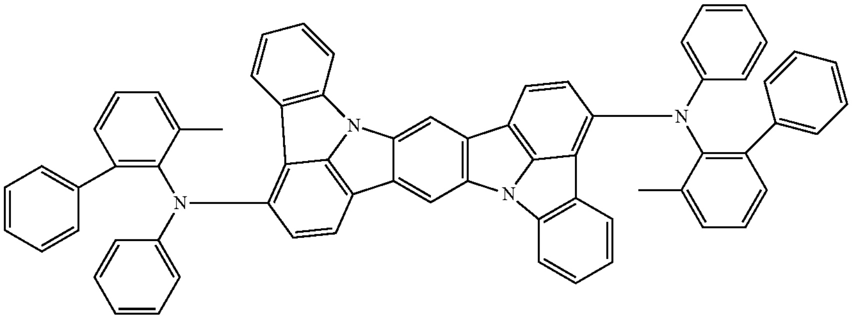
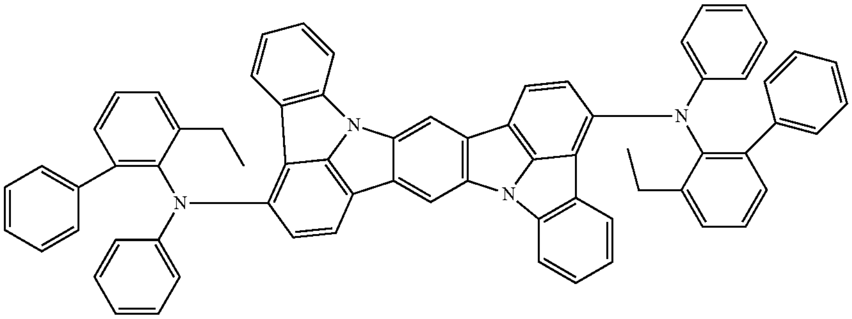
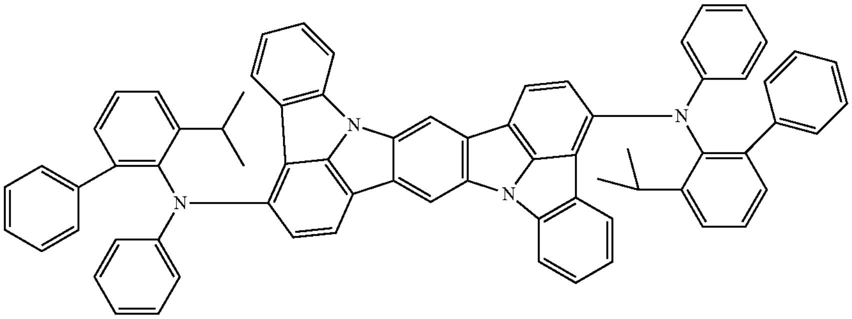

-continued
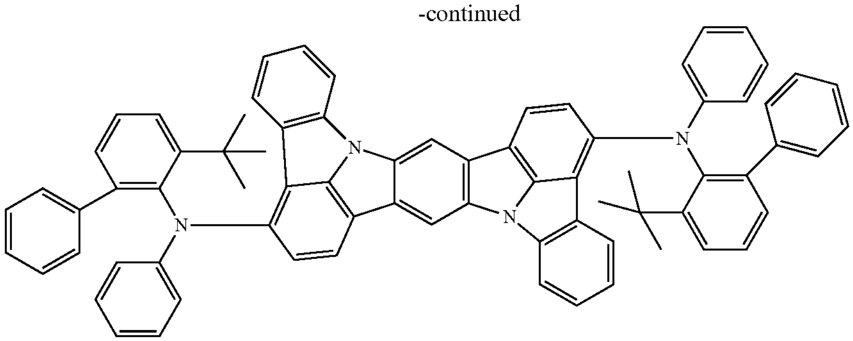
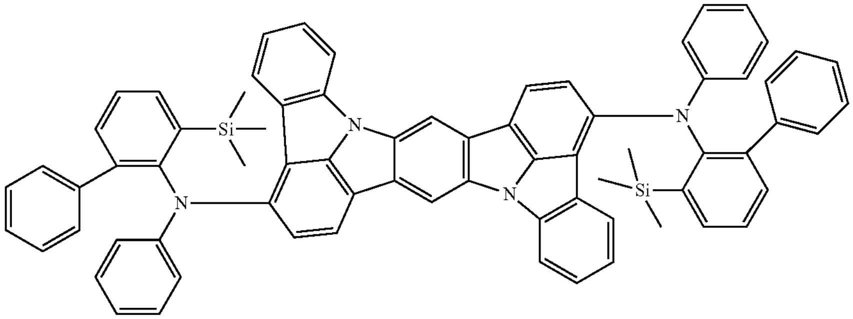
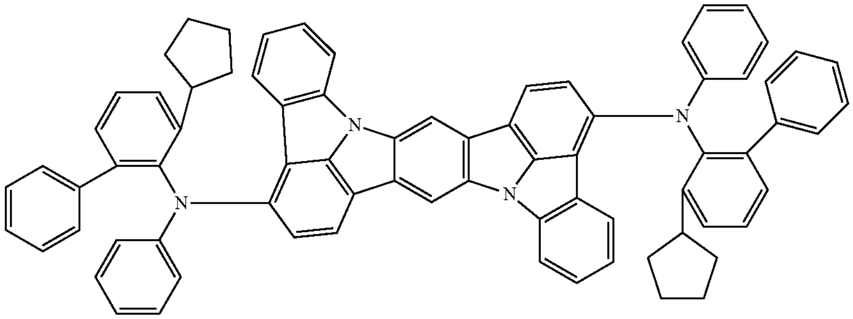
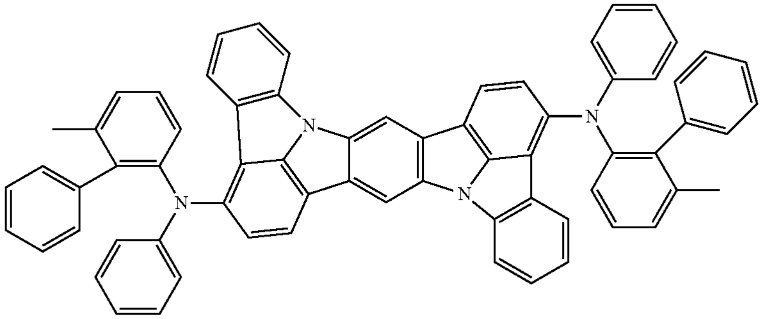
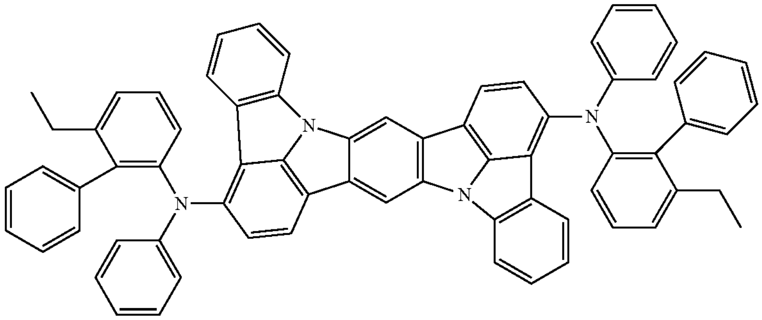

-continued
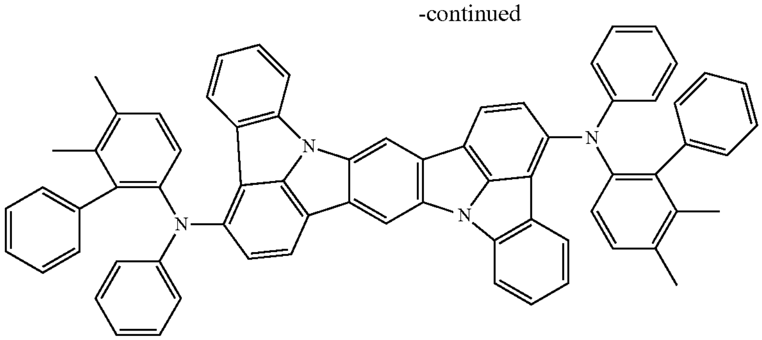
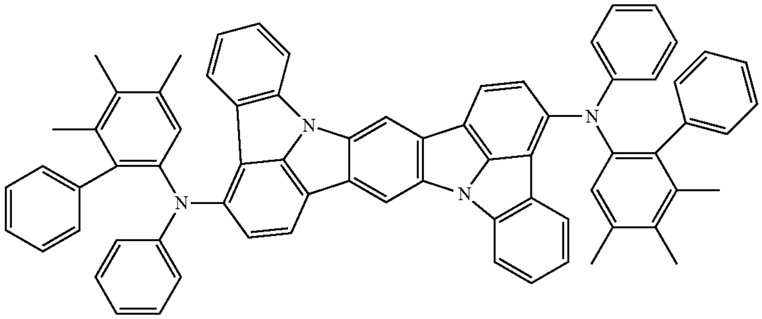
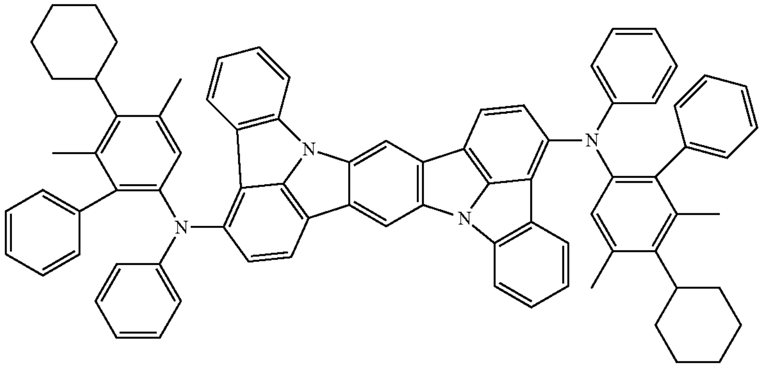
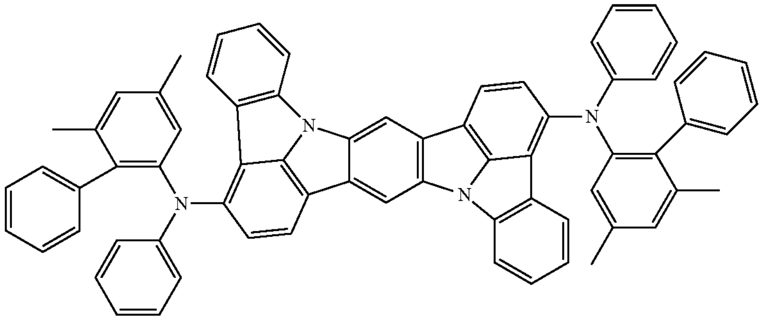
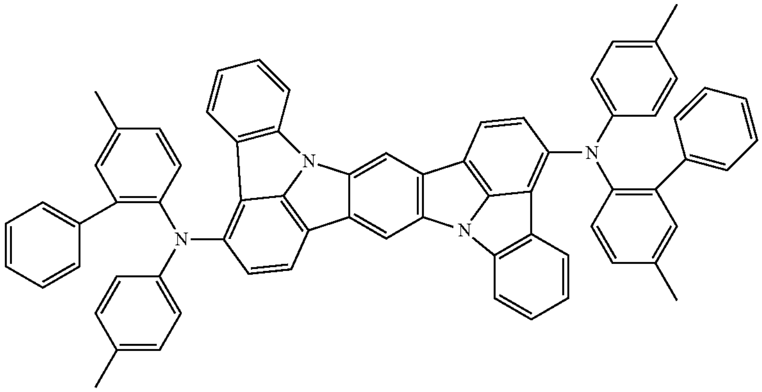

-continued
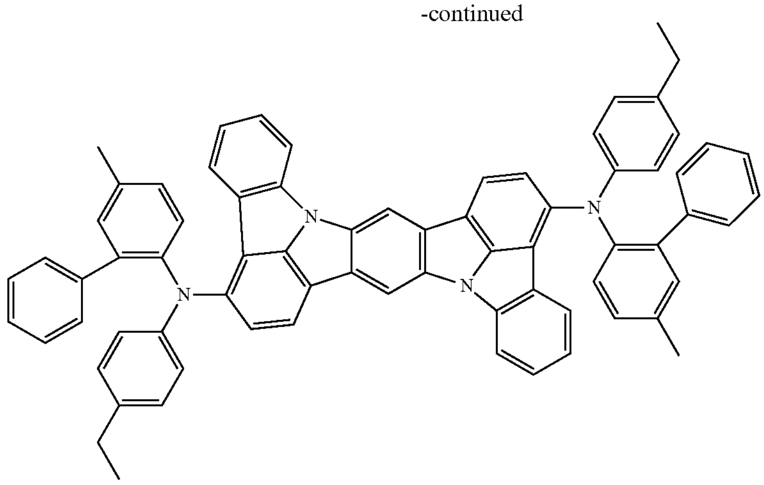
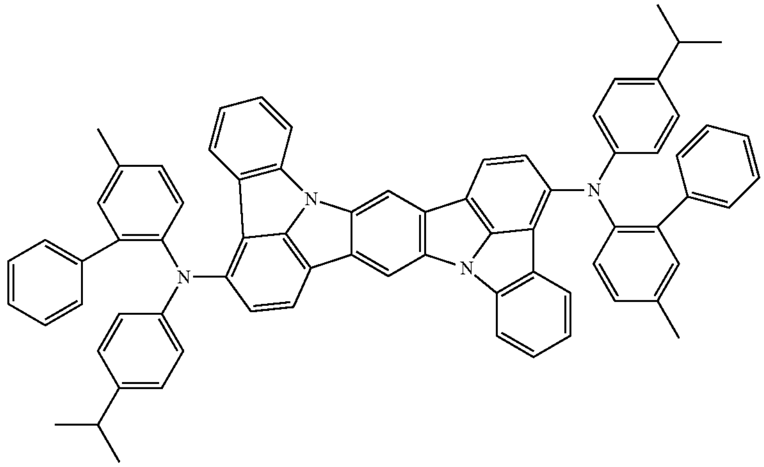
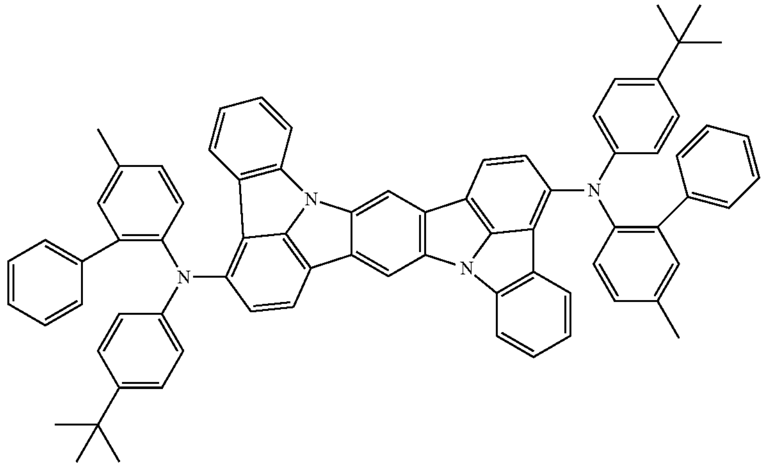

-continued
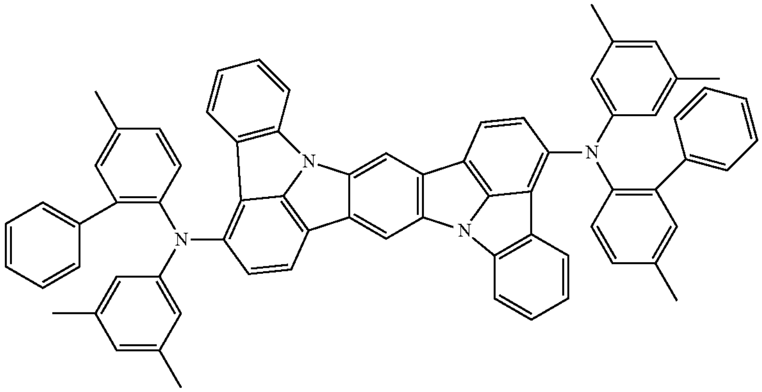
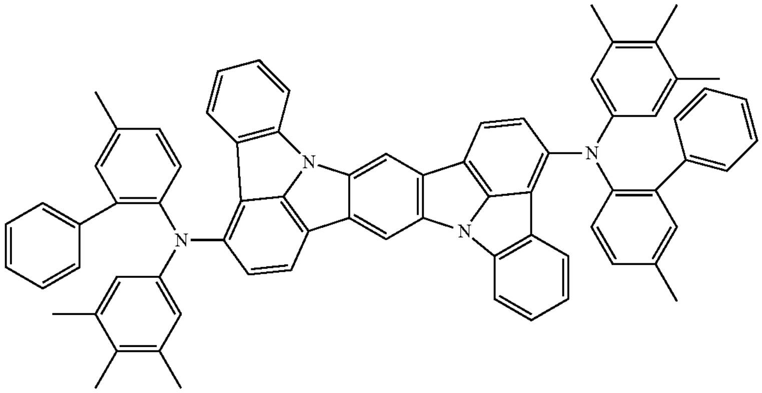
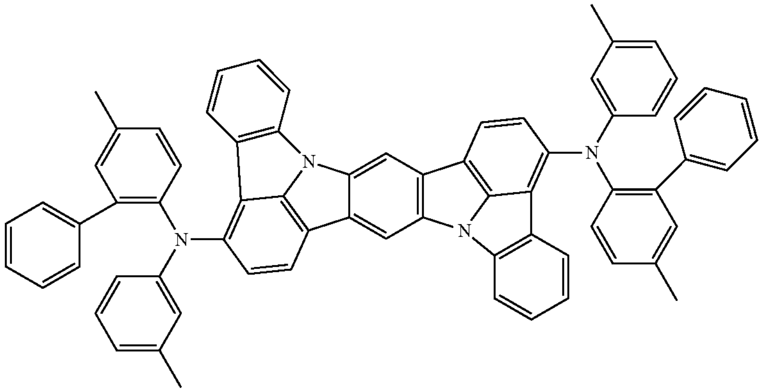
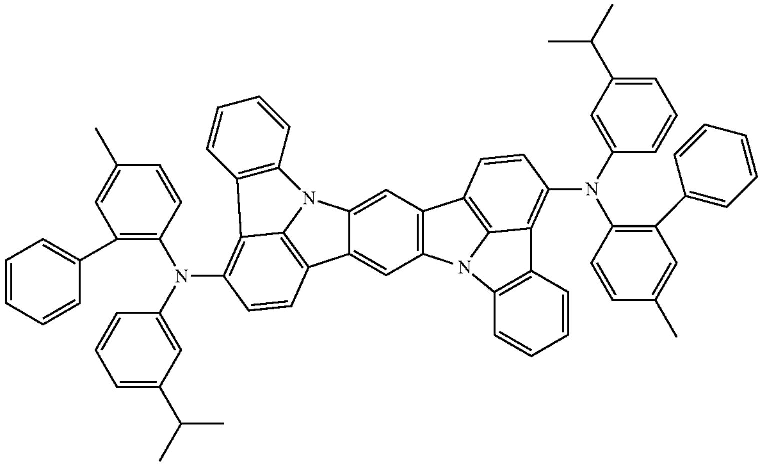

-continued
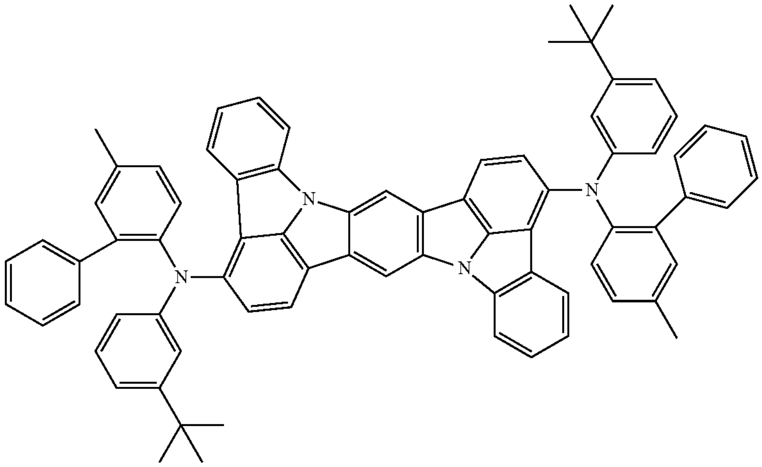
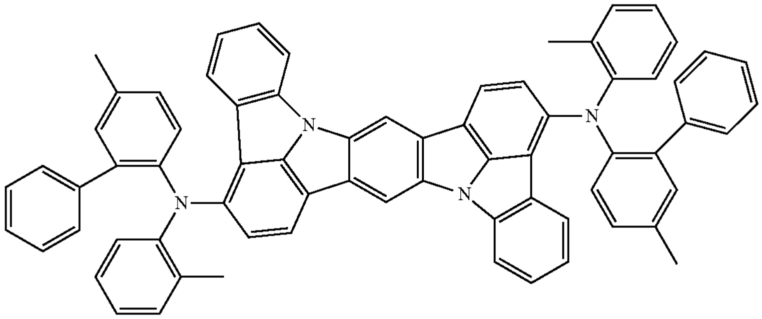
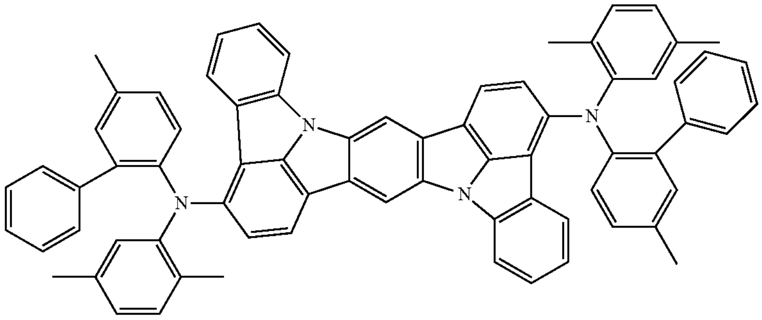
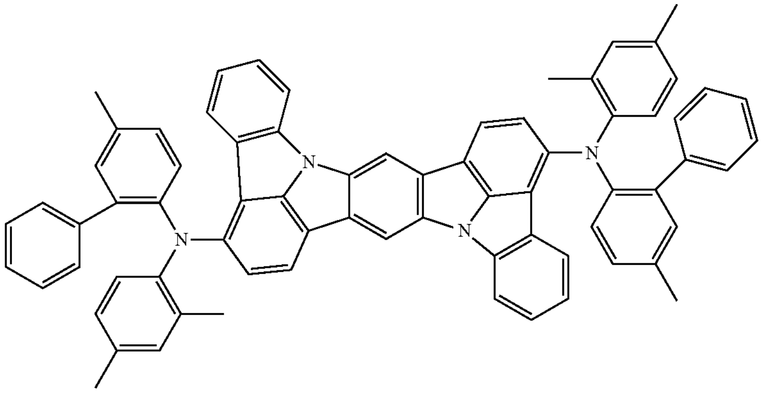

-continued
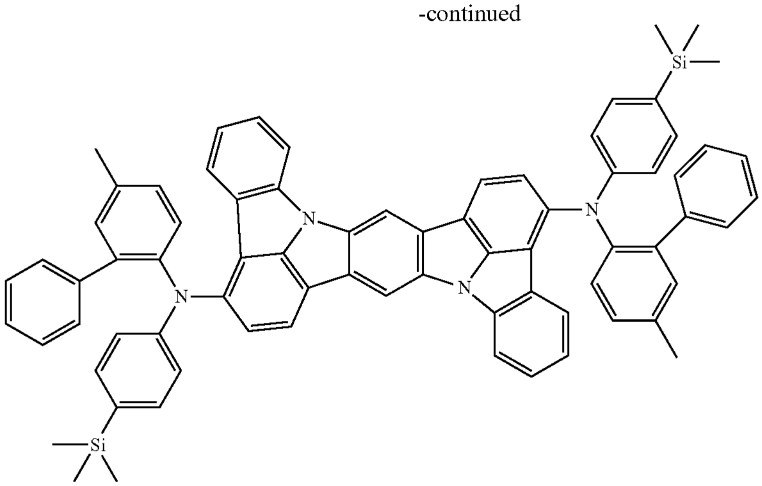
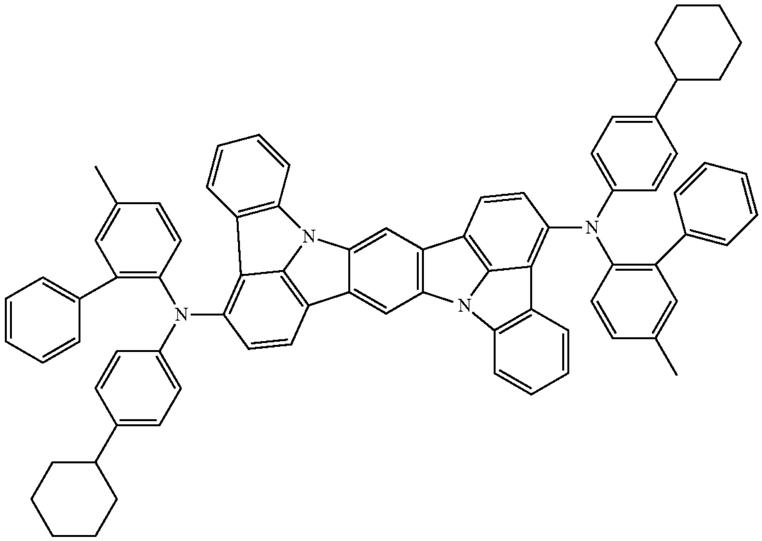
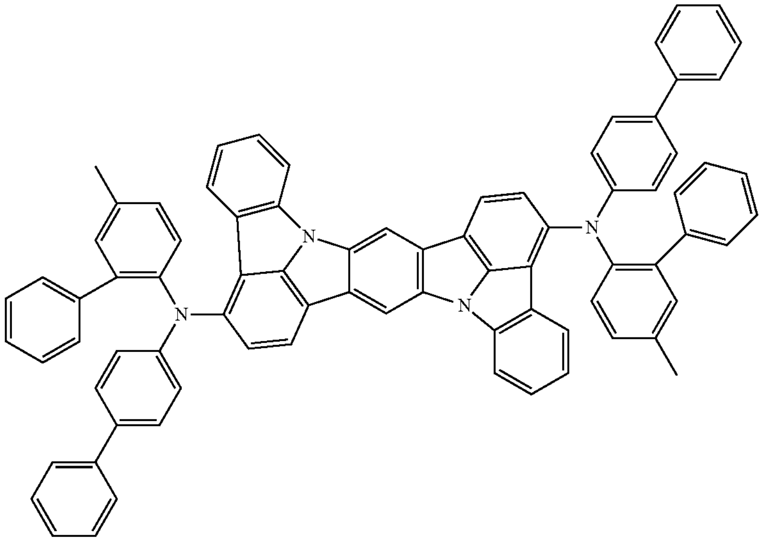

-continued
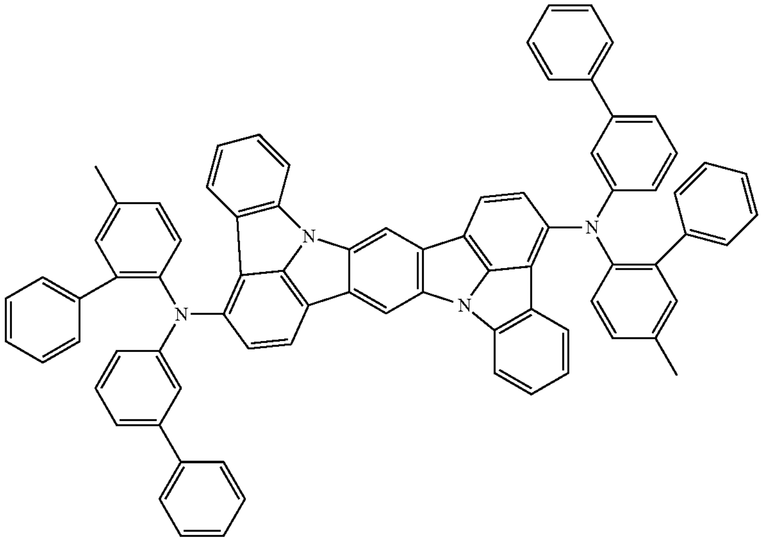
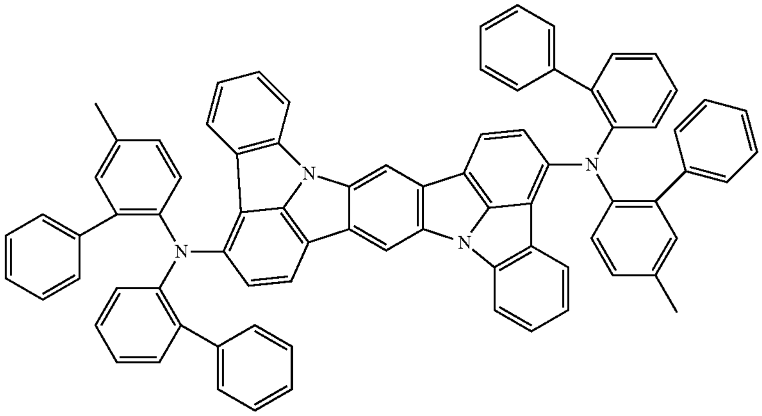
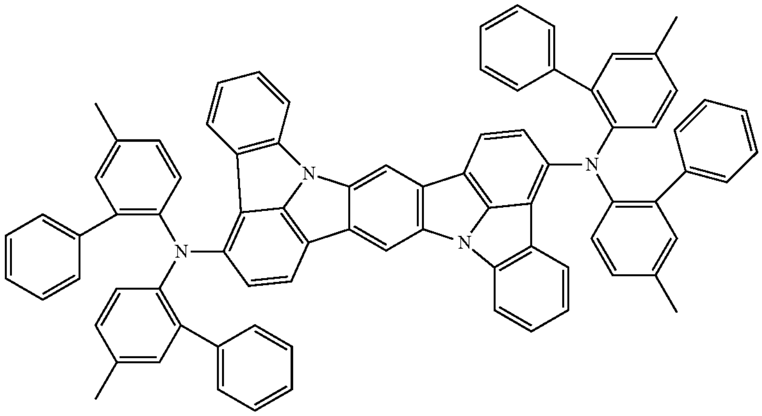

-continued
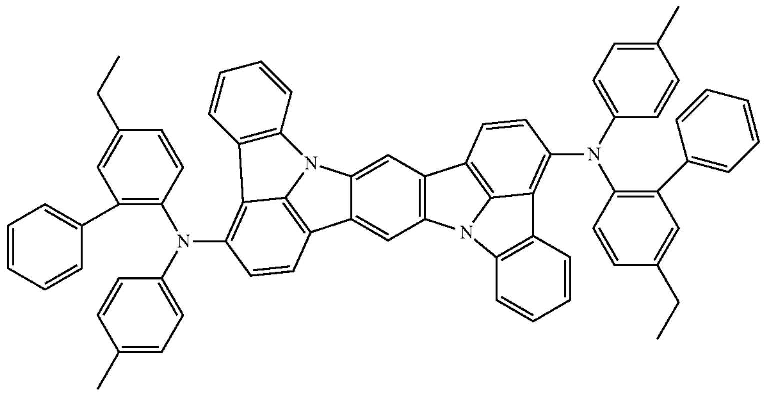
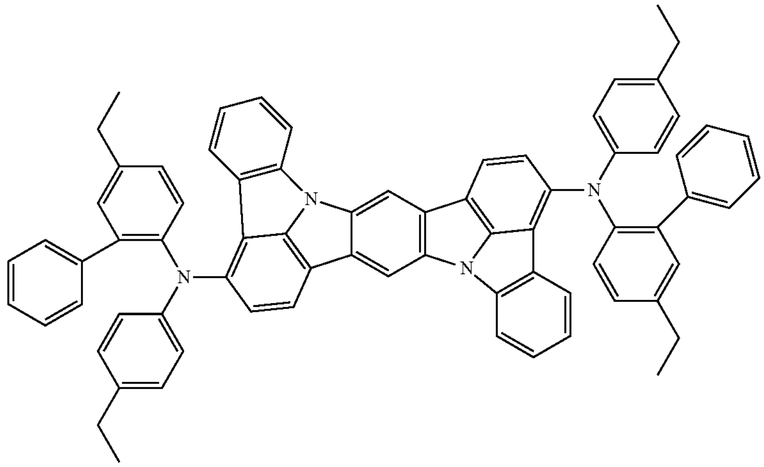
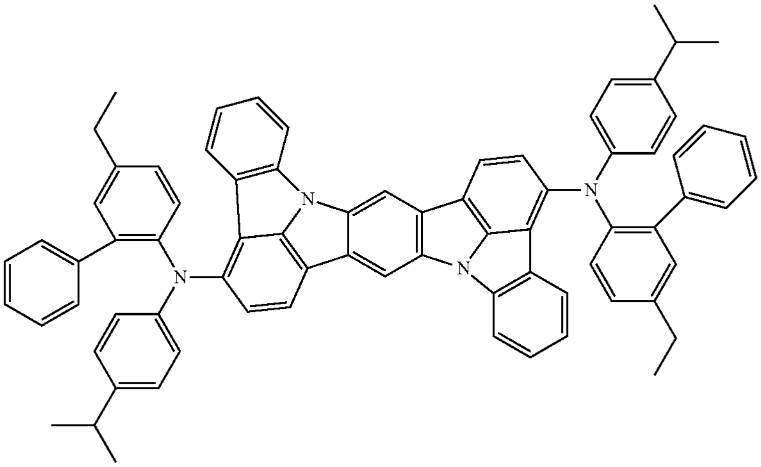

-continued
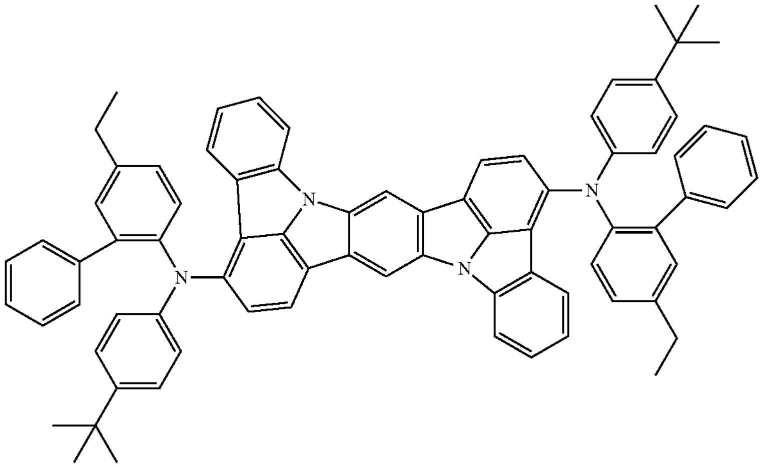
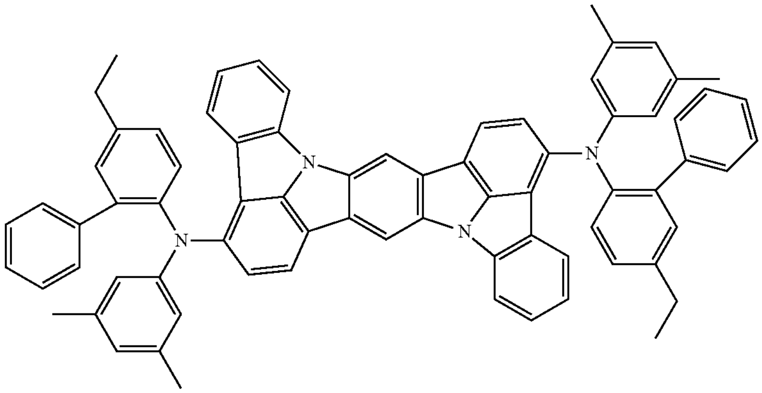
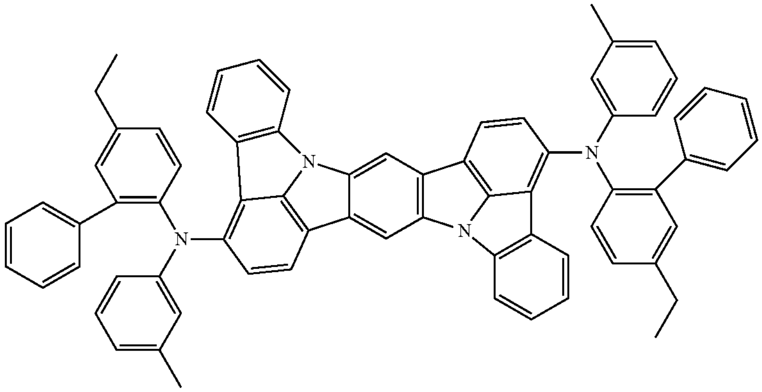
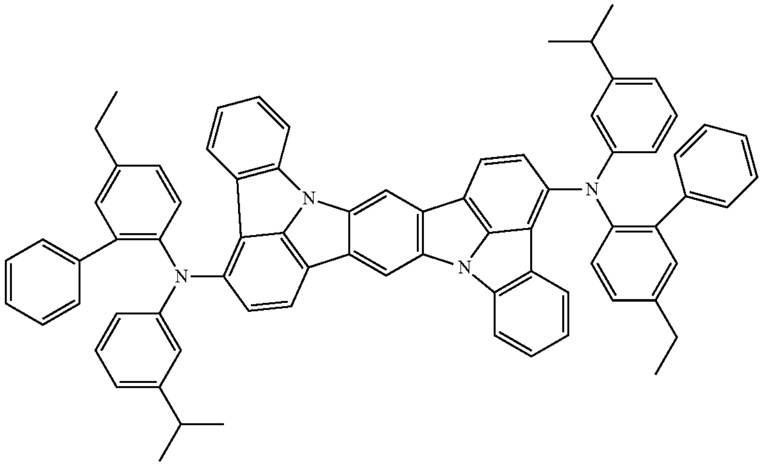

-continued
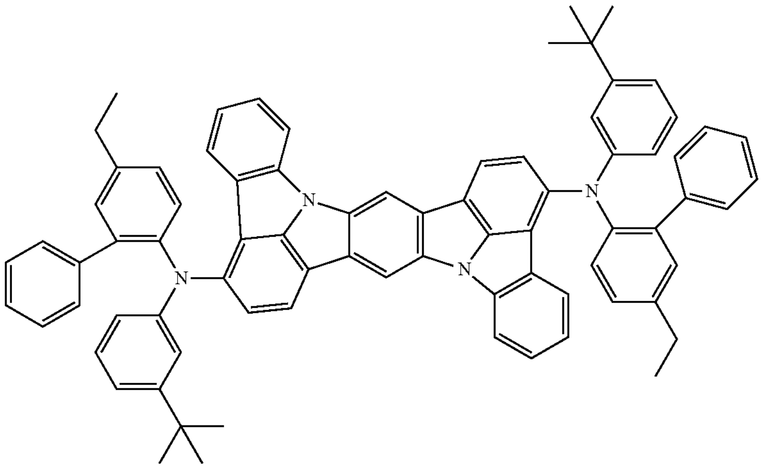
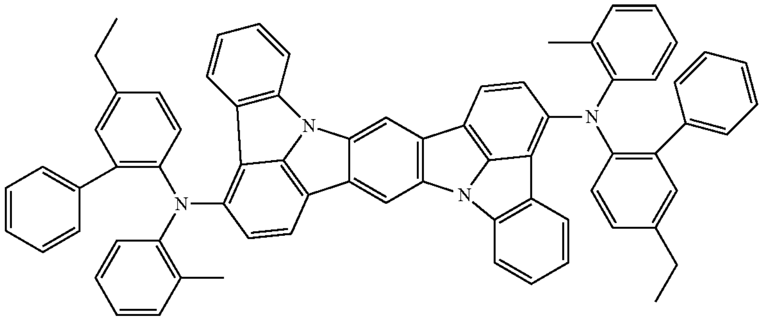
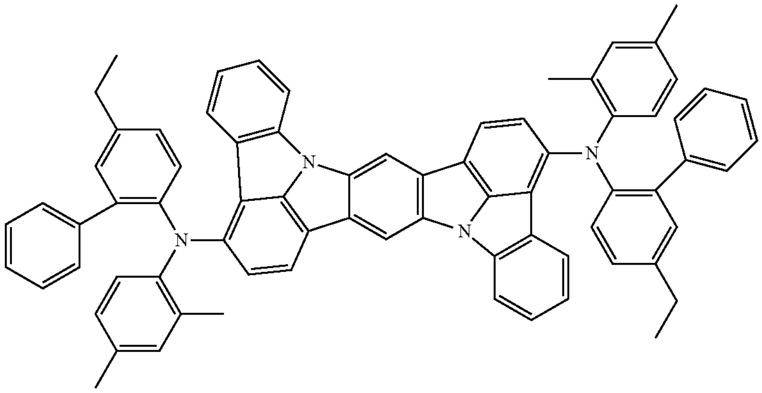
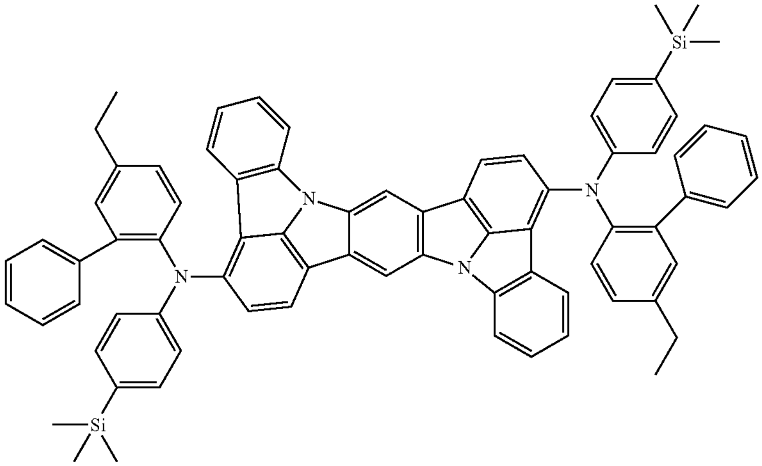

-continued
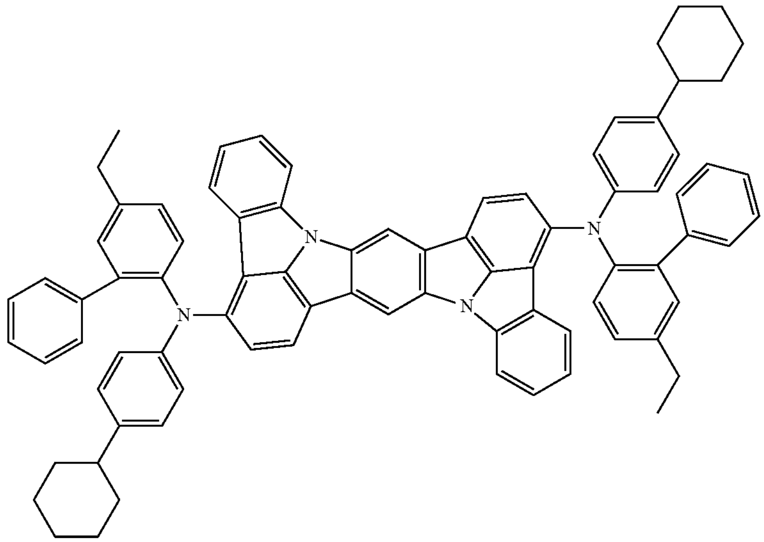
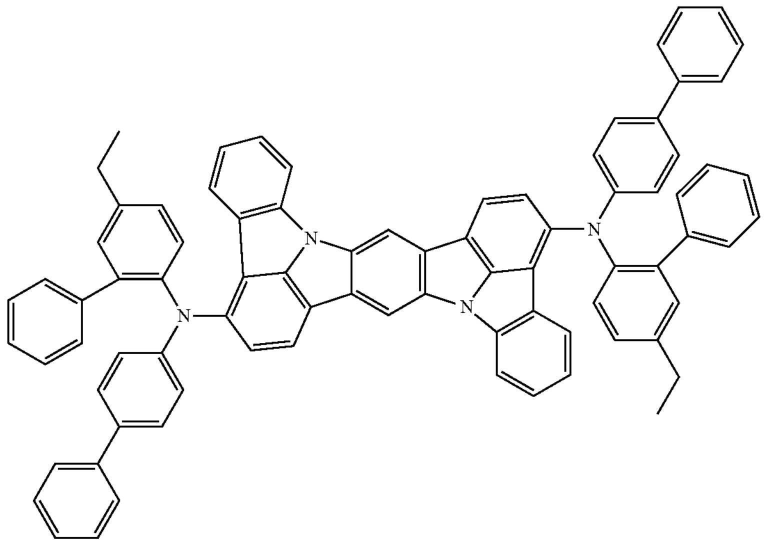
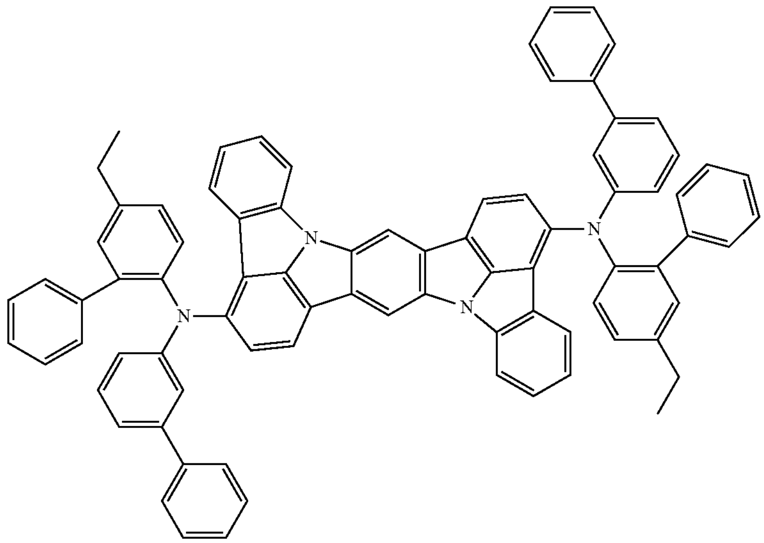

-continued
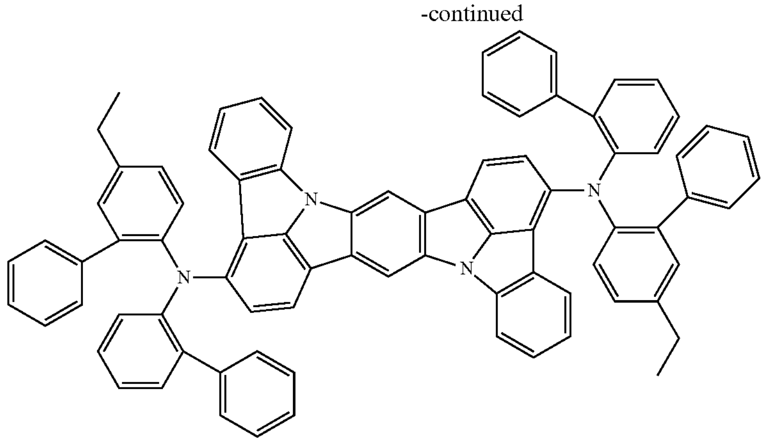
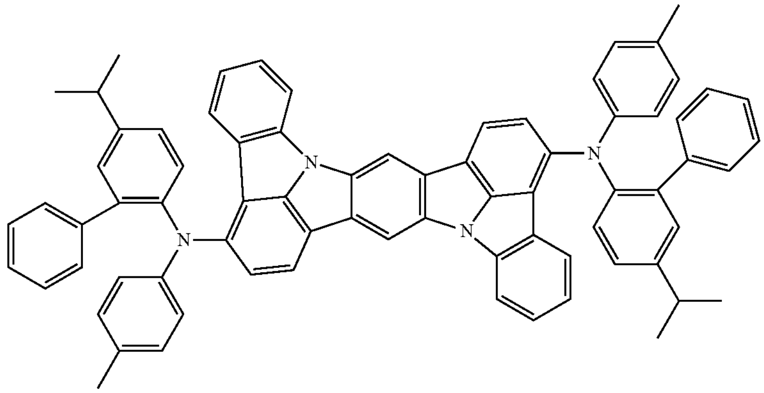
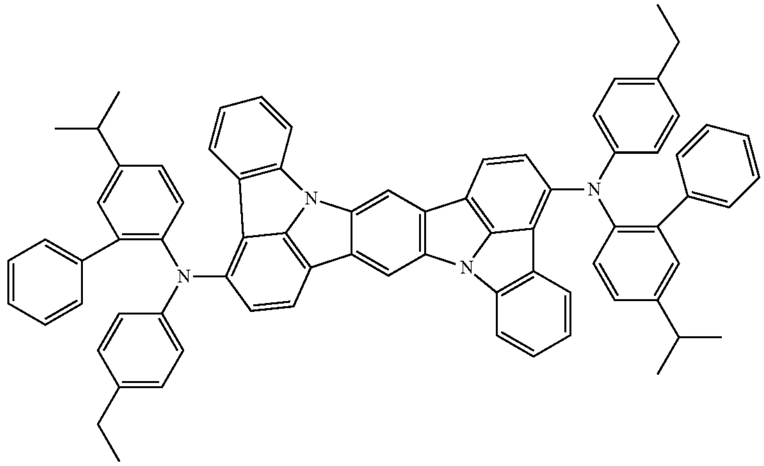

-continued
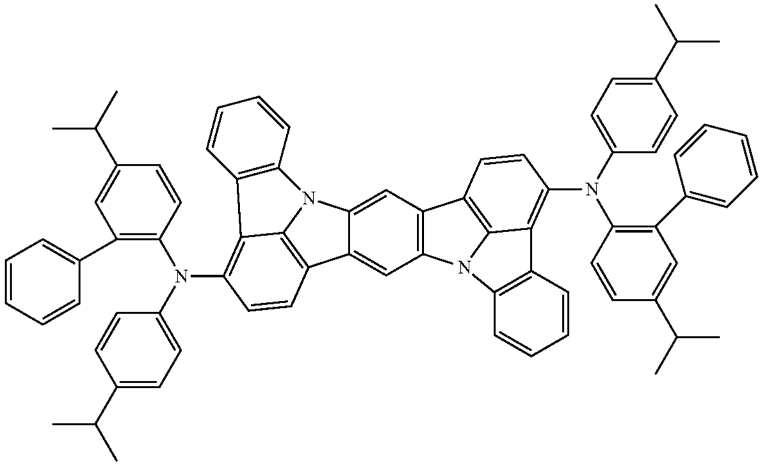
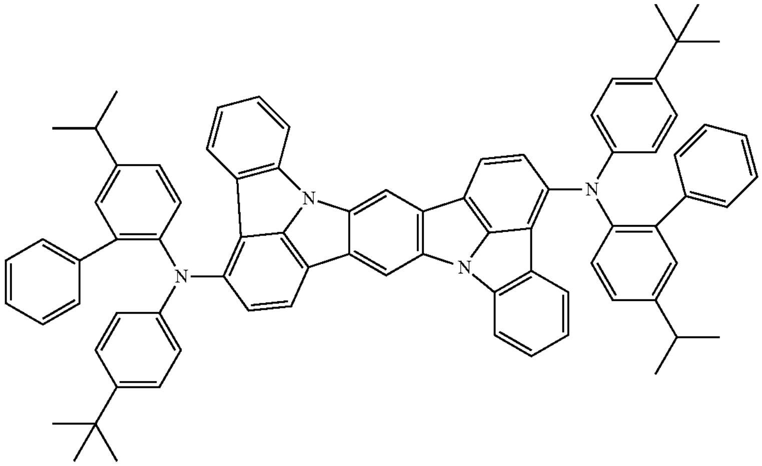
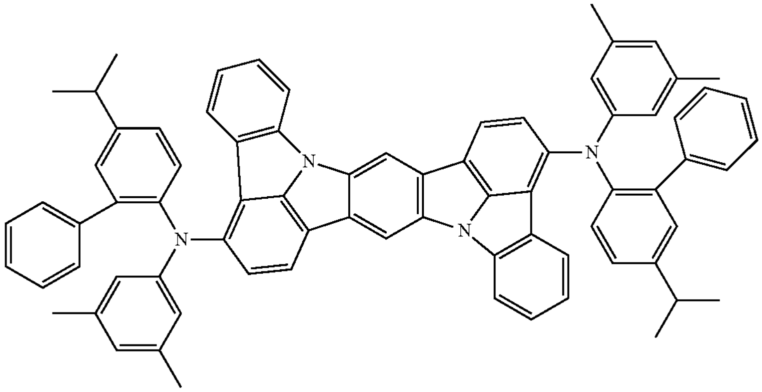
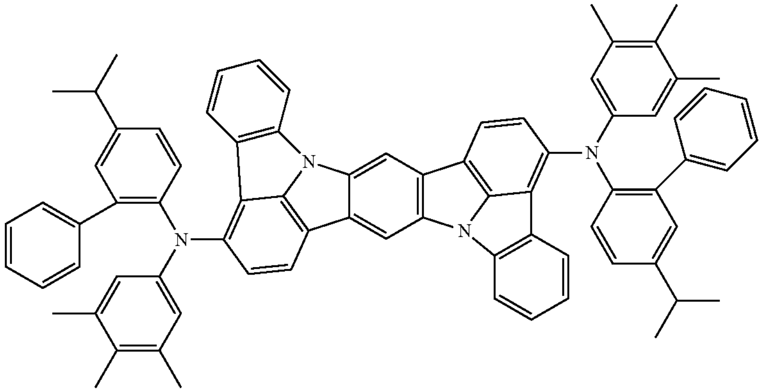

-continued
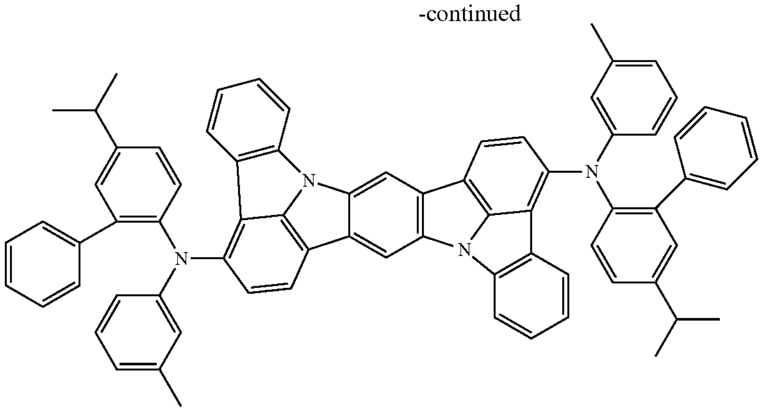
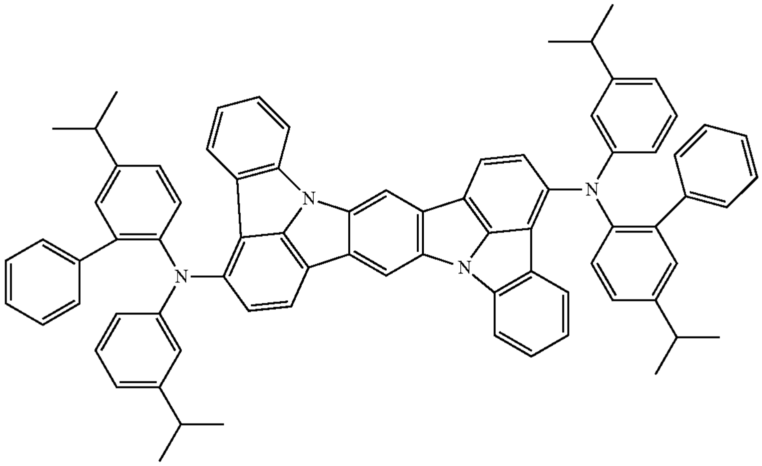
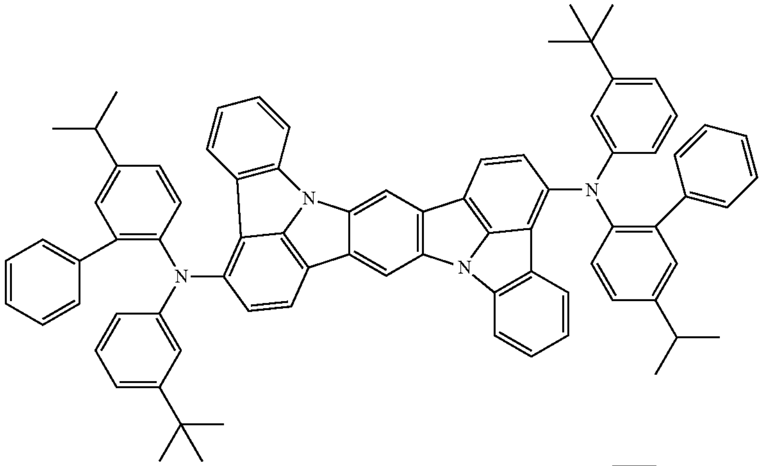
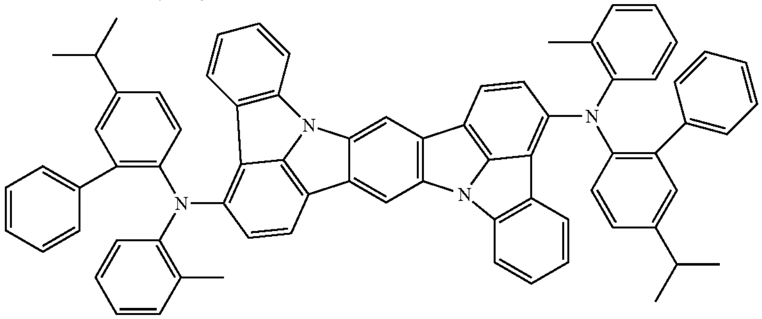

-continued
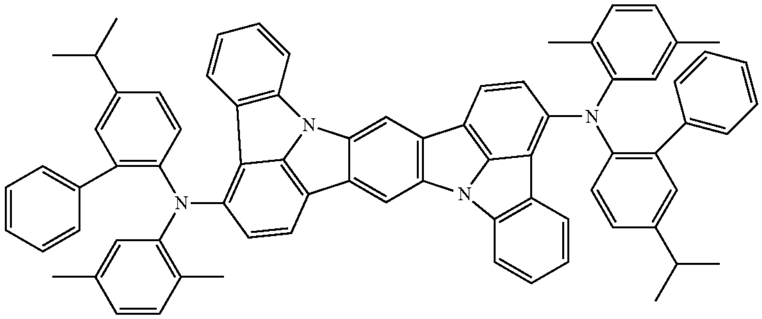
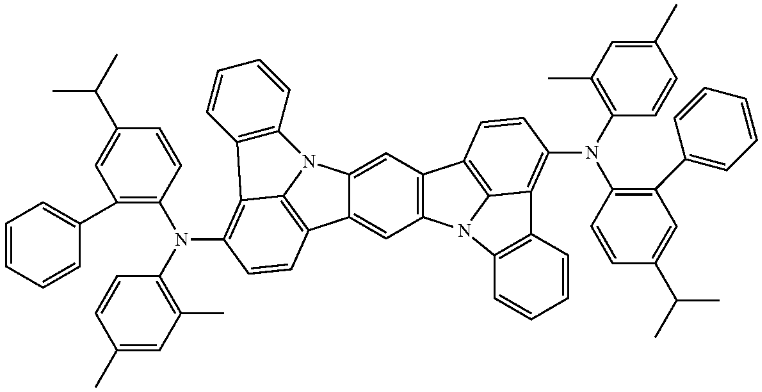
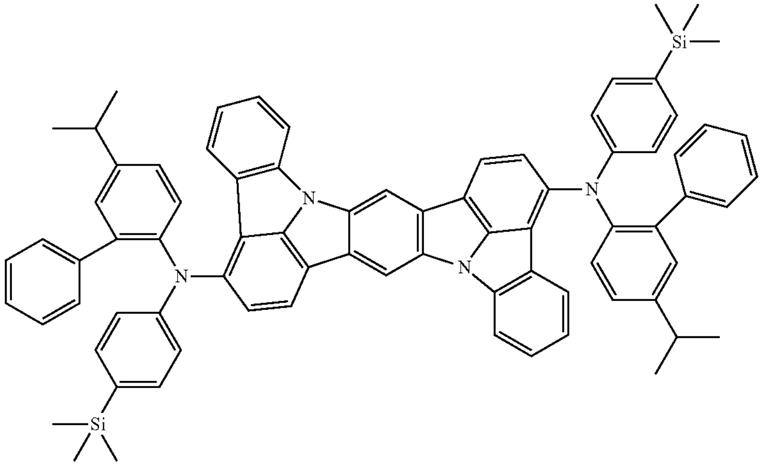
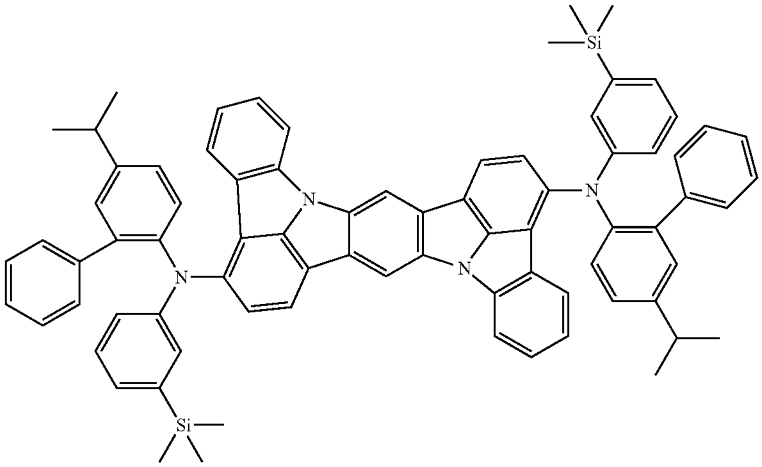

-continued
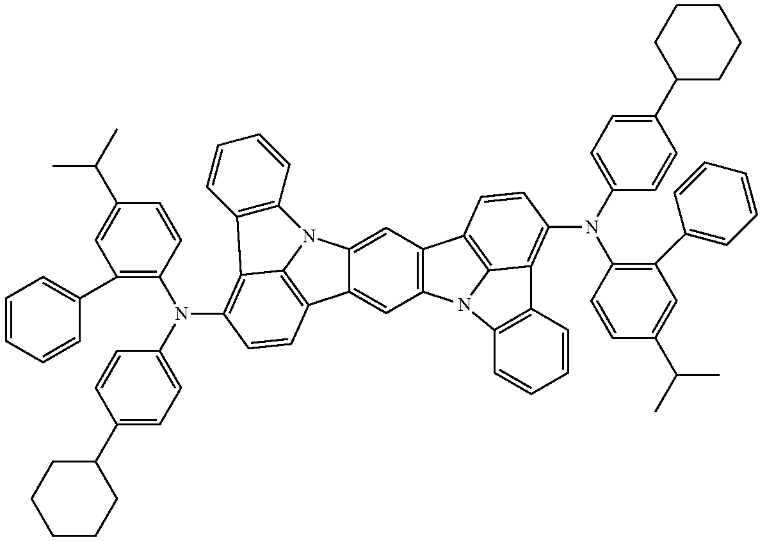
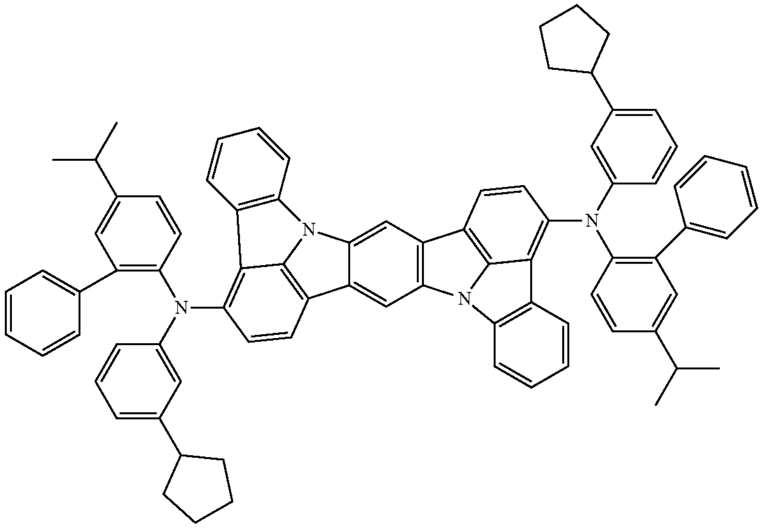
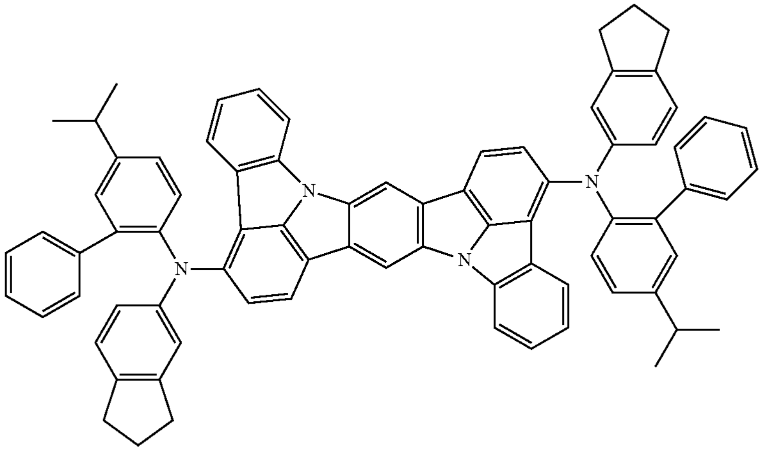

-continued
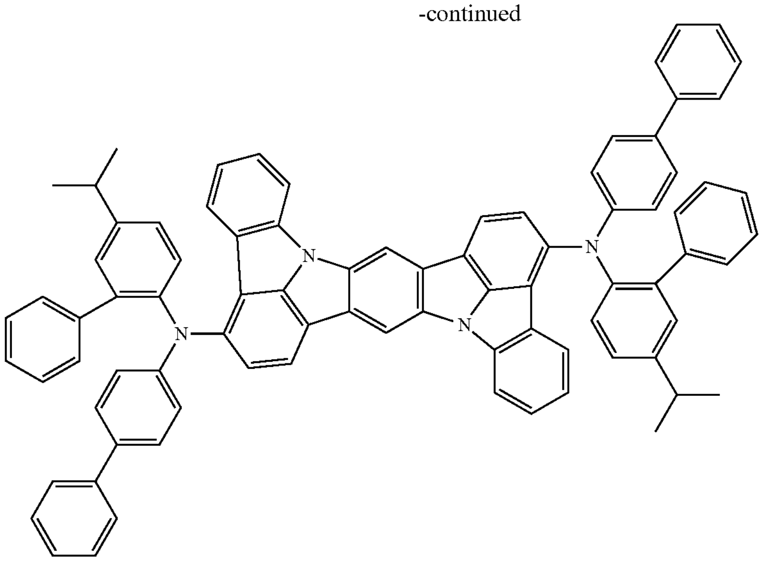
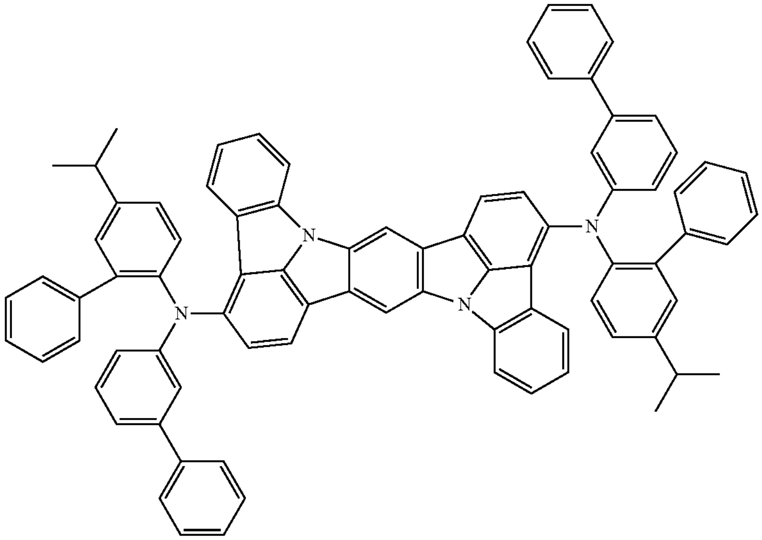
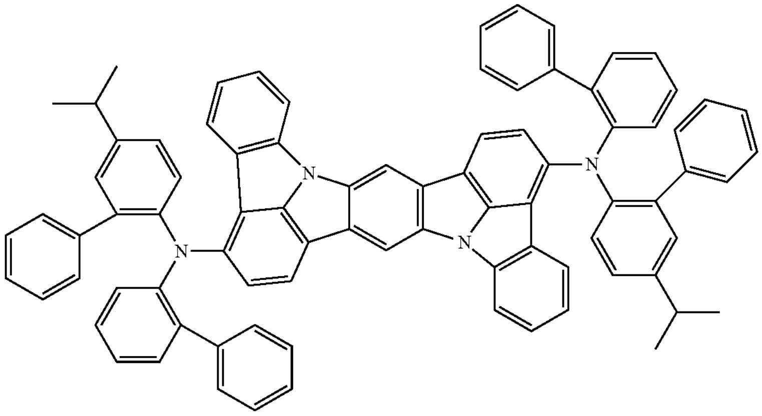

-continued
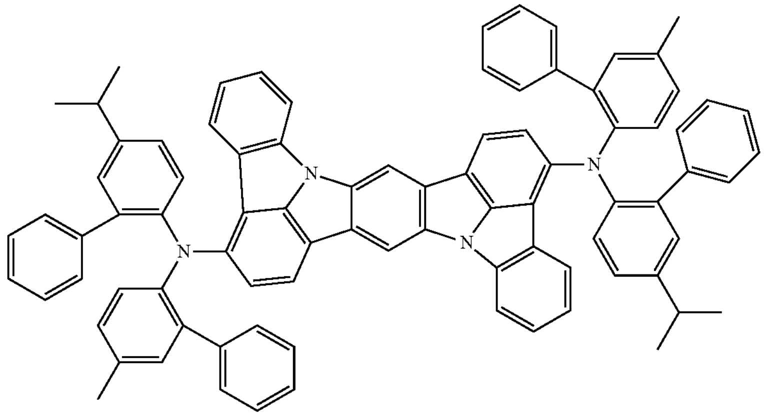
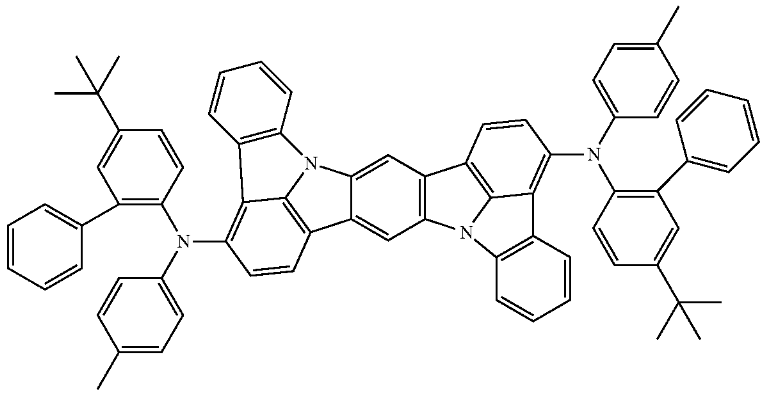
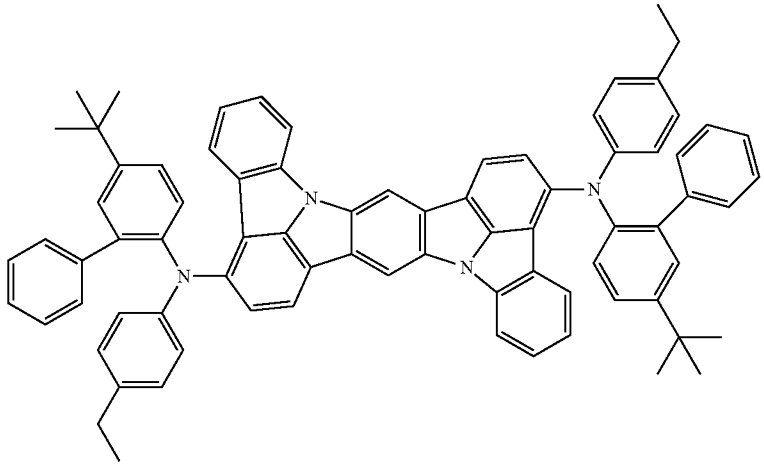

-continued
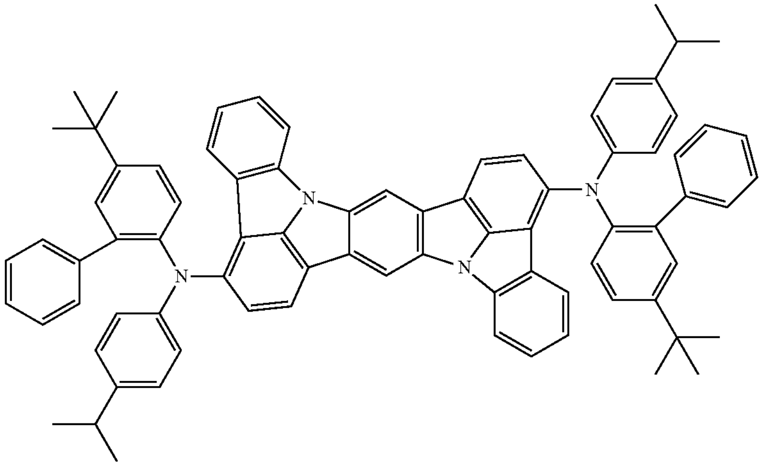
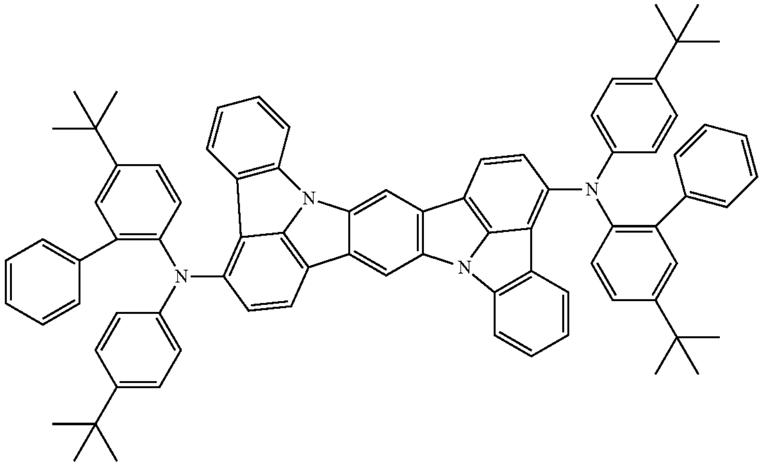
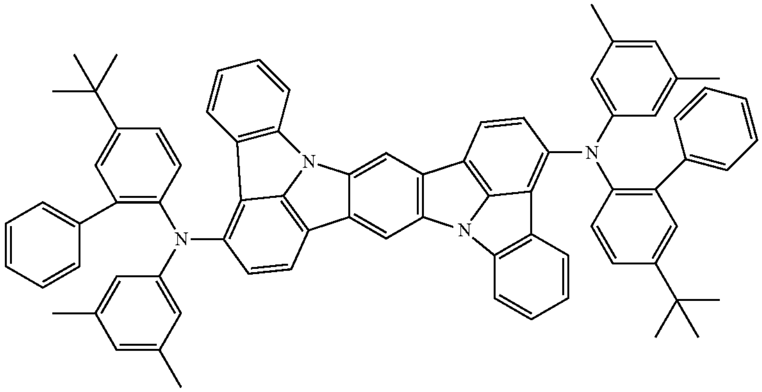
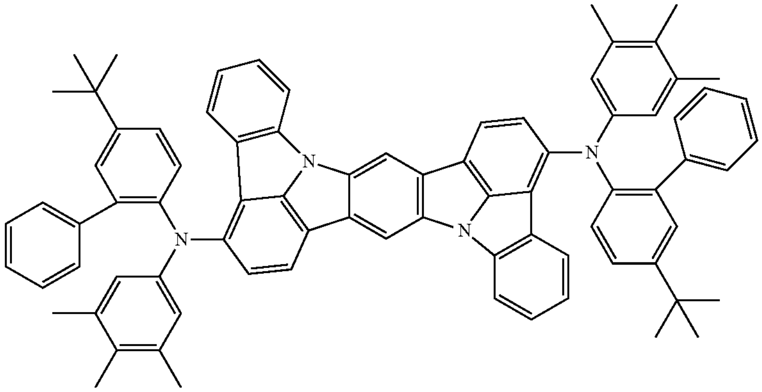

-continued
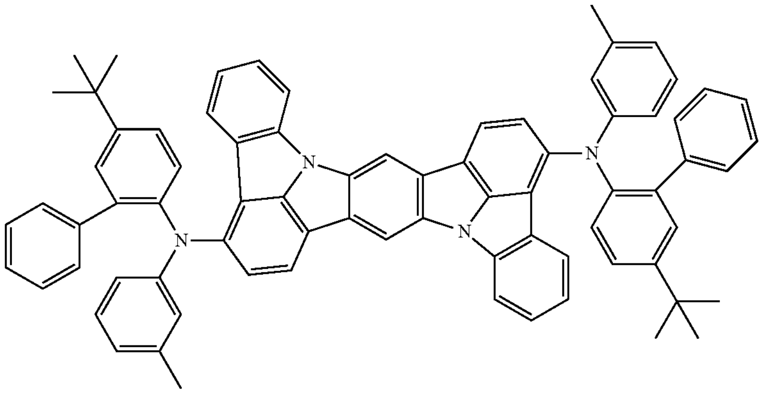
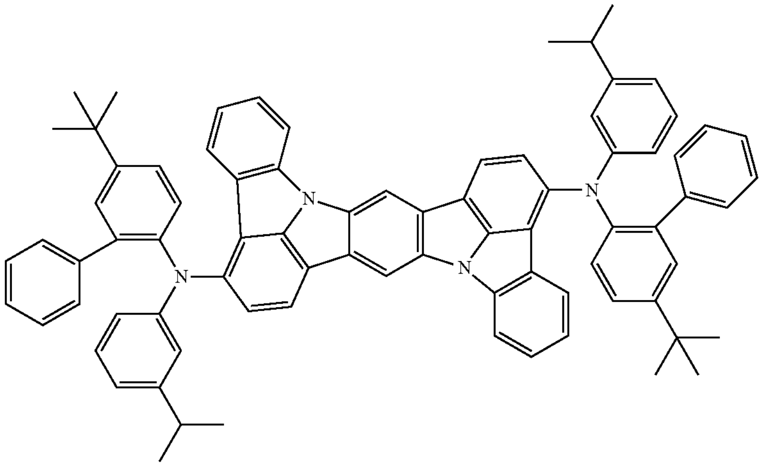
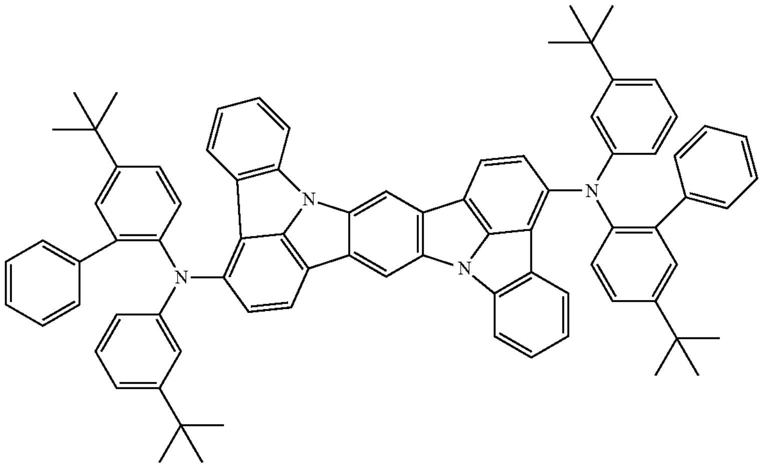
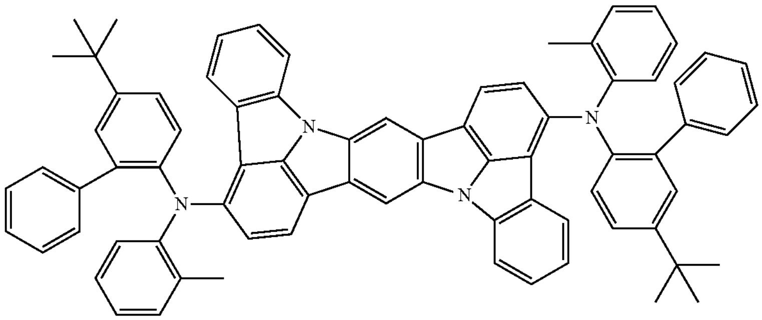

-continued
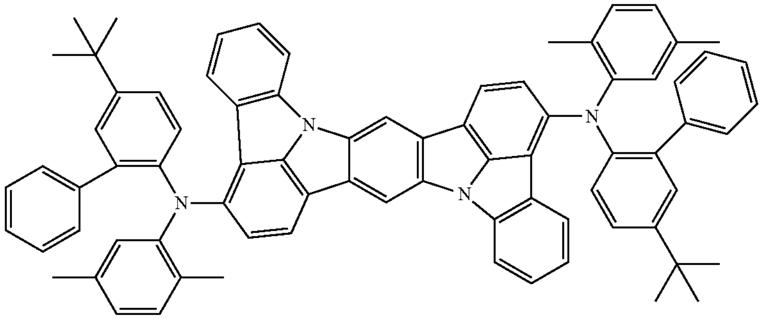
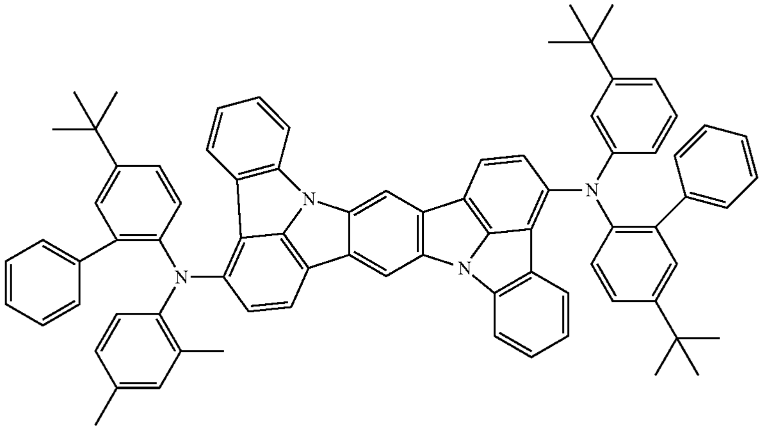
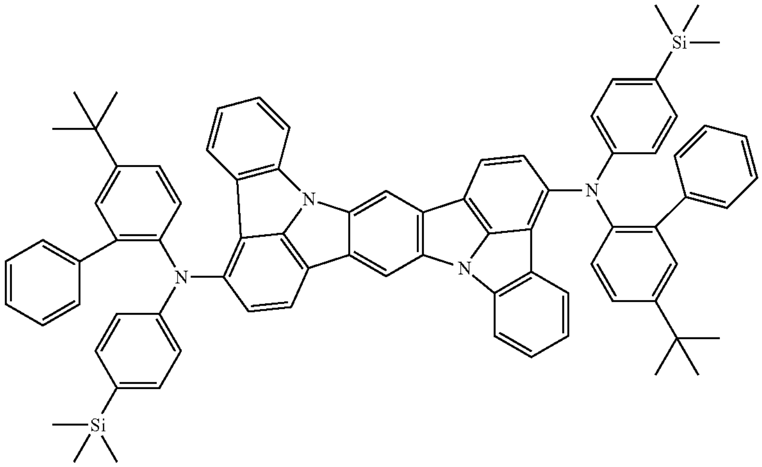
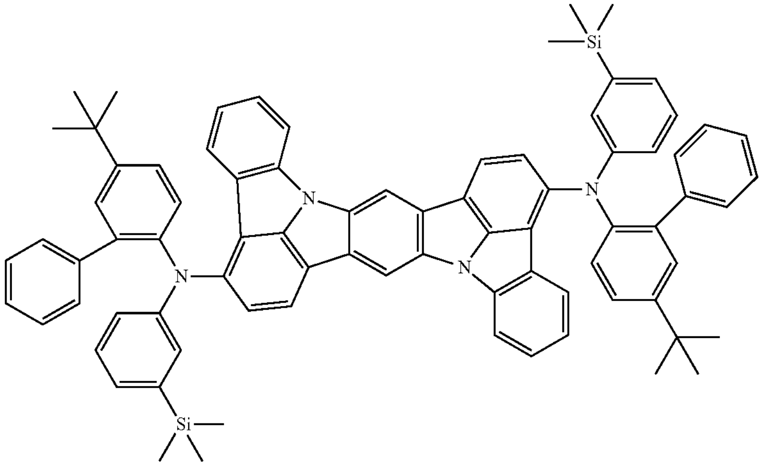

-continued
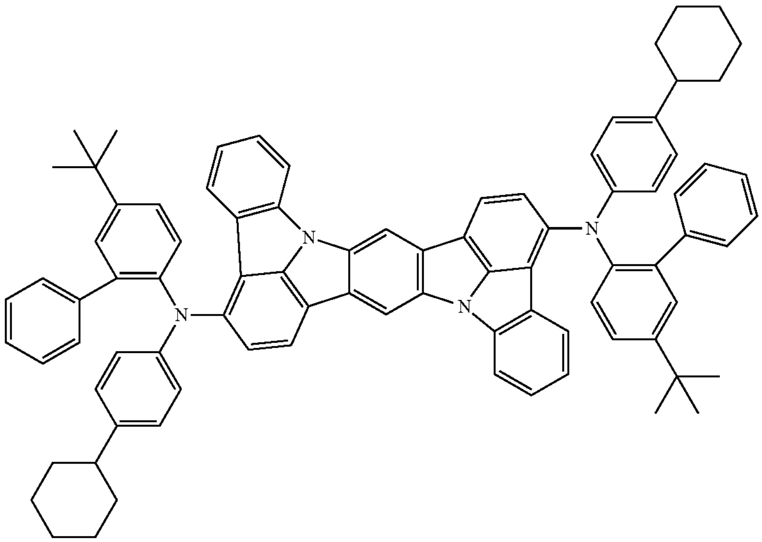
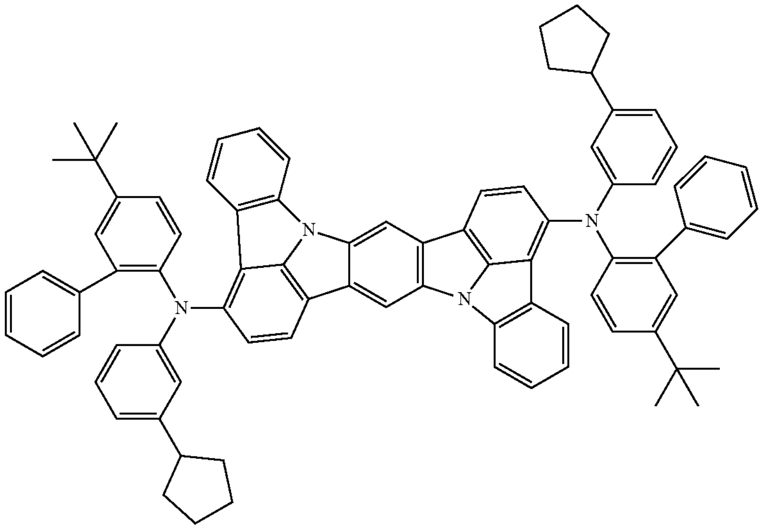
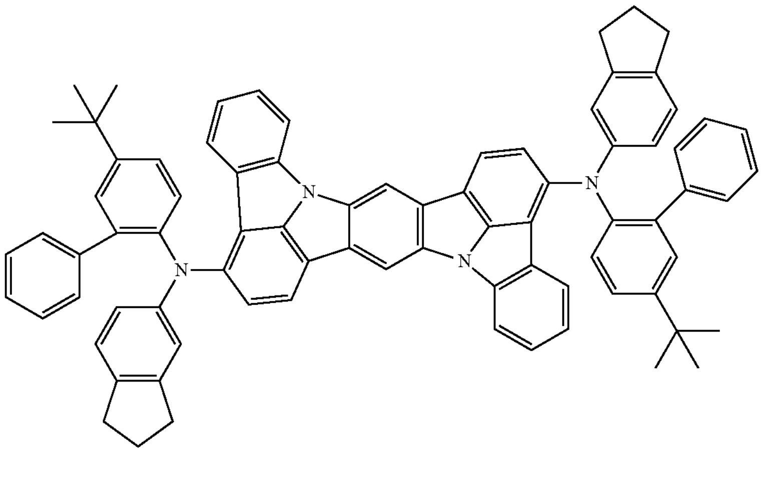

-continued
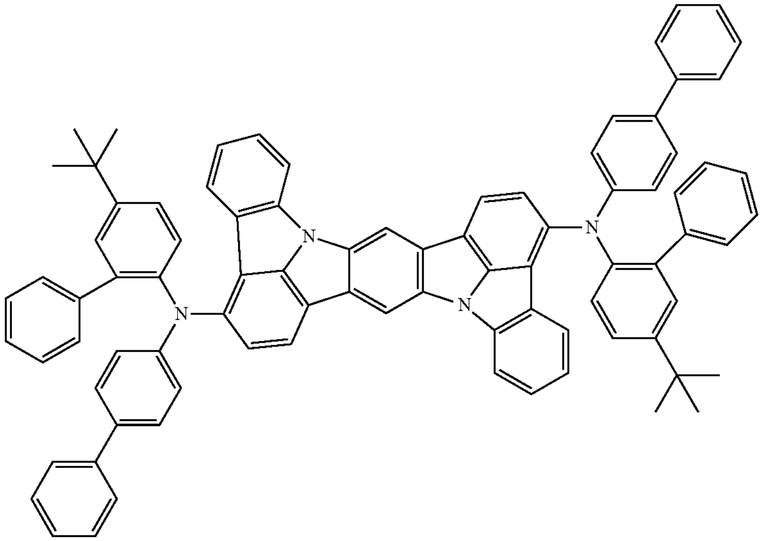
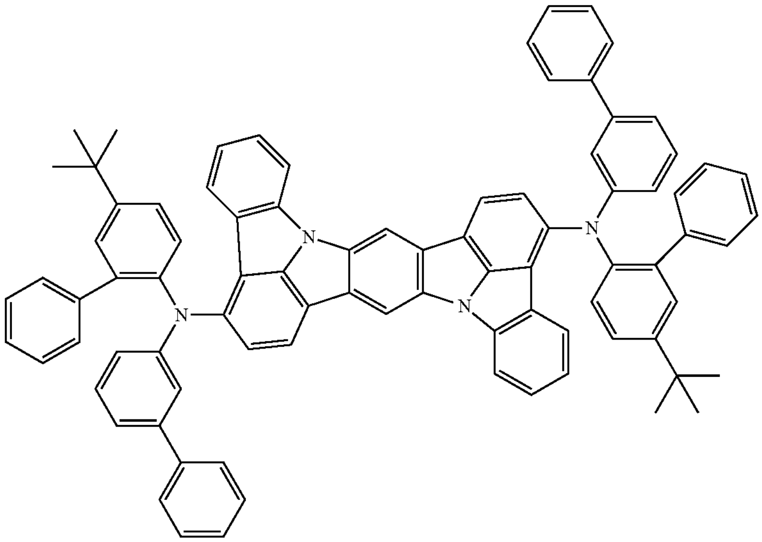
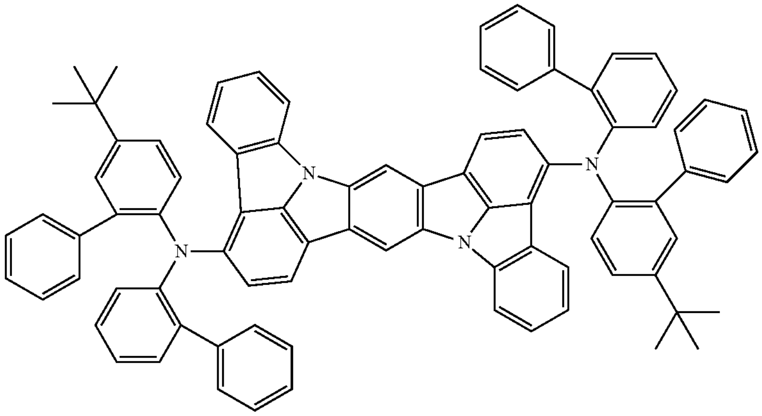

-continued
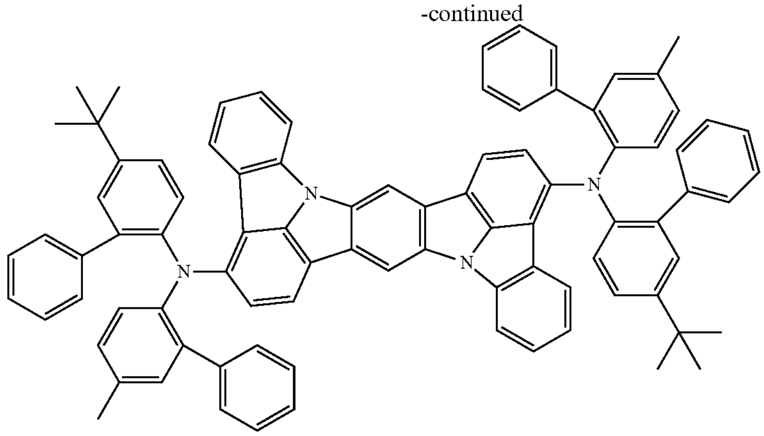
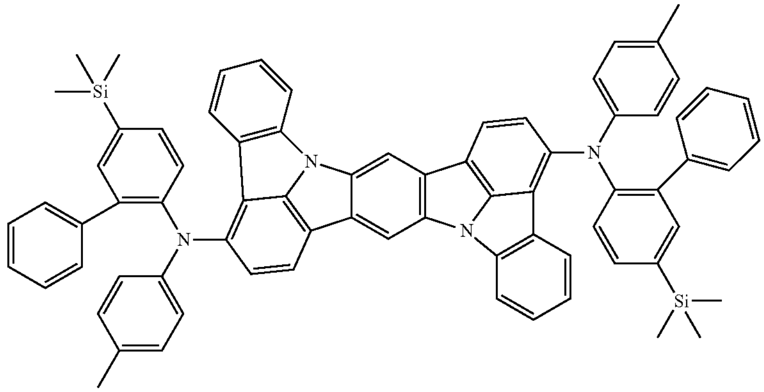
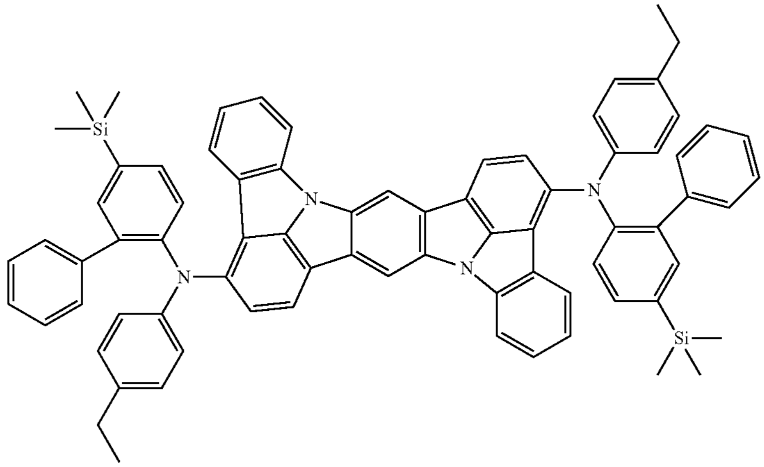

-continued
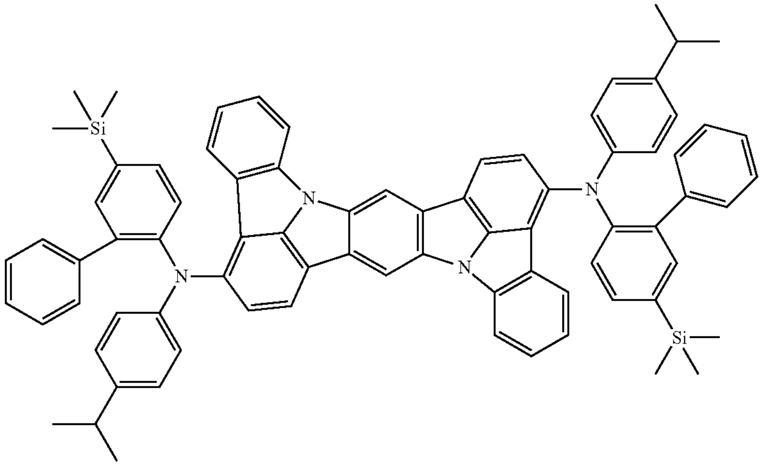
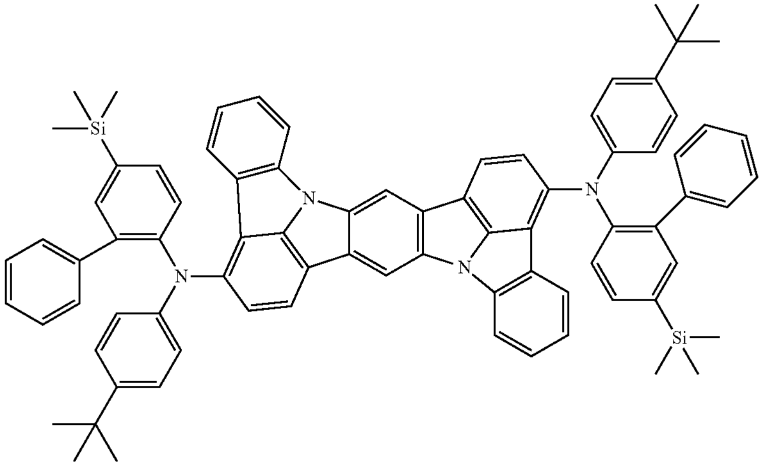
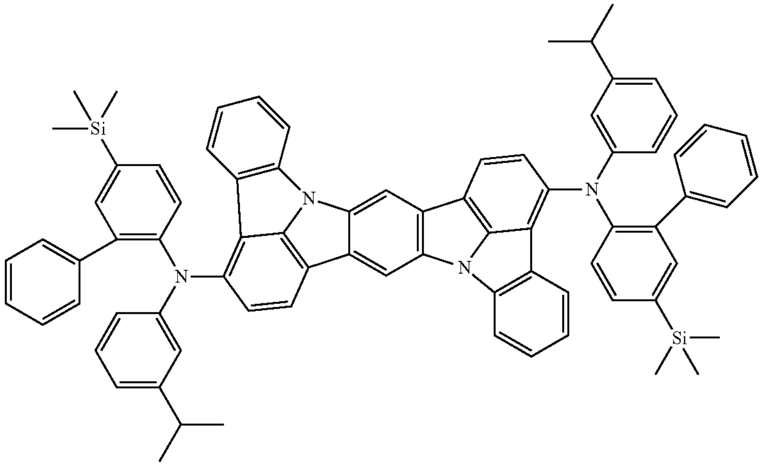

-continued
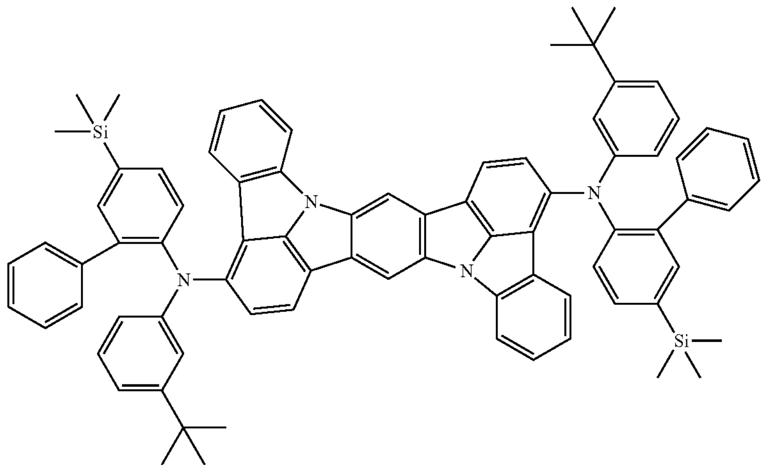
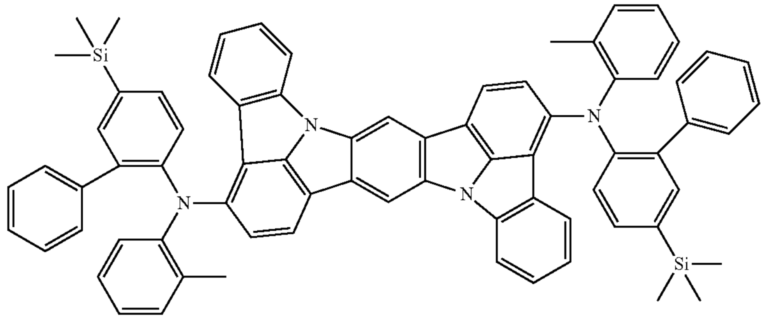
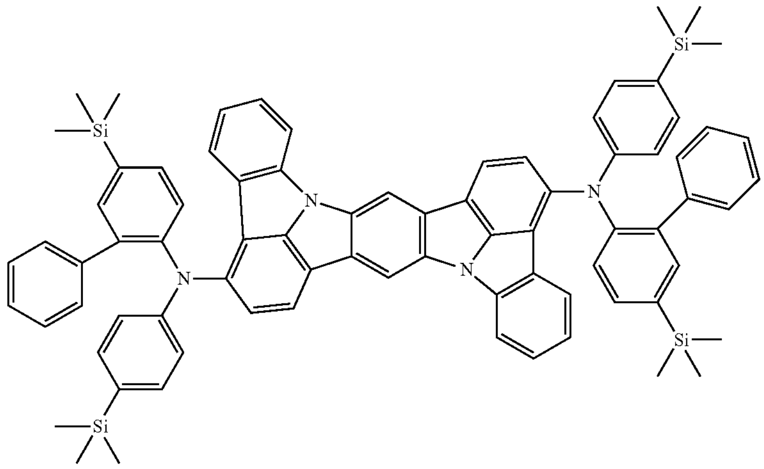

-continued
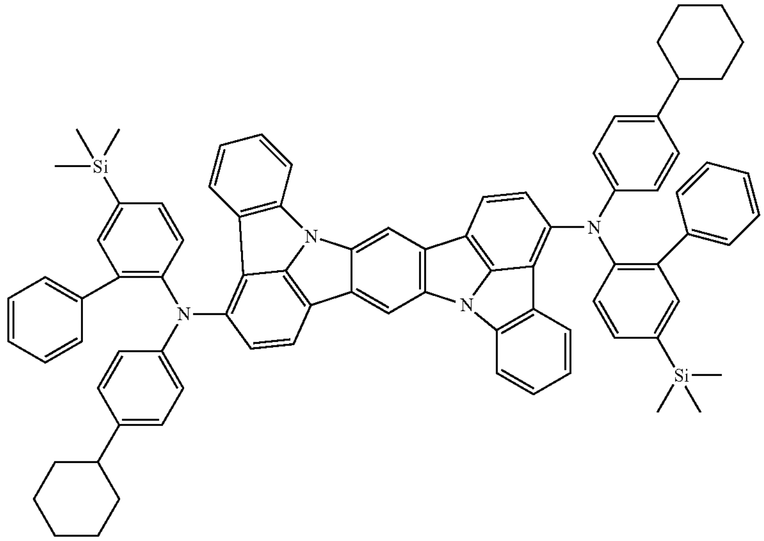
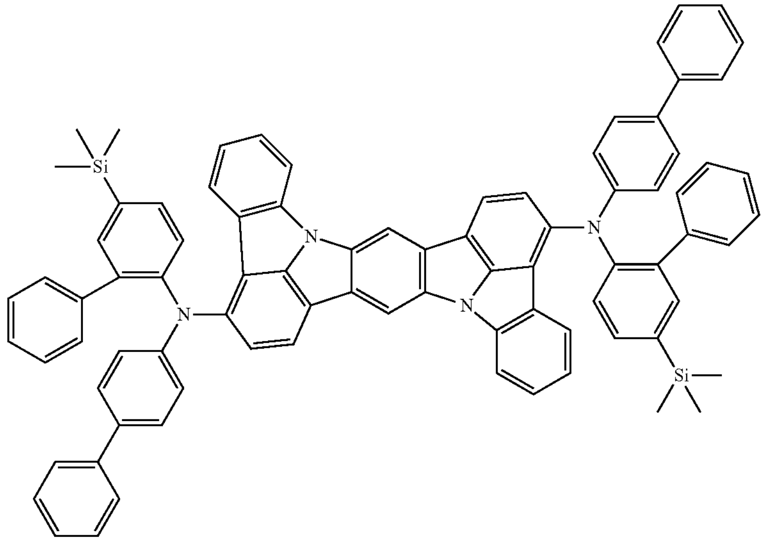
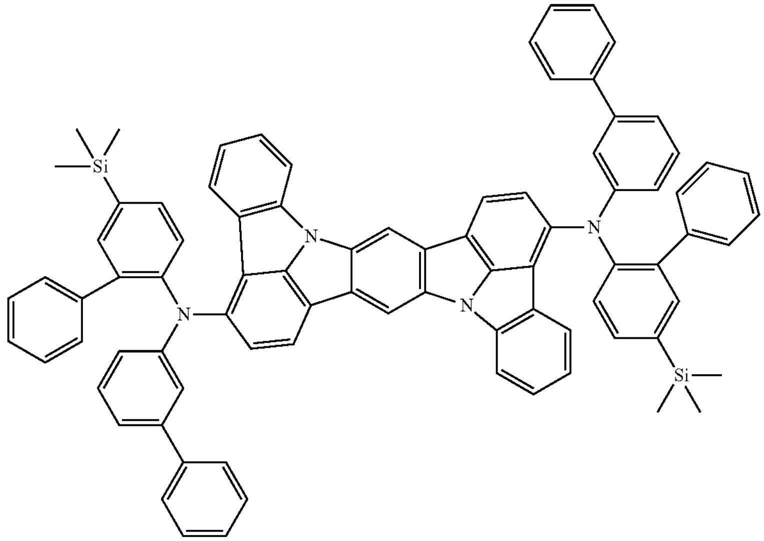

-continued
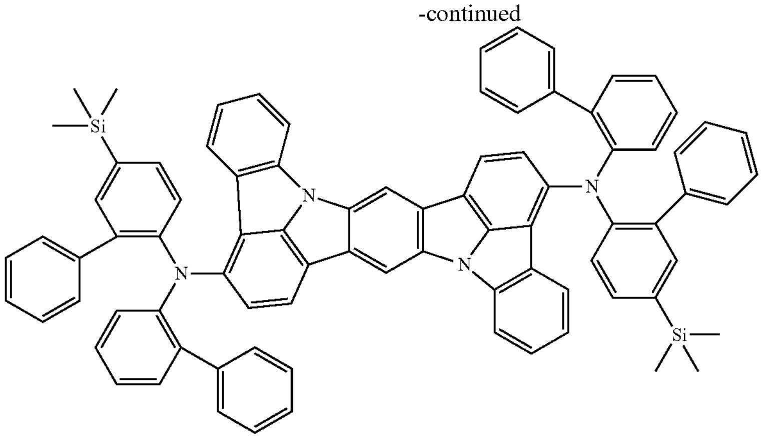
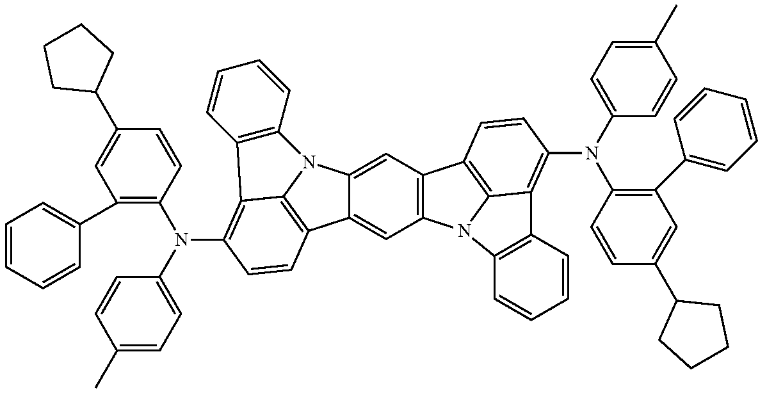
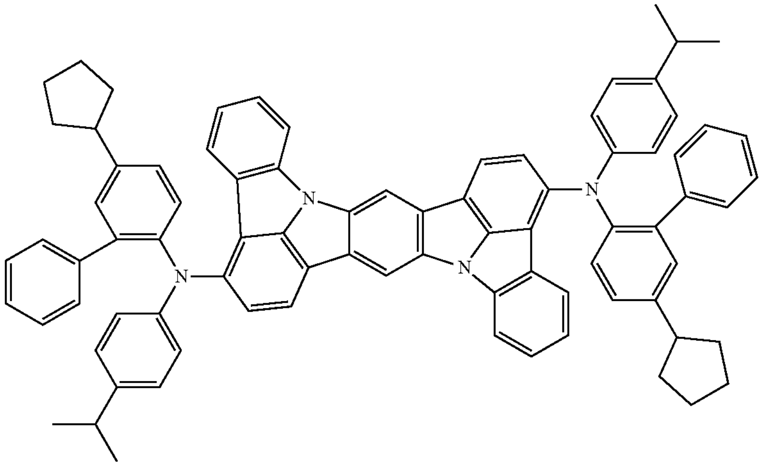

-continued
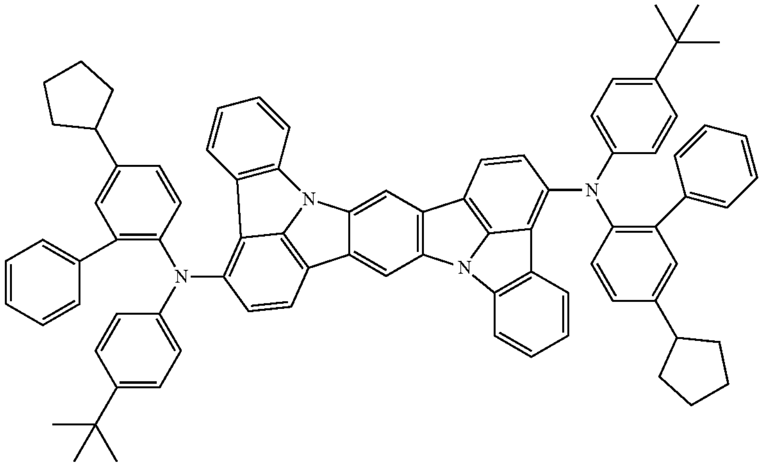
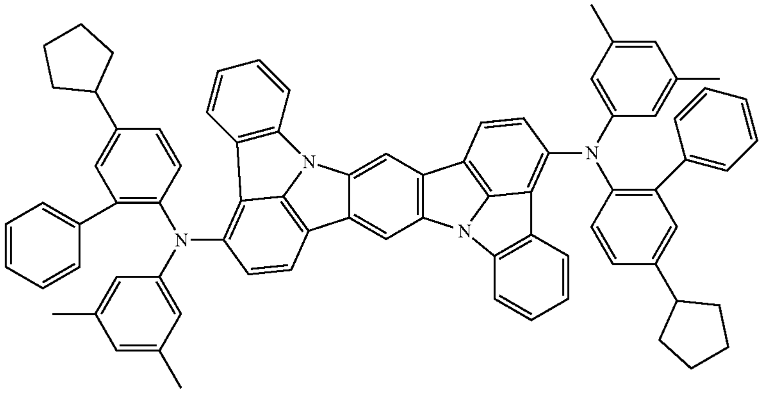
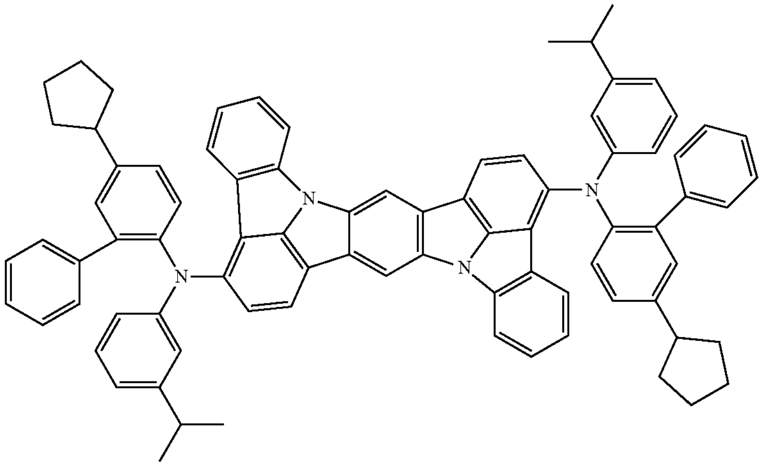

-continued
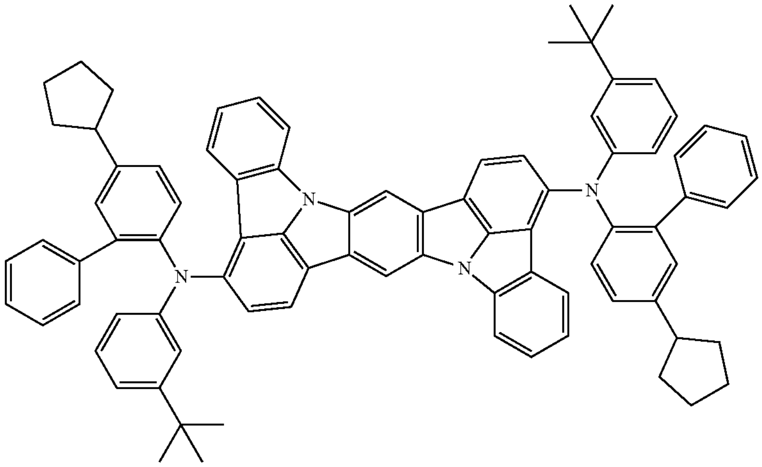
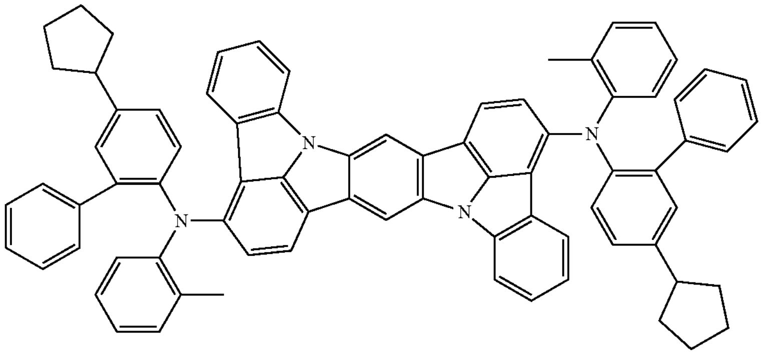
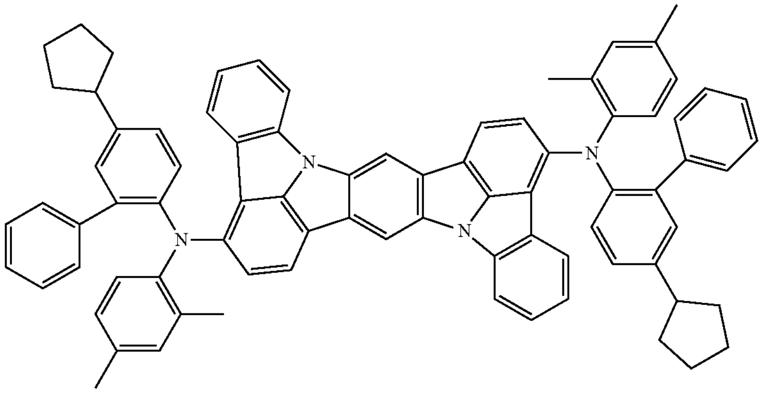
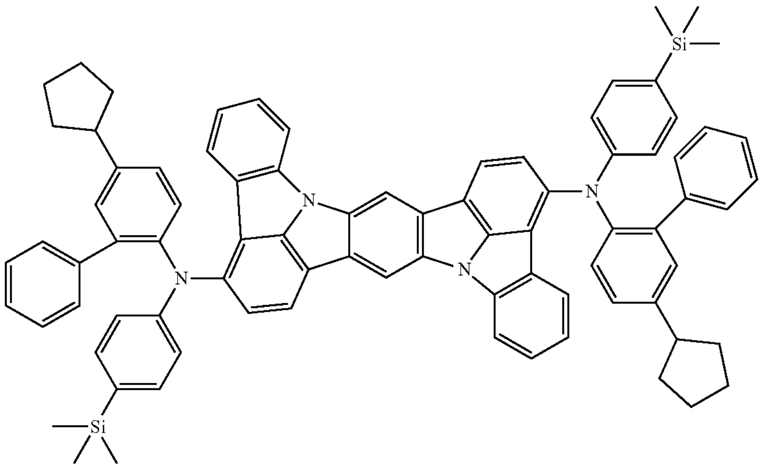

-continued
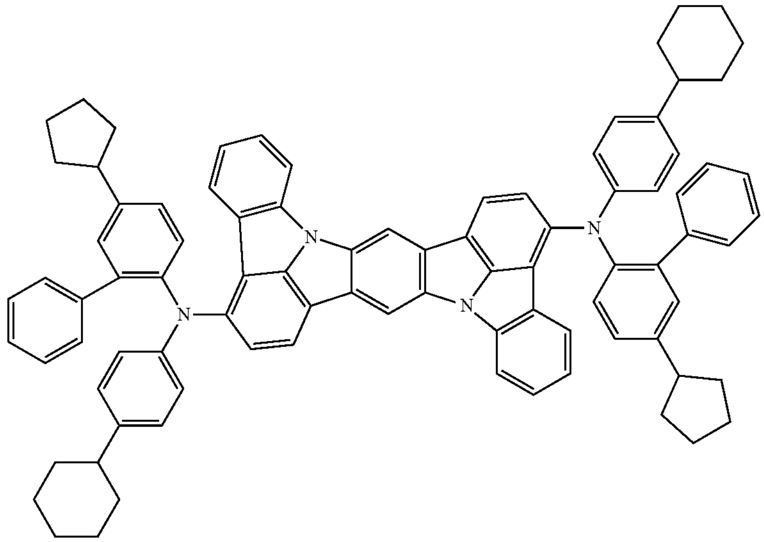
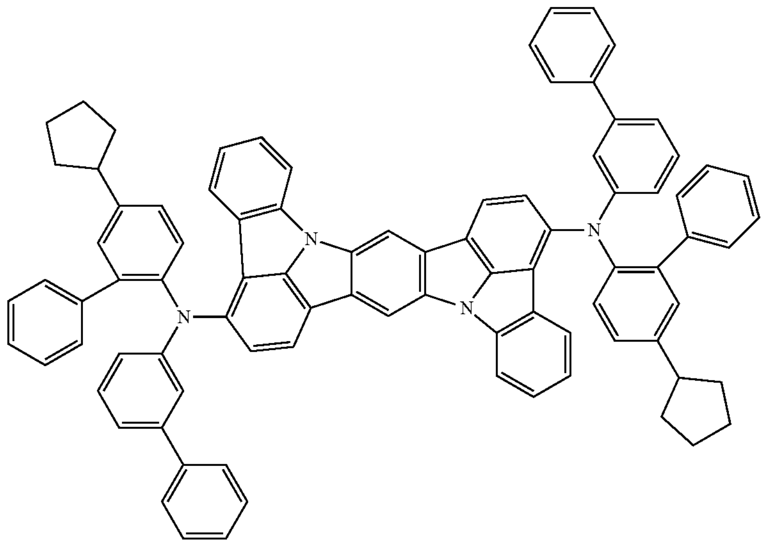
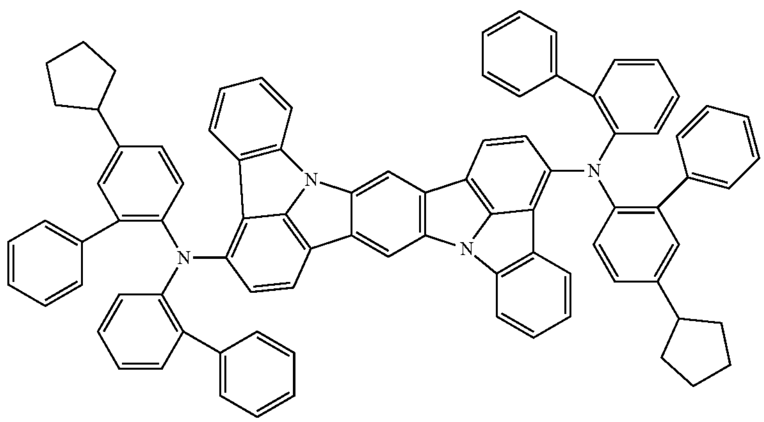

-continued
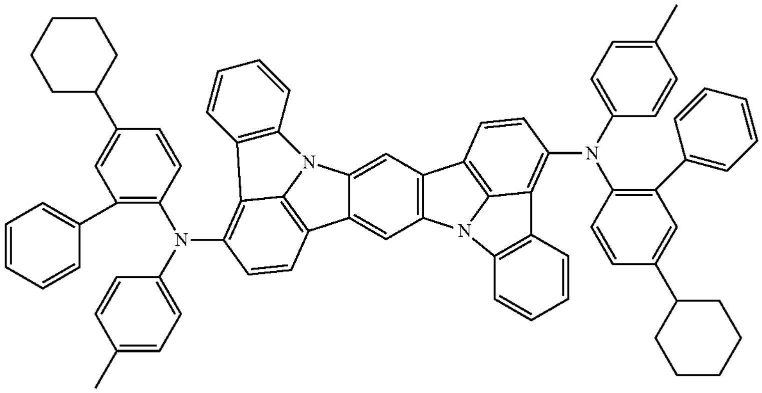
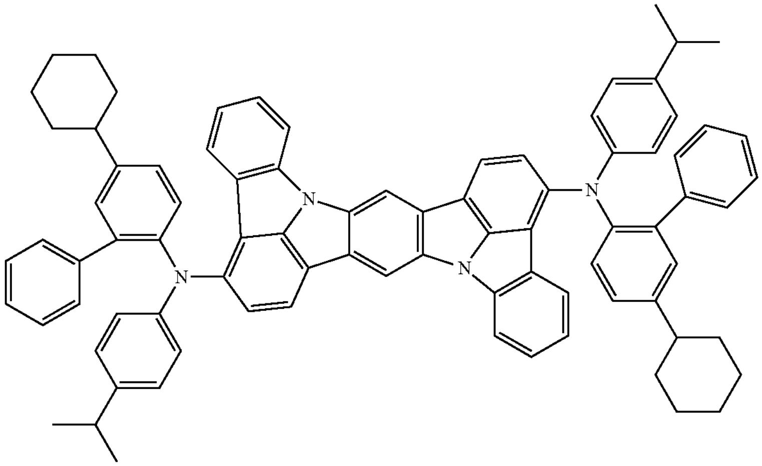
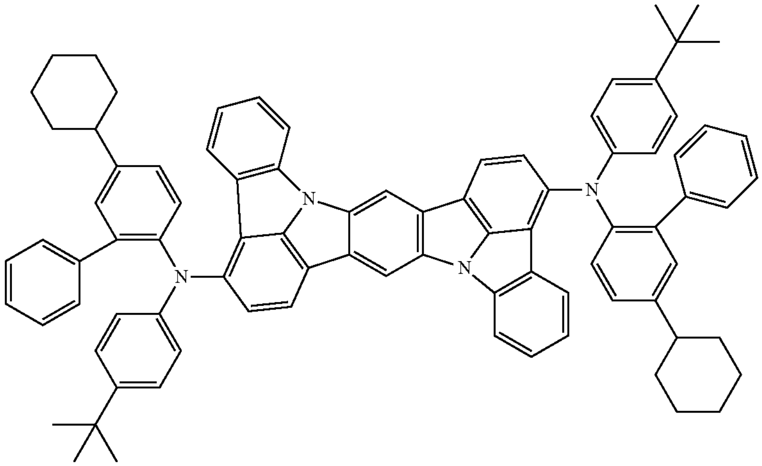

-continued
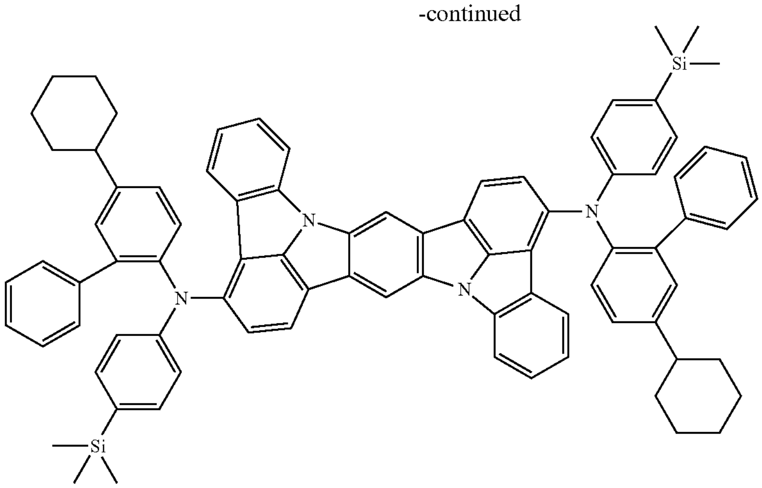
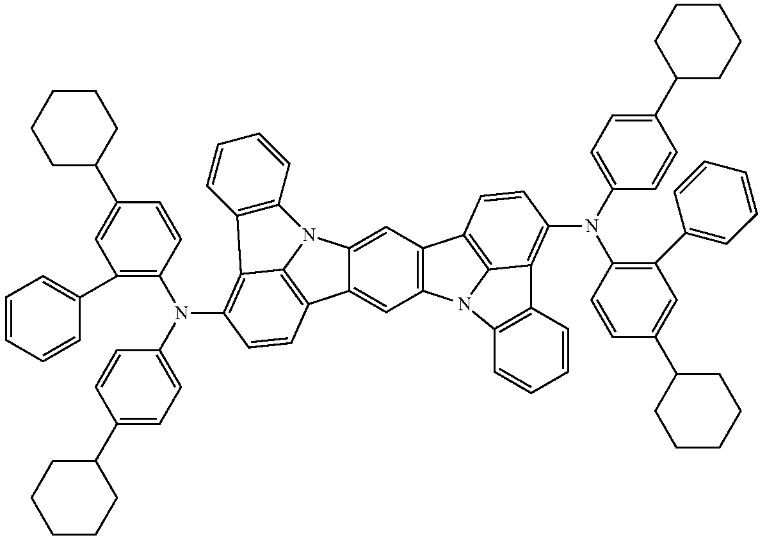
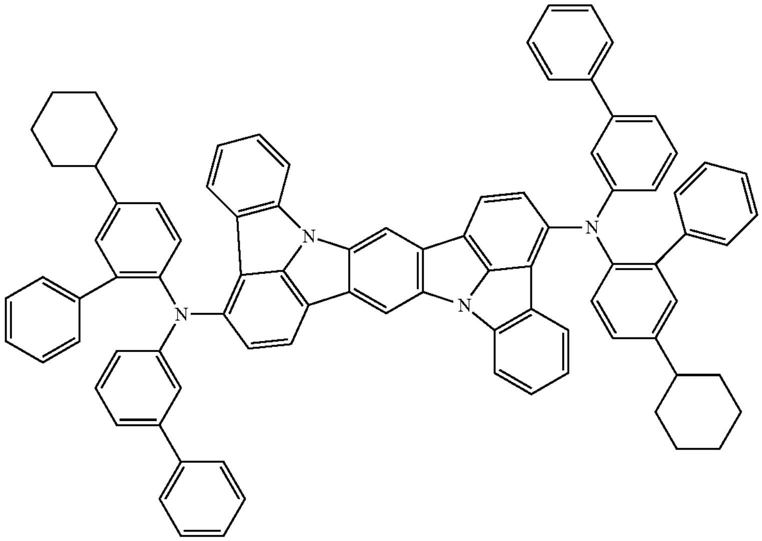

-continued
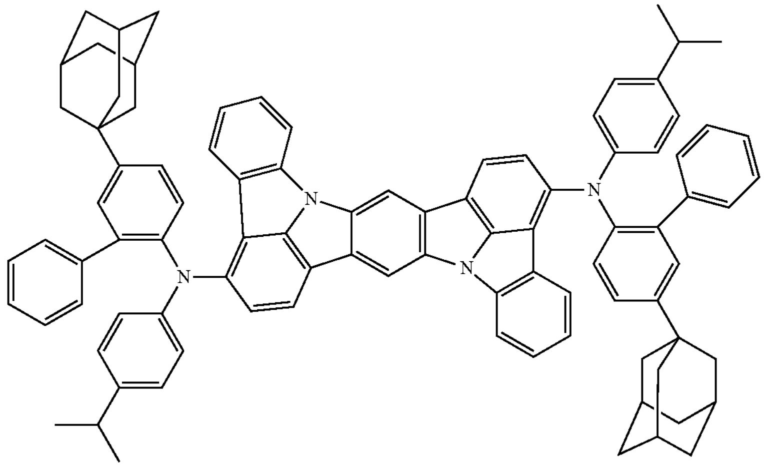
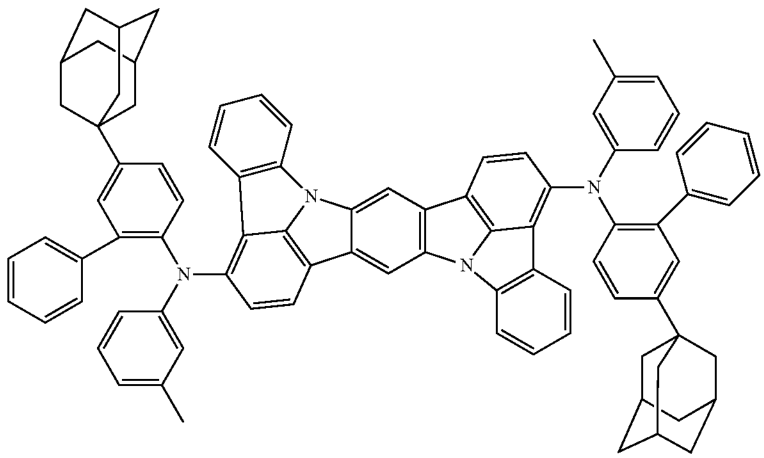
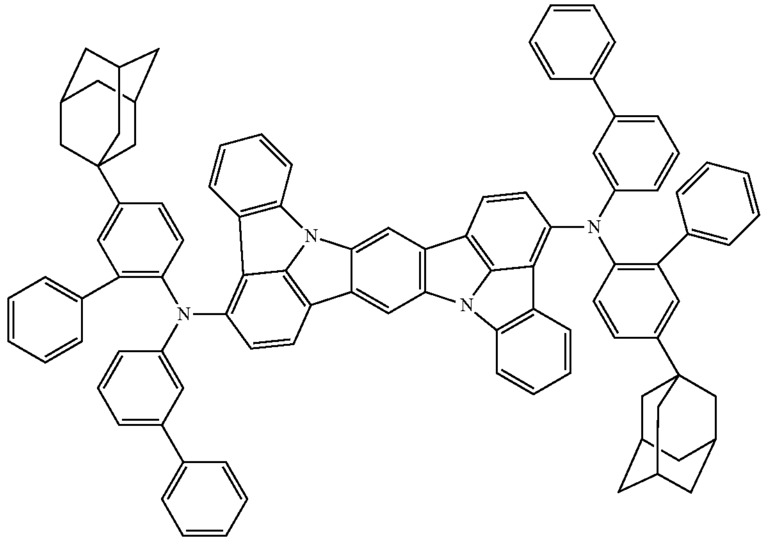

-continued
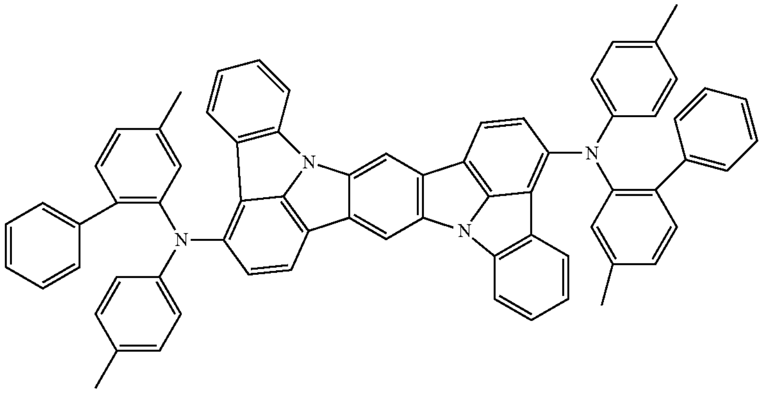
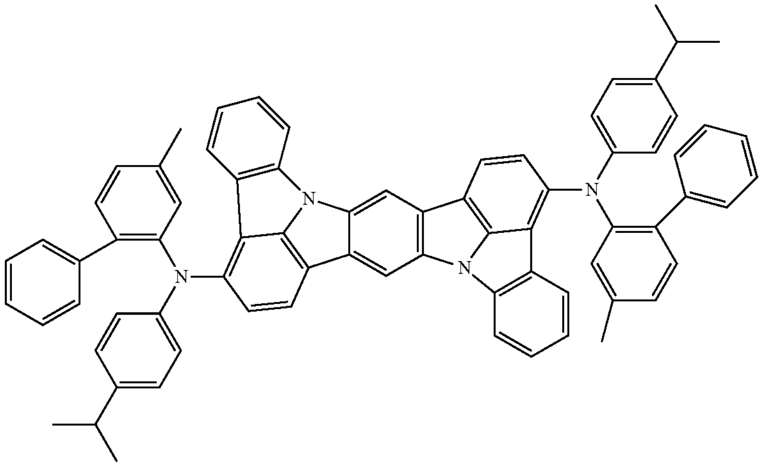
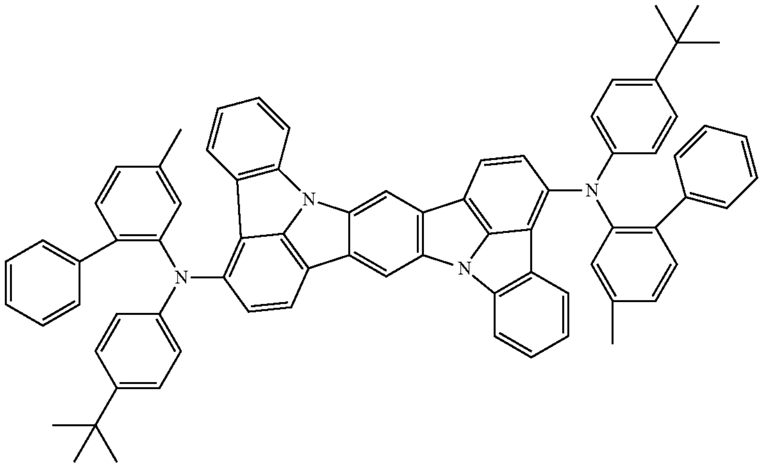

-continued
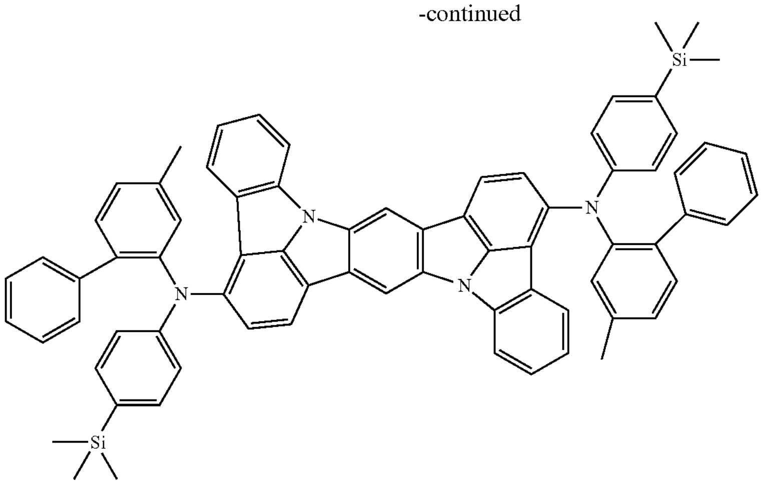
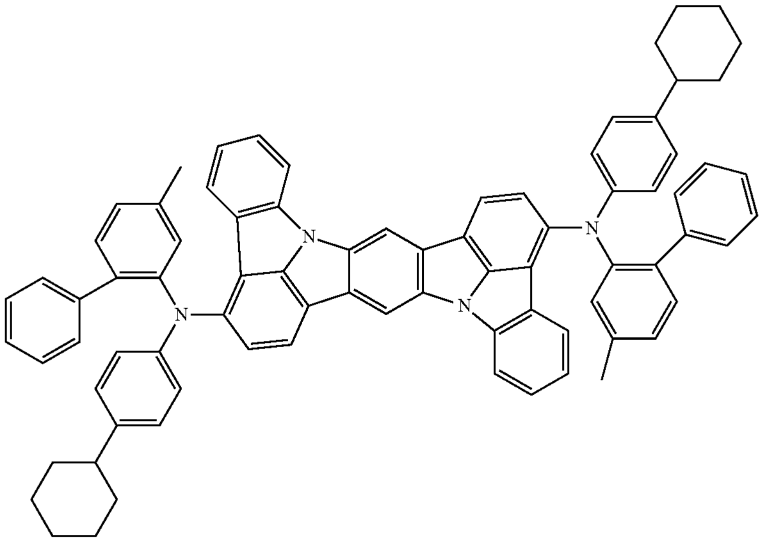
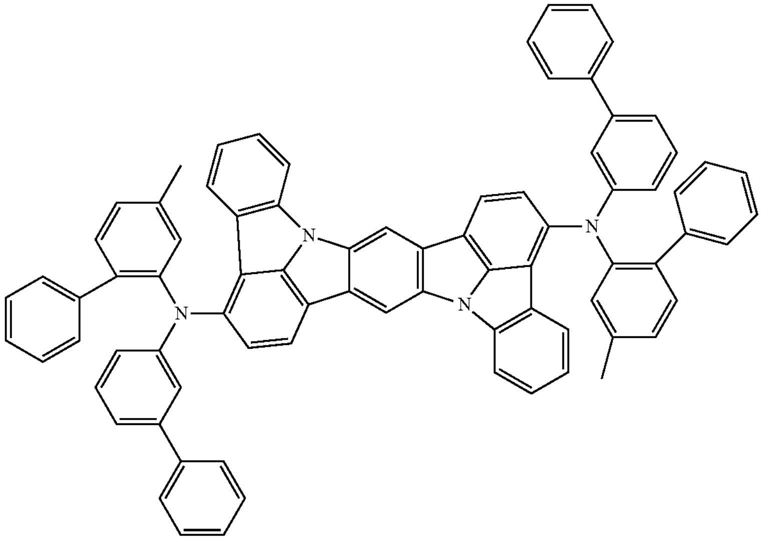

-continued
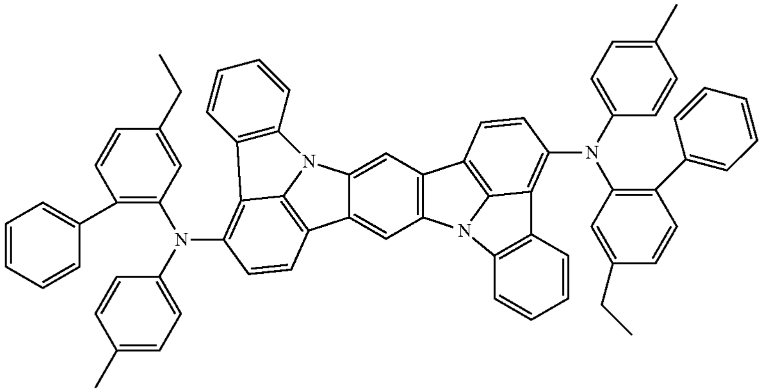
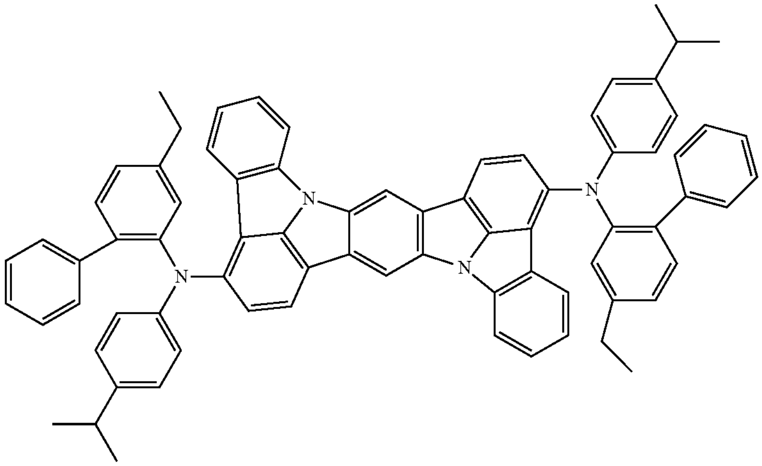
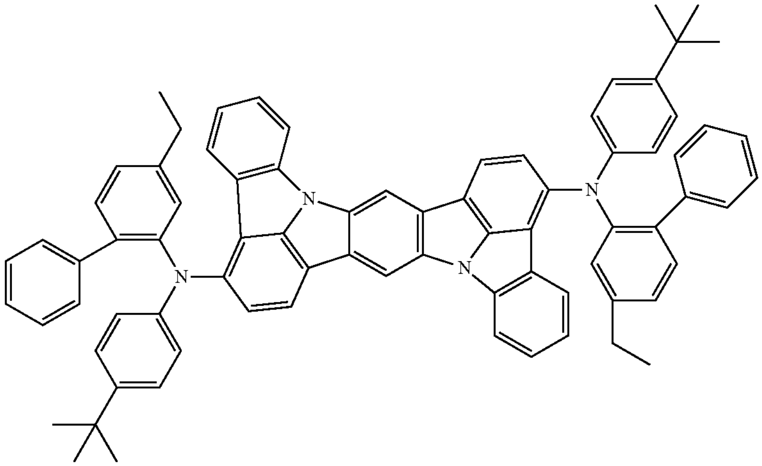

-continued
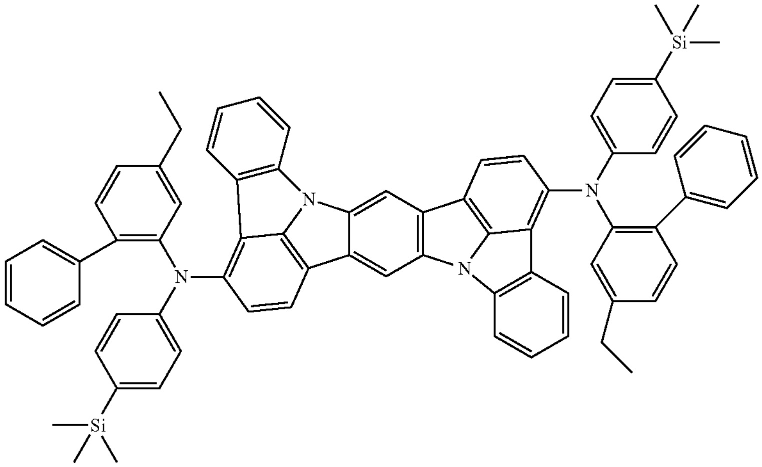
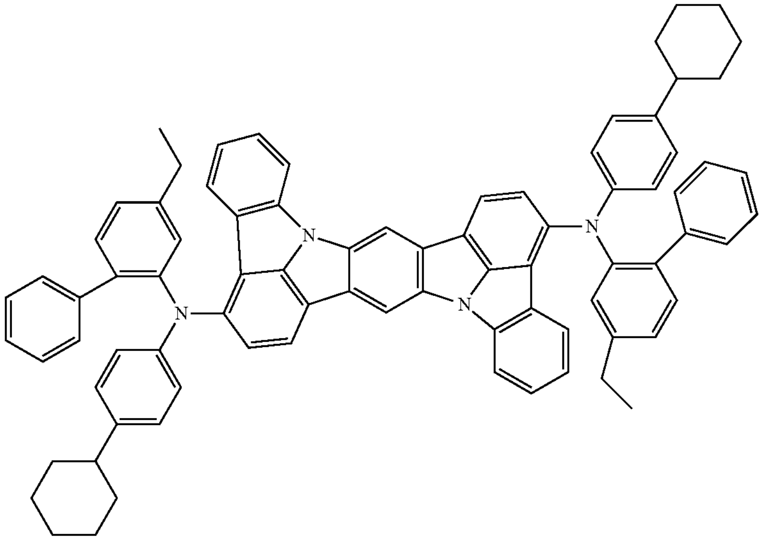
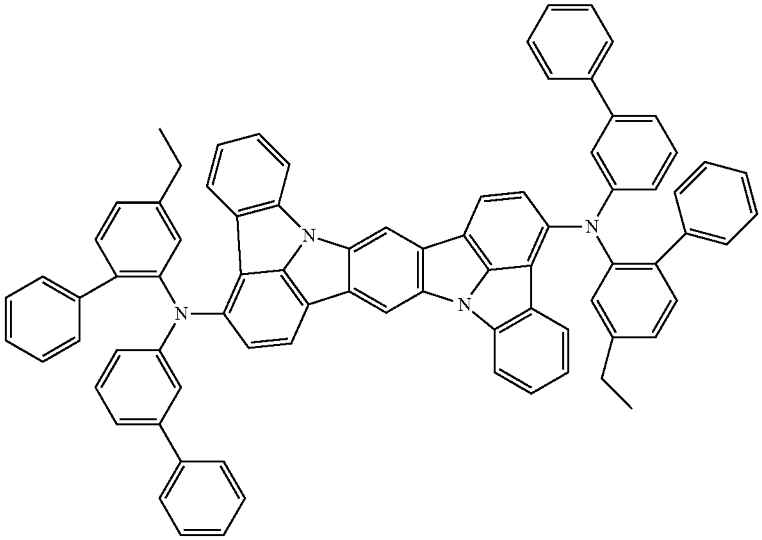

-continued
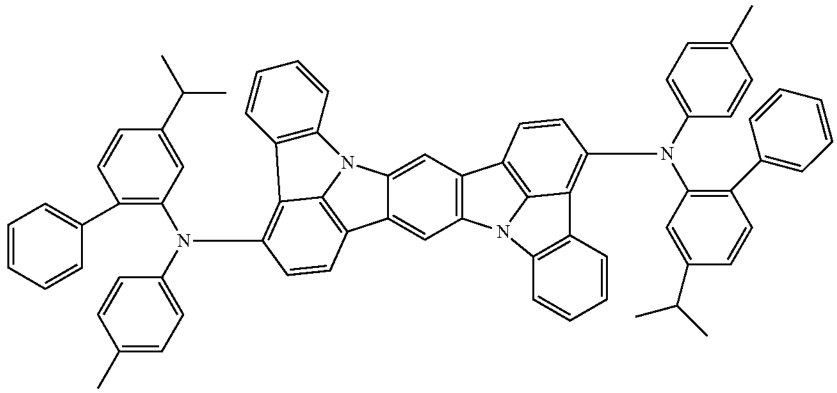
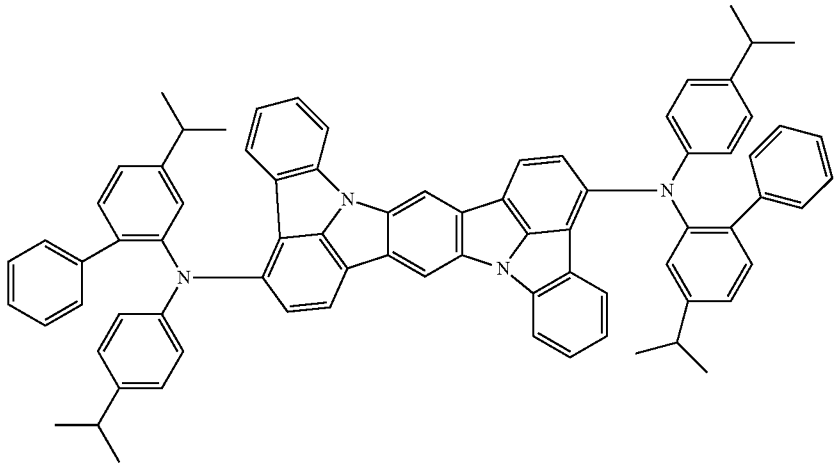
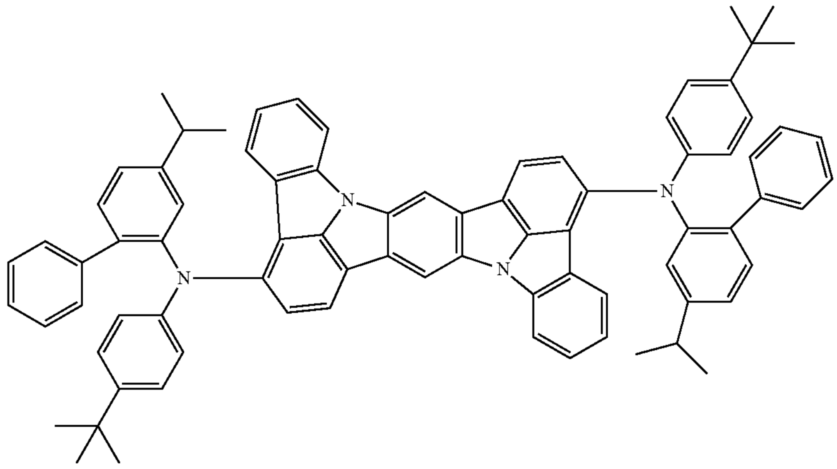

-continued
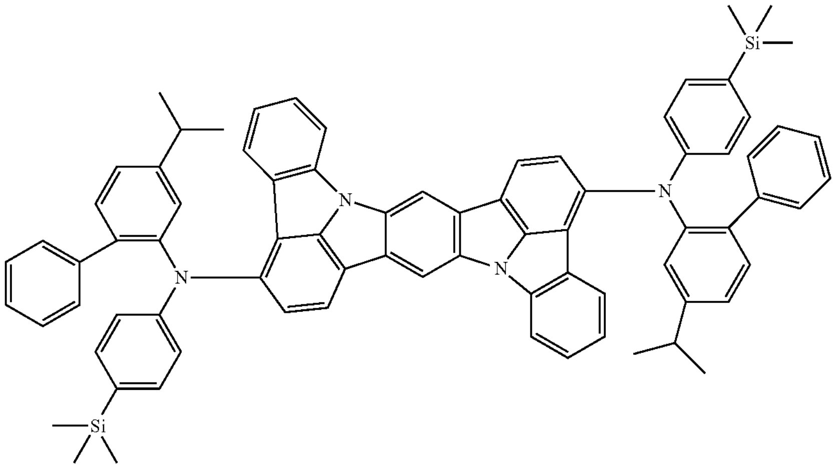
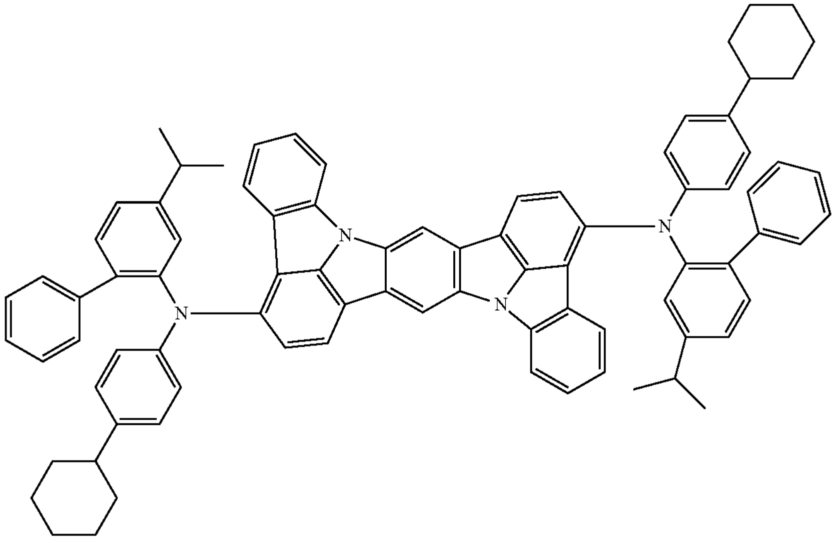
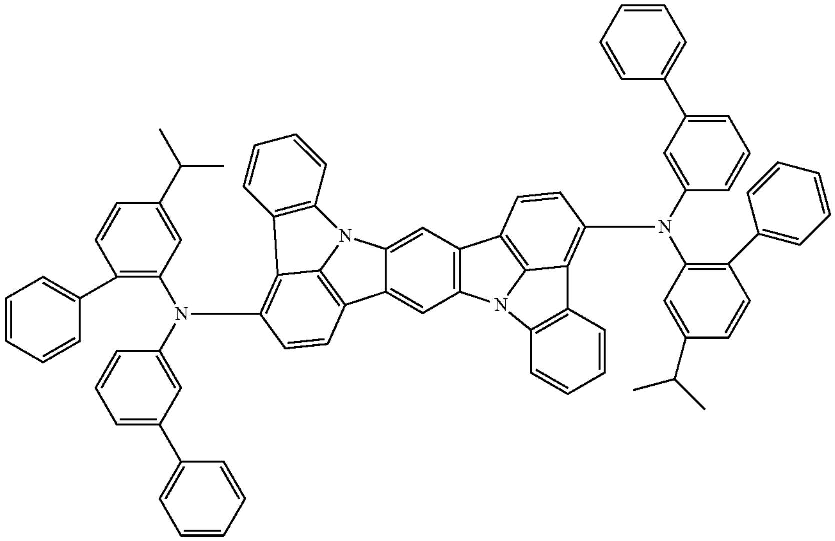

-continued
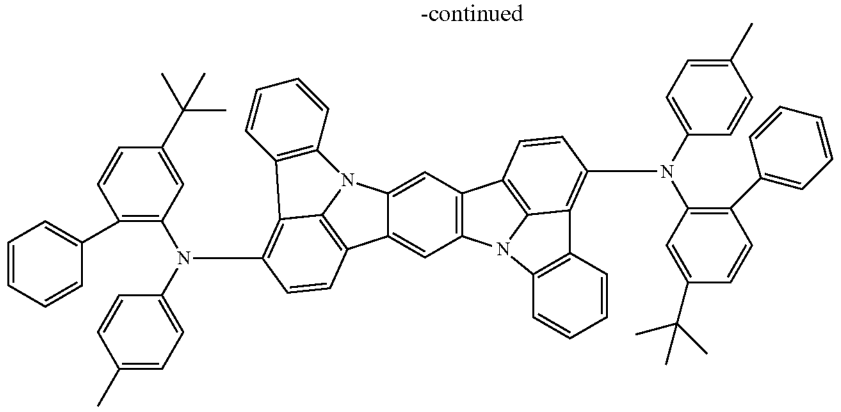
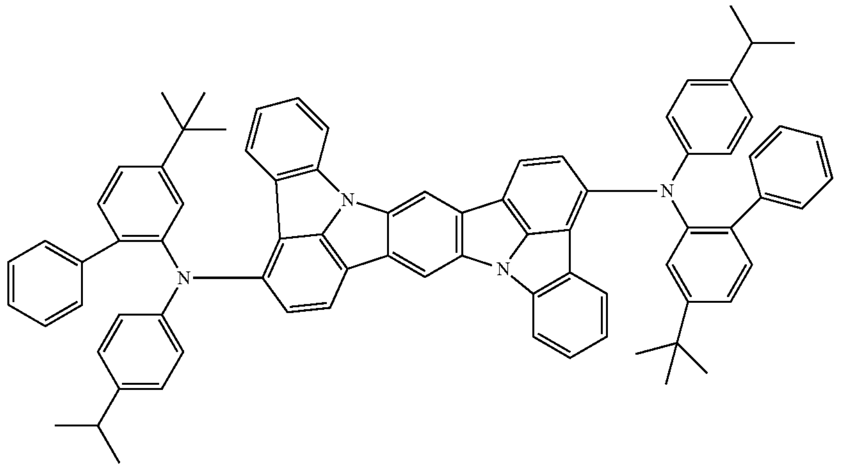
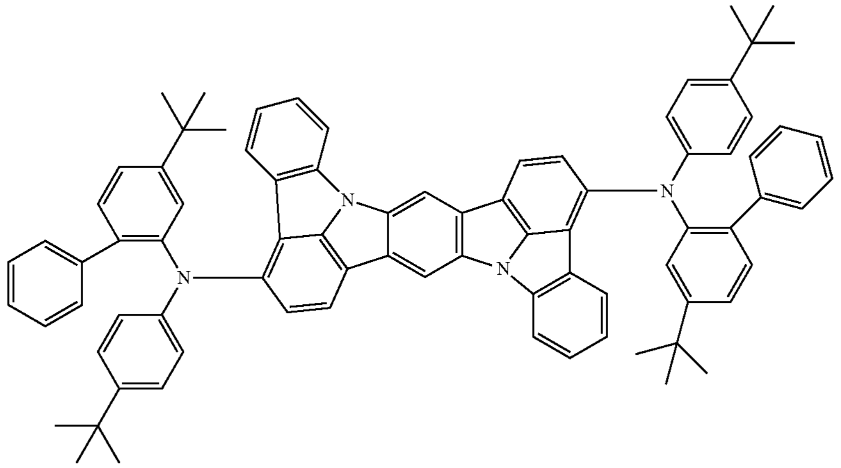

-continued
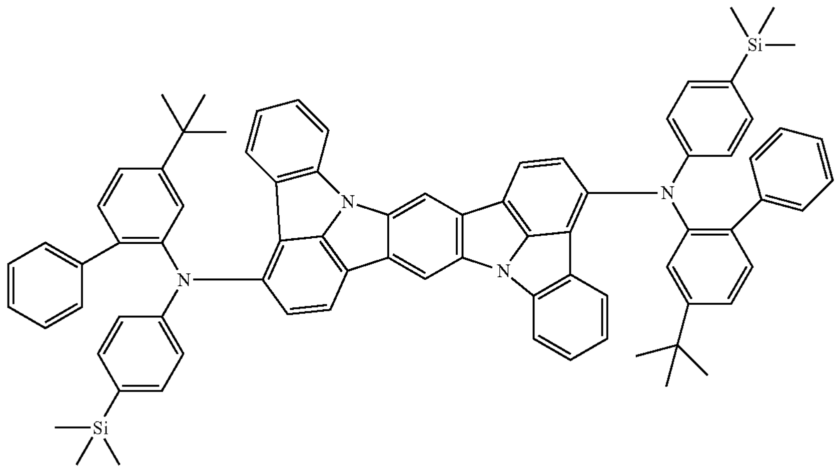
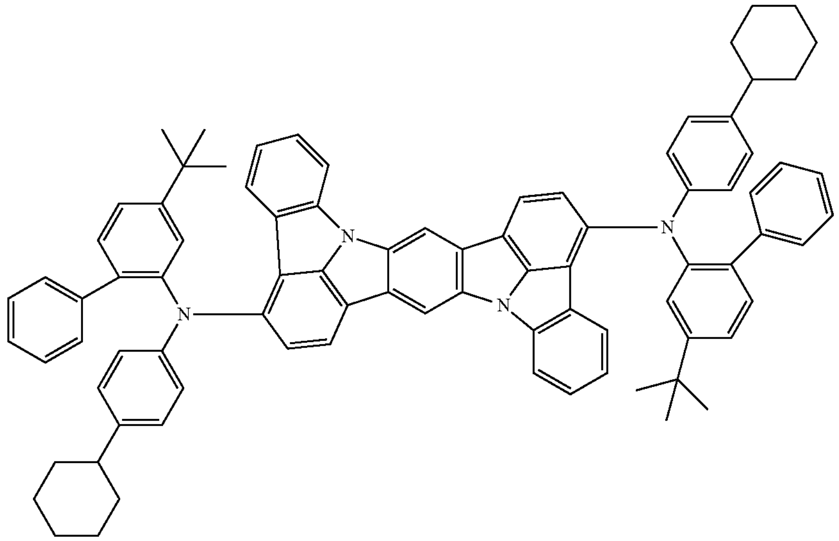
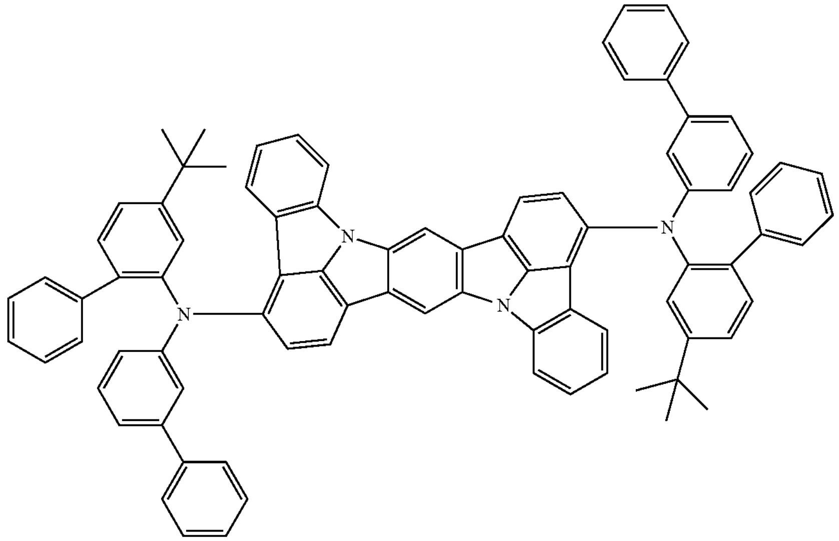

-continued
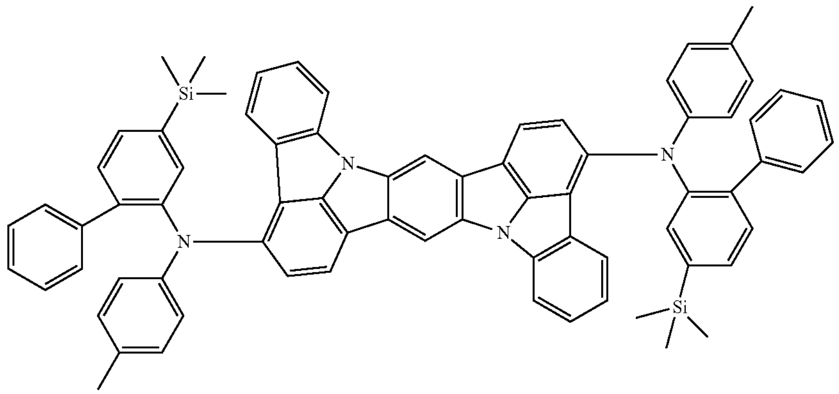
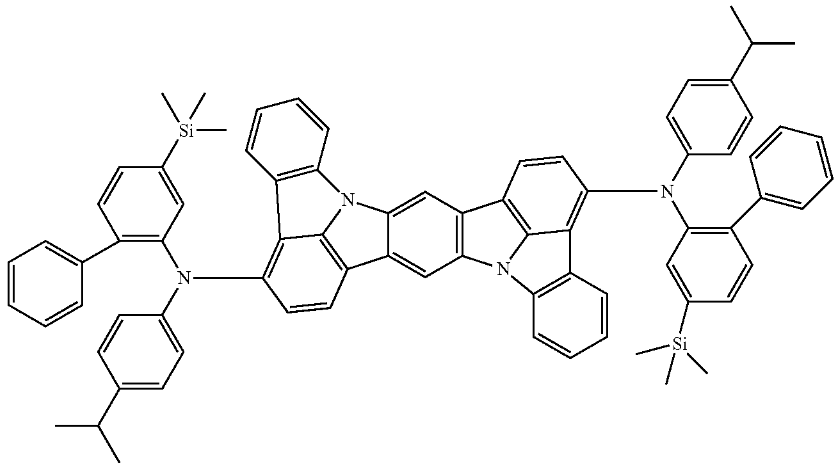
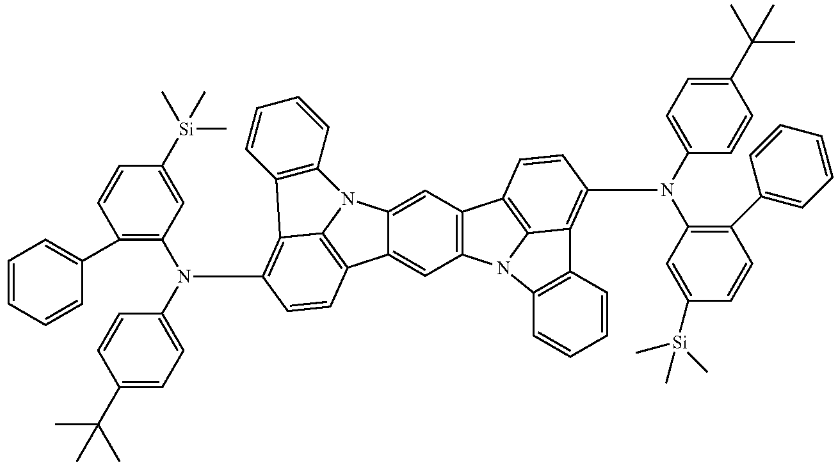

-continued
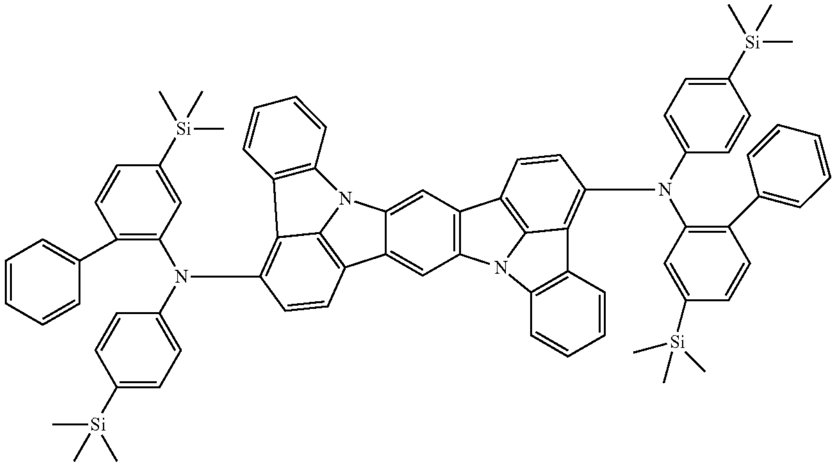
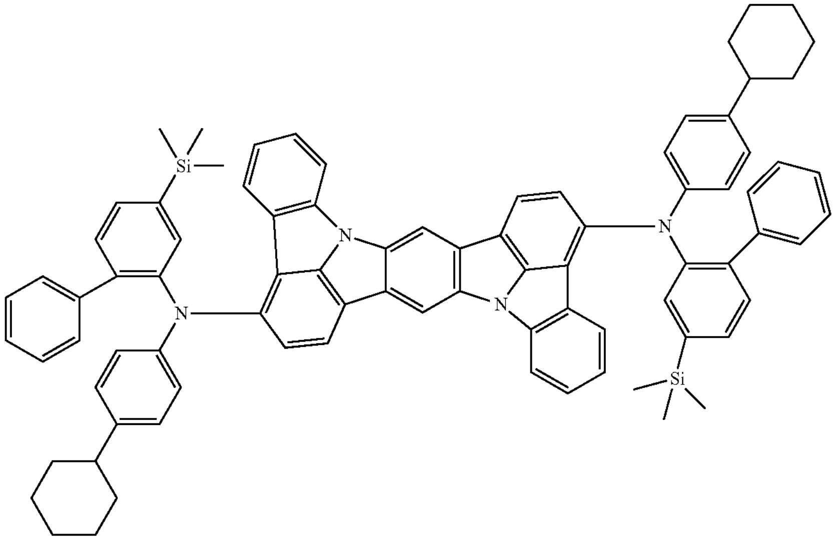
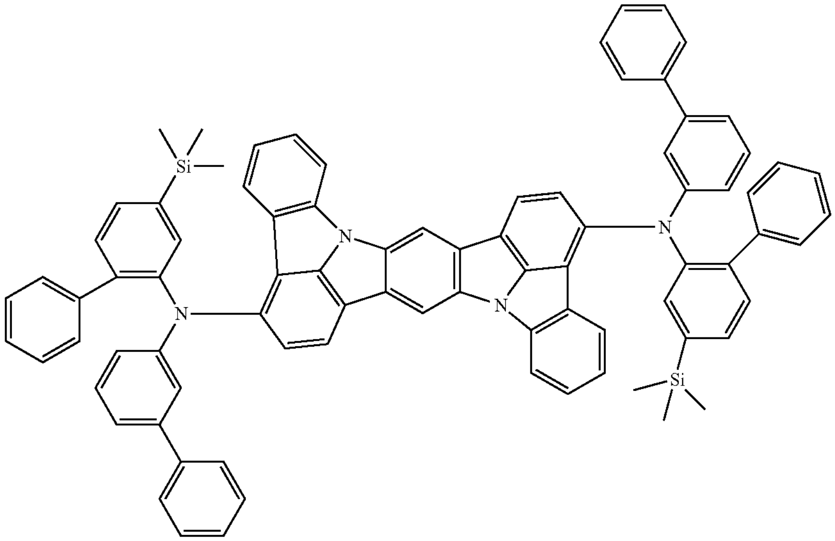

-continued
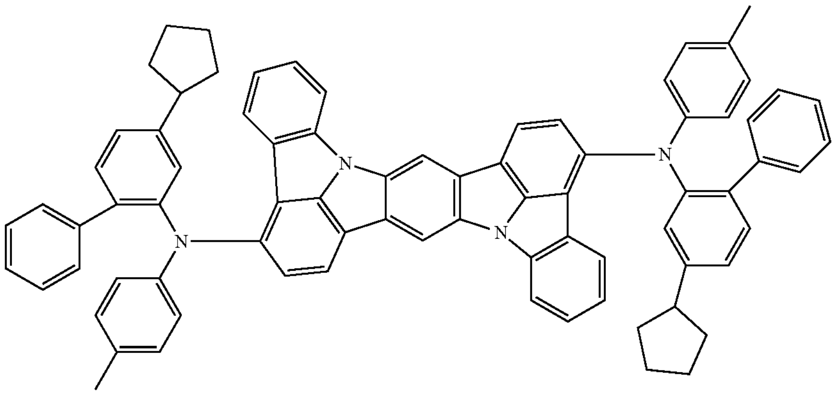
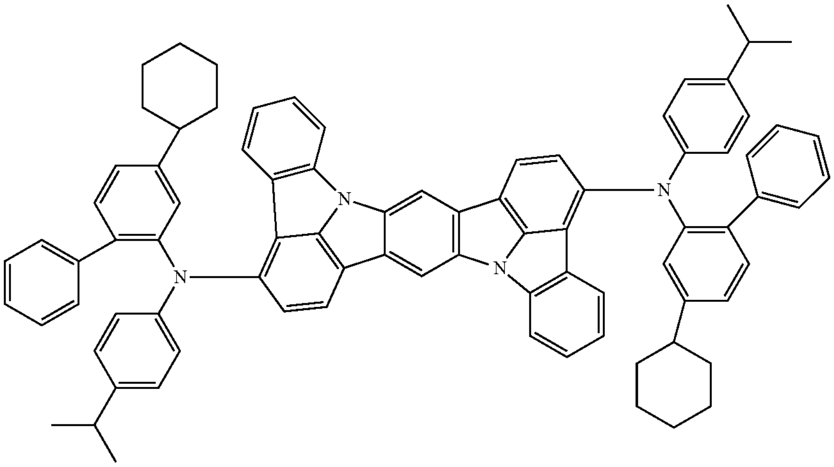
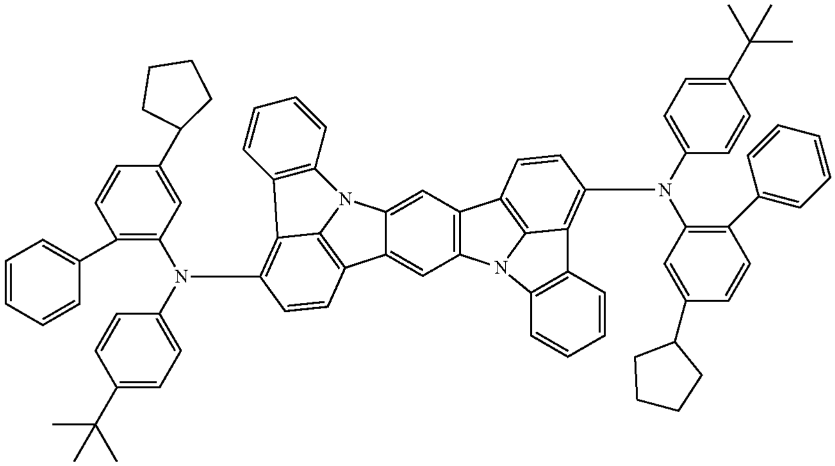

-continued
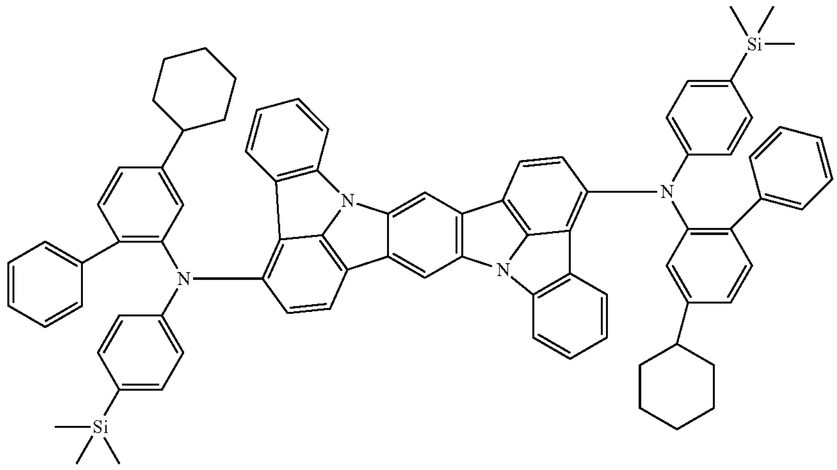
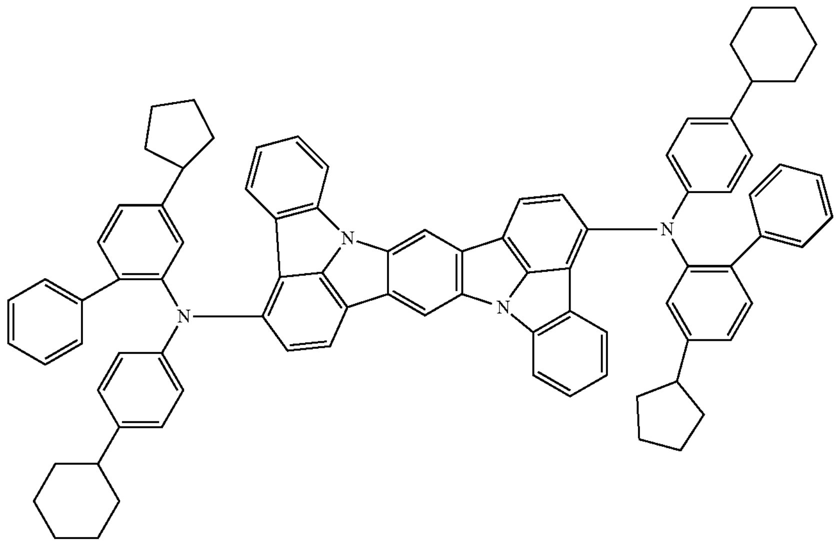
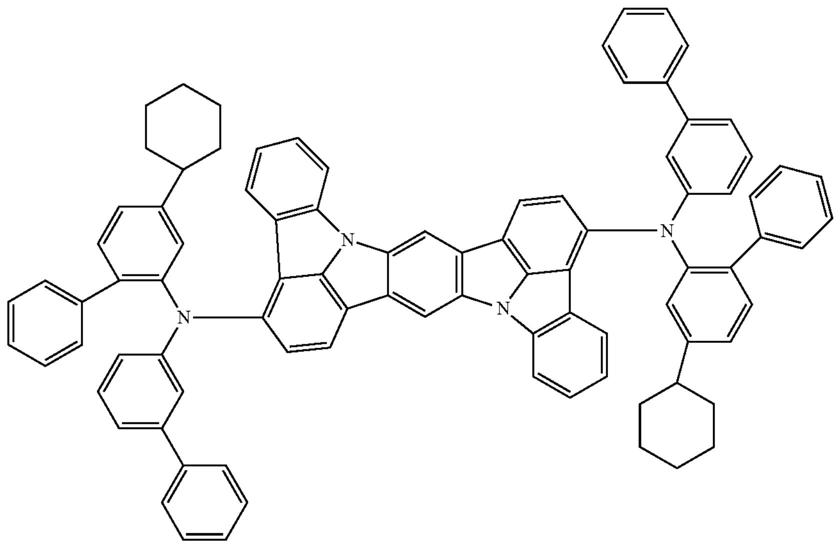

-continued
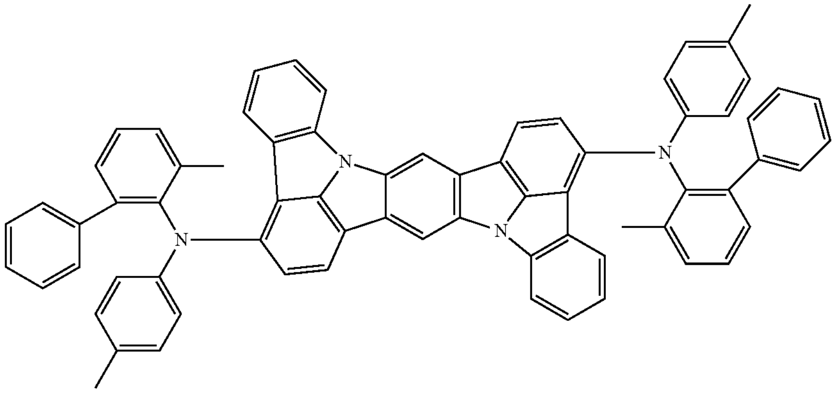
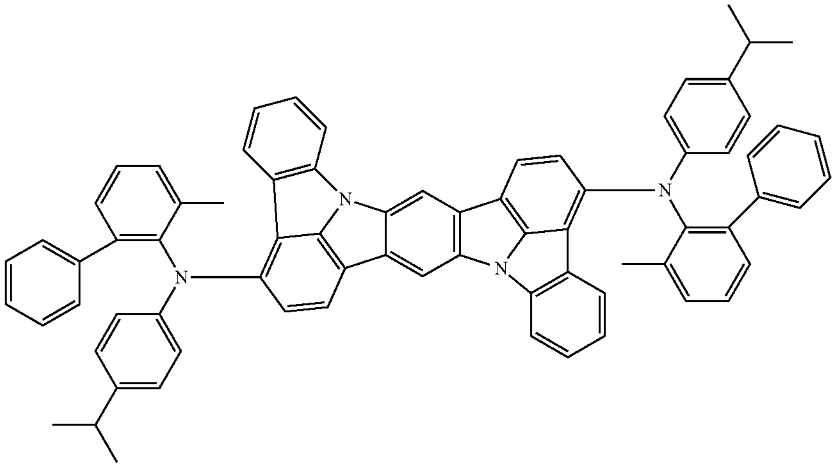
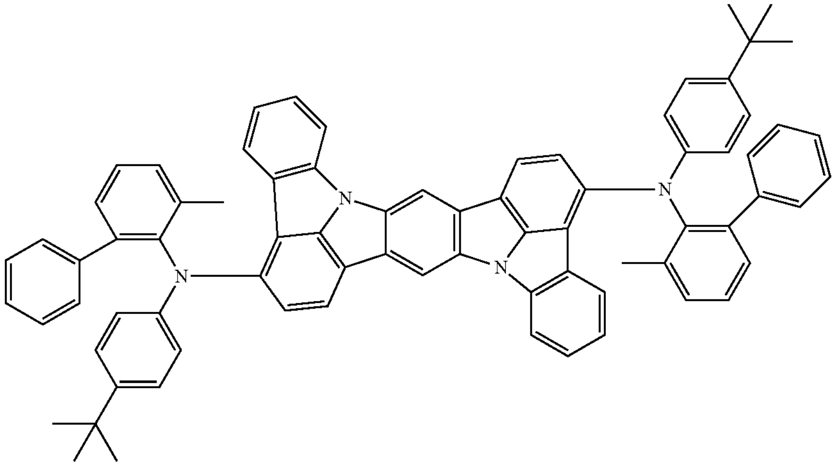
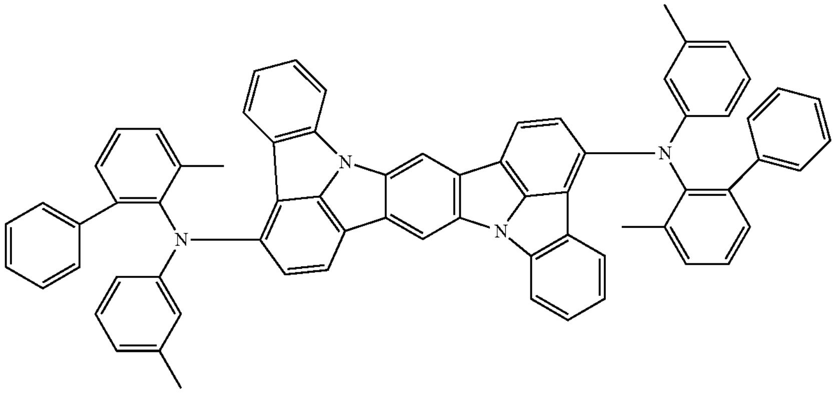

-continued
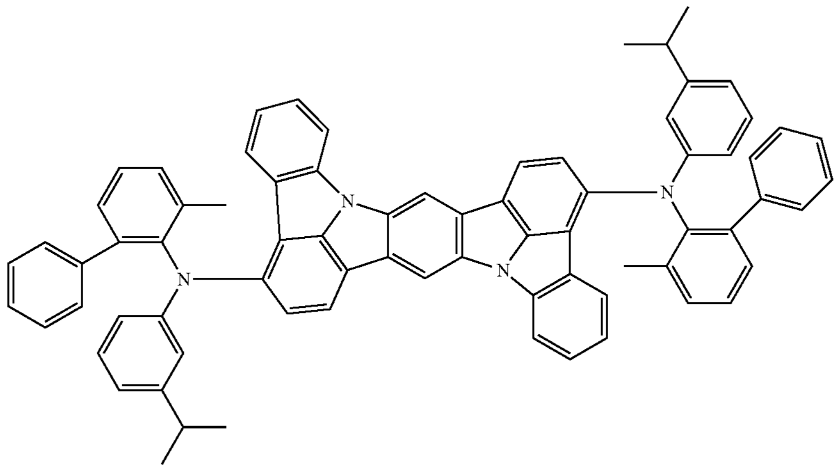
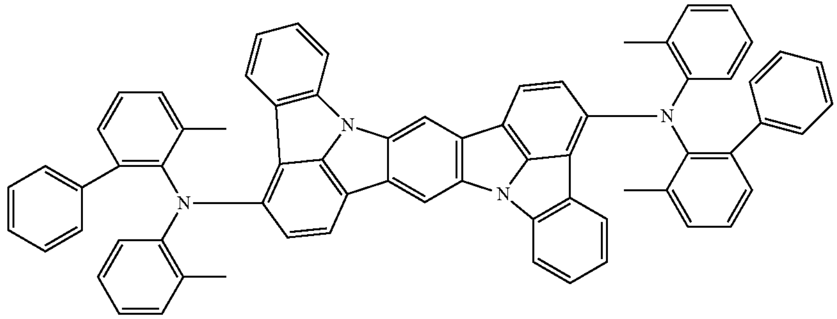
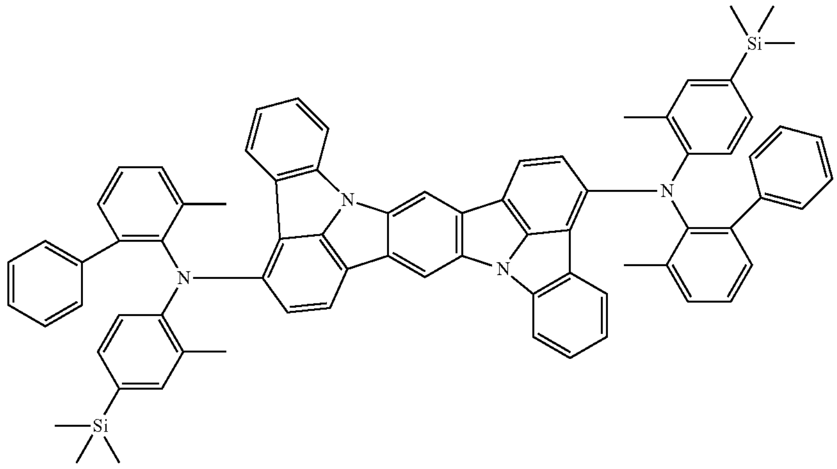

-continued
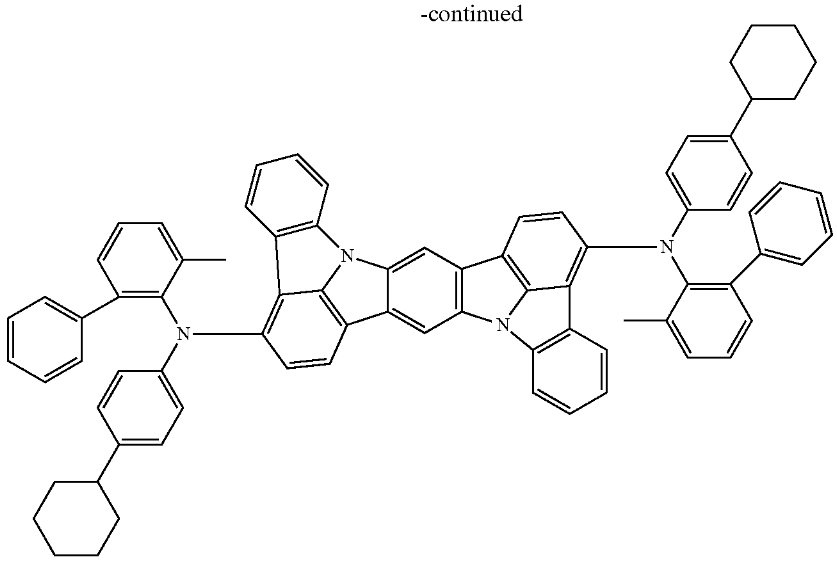
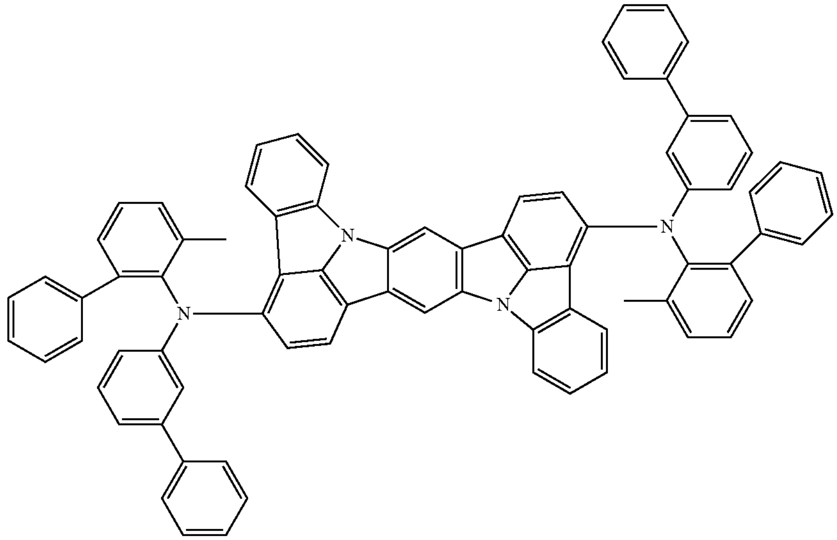
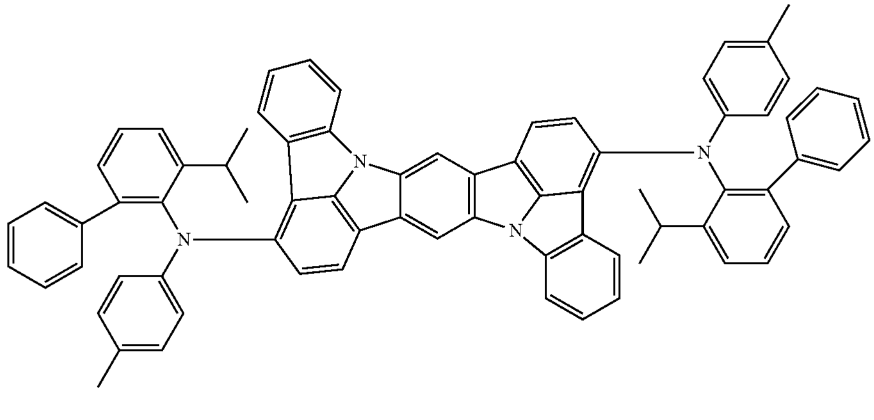

-continued
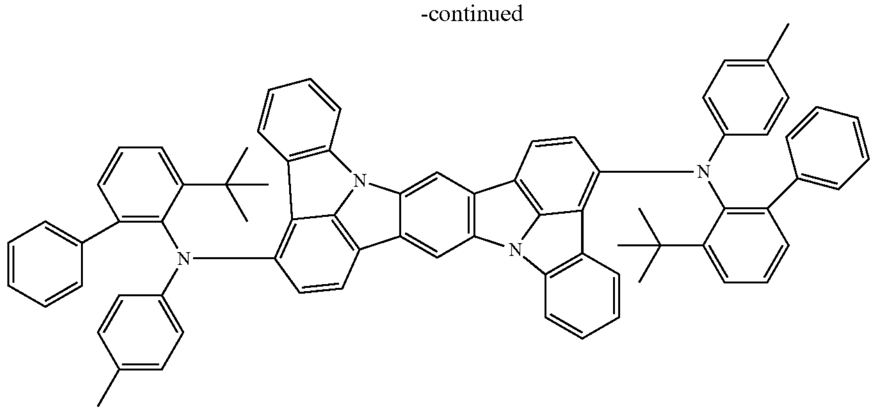
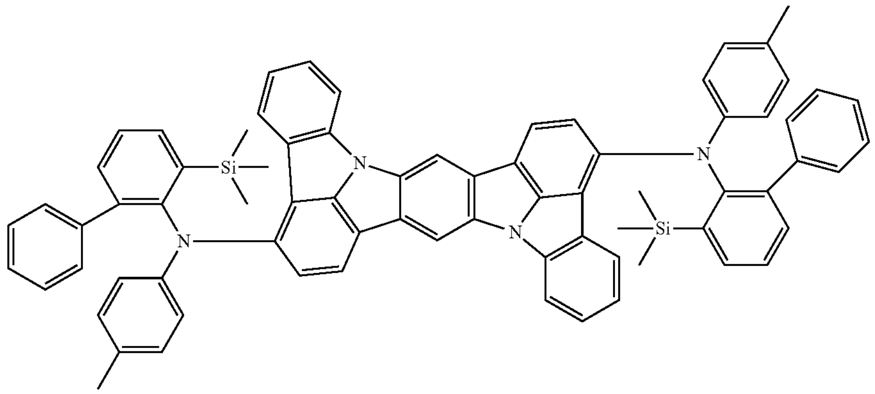
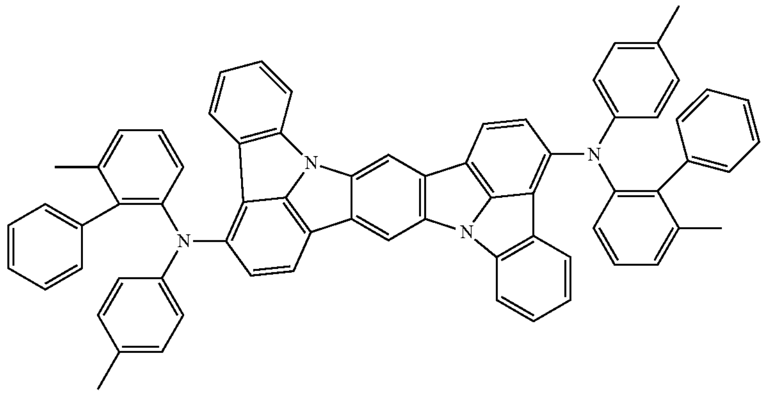
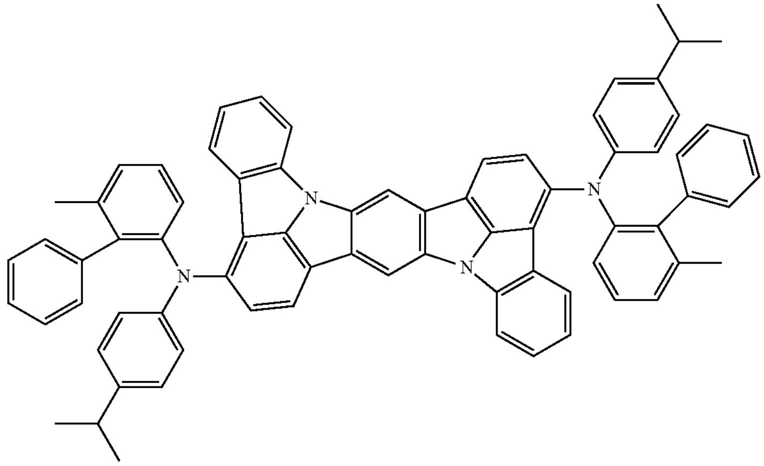

-continued
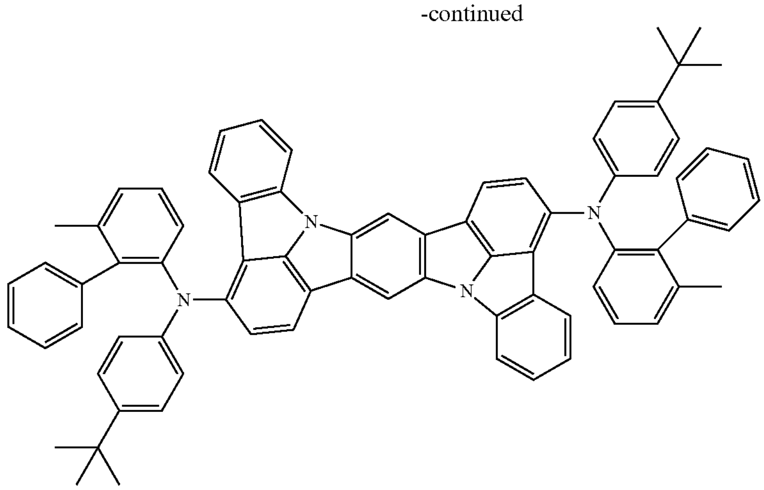
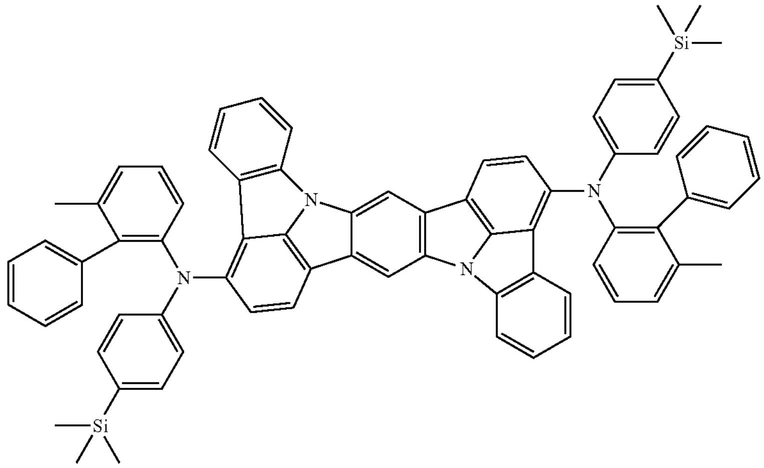
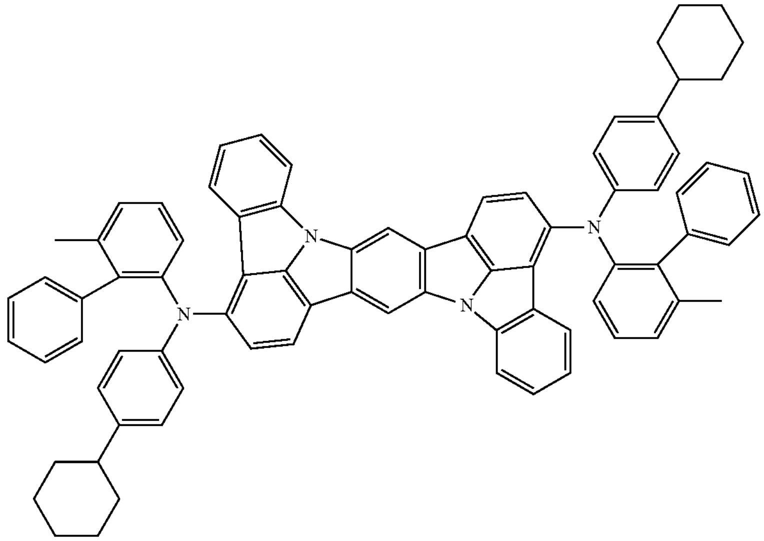

-continued
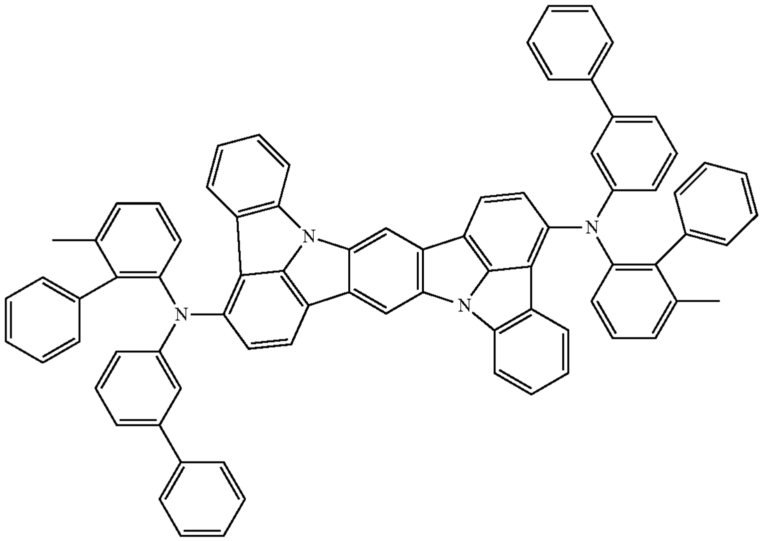
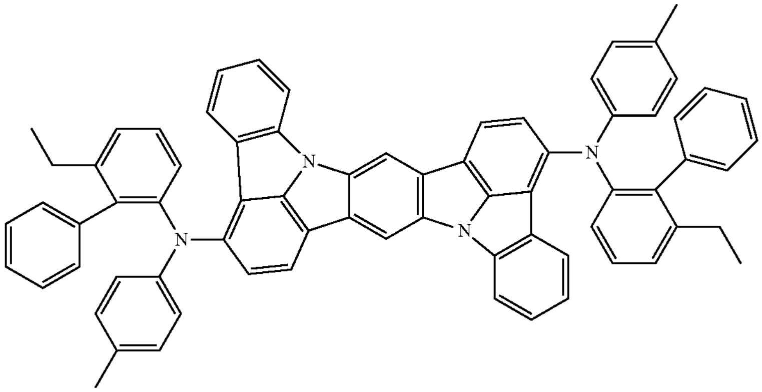
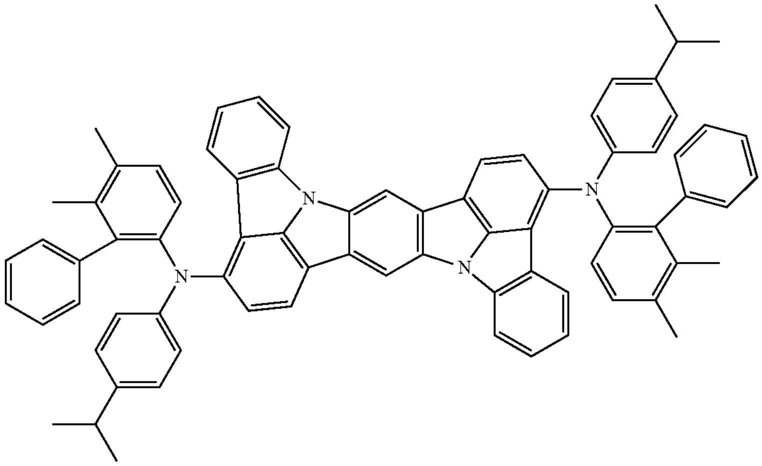

-continued
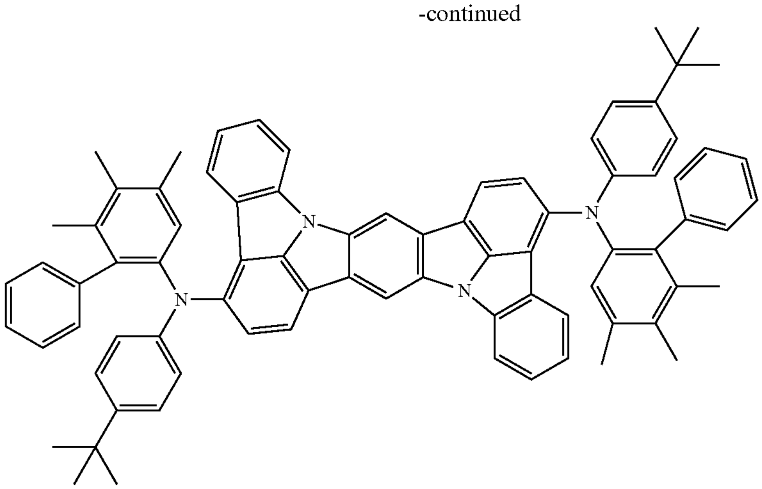
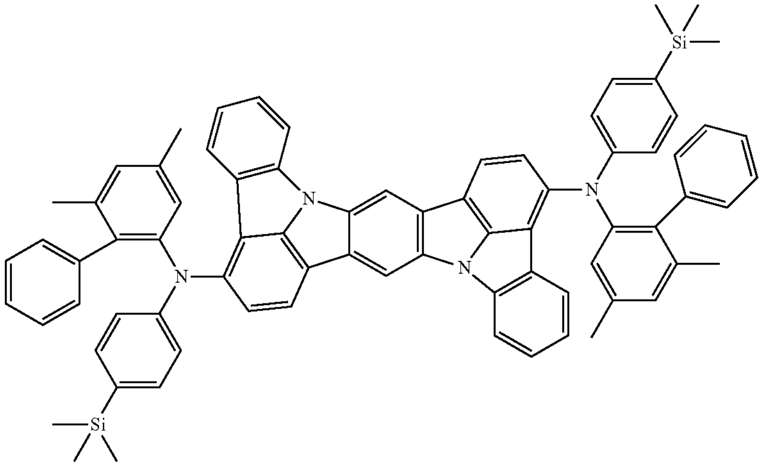
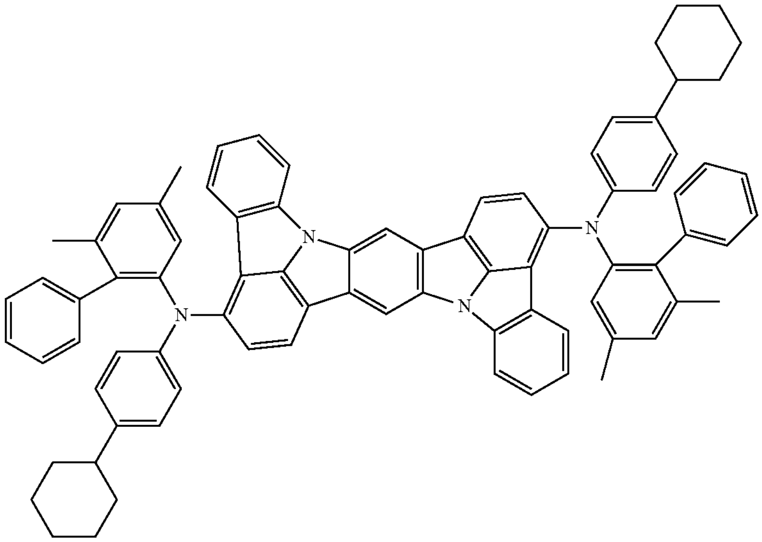

-continued
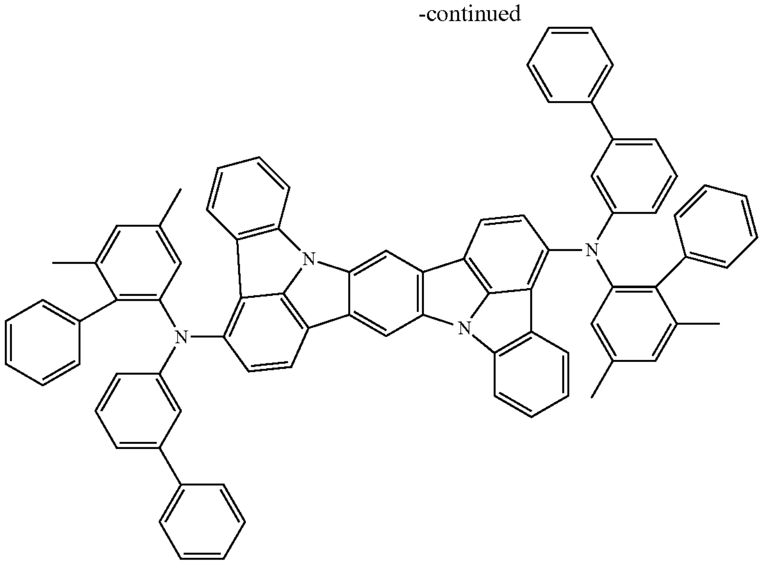
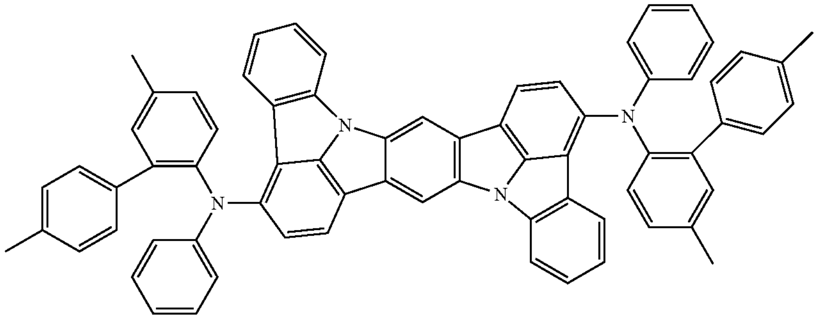
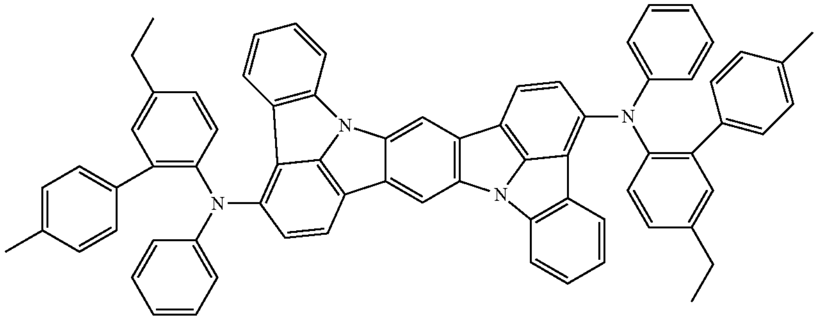
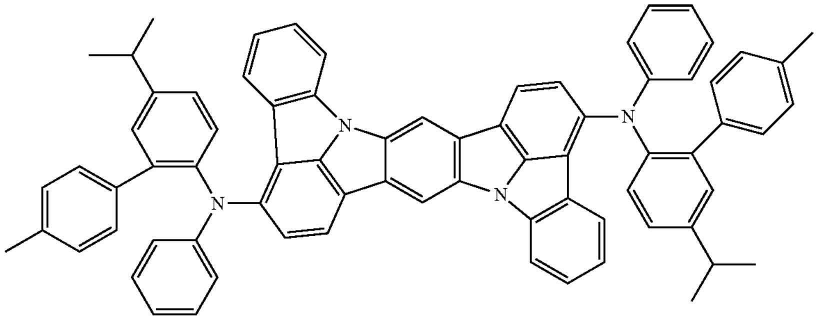

-continued
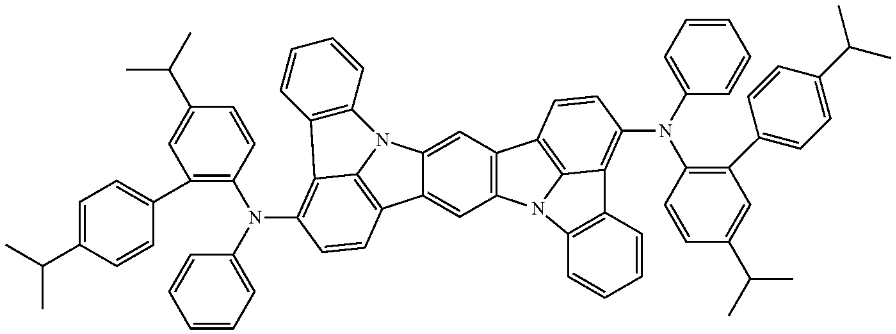
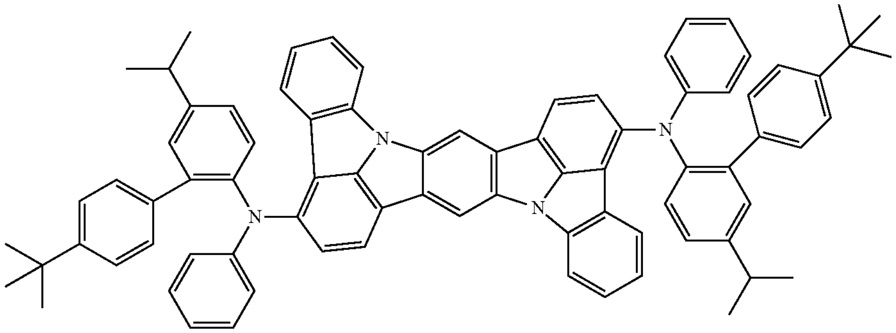
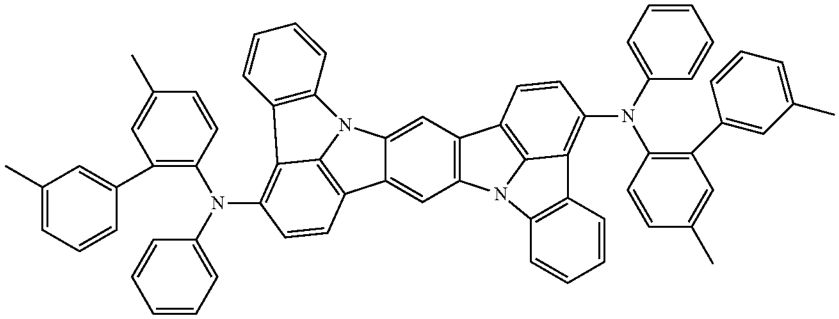
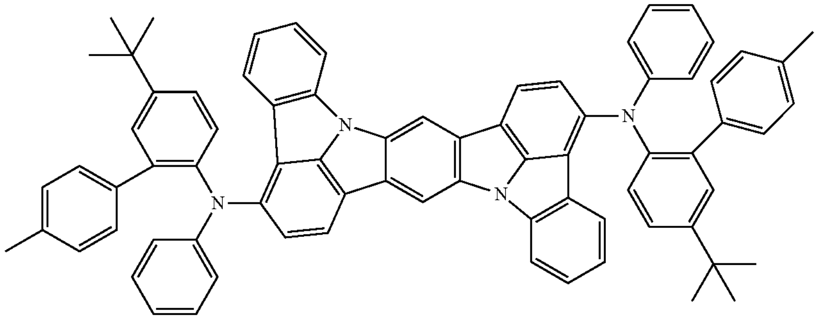
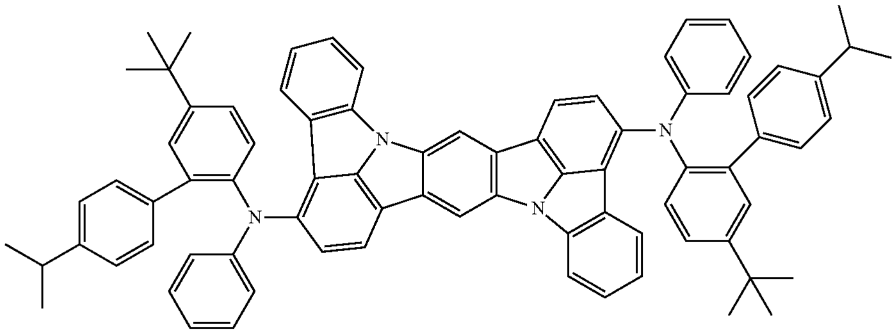

-continued
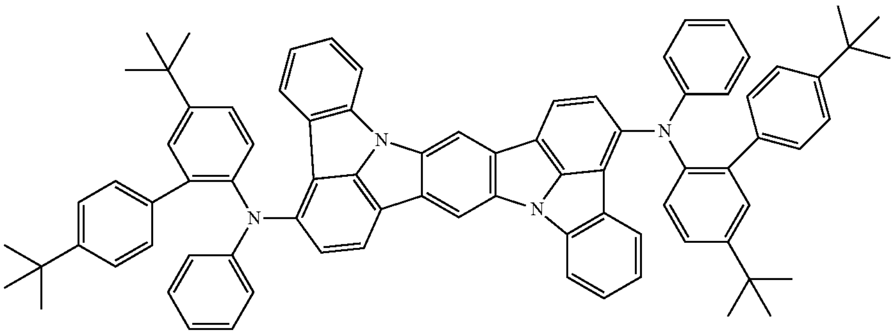
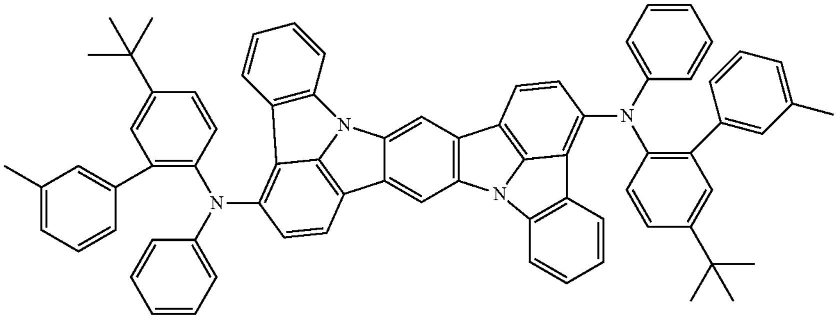
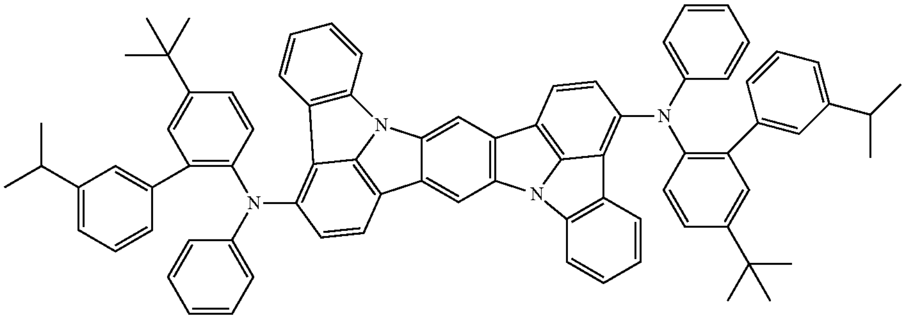
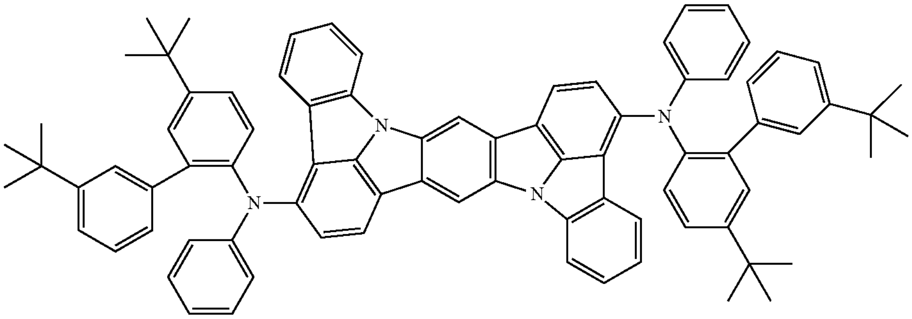
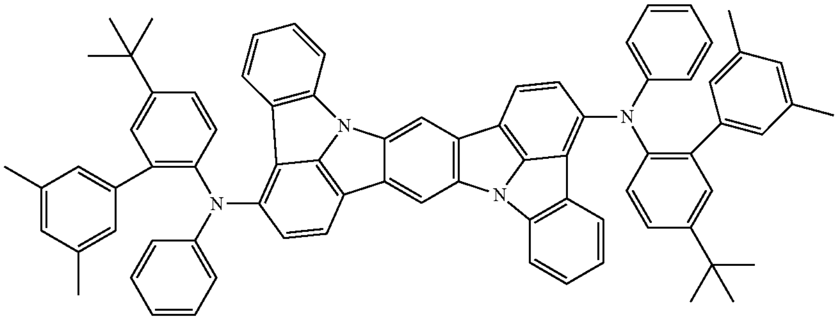

-continued
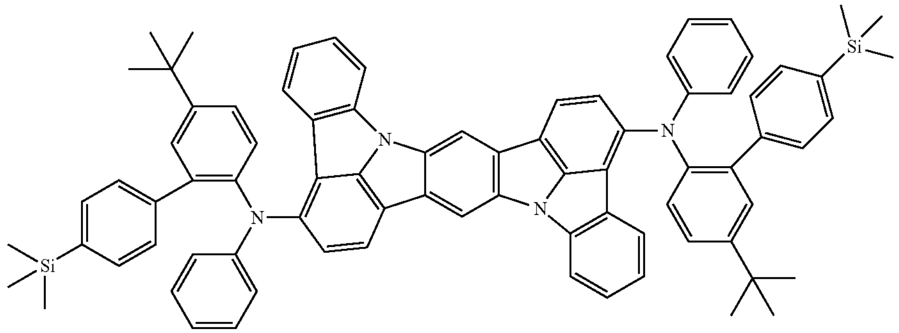
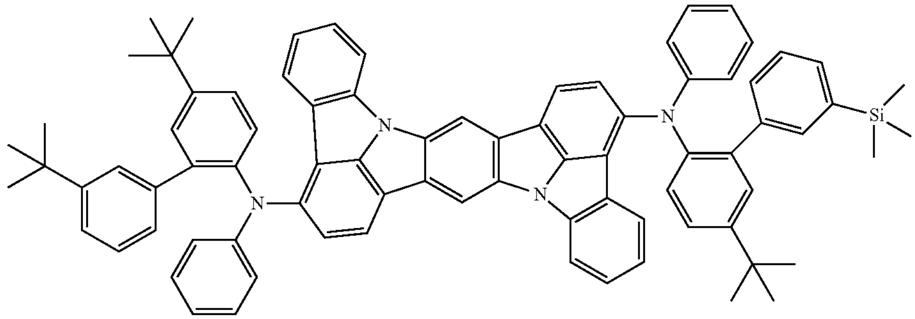
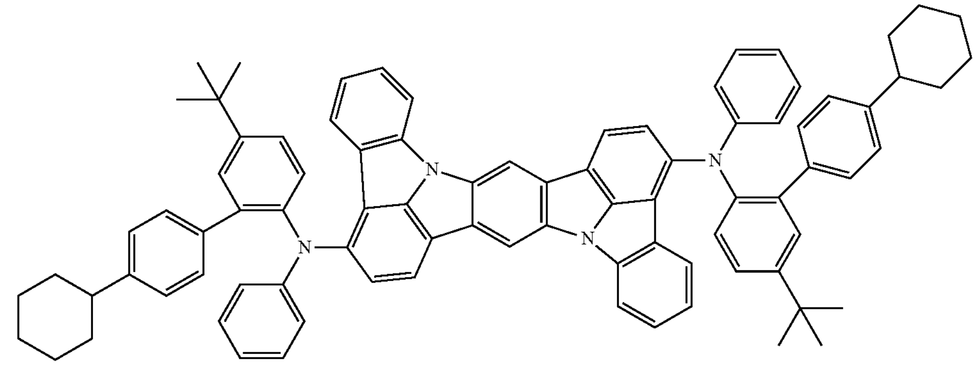
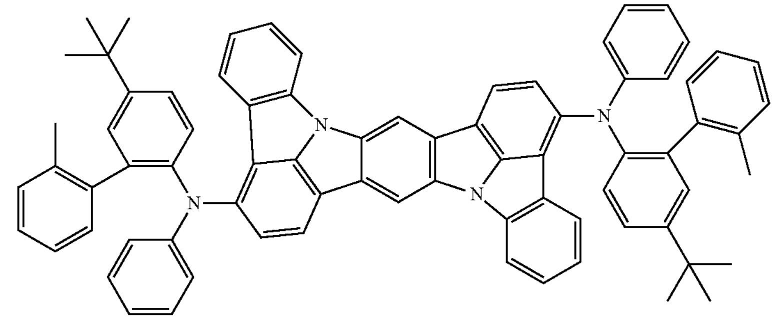
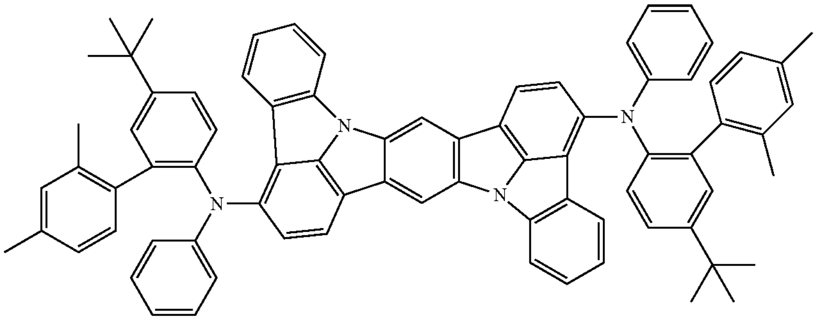

-continued
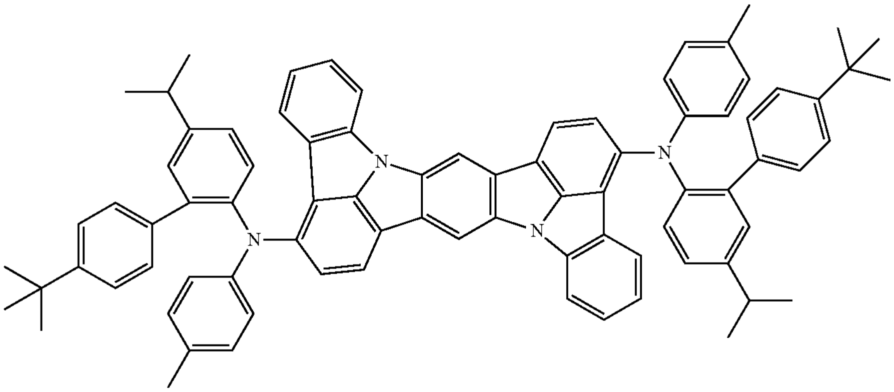
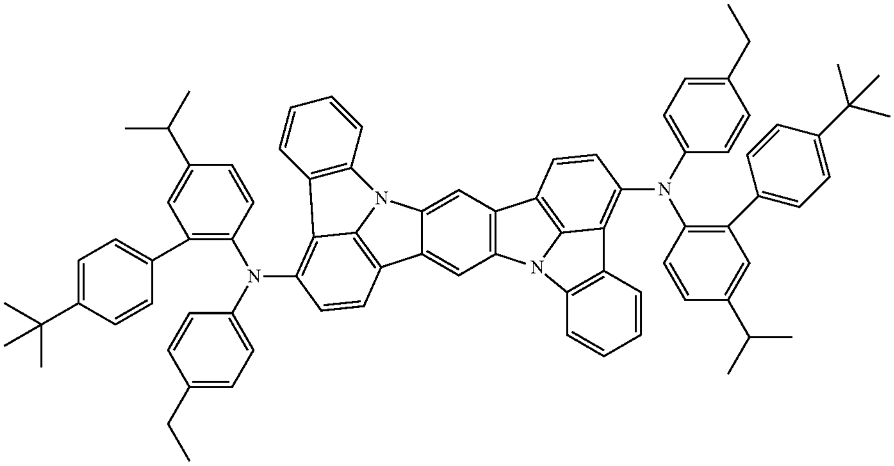
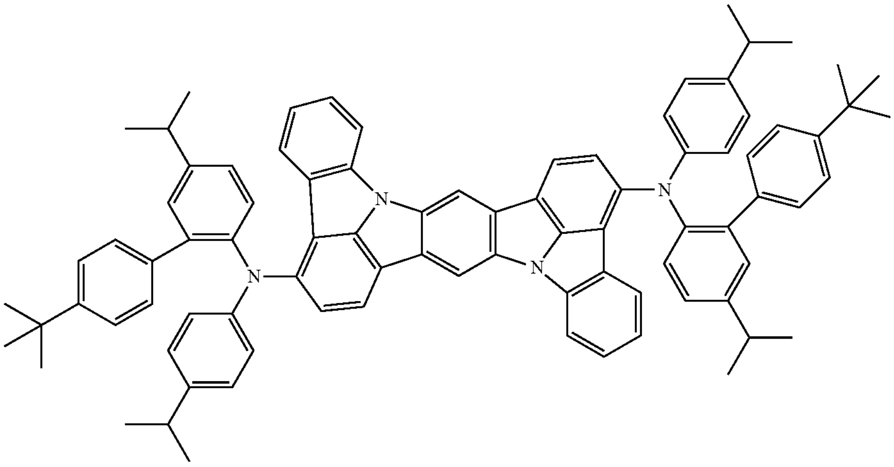 [SMILES: CC(C)c1ccc(N(c2ccc(C(C)C)cc2-c2ccc(C(C)(C)C)cc2)c2ccc3c4cc5c(cc4n4c6ccccc6c2c34)c2ccc(N(c3ccc(C(C)C)cc3)c3ccc(C(C)C)cc3-c3ccc(C(C)(C)C)cc3)c3c4ccccc4n5c23)cc1]

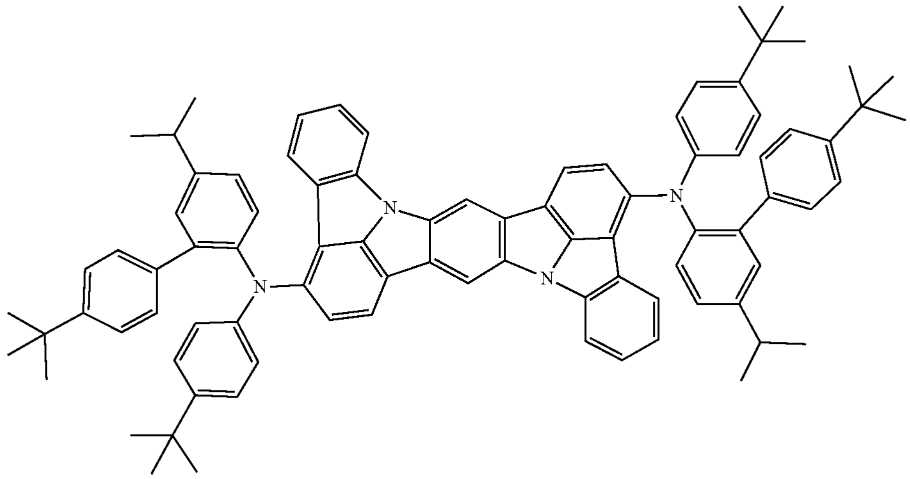
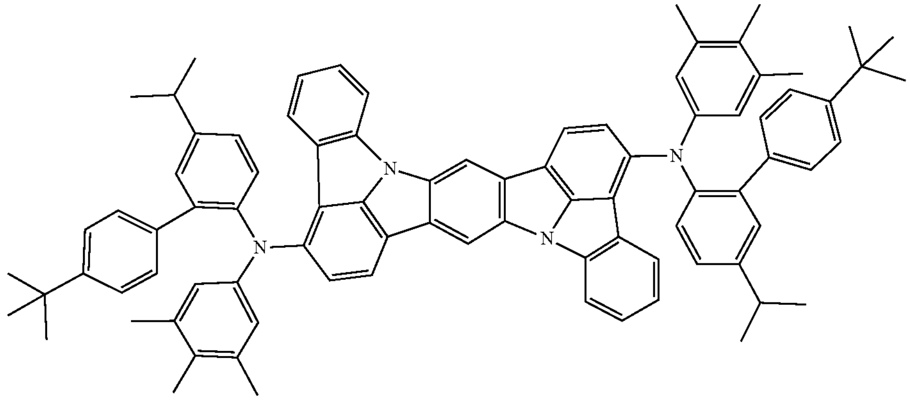
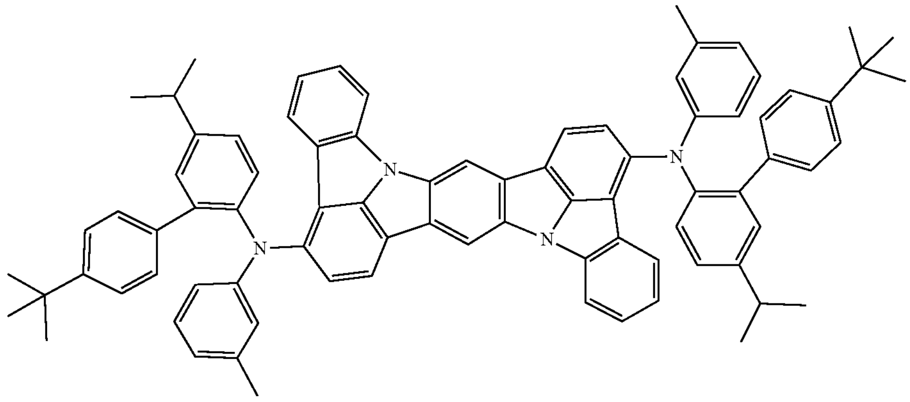

-continued
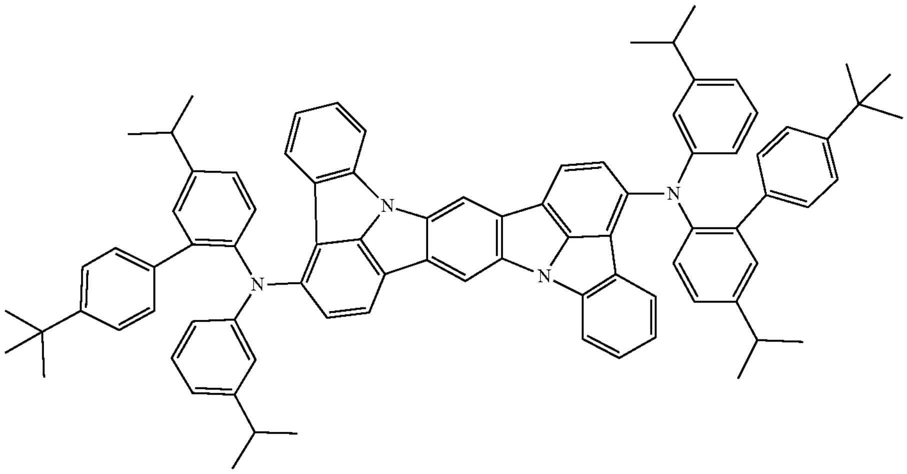
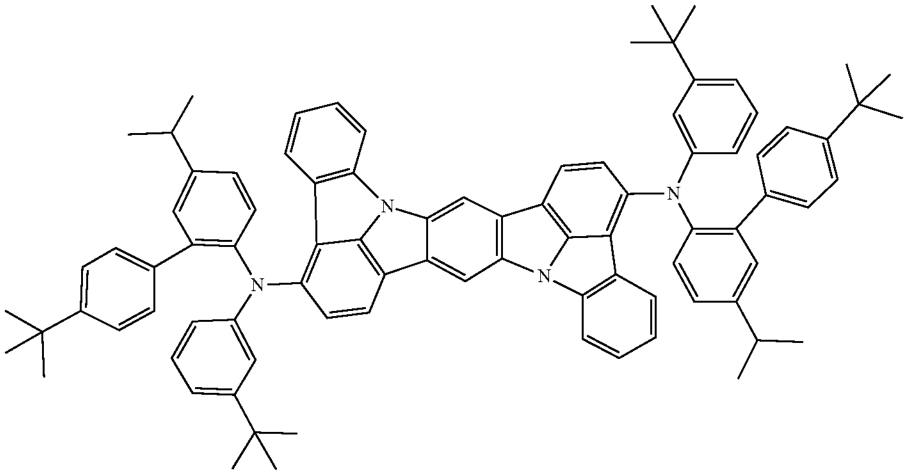
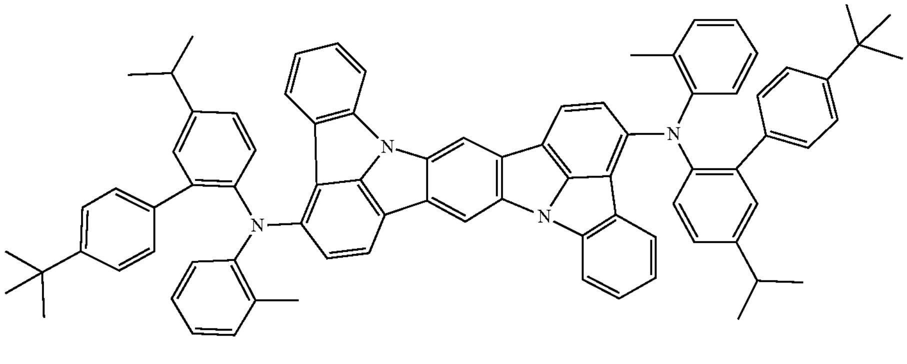

-continued
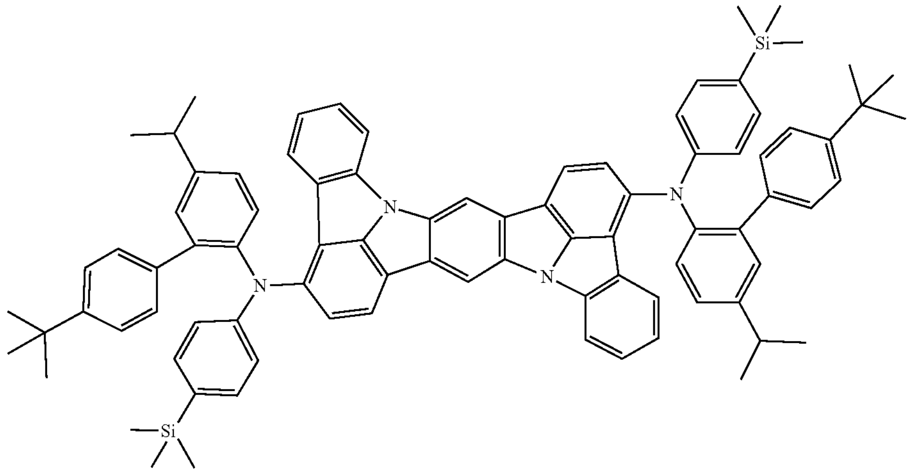
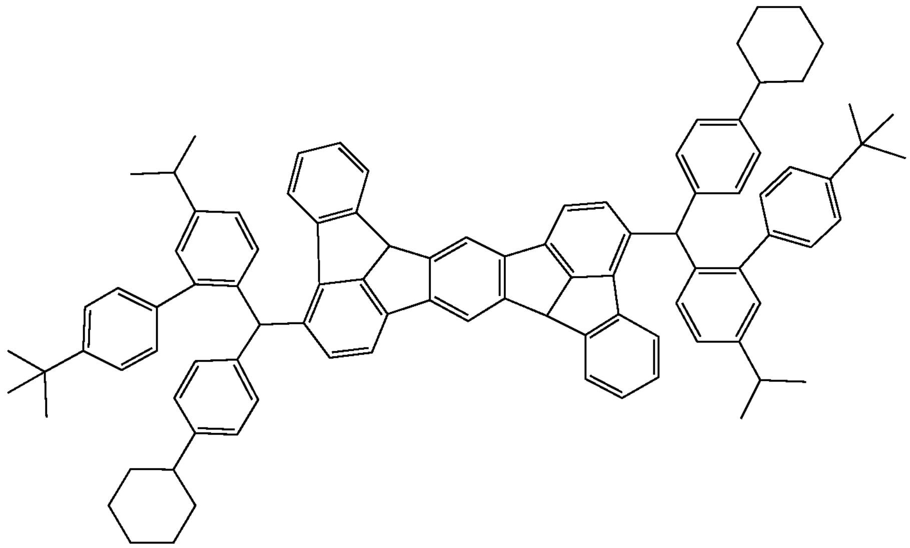
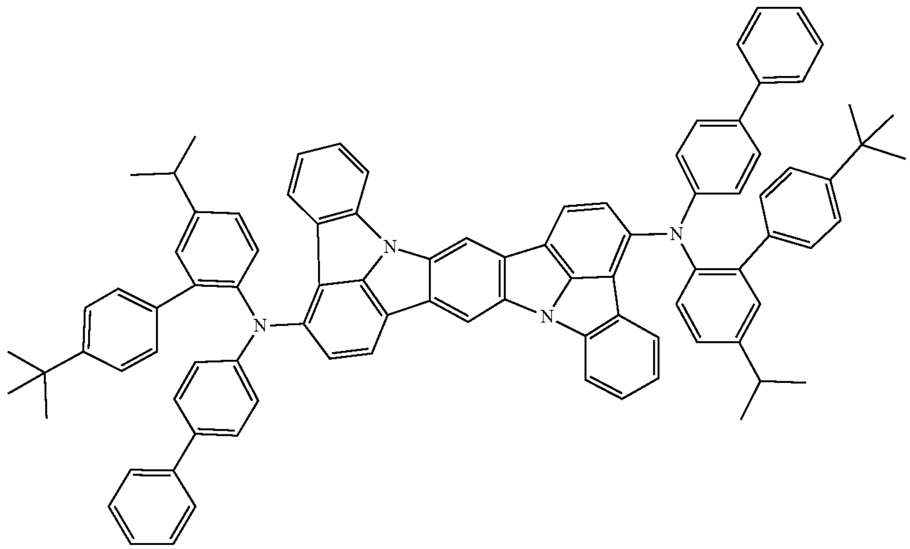

-continued
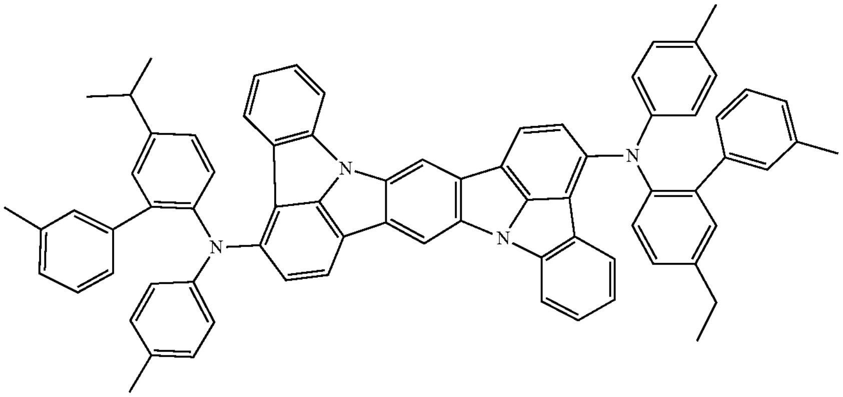
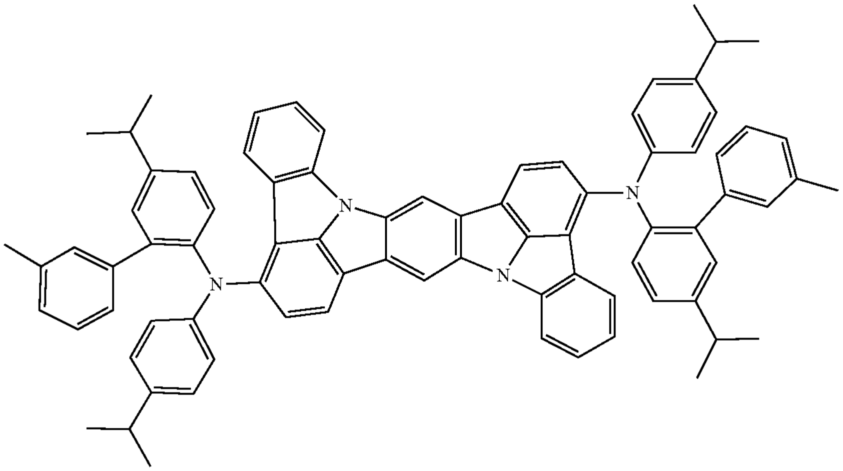
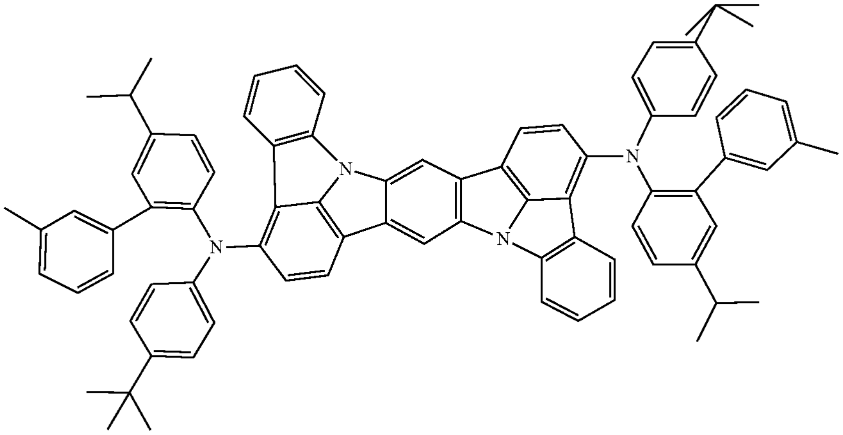
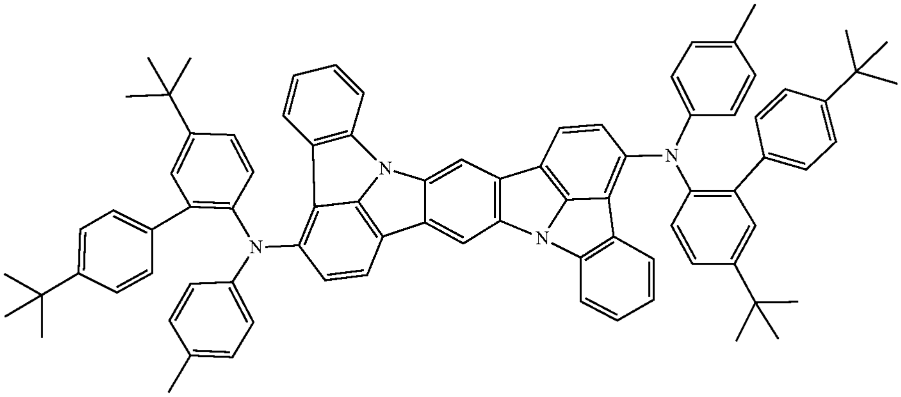

-continued
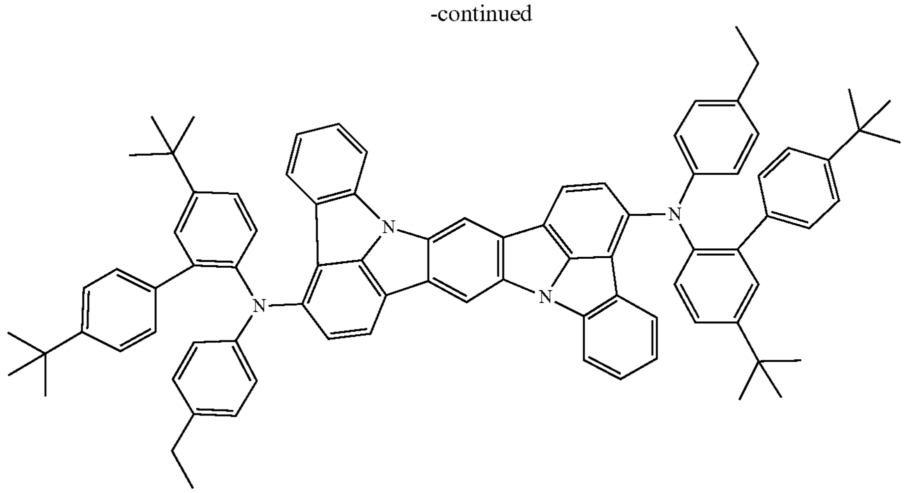
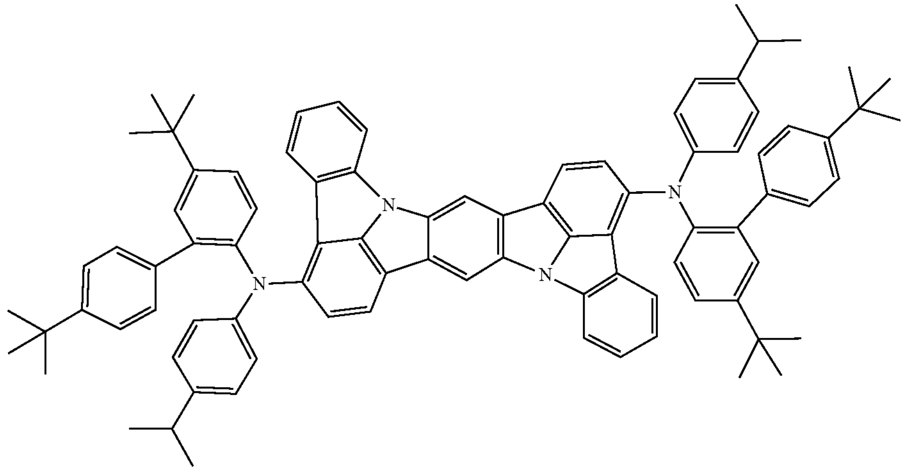
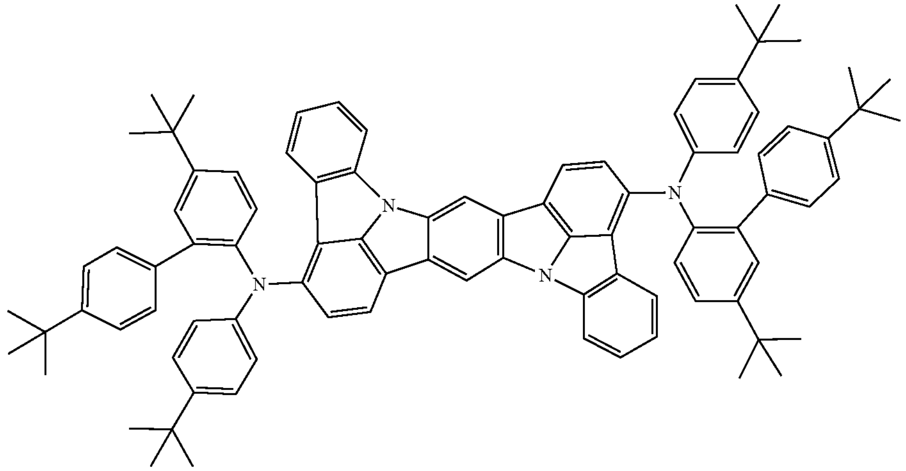

-continued
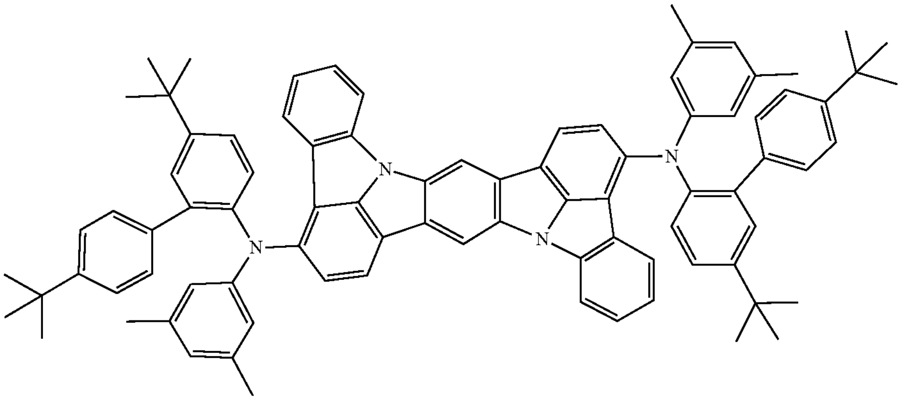
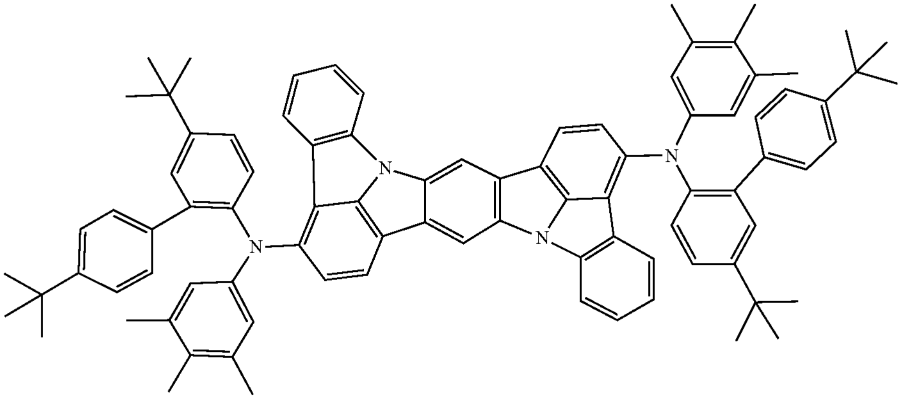
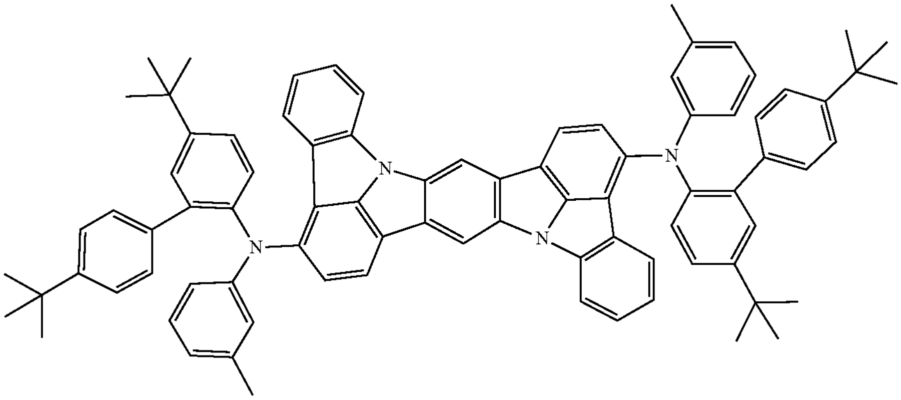
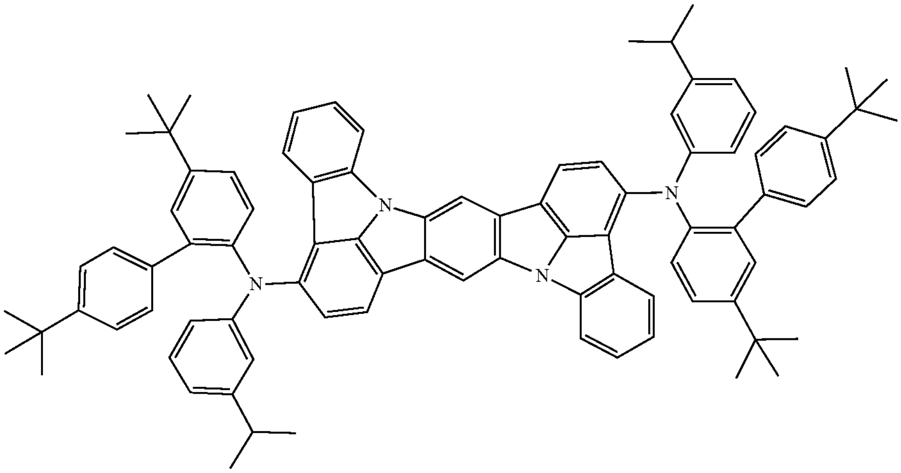

-continued
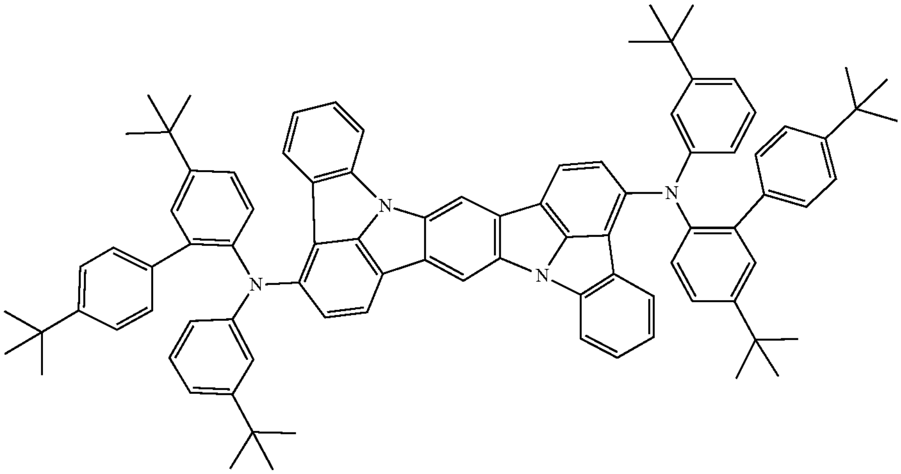
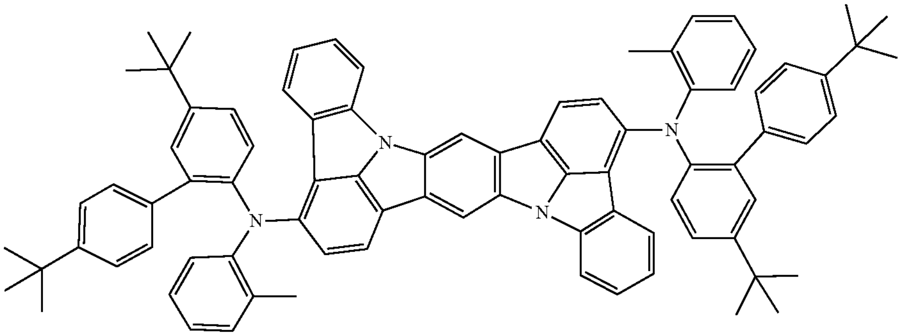
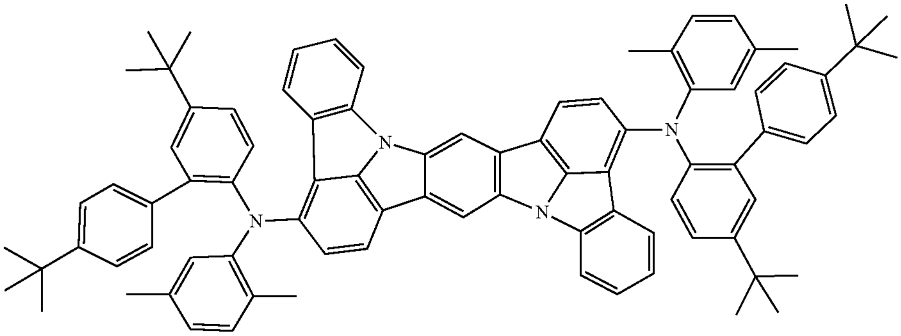
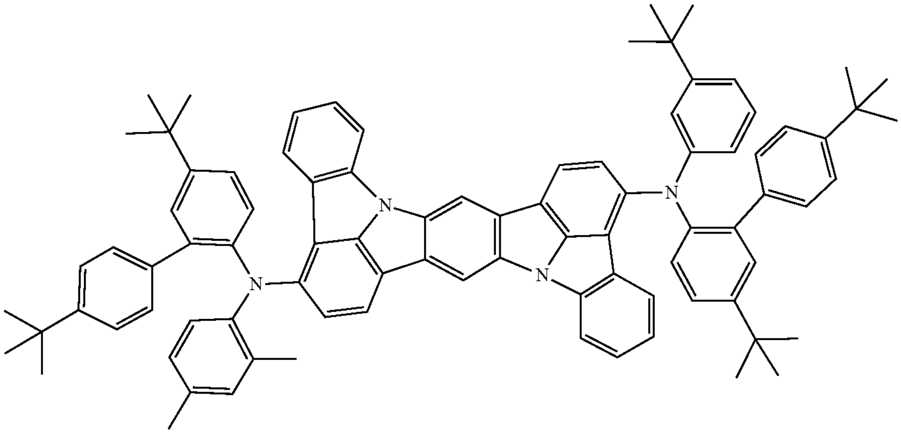

-continued
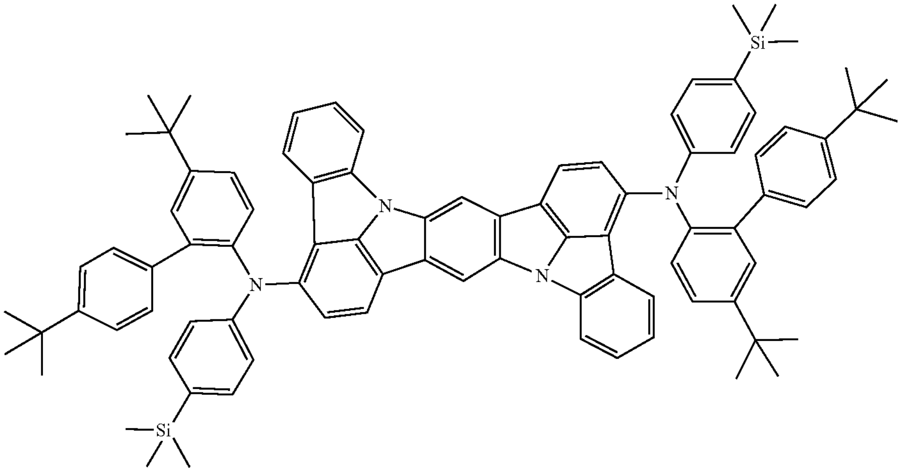
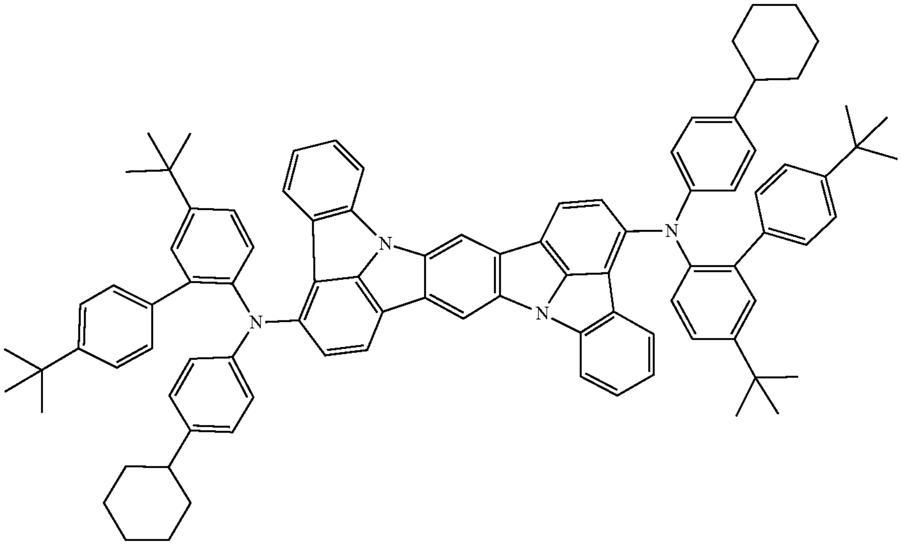
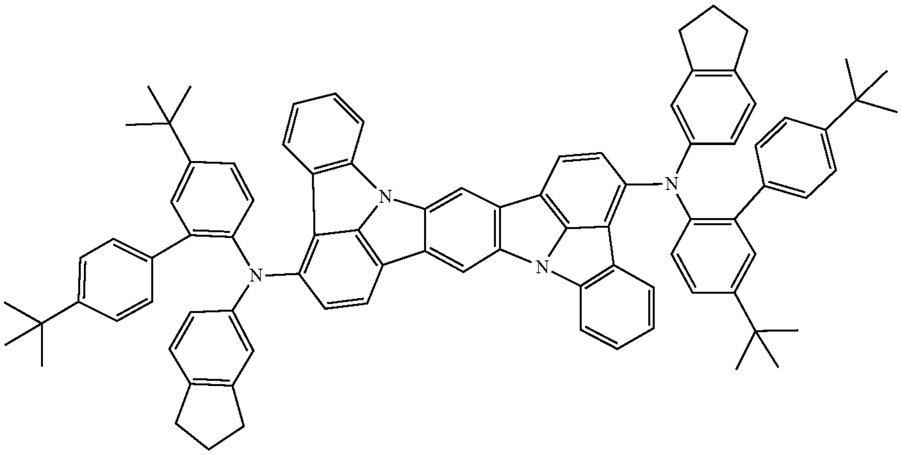

-continued
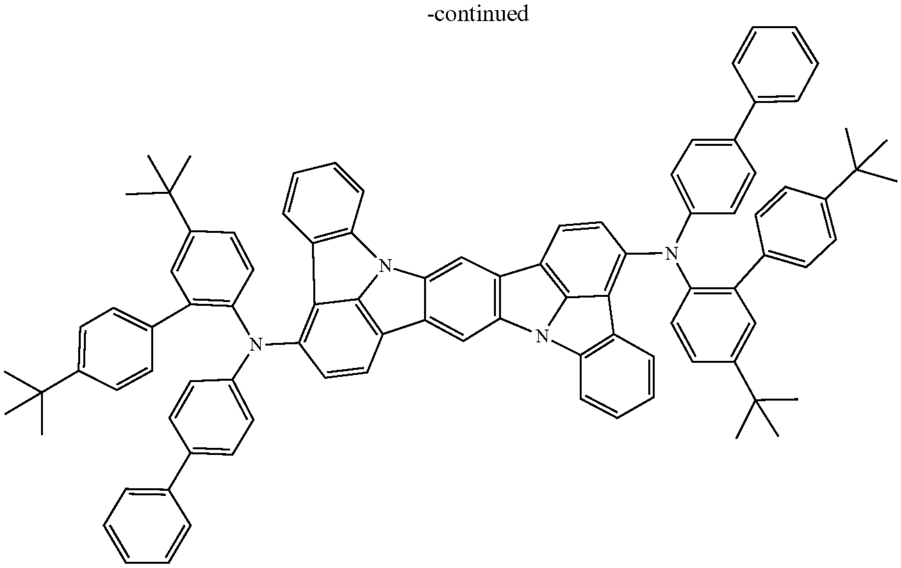
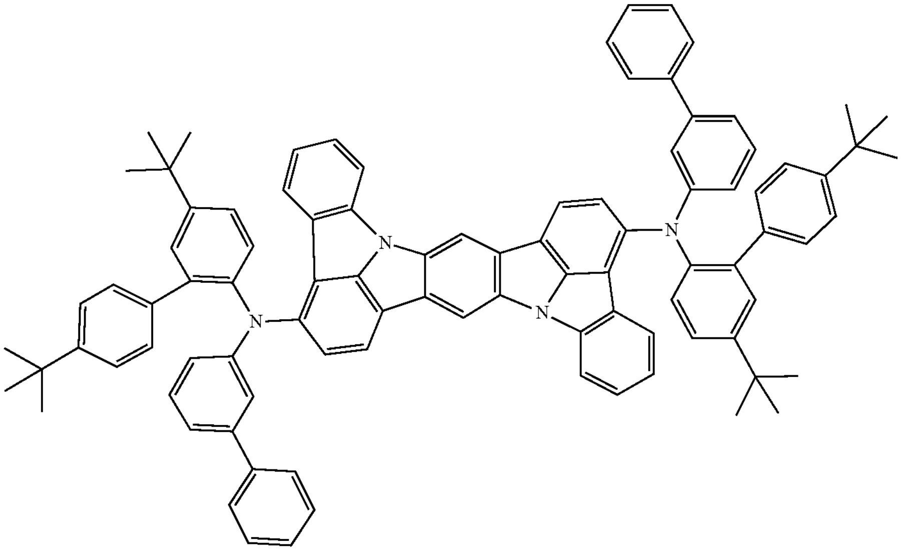
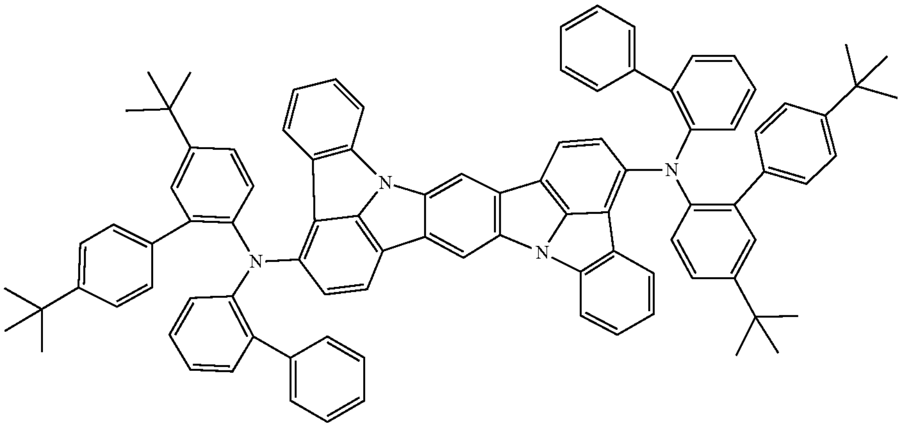

-continued
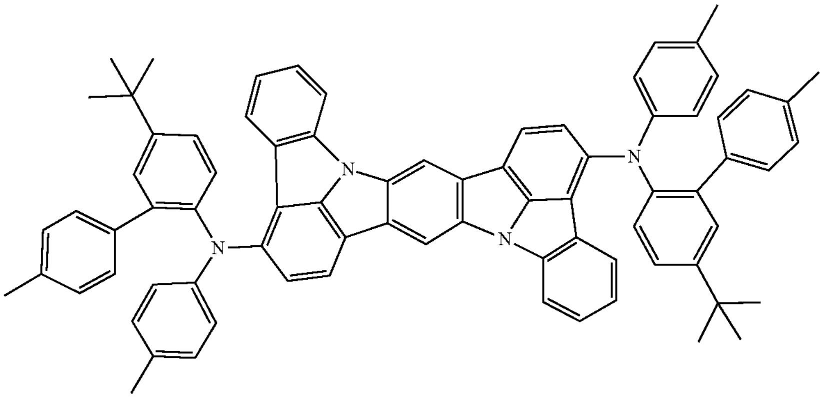
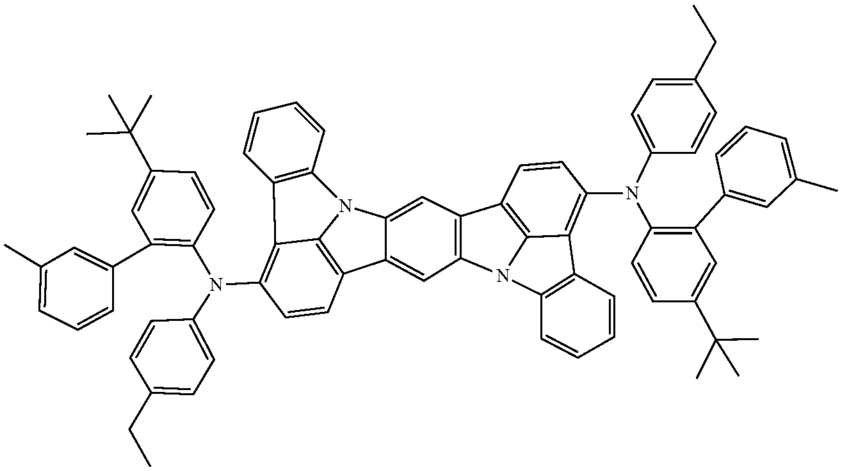
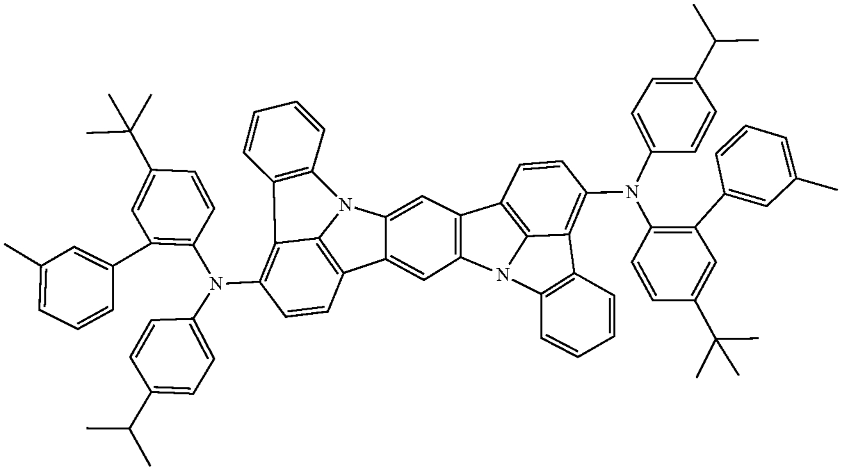

-continued
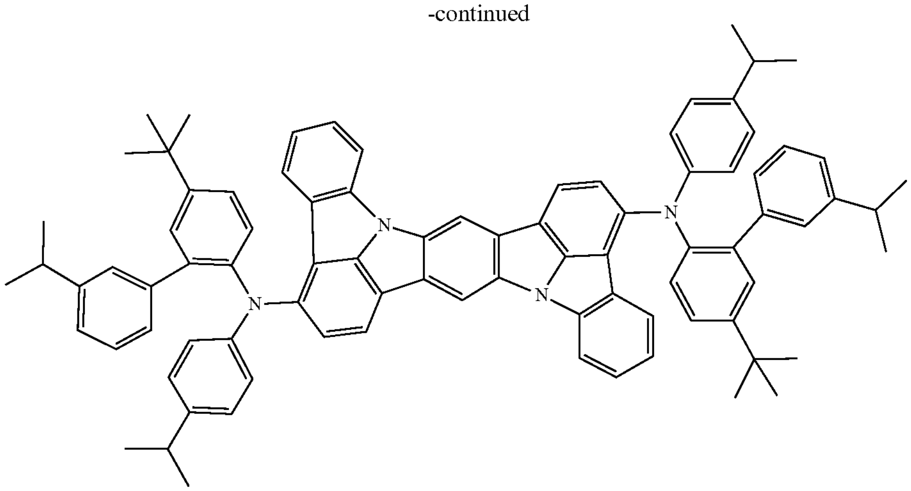
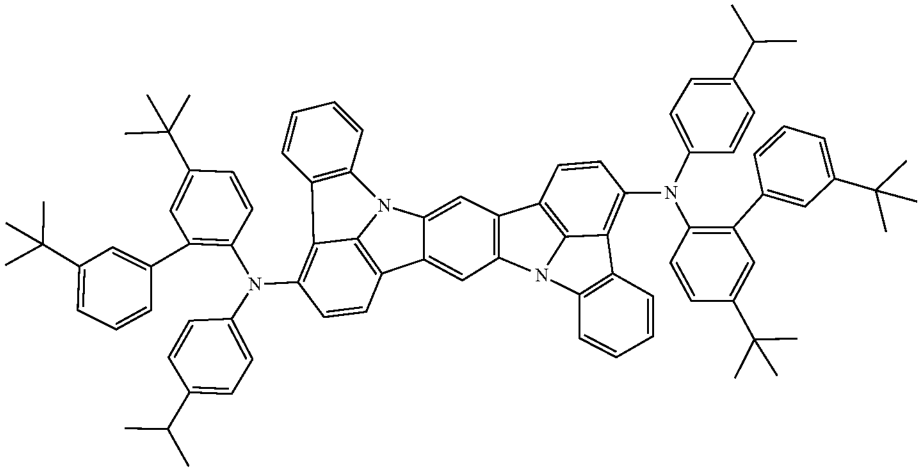
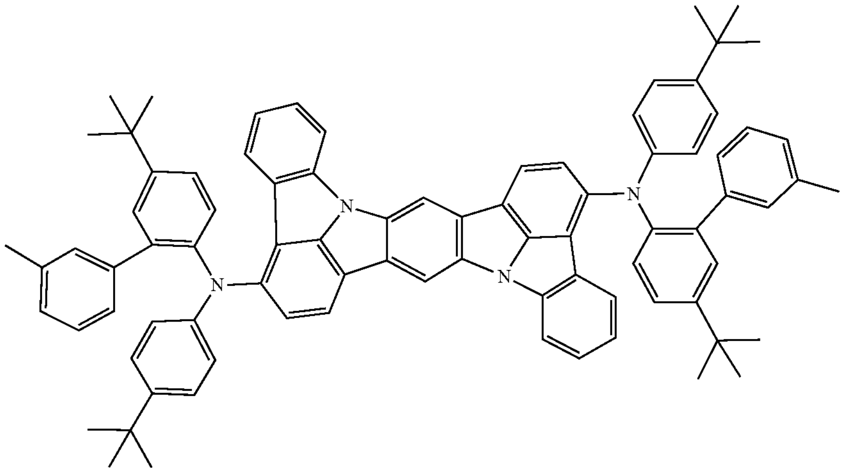

-continued
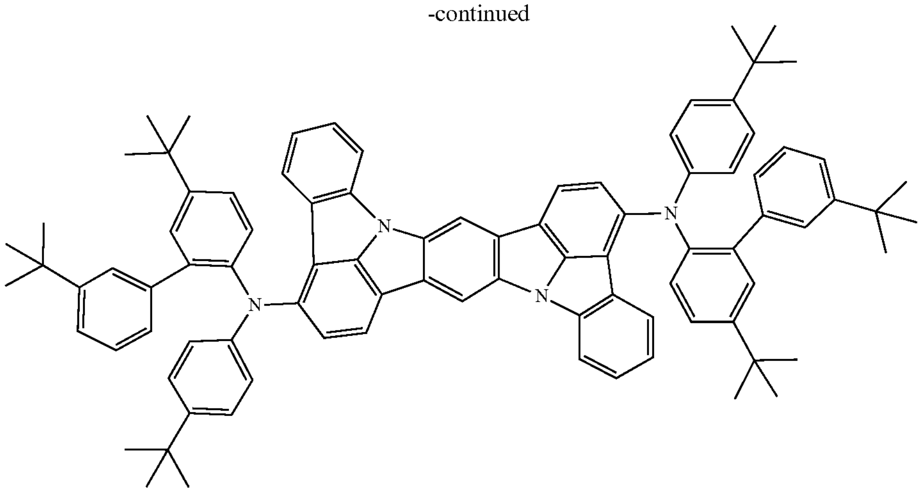
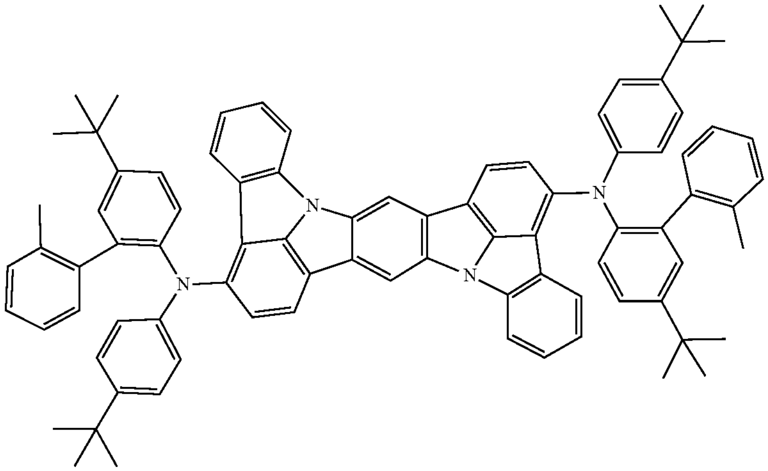
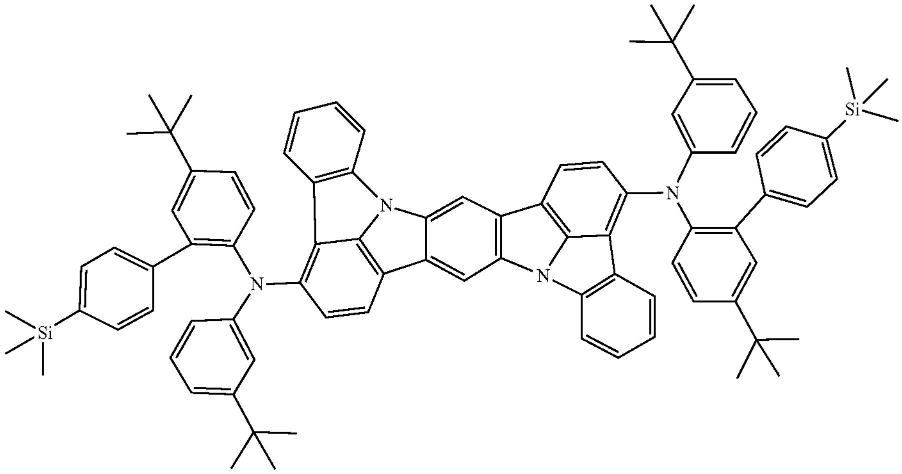

-continued
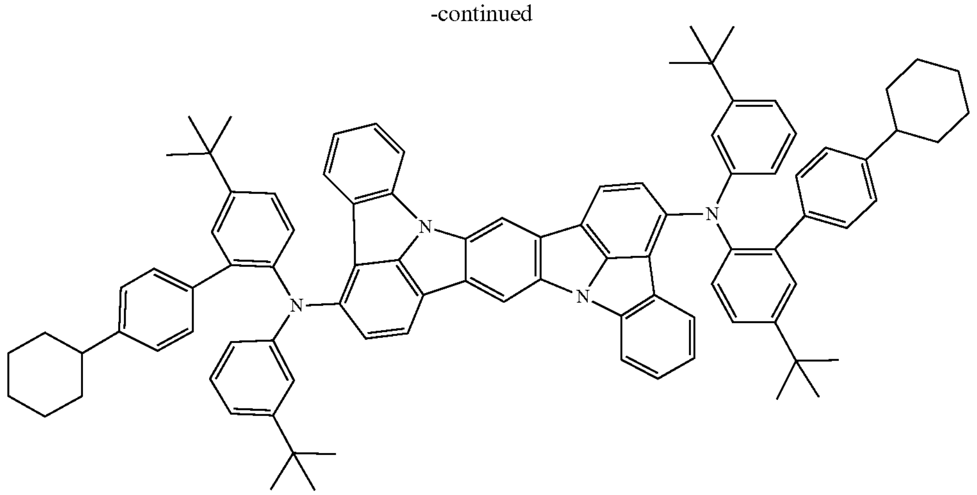
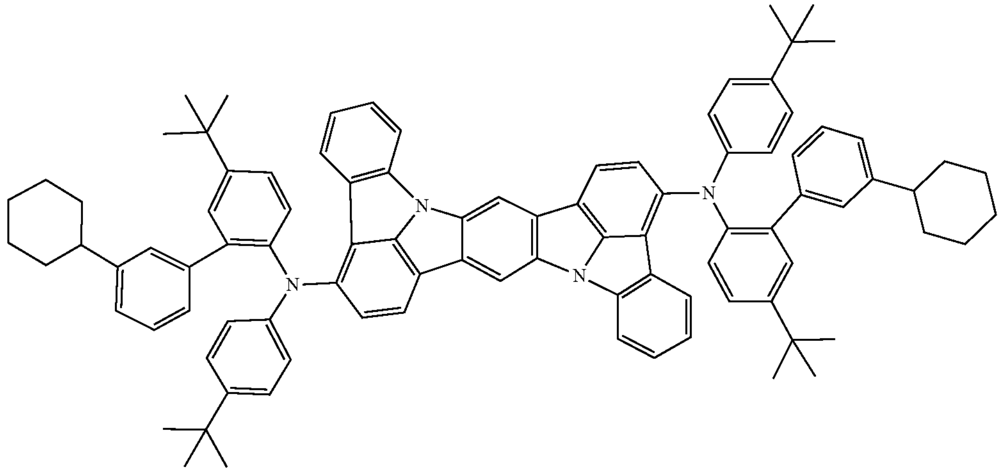
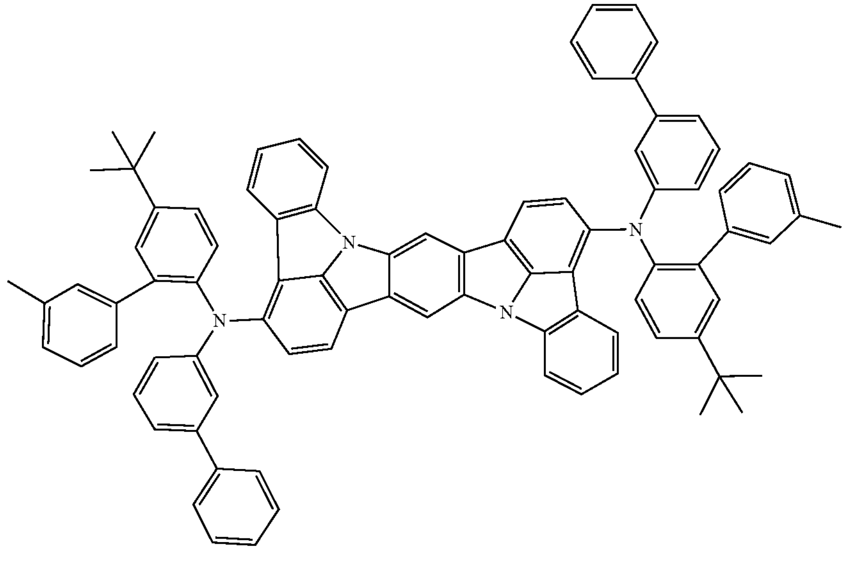

-continued
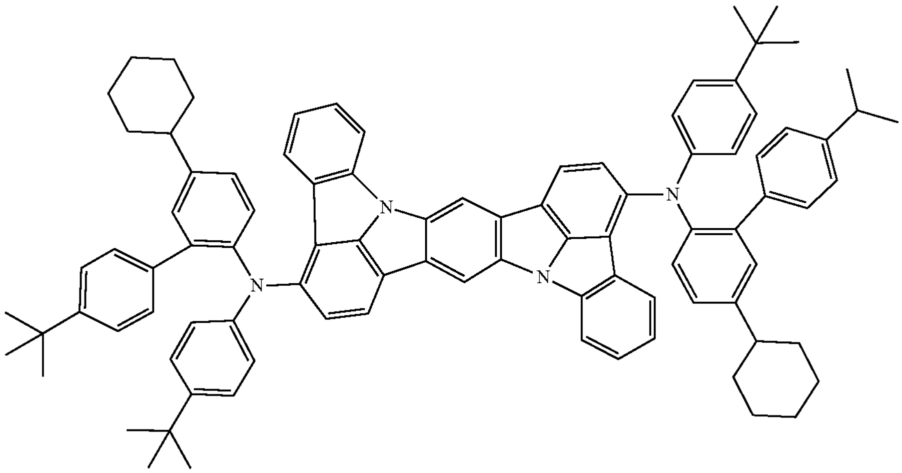
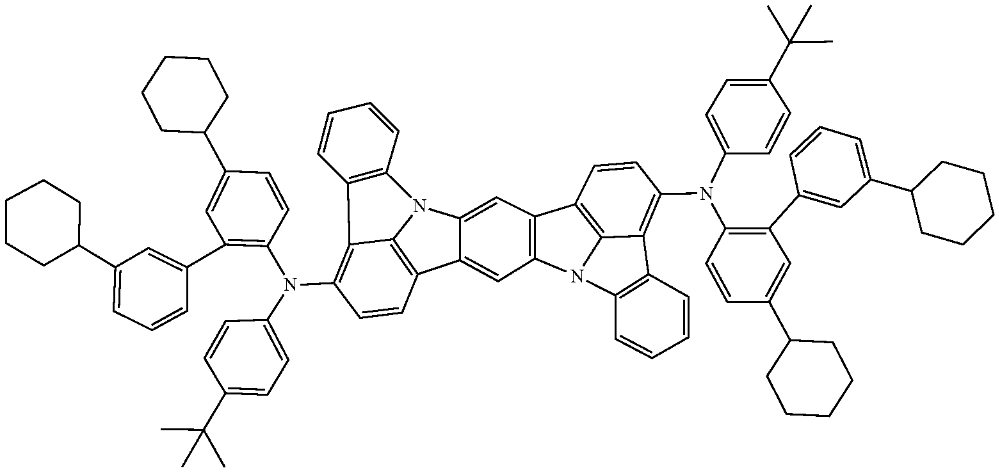
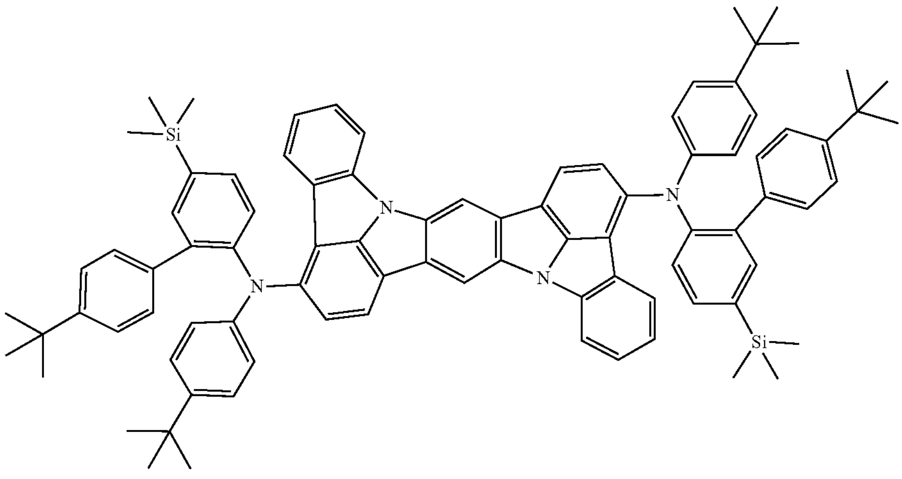

-continued
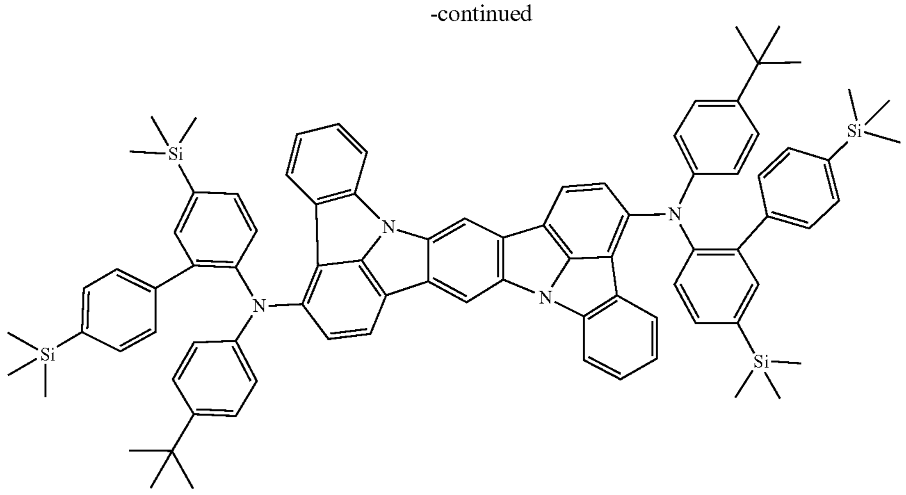
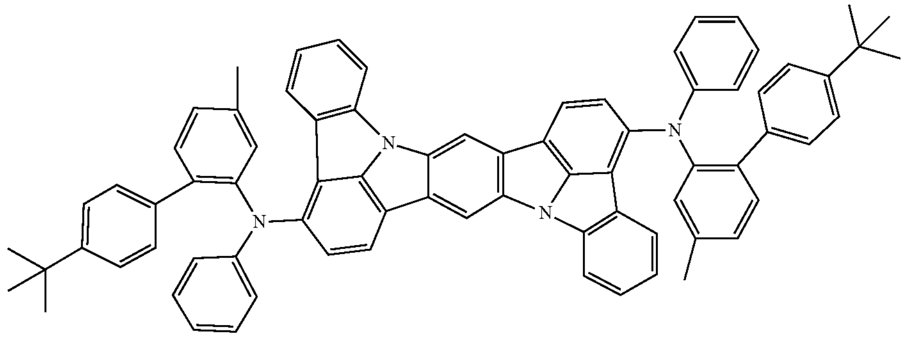
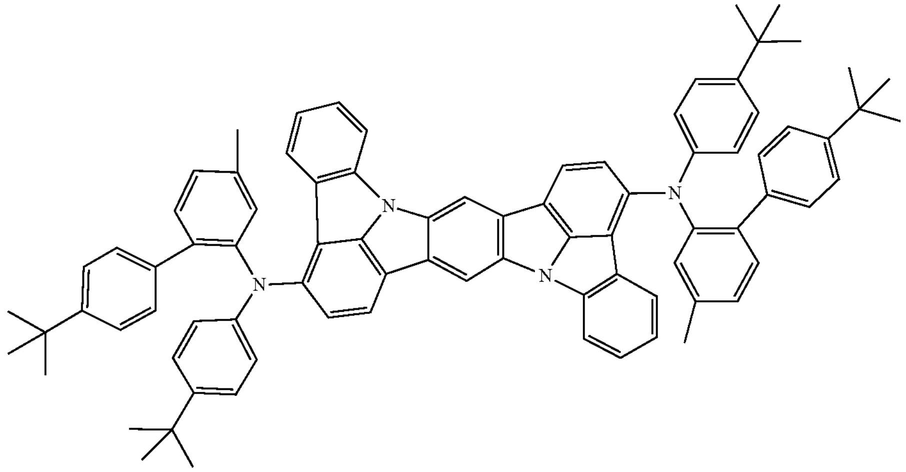
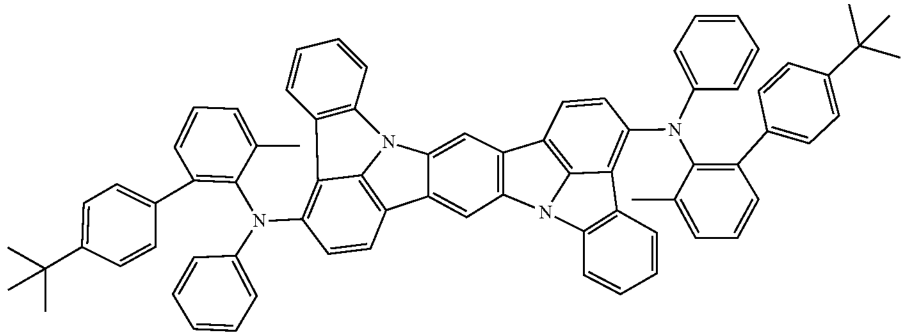

-continued
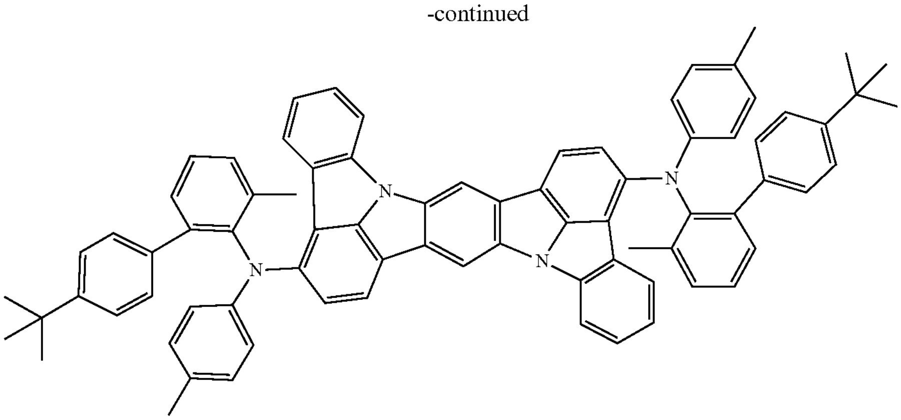
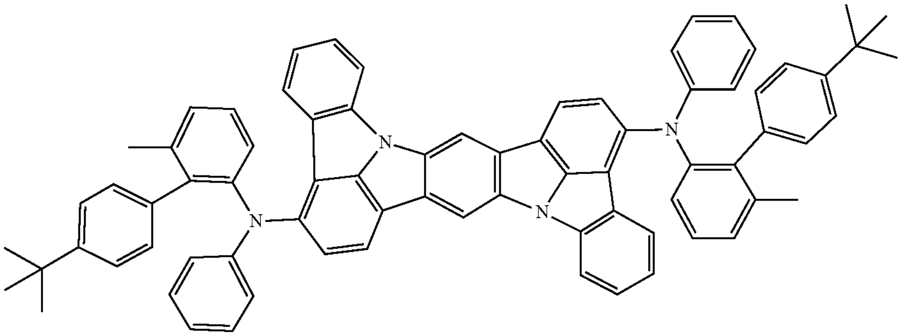
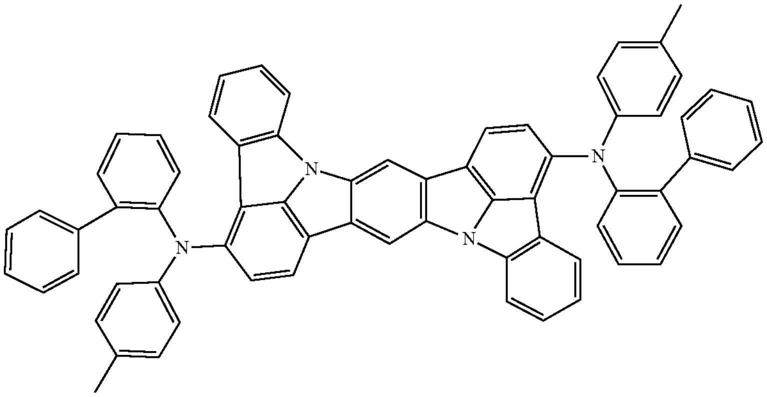
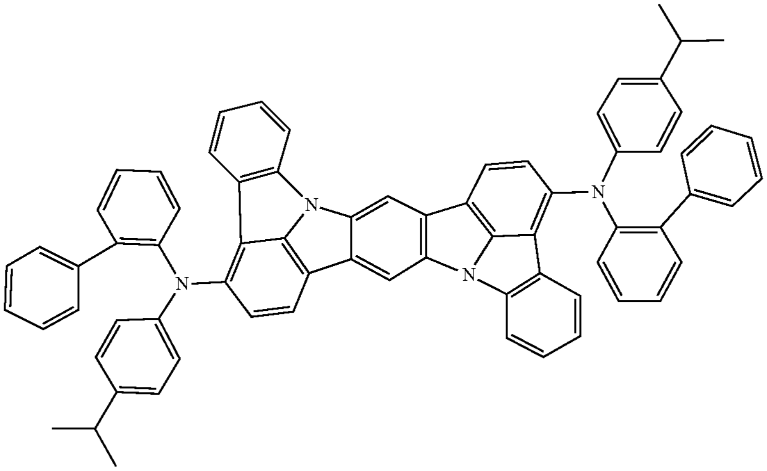

-continued
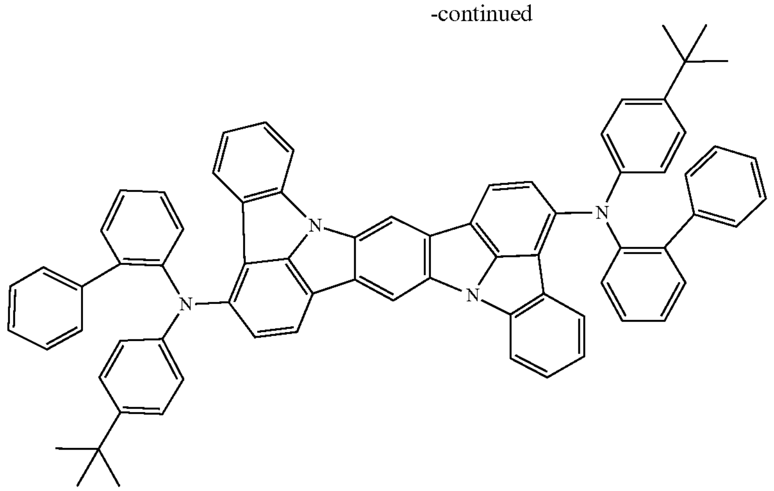
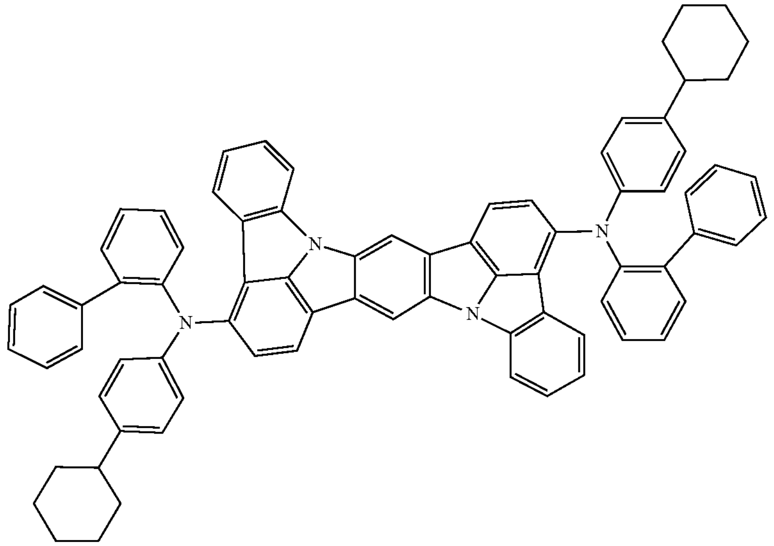
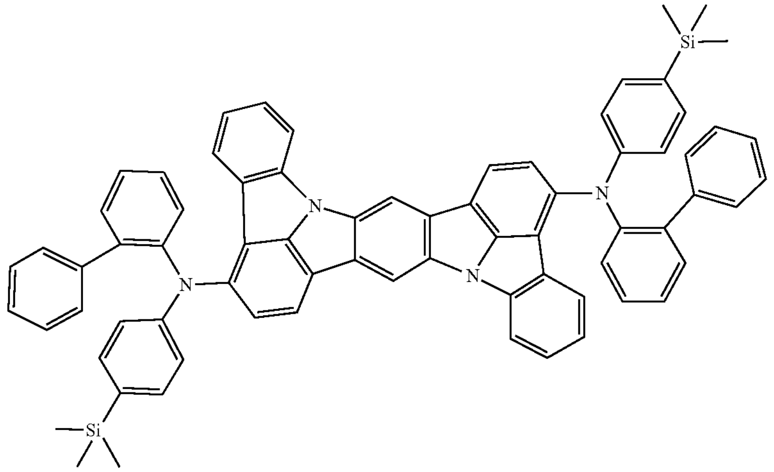

-continued
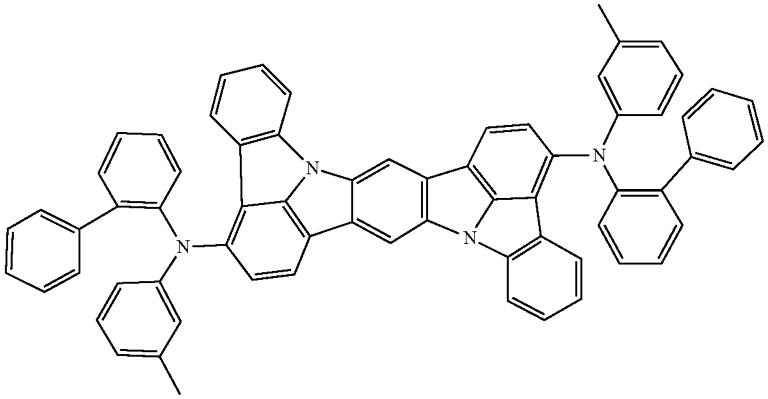
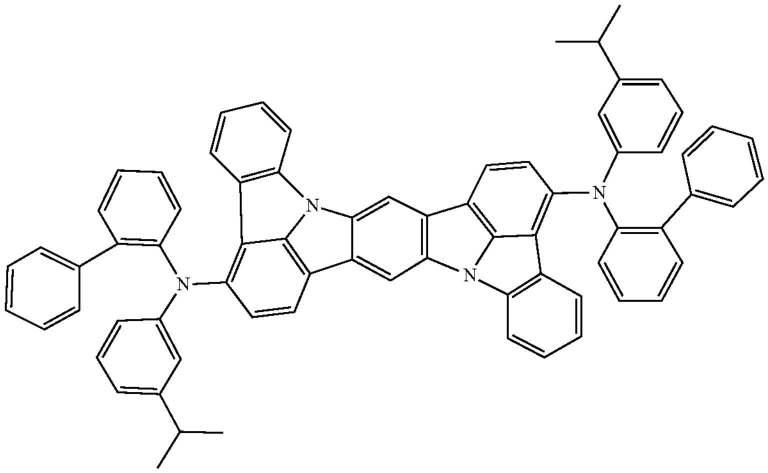
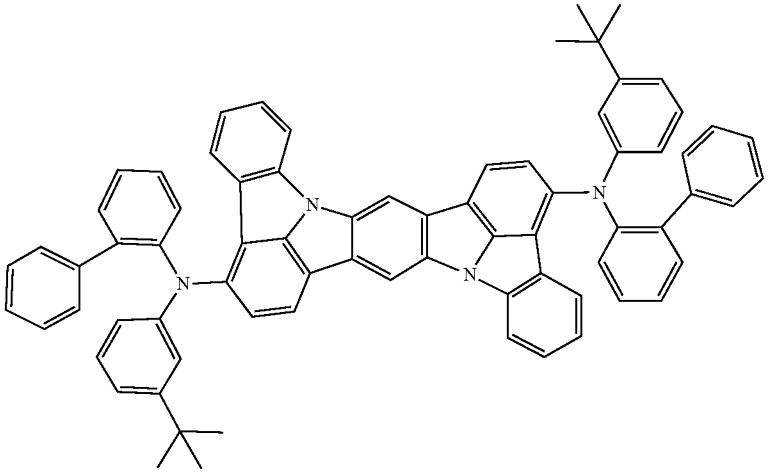

-continued
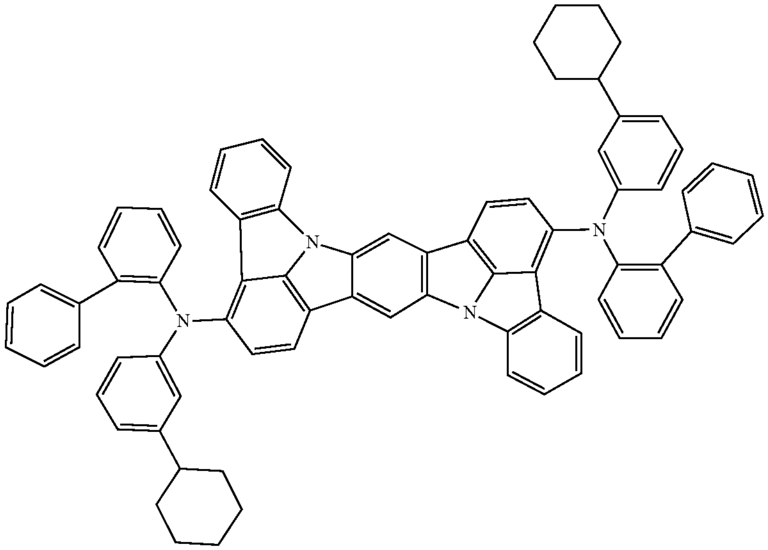
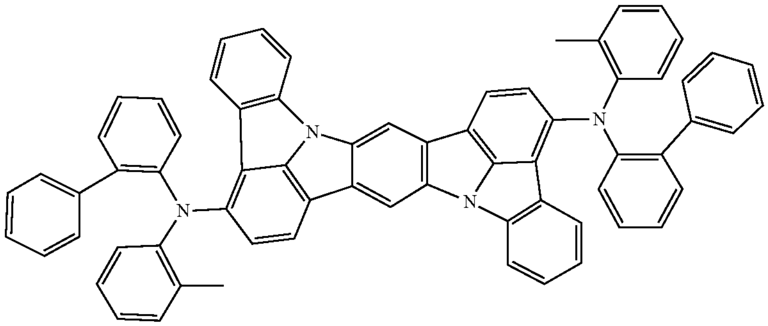
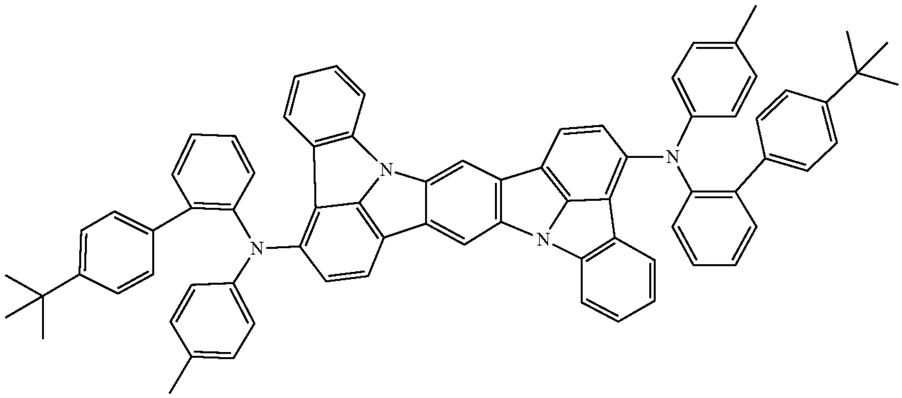

-continued
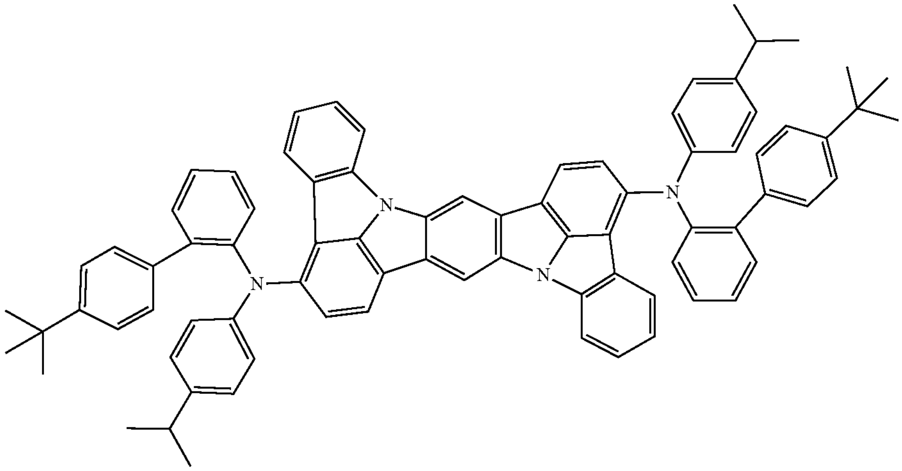
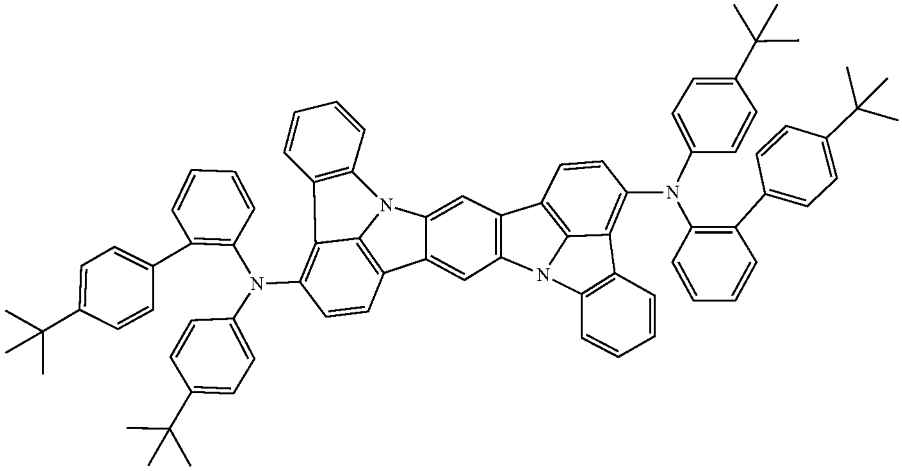
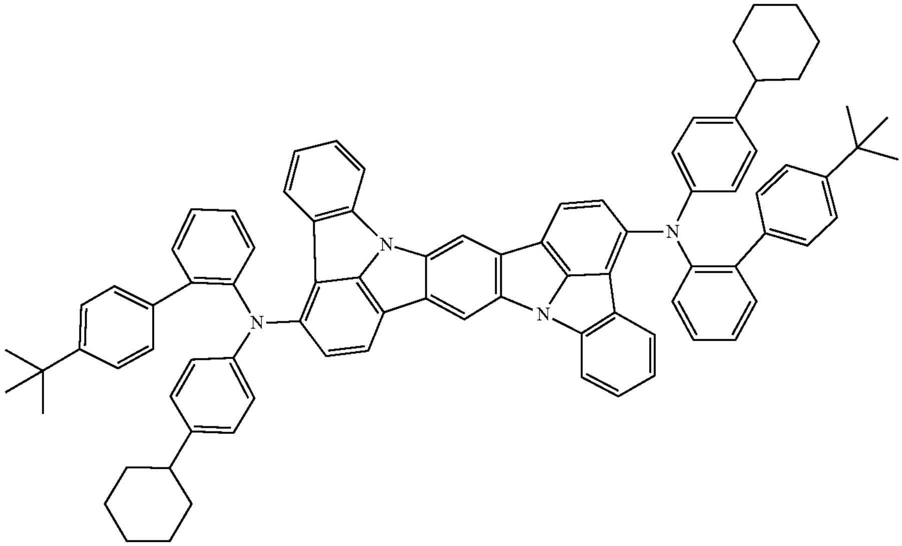

-continued
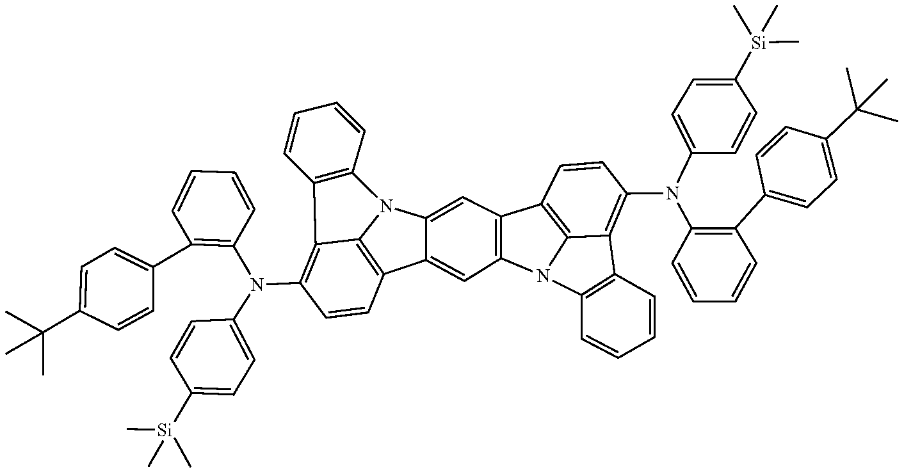
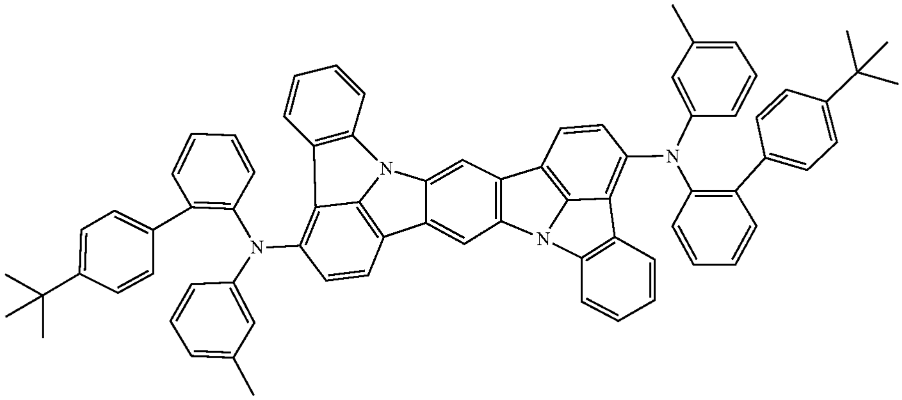
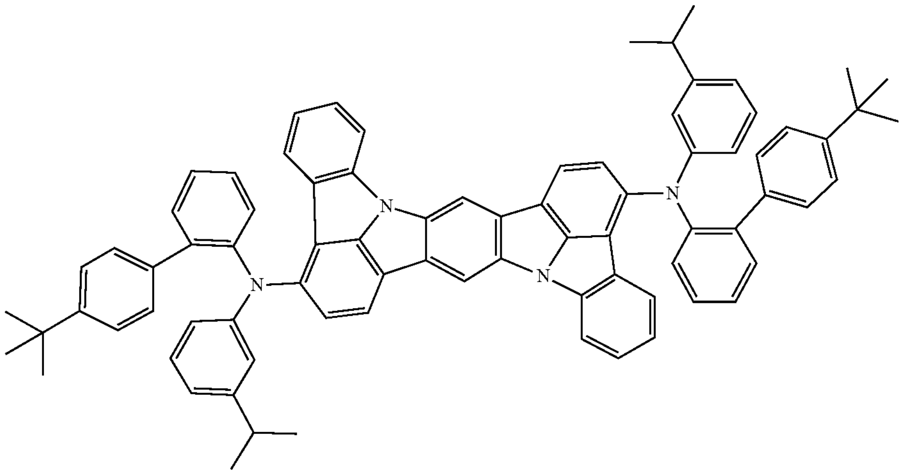
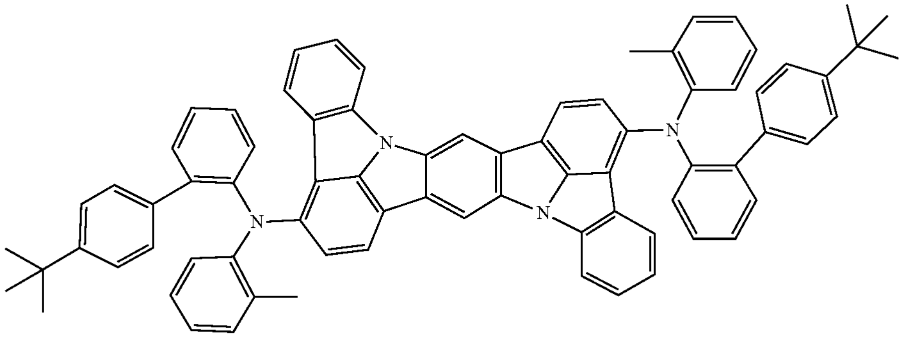

-continued
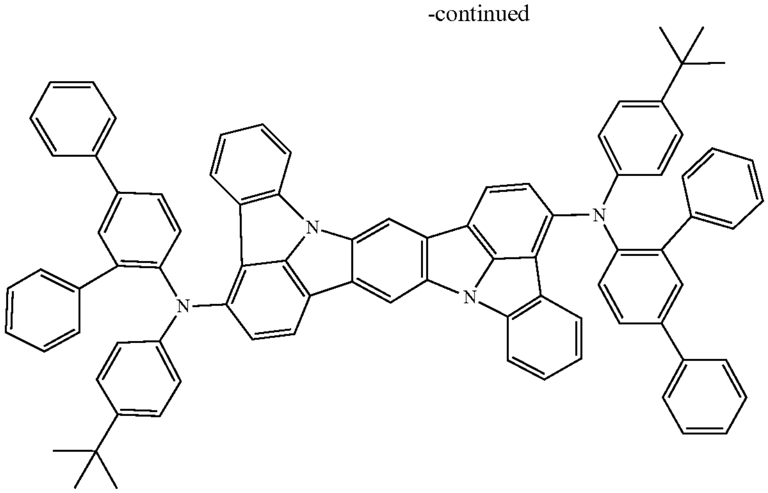
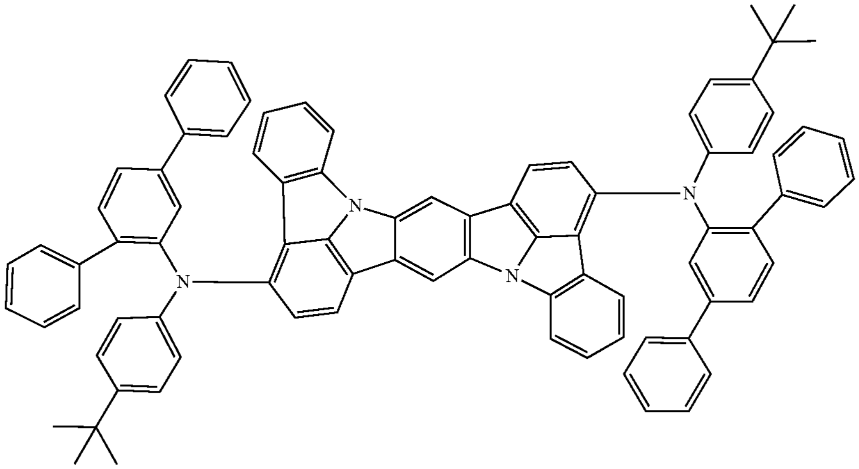
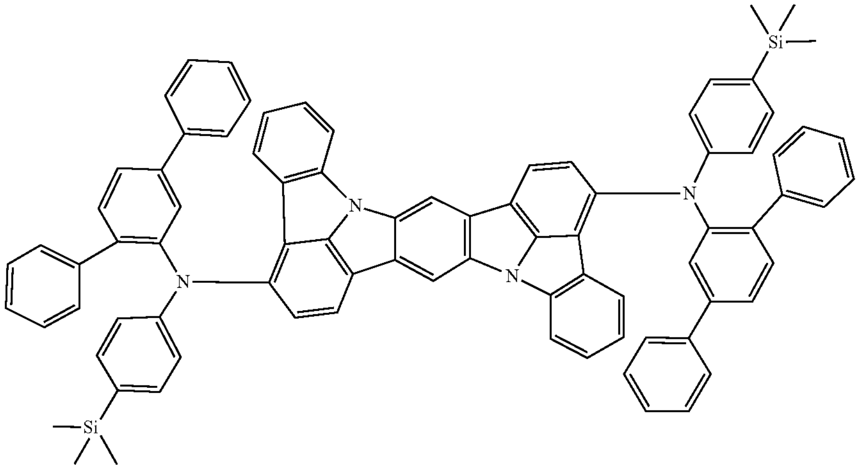
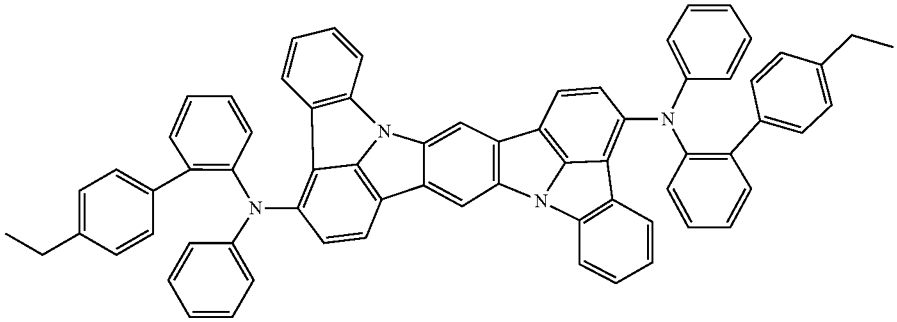

-continued
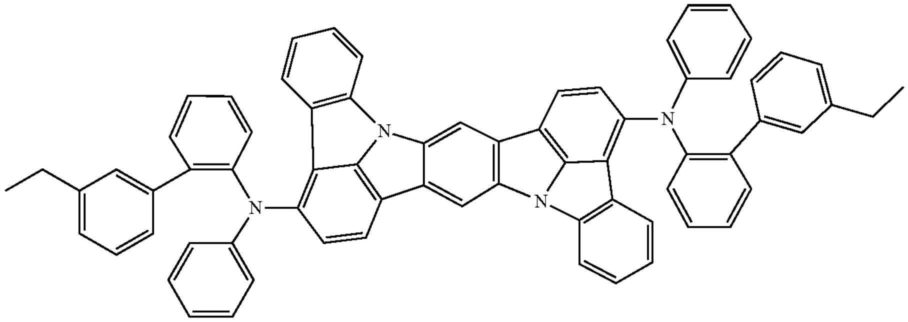
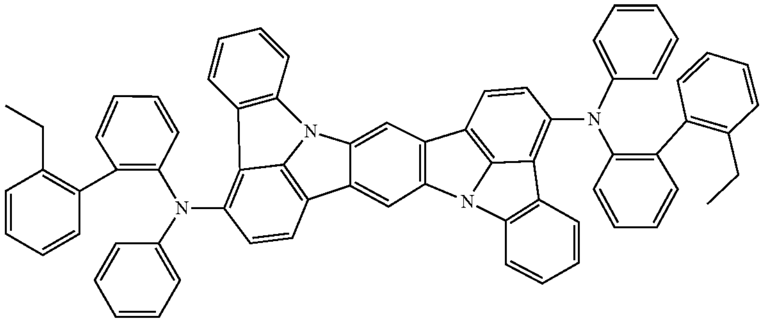
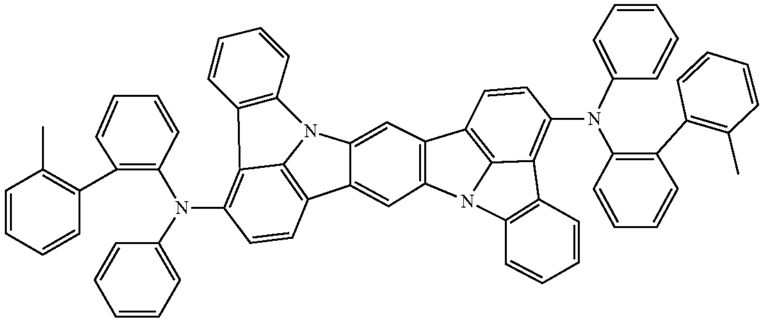
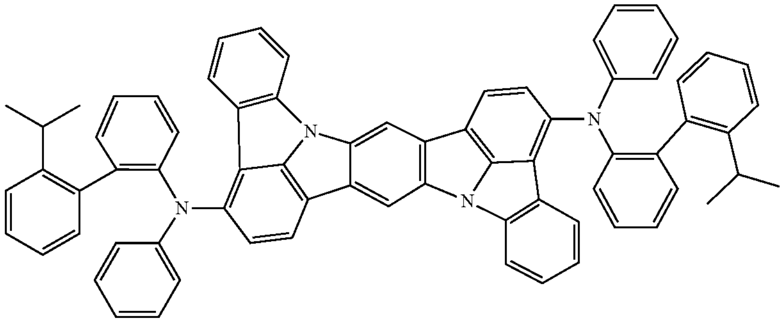
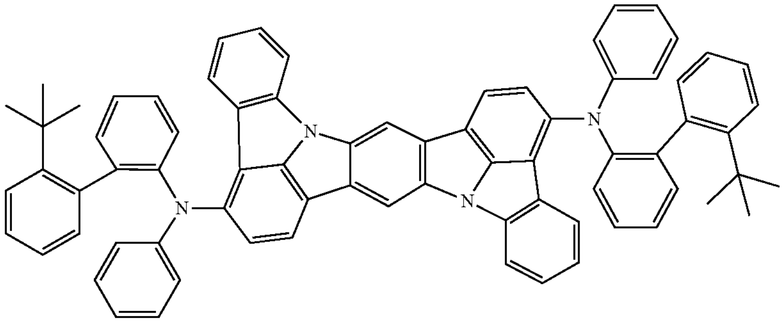

-continued
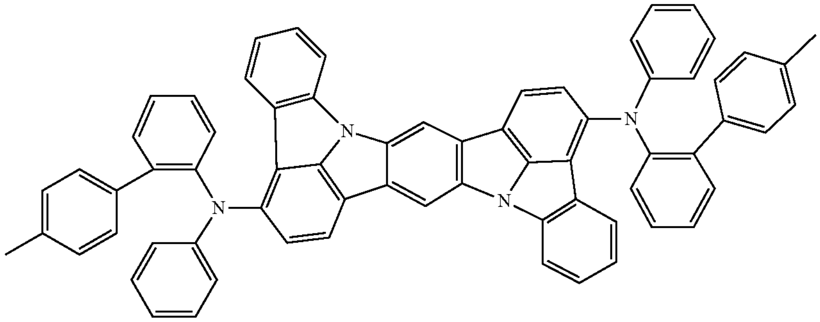
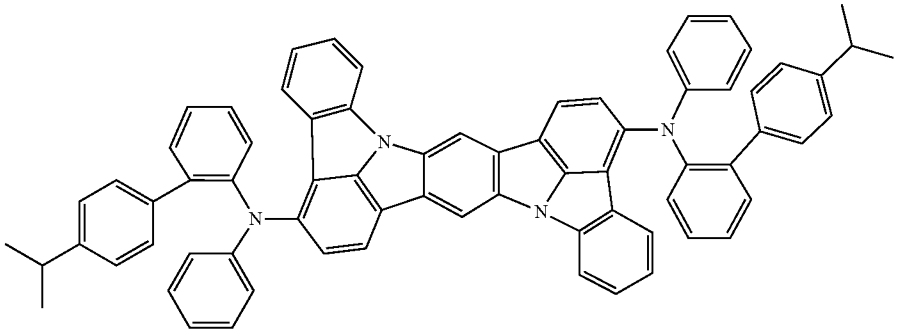
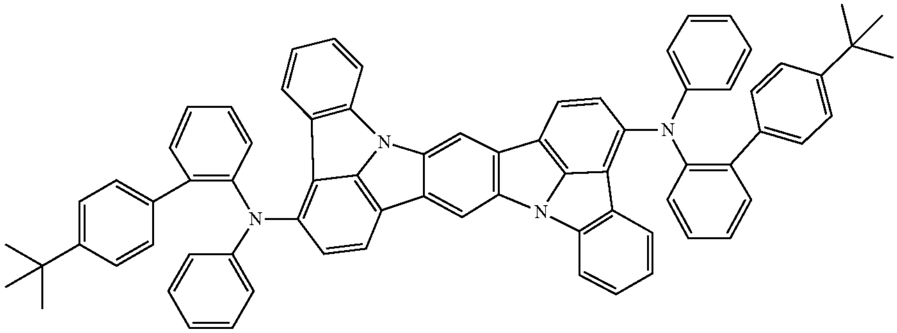
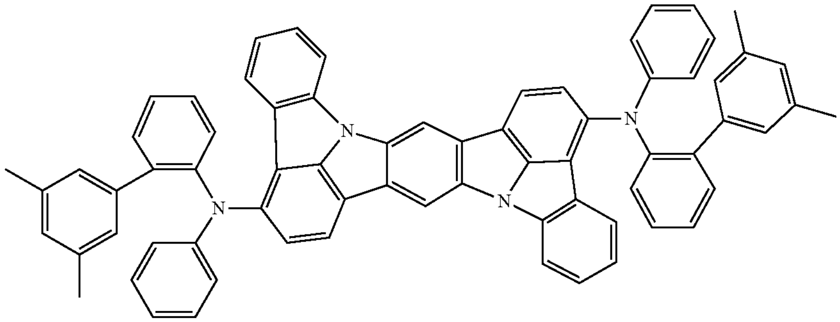
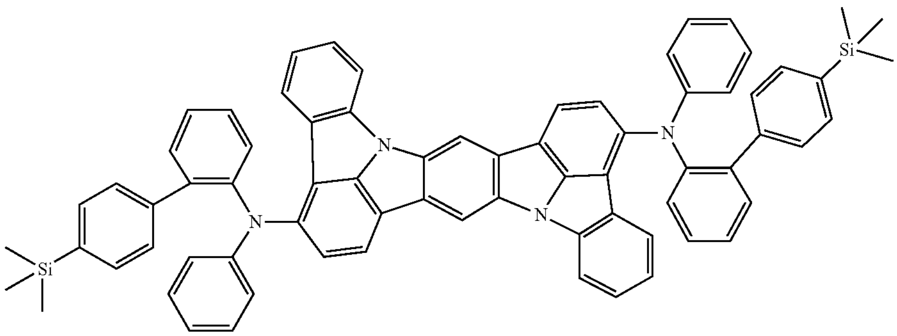

-continued
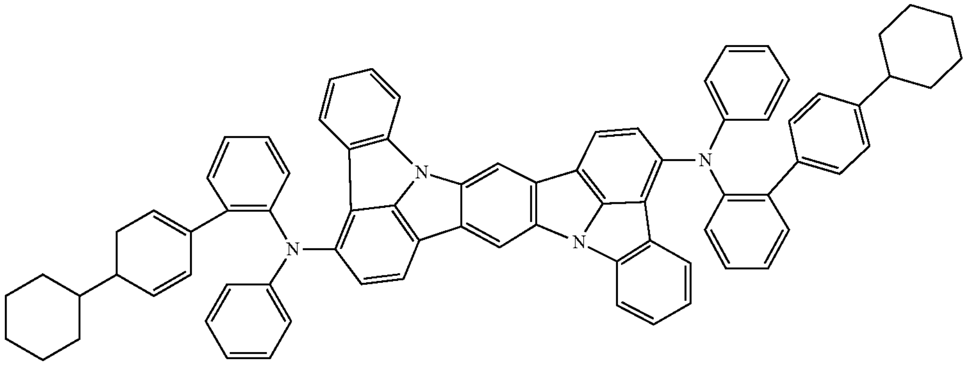
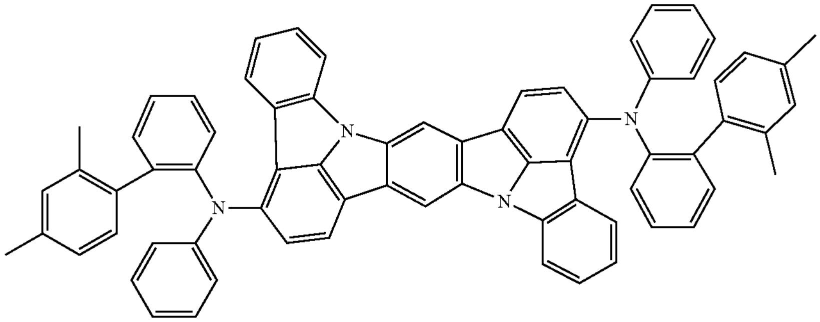
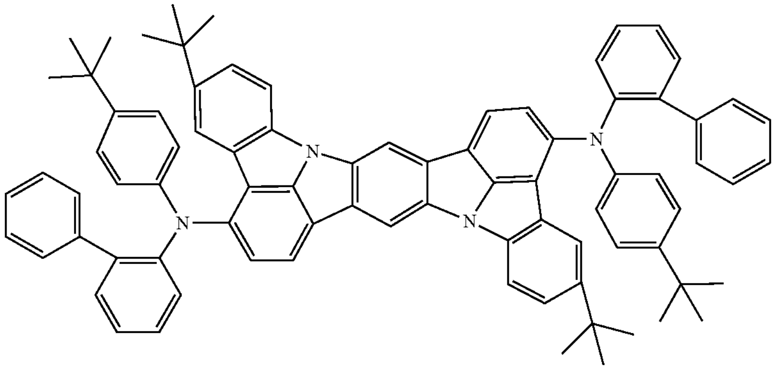
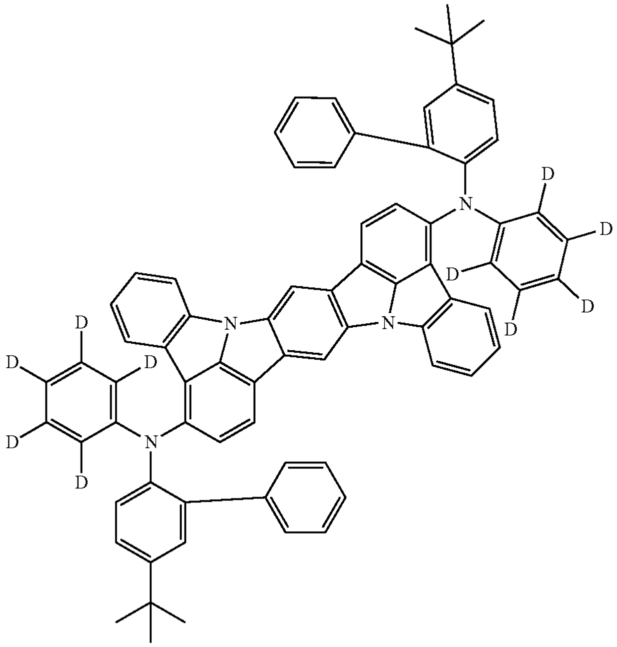

-continued
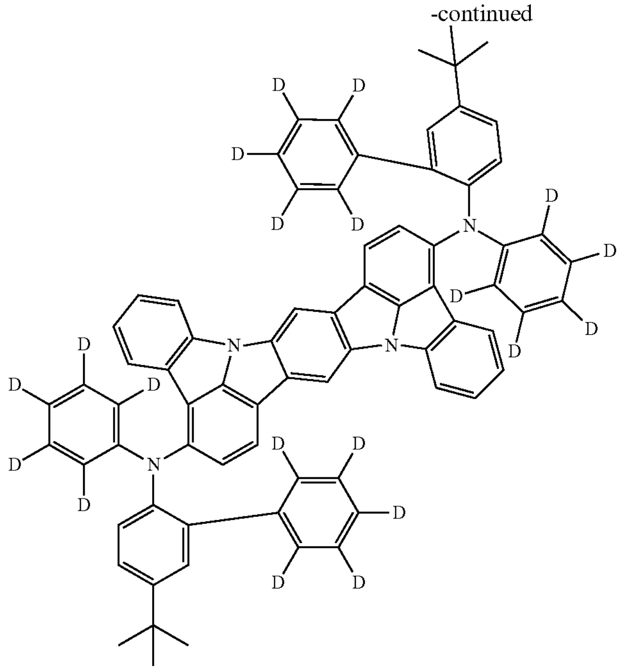
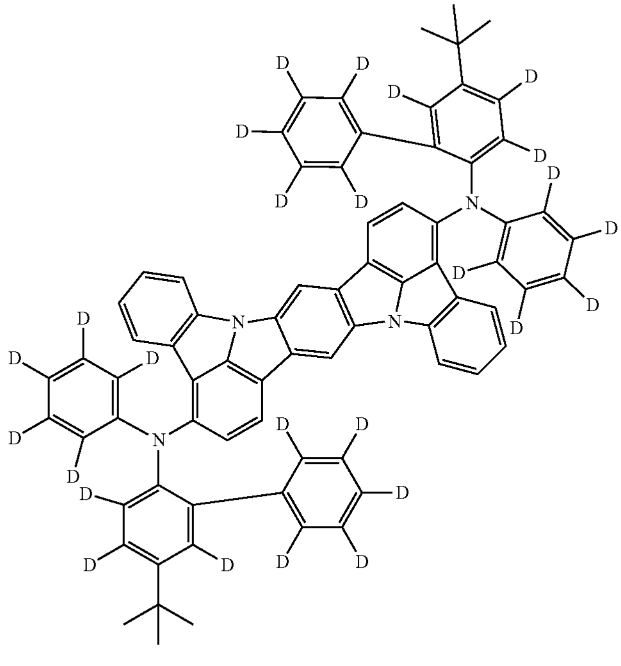

-continued
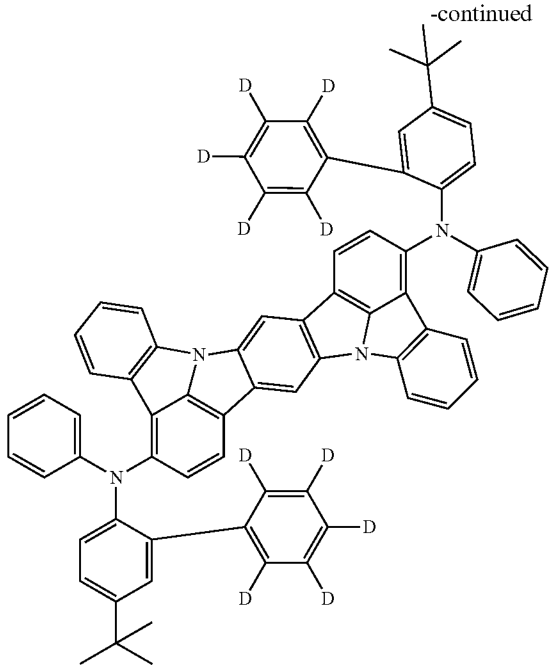
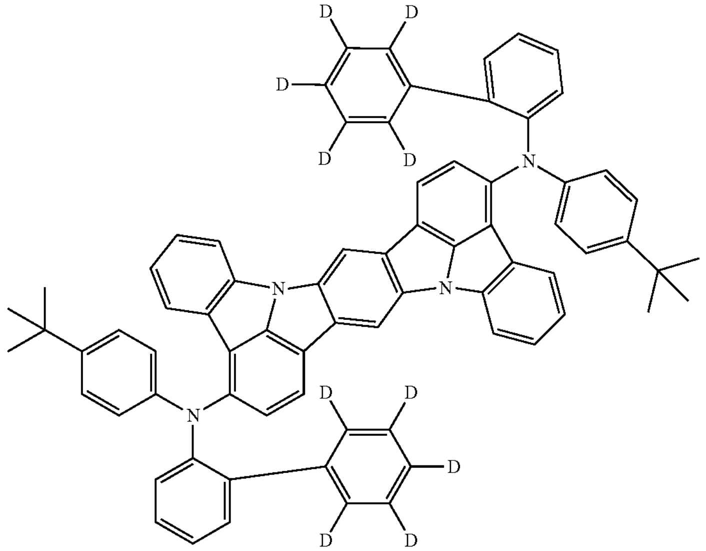

-continued
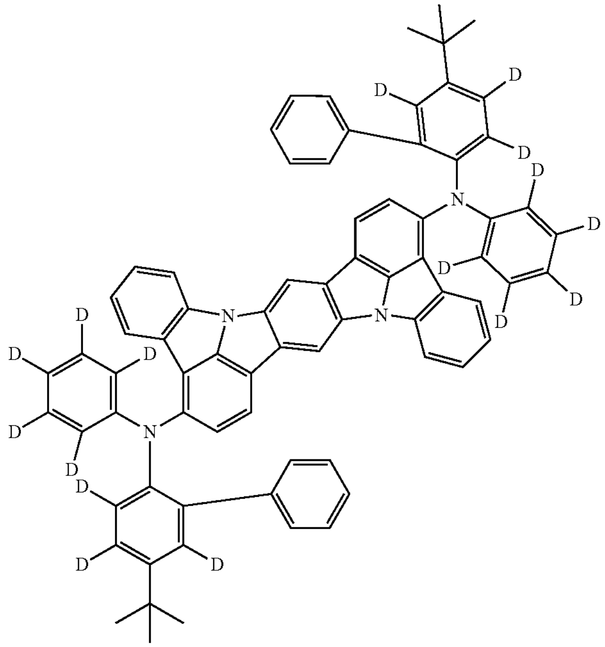
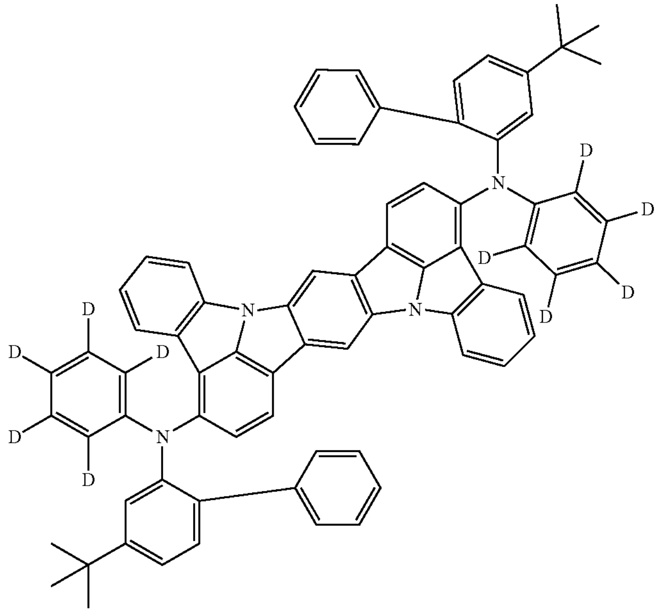

-continued
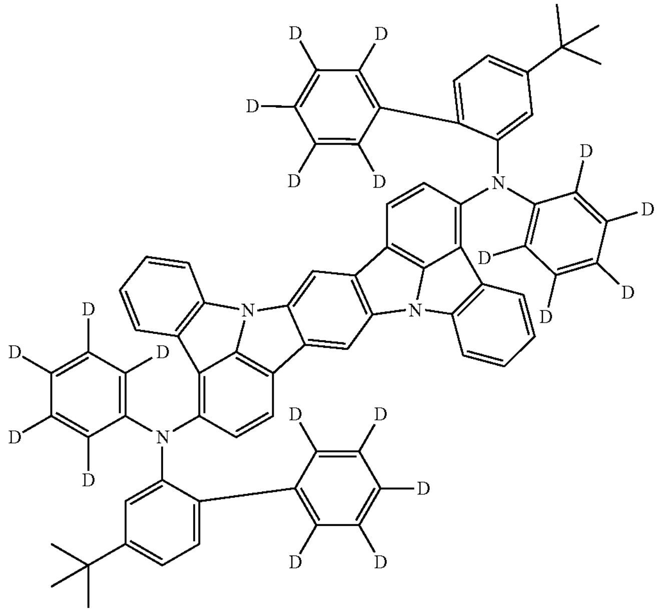
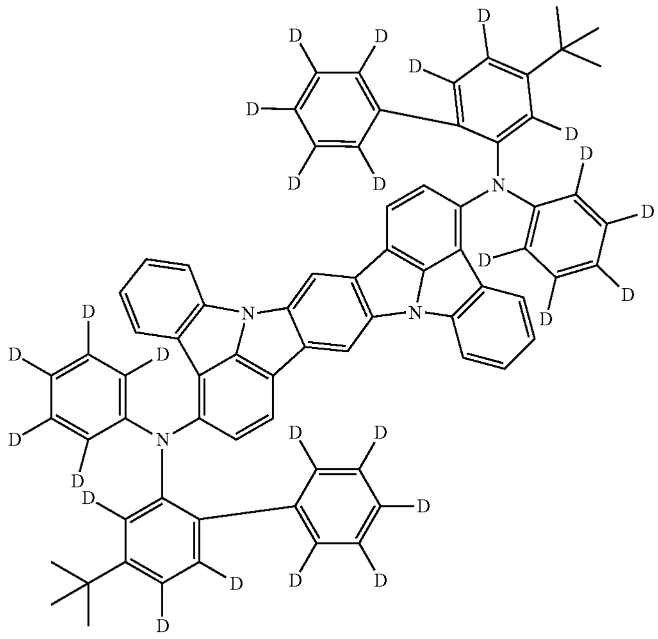

-continued
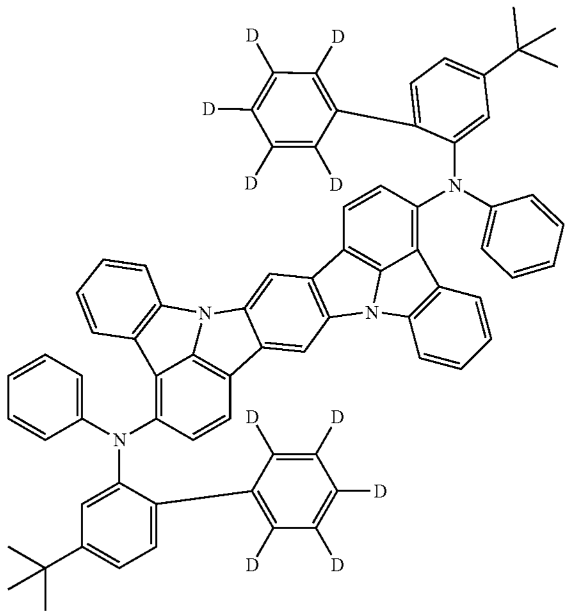
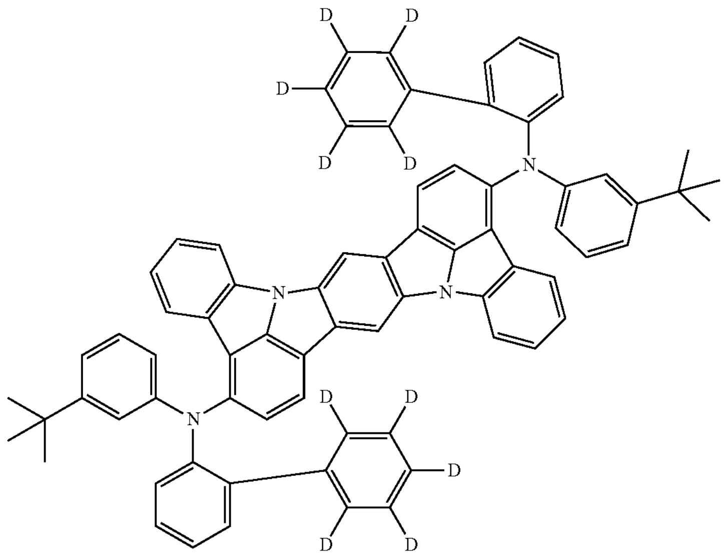

-continued
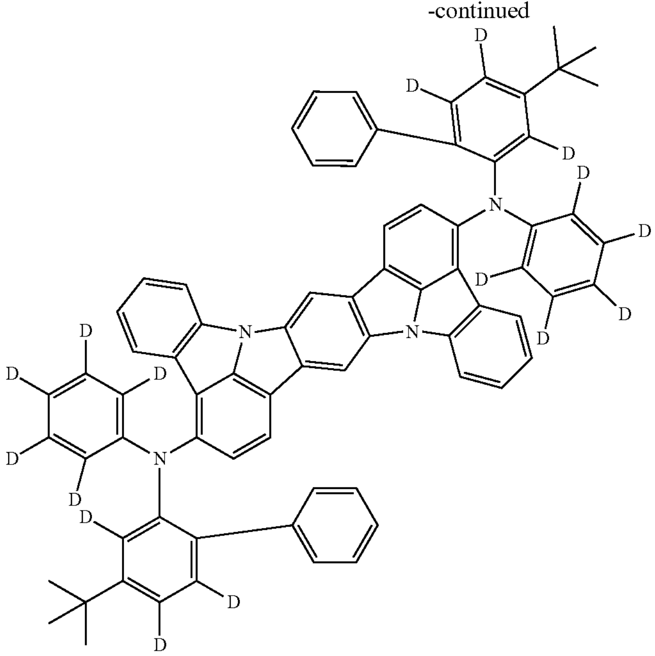
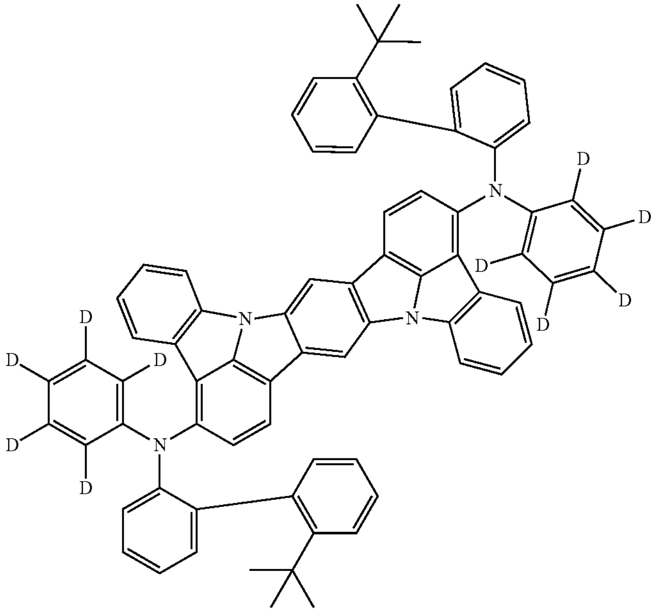

-continued

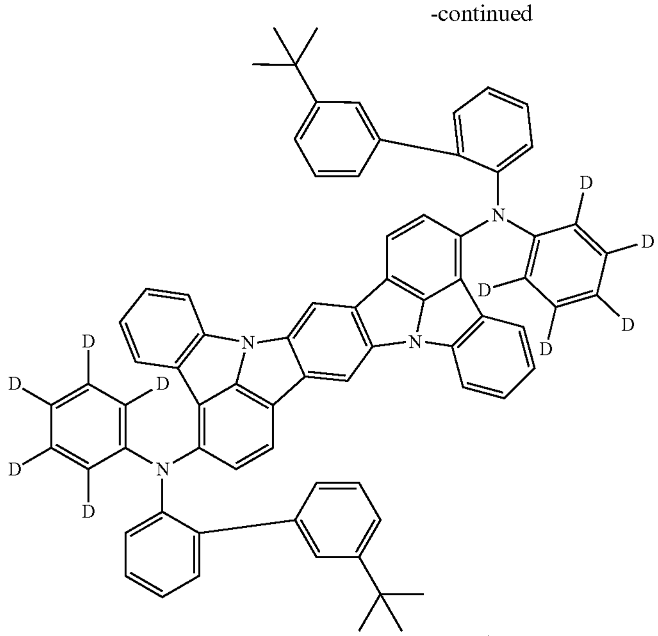

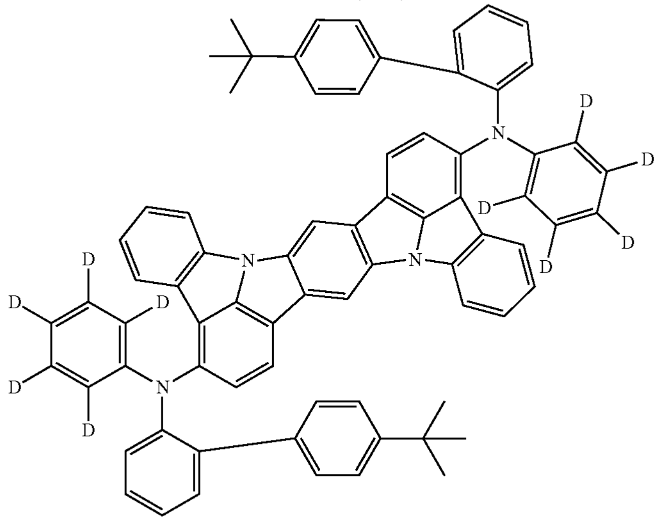

[Material for Organic EL Device]

The compound according to an aspect of the invention is useful as a material for an organic EL device, is useful as a material for an emitting layer of an organic EL device, and is particularly useful as a dopant material for an emitting layer.

By using the compound according to an aspect of the invention for an emitting layer of an organic EL device, an organic EL device having a long lifetime can be obtained.

[Organic EL Device]

An organic EL device according to an aspect of the invention has a cathode, an anode, and at least one organic layer disposed between the cathode and the anode, and at least one of the at least one organic layer contains a compound represented by the formula (1).

A schematic configuration of the organic EL device according to an aspect of the invention will be described with reference to The FIGURE.

The organic EL device 1 according to an aspect of the invention has a substrate 2, an anode 3, an emitting layer 5 as an organic layer, a cathode 10, an organic layer 4 disposed between the anode 3 and the emitting layer 5, and an organic layer 6 disposed between the emitting layer 5 and the cathode 10.

Each of the organic layer 4 and the organic layer 6 may be a single layer or may consist of a plurality of layers.

Further, the organic layer 4 may include a hole-transporting zone. The hole-transporting zone may include a hole-injecting layer, a hole-transporting layer, an electron barrier layer, and the like. The organic layer 6 may include an electron-transporting zone. The electron-transporting zone may include an electron-injecting layer, an electron-transporting layer, a hole barrier layer, and the like.

The compound represented by the formula (1) is contained in the organic layer 4, the emitting layer 5, or the organic layer 6. In one embodiment, the compound represented by the formula (1) is contained in the emitting layer 5. The compound represented by the formula (1) can function as a dopant material in the emitting layer 5.

In the organic EL device according to an aspect of the invention, at least one of the at least one organic layer contains a first compound and a second compound, and the first compound is the compound represented by the formula (1).

In the organic EL device according to an aspect of the invention, the second compound is a heterocyclic compound or a fused aromatic compound.

In the organic EL device according to an aspect of the invention, the second compound is an anthracene derivative.

In the organic EL device according to an aspect of the invention, the second compound is a compound represented by the following formula (10).

<Compound Represented by the Formula (10)>

A compound represented by the formula (10) will be described.

(10)

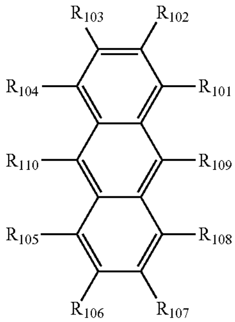

wherein in the formula (10), one or more sets of adjacent two or more of $R_{101}$ to $R_{110}$ form a substituted or unsubstituted, saturated or unsaturated ring, or do not form the substituted or unsubstituted, saturated or unsaturated ring;

$R_{101}$ to $R_{110}$ which do not form the substituted or unsubstituted, saturated or unsaturated ring are independently a hydrogen atom,
a substituent R, or
a group represented by the following formula (11):

$$-L_{101}-Ar_{101} \quad (11)$$

wherein in the formula (11), $L_{101}$ is a single bond,
a substituted or unsubstituted arylene group including 6 to 50 ring carbon atoms, or
a substituted or unsubstituted divalent heterocyclic group including 5 to 50 ring atoms;

$Ar_{101}$ is a substituted or unsubstituted aryl group including 6 to 50 ring carbon atoms, or
a substituted or unsubstituted monovalent heterocyclic group including 5 to 50 ring atoms;

the substituent R is a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
$—Si(R_{901})(R_{902})(R_{903})$,
$—O—(R_{904})$,
$—S—(R_{906})$,
$—N(R_{906})(R_{907})$,
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms;

when two or more of the substituent R's are present, the two or more of the substituent R's may be the same as or different from each other;

$R_{901}$ to $R_{907}$ are independently a hydrogen atom,
a substituted or unsubstituted alkyl group including 1 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted monovalent heterocyclic group including 5 to 50 ring atoms;

when two or more of each of $R_{901}$ to $R_{907}$ are present, the two or more of each of $R_{901}$ to $R_{907}$ may be the same as or different from each other; and provided that at least one of $R_{101}$ to $R_{110}$ which do not form the substituted or unsubstituted, saturated or unsaturated ring is a group represented by the formula (11); and when two or more of the groups represented by the formula (11) are present, the two or more of the groups represented by the formula (11) may be the same as or different from each other.

The compound represented by the formula (10) may have a deuterium atom as a hydrogen atom.

In one embodiment, at least one $Ar_{101}$ in the formula (10) is a substituted or unsubstituted aryl group including 6 to 50 ring carbon atoms.

In one embodiment, at least one $Ar_{101}$ in the formula (10) is a substituted or unsubstituted monovalent heterocyclic group including 5 to 50 ring atoms.

In one embodiment, all of $Ar_{101}$'s in the formula (10) are substituted or unsubstituted aryl groups including 6 to 50 ring carbon atoms. The plurality of $Ar_{101}$'s may be the same as or different from each other.

In one embodiment, one of $Ar_{101}$'s in the formula (10) is a substituted or unsubstituted monovalent heterocyclic group including 5 to 50 ring atoms, and the remaining of $Ar_{101}$'s is a substituted or unsubstituted aryl group including 6 to 50 ring carbon atoms. The plurality of $Ar_{101}$'s may be the same as or different from each other.

In one embodiment, at least one of $L_{101}$'s in the formula (10) is a single bond.

In one embodiment, all of $L_{101}$'s in the formula (10) are single bonds.

In one embodiment, at least one of $L_{101}$'s in the formula (10) is a substituted or unsubstituted arylene group including 6 to 50 ring carbon atoms.

In one embodiment, at least one of $L_{101}$'s in the formula (10) is a substituted or unsubstituted phenylene group, or a substituted or unsubstituted naphthyl group.

In one embodiment, the group represented by $-L_{101}-Ar_{101}$ in the formula (10) is selected from the group consisting of:

a substituted or unsubstituted phenyl group,
a substituted or unsubstituted naphthyl group,
a substituted or unsubstituted biphenyl group,
a substituted or unsubstituted phenanthrenyl group,
a substituted or unsubstituted benzophenanthrenyl group,
a substituted or unsubstituted fluorenyl group,
a substituted or unsubstituted benzofluorenyl group,
a substituted or unsubstituted dibenzofuranyl group, a substituted or unsubstituted naphthobenzofuranyl group, a substituted or unsubstituted dibenzothiophenyl group, and a substituted or unsubstituted carbazolyl group.

In one embodiment, the substituent R's in the formula (10) are independently a substituted or unsubstituted alkyl group including 1 to 50 carbon atoms, a substituted or unsubstituted cycloalkyl group including 3 to 50 ring carbon atoms, $-Si(R_{901})(R_{902})(R_{903})$, $-O-(R_{904})$, $-S-(R_{906})$, $-N(R_{906})(R_{907})$, a halogen atom, a cyano group, a nitro group, or a substituted or unsubstituted aryl group including 6 to 50 ring carbon atoms.

$R_{901}$ to $R_{907}$ are as defined in the formula (10).

In one embodiment, the substituents in the case of the "substituted or unsubstituted" in the formula (10) are independently a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, $-Si(R_{901})(R_{902})(R_{903})$, $-O-(R_{904})$, $-S-(R_{905})$, $-N(R_{906})(R_{907})$, a halogen atom, a cyano group, a nitro group, a substituted or unsubstituted aryl group including 6 to 50 ring carbon atoms, or a substituted or unsubstituted monovalent heterocyclic group including 5 to 50 ring atoms.

$R_{901}$ to $R_{907}$ are as defined in the formula (10).

In one embodiment, the substituents in the case of the "substituted or unsubstituted" in the formula (10) are independently a substituted or unsubstituted alkyl group including 1 to 50 carbon atoms, a substituted or unsubstituted cycloalkyl group including 3 to 50 ring carbon atoms, $-Si(R_{901})(R_{902})(R_{903})$, $-O-(R_{904})$, $-S-(R_{905})$, $-N(R_{906})(R_{907})$, a halogen atom, a cyano group, a nitro group, or a substituted or unsubstituted aryl group including 6 to 50 ring carbon atoms.

$R_{901}$ to $R_{907}$ are as defined in the formula (10).

In one embodiment, the substituent in the case of the "substituted or unsubstituted" in the formula (10) is selected from the group consisting of an alkyl group including 1 to 18 carbon atoms, an aryl group including 6 to 18 ring carbon atoms, and a monovalent heterocyclic group including 5 to 18 ring atoms.

In one embodiment, the substituent in the case of the "substituted or unsubstituted" in the formula (10) is an alkyl group including 1 to 5 carbon atoms.

In one embodiment, the compound represented by the formula (10) is a compound represented by the following formula (20).

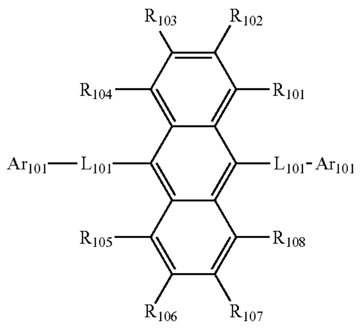

(20)

wherein in the formula (20), $R_{101}$ to $R_{108}$, $L_{101}$, and $Ar_{101}$ are as defined in the formula (10).

The compound represented by the formula (20) may have a deuterium atom as a hydrogen atom.

In other words, in one embodiment, the compound represented by the formula (10) or the formula (20) has at least two groups represented by the formula (11).

In one embodiment, the compound represented by the formula (10) or the formula (20) has two or three groups represented by the formula (11).

In one embodiment, $R_{101}$ to $R_{110}$ in the formulas (10) and (20) do not form the substituted or unsubstituted, saturated or unsaturated ring.

In one embodiment, $R_{101}$ to $R_{110}$ in the formulas (10) and (20) are hydrogen atoms.

In one embodiment, the compound represented by the formula (20) is a compound represented by the following formula (30).

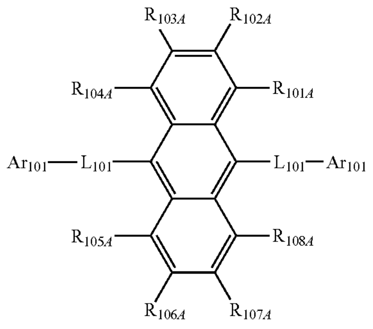

(30)

wherein in the formula (30), $L_{101}$ and $Ar_{101}$ are as defined in the formula (10);

adjacent two of $R_{101A}$ to $R_{108A}$ do not form a substituted or unsubstituted, saturated or unsaturated ring;

$R_{101A}$ to $R_{108A}$ are independently a hydrogen atom, or a substituent R; and the substituent R is as defined in the formula (10).

In other words, the compound represented by the formula (30) is a compound having the two groups represented by the formula (11).

The compound represented by the formula (30) has substantially only protium atoms as hydrogen atoms.

Note that “having substantially only protium atoms” means the case where the ratio of the compound which has only protium atoms as hydrogen atoms (“protium compound”), based on the total moles of the protium compound, and the compound which has the structure same as the protium compound and which has a deuterium atom as a hydrogen atom (“deuterium compound”), is 90 mol % or more, 95 mol % or more, or 99 mol % or more.

In one embodiment, the compound represented by the formula (30) is a compound represented by the following formula (31).

(31)

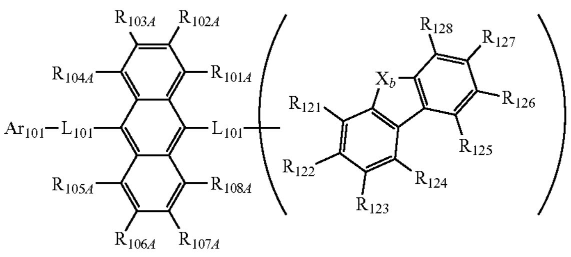

wherein in the formula (31), $L_{101}$ and $Ar_{101}$ are as defined in the formula (10);

$R_{101A}$ to $R_{108A}$ are as defined in the formula (30);

$X_b$ is O, S, N ($R_{131}$), or C($R_{132}$)($R_{133}$);

one of $R_{121}$ to $R_{128}$ and $R_{131}$ to $R_{133}$ is a single bond which bonds with $L_{101}$;

one or more sets of adjacent two or more of the $R_{121}$ to $R_{128}$ which are not the single bond which bonds with $L_{101}$ form a substituted or unsubstituted, saturated or unsaturated ring, or do not form the substituted or unsubstituted, saturated or unsaturated ring;

$R_{121}$ to $R_{128}$ which are not the single bond which bonds with $L_{101}$ and which do not form the substituted or unsubstituted, saturated or unsaturated ring are independently a hydrogen atom, or a substituent R;

the substituent R is as defined in the formula (10);

$R_{131}$ to $R_{133}$ which are not the single bond which bonds with $L_{101}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms; and when two or more of each of $R_{131}$ to $R_{133}$ are present, the two or more of each of $R_{131}$ to $R_{133}$ may be the same as or different from each other.

In one embodiment, the compound represented by the formula (31) is a compound represented by the following formula (32).

(32)

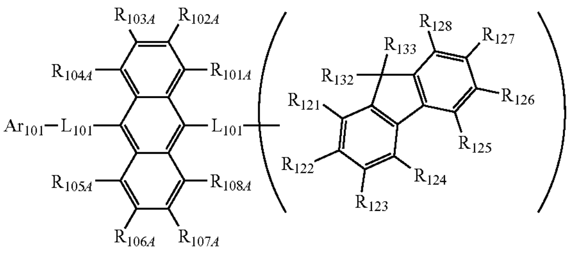

wherein in the formula (32), $R_{101A}$ to $R_{108A}$, $L_{101}$, $Ar_{101}$, $R_{121}$ to $R_{128}$, $R_{132}$, and $R_{133}$ are as defined in the formula (31).

In one embodiment, the compound represented by the formula (31) is a compound represented by the following formula (33).

(33)

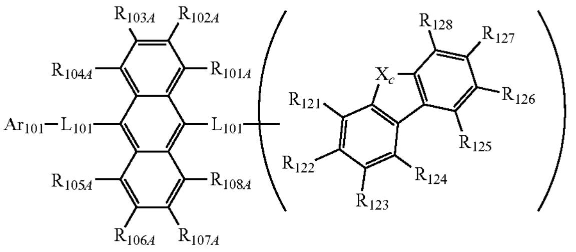

wherein in the formula (33), $R_{101A}$ to $R_{108A}$, $L_{101}$, $Ar_{101}$, and $R_{121}$ to $R_{128}$ are as defined in the formula (31);

$X_c$ is O, S, or $NR_{131}$;

$R_{131}$ is as defined in the formula (31).

In one embodiment, the compound represented by the formula (31) is a compound represented by the following formula (34).

(34)

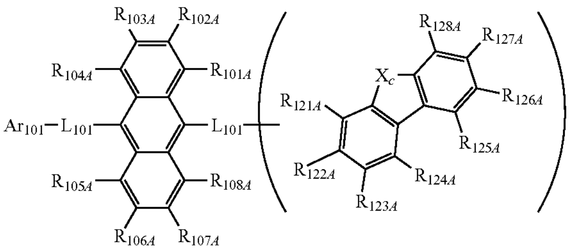

wherein in the formula (34), $R_{101A}$ to $R_{108A}$, $L_{101}$, and $Ar_{101}$ are as defined in the formula (31);

$X_c$ is O, S or $NR_{131}$;

$R_{131}$ is as defined in the formula (31);

one of $R_{121A}$ to $R_{128A}$ is a single bond which bonds with $L_{101}$;

one or more sets of adjacent two or more of Rum to Rum which are not the single bond which bonds with $L_{101}$ do not form a substituted or unsubstituted, saturated or unsaturated ring;

$R_{121A}$ to $R_{128A}$ which are not the single bond which bonds with $L_{101}$ are independently a hydrogen atom, or
a substituent R; and
the substituent R is as defined in the formula (10).

In one embodiment, the compound represented by the formula (31) is a compound represented by the following formula (35).

(35)

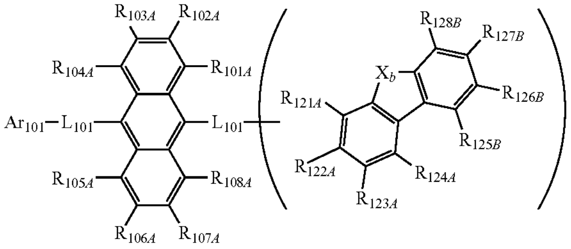

wherein in the formula (35), $R_{101A}$ to $R_{108A}$, $L_{101}$, $Ar_{101}$, and $X_b$ are as defined in the formula (31);
one or more sets of adjacent two or more of $R_{121A}$ to $R_{124A}$ do not form a substituted or unsubstituted, saturated or unsaturated ring by bonding with each other;
one set of $R_{125B}$ and $R_{126B}$, $R_{126B}$ and $R_{127B}$, and $R_{127B}$ and $R_{128B}$ form a ring represented by the following formula (35a) or (35b) by bonding with each other.

(35a)

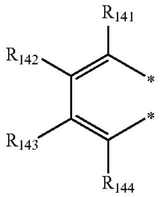

(35b)

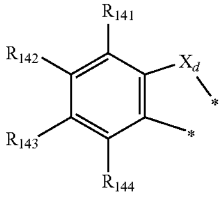

wherein in the formulas (35a) and (35b),
two *'s respectively bond with one set of $R_{125B}$ and $R_{126B}$, $R_{126B}$ and $R_{127B}$, and $R_{127B}$ and $R_{128B}$,
$R_{141}$ to $R_{144}$ are independently
a hydrogen atom, or
a substituent R;
the substituent R is as defined in the formula (10);
$X_d$ is O or S;
one of $R_{121A}$ to $R_{124A}$ and $R_{125B}$ to $R_{128B}$ which do not form the ring represented by the formula (35a) or (35b), and $R_{141}$ to $R_{144}$ is a single bond which bonds with $L_{101}$;
$R_{121A}$ to $R_{124A}$ which are not the single bond which bonds with $L_{101}$, and $R_{125B}$ to $R_{128B}$ which are not the single bond which bonds with $L_{101}$ and do not form the ring represented by the formula (35a) or (35b) are independently
a hydrogen atom, or
a substituent R; and
the substituent R is as defined in the formula (10).

In one embodiment, the compound represented by the formula (35) is a compound represented by the following formula (36).

(36)

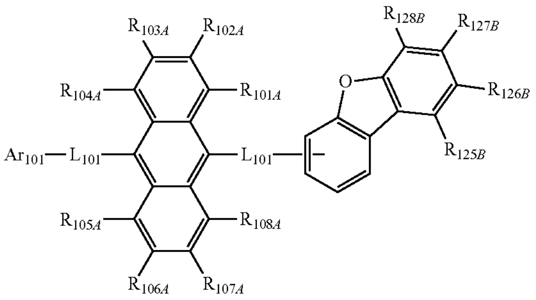

wherein in the formula (36), $R_{101A}$ to $R_{108A}$, $L_{101}$, $Ar_{101}$, and $R_{125B}$ to $R_{128B}$ are as defined in the formula (35).

In one embodiment, the compound represented by the formula (34) is a compound represented by the following formula (37).

(37)

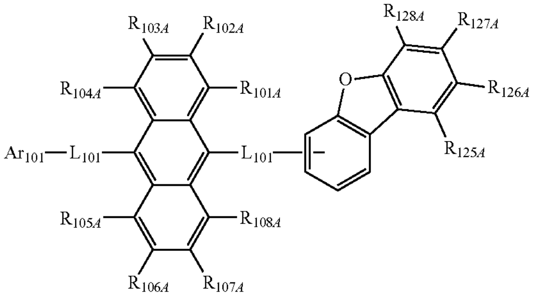

wherein in the formula (37), $R_{101A}$ to $R_{108A}$, $R_{125A}$ to $R_{128A}$, $L_{101}$, and $Ar_{101}$ are as defined in the formula (34).

In one embodiment, $R_{101A}$ to $R_{108A}$ in the formulas (30) to (37) are hydrogen atoms.

In one embodiment, the compound represented by the formula (10) is a compound represented by the following formula (40).

(40)

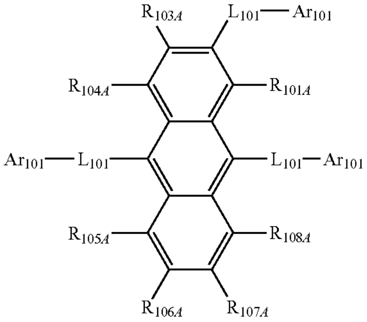

wherein in the formula (40), $L_{101}$ and $Ar_{101}$ are as defined in the formula (10);

one or more sets of adjacent two or more of $R_{101A}$ and $R_{103A}$ to $R_{108A}$ form a substituted or unsubstituted, saturated or unsaturated ring, or do not form the substituted or unsubstituted, saturated or unsaturated ring;

$R_{101A}$ and $R_{103A}$ to $R_{108A}$ which do not form the substituted or unsubstituted, saturated or unsaturated ring are independently a hydrogen atom, or a substituent R; and the substituent R is as defined in the formula (10).

In other words, the compound represented by the formula (40) is a compound having three groups represented by the formula (11). The compound represented by the formula (40) has substantially only protium atoms as hydrogen atoms.

In one embodiment, the compound represented by the formula (40) is a compound represented by the following formula (41).

(41)

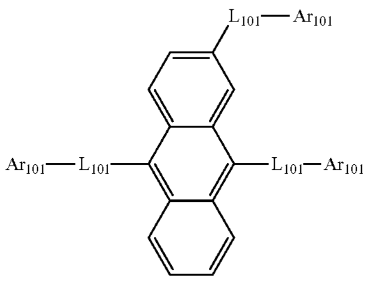

wherein in the formula (41), $L_{101}$ and $Ar_{101}$ are as defined in the formula (40).

In one embodiment, the compound represented by the formula (40) is a compound represented by any of the following formulas (42-1) to (42-3).

(42-1)

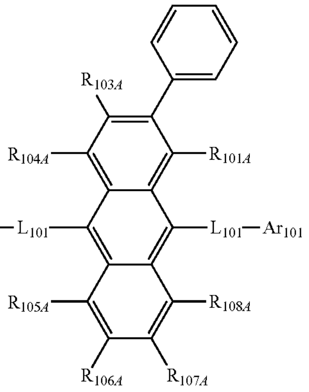

-continued (42-2)

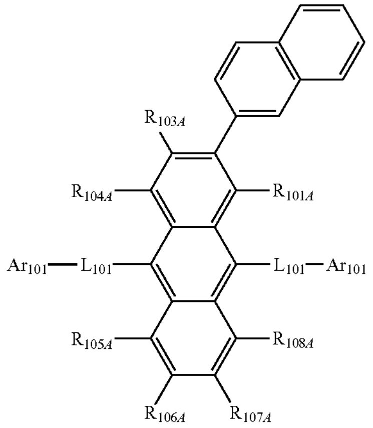

(42-3)

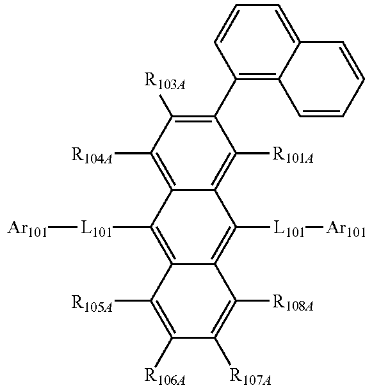

wherein in the formulas (42-1) to (42-3), $R_{101A}$ to $R_{108A}$, $L_{101}$, and $Ar_{101}$ are as defined in the formula (40).

In one embodiment, the compounds represented by each of the formulas (42-1) to (42-3) are compounds represented by each of the following formulas (43-1) to (43-3), respectively.

(43-1)

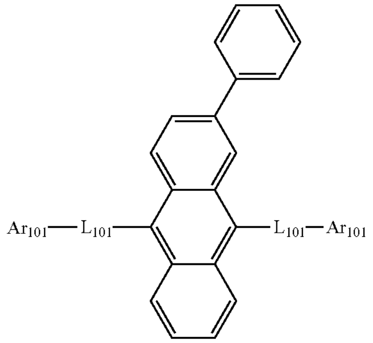

-continued (43-2)

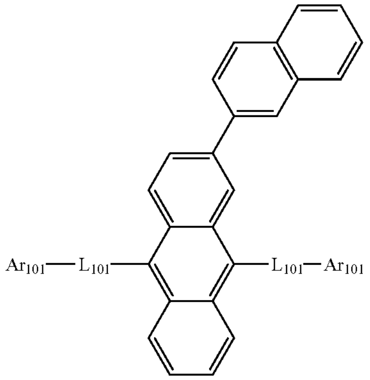

(43-3)

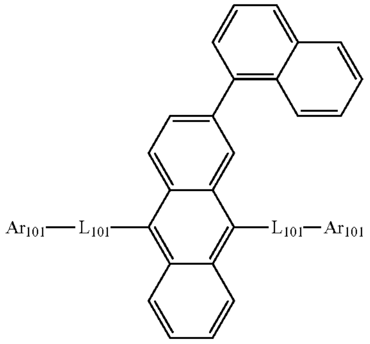

wherein in the formulas (43-1) to (43-3), $L_{101}$ and $Ar_{101}$ are as defined in the formula (40).

In one embodiment, the group represented by $-L_{101}-Ar_{101}$ in each of the formulas (40), (41), (42-1) to (42-3), and (43-1) to (43-3) is selected from the group consisting of a substituted or unsubstituted phenyl group,
a substituted or unsubstituted naphthyl group,
a substituted or unsubstituted biphenyl group,
a substituted or unsubstituted phenanthrenyl group,
a substituted or unsubstituted benzophenanthrenyl group,
a substituted or unsubstituted fluorenyl group,
a substituted or unsubstituted benzofluorenyl group,
a substituted or unsubstituted dibenzofuranyl group,
a substituted or unsubstituted naphthobenzofuranyl group,
a substituted or unsubstituted dibenzothiophenyl group, and
a substituted or unsubstituted carbazolyl group.

In one embodiment, the compound represented by the formula (10) or the formula (20) include a compound in which at least one hydrogen atom possessed by these compounds is a deuterium atom.

In one embodiment, in the formula (20), at least one of
$R_{101}$ to $R_{108}$ which are hydrogen atoms,
hydrogen atoms possessed by $R_{101}$ to $R_{108}$ which are the substituent R,
hydrogen atoms possessed by $L_{101}$,
hydrogen atoms possessed by substituents on $L_{101}$,
hydrogen atoms possessed by $Ar_{101}$, and
hydrogen atoms possessed by substituents on $Ar_{101}$
is a deuterium atom.

The compounds represented by each of the formulas (30) to (37) include compounds in which at least one hydrogen atom possessed by these compounds is a deuterium atom.

In one embodiment, at least one hydrogen atom which is bonded with a carbon atom constituting the anthracene skeleton in the compounds represented by each of the formulas (30) to (37) is a deuterium atom.

In one embodiment, the compound represented by the formula (30) is a compound represented by the following formula (30D).

(30D)

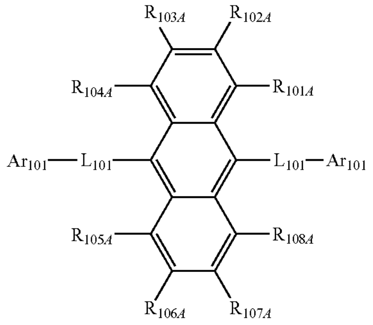

wherein in the formula (30D), $R_{101A}$ to $R_{108A}$, $L_{101}$, and $Ar_{101}$ are as defined in the formula (30); and
provided that at least one of
$R_{101A}$ to $R_{110A}$ which are hydrogen atoms,
hydrogen atoms possessed by $R_{101A}$ to $R_{110A}$ which are the substituent R,
hydrogen atoms possessed by $L_{101}$,
hydrogen atoms possessed by substituents on $L_{101}$,
hydrogen atoms possessed by $Ar_{101}$, and
hydrogen atoms possessed by substituents on $Ar_{101}$
is a deuterium atom.

In other words, the compound represented by the formula (30D) is a compound in which at least one hydrogen atom possessed by the compound represented by the formula (30) is a deuterium atom.

In one embodiment, at least one of $R_{101A}$ to $R_{108A}$ which are hydrogen atoms in the formula (30D) is a deuterium atom.

In one embodiment, the compound represented by the formula (30D) is a compound represented by the following formula (31D).

(31D)

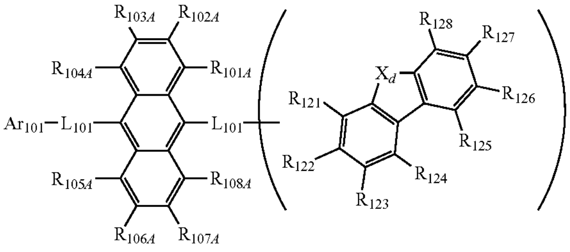

wherein in the formula (31D), $R_{101A}$ to $R_{108A}$, $L_{101}$, and $Ar_{101}$ are as defined in the formula (30D);
$X_d$ is O or S;
one of $R_{121}$ to $R_{128}$ is a single bond which bonds with $L_{101}$;
one or more sets of adjacent two or more of $R_{121}$ to $R_{128}$ which are not the single bond which bonds with $L_{101}$ form a substituted or unsubstituted, saturated or unsaturated ring, or do not form a substituted or unsubstituted, saturated or unsaturated ring;

$R_{121}$ to $R_{128}$ which are not single bonds bonding with $L_{101}$ and which do not form the substituted or unsubstituted, saturated or unsaturated ring are independently a hydrogen atom, or a substituent R;

the substituent R is as defined in the formula (10); and provided that at least one of $R_{101A}$ to $R_{110A}$ which are hydrogen atoms, hydrogen atoms possessed by $R_{101A}$ to $R_{110A}$ which are the substituent R, hydrogen atoms possessed by $L_{101}$, hydrogen atoms possessed by substituents on $L_{101}$, hydrogen atoms possessed by $Ar_{101}$, hydrogen atoms possessed by substituents on $Ar_{101}$, $R_{121}$ to $R_{128}$ which are hydrogen atoms, and hydrogen atoms possessed by $R_{121}$ to $R_{128}$ which are the substituent R is a deuterium atom.

In one embodiment, the compound represented by the formula (31D) is a compound represented by the following formula (32D).

(32D)

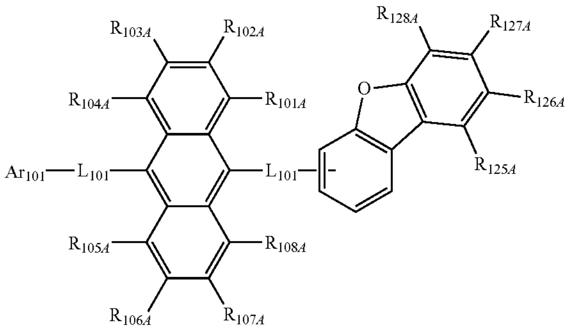

wherein in the formula (32D), $R_{101A}$ to $R_{108A}$, $R_{125A}$ to $R_{128A}$, $L_{101}$, and $Ar_{101}$ are as defined in the formula (31D); and provided that at least one of $R_{101A}$ to $R_{108A}$ which are hydrogen atoms, hydrogen atoms possessed by $R_{101A}$ to $R_{108A}$ which are the substituent R, $R_{125A}$ to $R_{128A}$ which are hydrogen atoms, hydrogen atoms possessed by $R_{125A}$ to $R_{128A}$ which are the substituent R, hydrogen atoms which bond with the carbon atoms of the dibenzofuran skeleton in the formula (32D), hydrogen atoms possessed by $L_{101}$, hydrogen atoms possessed by substituents on $L_{101}$, hydrogen atoms possessed by $Ar_{101}$, and hydrogen atoms possessed by substituents on $Ar_{101}$ is a deuterium atom.

In one embodiment, the compound represented by the formula (32D) is a compound represented by the following formula (32D-1) or (32D-2).

(32D-1)

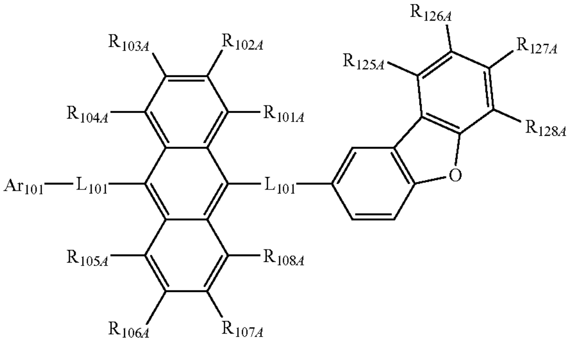

(32D-2)

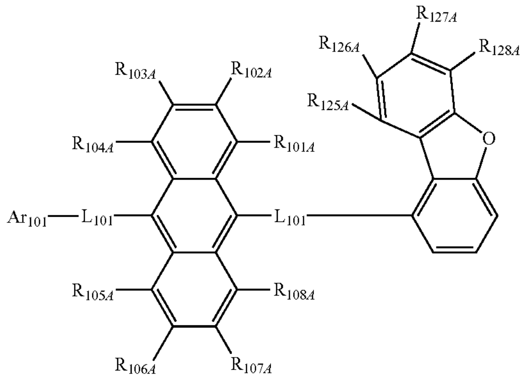

wherein in the formulas (32D-1) and (32D-2), $R_{101A}$ to $R_{108A}$, $R_{125A}$ to $R_{128A}$, $L_{101}$, and $Ar_{101}$ are as defined in the formula (32D); and provided that at least one of $R_{101A}$ to $R_{108A}$ which are hydrogen atoms, hydrogen atoms possessed by $R_{101A}$ to $R_{108A}$ which are the substituent R, $R_{125A}$ to $R_{128A}$ which are hydrogen atoms, Hydrogen atoms possessed by $R_{125A}$ to $R_{128A}$ which are the substituent R, hydrogen atoms which bond with the carbon atoms of the dibenzofuran skeleton in the formulas (32D-1) and (32D-2), hydrogen atoms possessed by $L_{101}$, hydrogen atoms possessed by substituents on $L_{101}$, hydrogen atoms possessed by $Ar_{101}$, and hydrogen atoms possessed by substituents on $Ar_{101}$.

is a deuterium atom.

In one embodiment, at least one hydrogen atom possessed by the compounds represented by each of the formulas (40), (41), (42-1) to (42-3), and (43-1) to (43-3) is a deuterium atom.

In one embodiment, at least one of the hydrogen atoms which bond with the carbon atoms constituting the anthracene skeleton in the compound represented by the formula (41)($R_{101A}$ to $R_{108A}$ which are hydrogen atoms) is a deuterium atom.

In one embodiment, the compound represented by the formula (40) is a compound represented by the following formula (40D).

(40D)

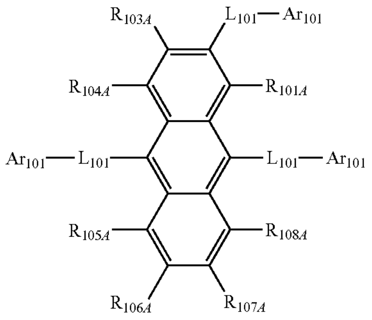

wherein in the formula (40D), $L_{101}$ and $Ar_{101}$ are as defined in the formula (10);

one or more sets of adjacent two or more of $R_{101A}$ and $R_{103A}$ to $R_{108A}$ do not form the substituted or unsubstituted, saturated or unsaturated ring;

$R_{101A}$ and $R_{103A}$ to $R_{108A}$ are independently a hydrogen atom, or a substituent R;

the substituent R is as defined in the formula (10); and provided that at least one of $R_{101A}$ and $R_{103A}$ to $R_{108A}$ which are hydrogen atoms, hydrogen atoms possessed by $R_{101A}$ and $R_{103A}$ to $R_{108A}$ which are the substituent R, hydrogen atoms possessed by $L_{101}$, hydrogen atoms possessed by substituents on $L_{101}$, hydrogen atoms possessed by $Ar_{101}$, and hydrogen atoms possessed by substituents on $Ar_{101}$ is a deuterium atom.

In one embodiment, at least one of $R_{101A}$ and $R_{103A}$ to $R_{108A}$ in the formula (40D) is a deuterium atom.

In one embodiment, the compound represented by the formula (40D) is a compound represented by the following formula (41D).

(41D)

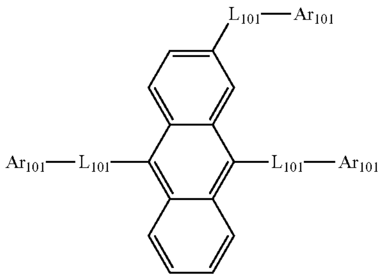

wherein in the formula (41D), $L_{101}$ and $Ar_{101}$ are as defined in the formula (40D); and provided that at least one of hydrogen atoms which bond with the carbon atoms constituting the anthracene skeleton hydrogen atoms possessed by $L_{101}$, hydrogen atoms possessed by substituents on $L_{101}$, hydrogen atoms possessed by $Ar_{101}$, and hydrogen atoms possessed by substituents on $Ar_{101}$ is a deuterium atom.

In one embodiment, the compound represented by the formula (40D) is a compound represented by any one of the following formulas (42D-1) to (42D-3).

(42D-1)

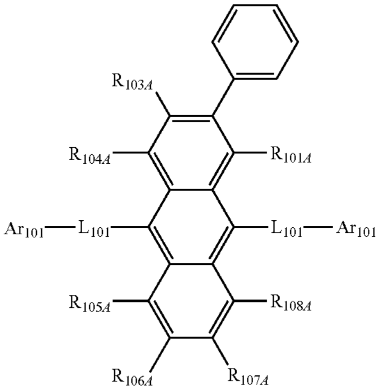

(42D-2)

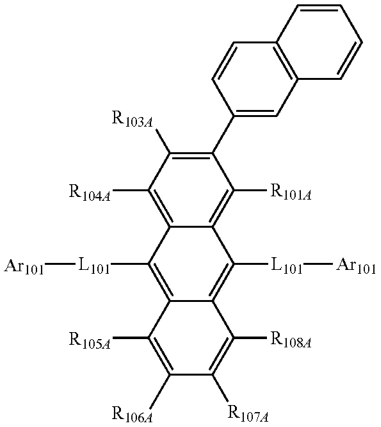

(42D-3)

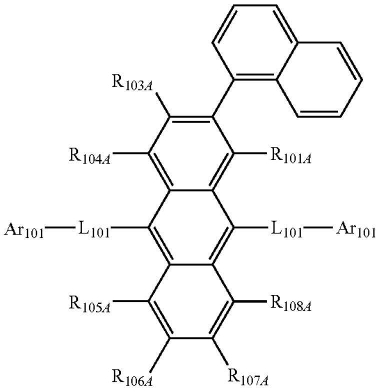

wherein in the formulas (42D-1) to (42D-3), $R_{101A}$ to $R_{108A}$, $L_{101}$, and $Ar_{101}$ are as defined in the formula (40D);

provided that, in the formula (42D-1), at least one of $R_{101A}$ and $R_{103A}$ to $R_{108A}$ which are hydrogen atoms, hydrogen atoms possessed by $R_{101A}$ and $R_{103A}$ to $R_{108A}$ which are the substituent R, hydrogen atoms possessed by $L_{101}$, hydrogen atoms possessed by substituents on $L_{101}$, hydrogen atoms possessed by $Ar_{101}$, hydrogen atoms possessed by substituents on $Ar_{101}$, and hydrogen atoms which bond with the carbon atoms constituting the phenyl group in the formula (42D-1) is a deuterium atom;

in the formula (42D-2), at least one of $R_{101A}$ and $R_{103A}$ to $R_{108A}$ which are hydrogen atoms, hydrogen atoms possessed by $R_{101A}$ and $R_{103A}$ to $R_{108A}$ which are the substituent R, hydrogen atoms possessed by $L_{101}$, hydrogen atoms possessed by substituents on $L_{101}$, hydrogen atoms possessed by $Ar_{101}$, hydrogen atoms possessed by substituents of $Ar_{101}$, and hydrogen atoms which bond with the carbon atoms constituting the naphthyl group in the formula (42D-2) is a deuterium atom; and in the formula (42D-3), at least one of $R_{101A}$ and $R_{103A}$ to $R_{108A}$ which are hydrogen atoms, hydrogen atoms possessed by $R_{101A}$ and $R_{103A}$ to $R_{108A}$ which are the substituent R, hydrogen atoms possessed by $L_{101}$, hydrogen atoms possessed by substituents on $L_{101}$, hydrogen atoms possessed by $Ar_{101}$, hydrogen atoms possessed by substituents on $Ar_{101}$, and hydrogen atoms which bond with the carbon atoms constituting the naphthyl group in the formula (42D-3) is a deuterium atom.

In one embodiment, the compounds represented by each of the formulas (42D-1) to (42D-3) are compounds represented by each of the following formulas (43D-1) to (43D-3), respectively.

(43D-1)

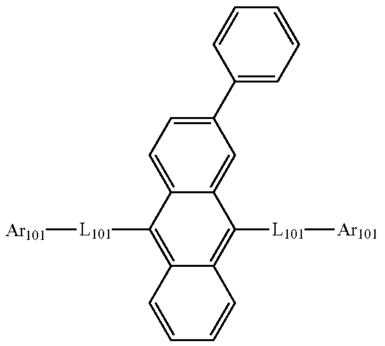

(43D-2)

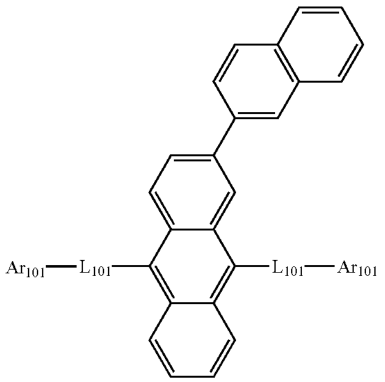

-continued (43D-3)

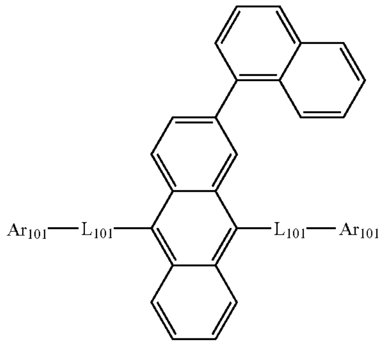

wherein in the formula (43D-1) to (43D-3), $L_{101}$ and $Ar_{101}$ are as defined in the formula (40D);

provided that, in the formula (43D-1), at least one of hydrogen atoms which bond with the carbon atoms constituting the anthracene skeleton, hydrogen atoms possessed by $L_{101}$, hydrogen atoms possessed by substituents on $L_{101}$, hydrogen atoms possessed by $Ar_{101}$, hydrogen atoms possessed by substituents on $Ar_{101}$, and hydrogen atoms which bond with the carbon atoms constituting the phenyl group in the formula (43D-1) is a deuterium atom;

in the formula (43D-2), at least one of hydrogen atoms which bond with the carbon atoms constituting the anthracene skeleton, hydrogen atoms possessed by $L_{101}$, hydrogen atoms possessed by substituents on $L_{101}$, hydrogen atoms possessed by $Ar_{101}$, hydrogen atoms possessed by substituents on $Ar_{101}$, and hydrogen atoms which bond with the carbon atoms constituting the naphthyl group in the formula (43D-2) is a deuterium atom; and in the formula (43D-3), at least one of hydrogen atoms which bond with the carbon atoms constituting the anthracene skeleton, hydrogen atoms possessed by $L_{101}$, hydrogen atoms possessed by substituents on $L_{101}$, hydrogen atoms possessed by $Ar_{101}$, hydrogen atoms possessed by substituents on $Ar_{101}$, and hydrogen atoms which bond with the carbon atoms constituting the naphthyl group in the formula (43D-3) is a deuterium atom.

In one embodiment, in the compound represented by the formula (20), at least one of $Ar_{101}$'s is a monovalent group having a structure represented by the following formula (50).

(50)

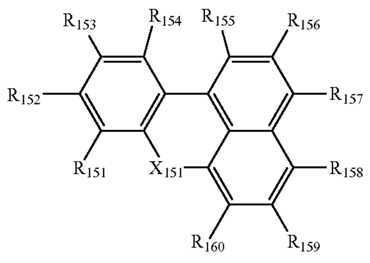

wherein in the formula (50), $X_{151}$ is O, S or $C(R_{161})(R_{162})$;

one of $R_{151}$ to $R_{160}$ is a single bond which bonds with $L_{101}$;

one or more sets of adjacent two or more of $R_{151}$ to $R_{154}$ and adjacent two or more of $R_{155}$ to $R_{160}$ which are not the single bond which bonds with $L_{101}$ form a substituted or unsubstituted, saturated or unsaturated ring by bonding with each other or do not form the substituted or unsubstituted, saturated or unsaturated ring;

$R_{161}$ and $R_{162}$ form a substituted or unsubstituted, saturated or unsaturated ring by bonding with each other, or do not form the substituted or unsubstituted, saturated or unsaturated ring;

$R_{161}$ and $R_{162}$ which do not form the substituted or unsubstituted, saturated or unsaturated ring, and $R_{151}$ to $R_{160}$ which are not the single bond which bonds with $L_{101}$ and do not form the substituted or unsubstituted, saturated or unsaturated ring are independently a hydrogen atom or a substituent R;

the substituent R is as defined in the formula (10); and $Ar_{101}$ which is not a monovalent group having a structure represented by the formula (50) is a substituted or unsubstituted aryl group including 6 to 50 ring carbon atoms, or a substituted or unsubstituted monovalent heterocyclic group including 5 to 50 ring atoms.

The position of the single bond which bonds with $L_{101}$ in the formula (50) is not particularly limited.

In one embodiment, one of $R_{161}$ to $R_{154}$ or one of $R_{155}$ to $R_{160}$ in the formula (50) is a single bond which bonds with $L_{101}$.

In one embodiment, $Ar_{101}$ is a monovalent group represented by the following formula (50-$R_{152}$), (50-$R_{153}$), (50-$R_{154}$), (50-$R_{157}$), or (50-$R_{158}$).

(50-$R_{152}$)

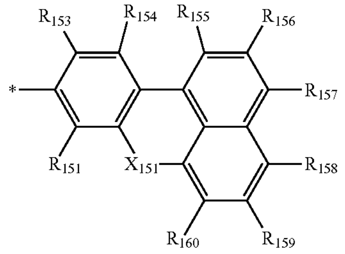

(50-$R_{153}$)

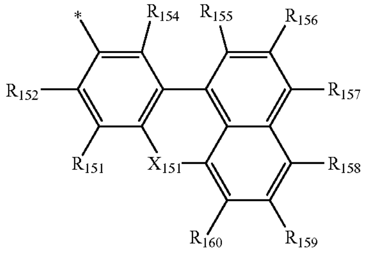

-continued (50-$R_{154}$)

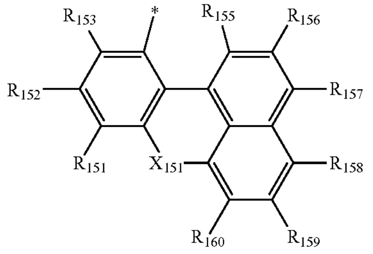

(50-$R_{157}$)

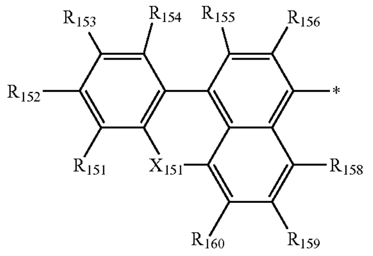

(50-$R_{158}$)

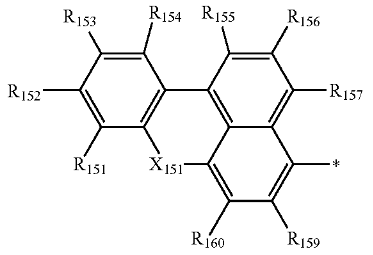

wherein in the formulas (50-$R_{152}$), (50-$R_{153}$), (50-$R_{154}$), (50-$R_{157}$), and (50-$R_{158}$), $X_{151}$ and $R_{151}$ to $R_{160}$ are as defined in the formula (50); and

* bonds with $L_{101}$.

Specific examples of the compound represented by the formula (10) include the following compounds. The compound represented by the formula (10) is not limited to these specific examples. In the following specific examples, "D" represents a deuterium atom.

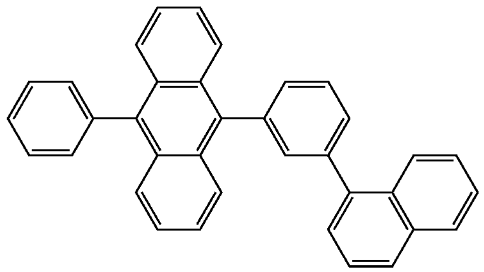

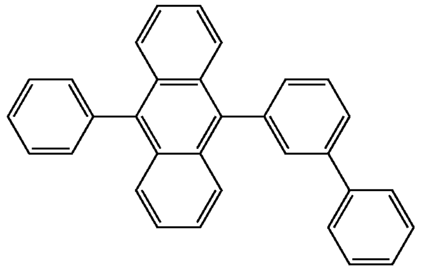

-continued
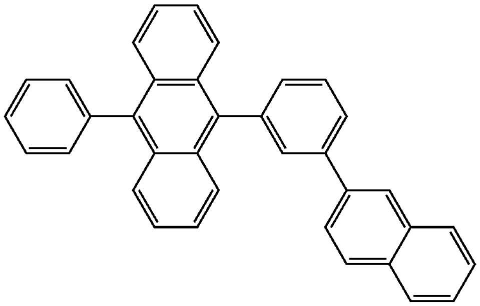
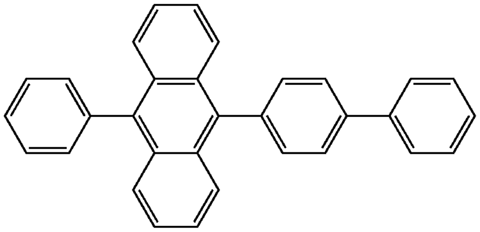
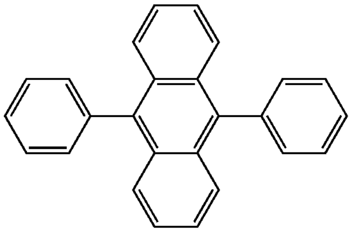
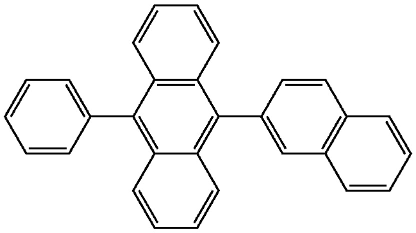
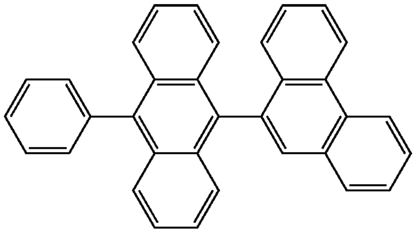
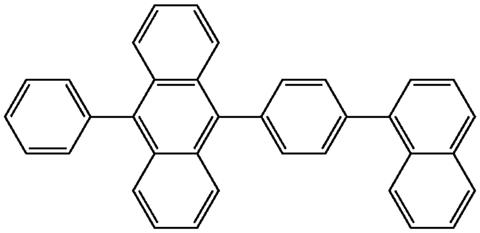
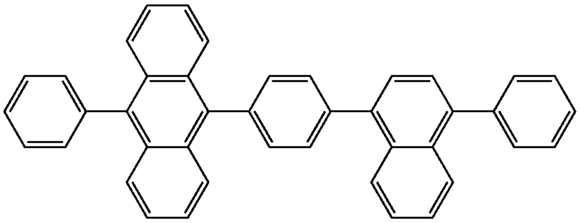
-continued
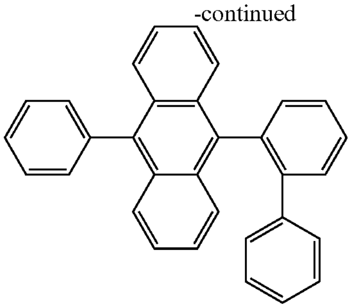
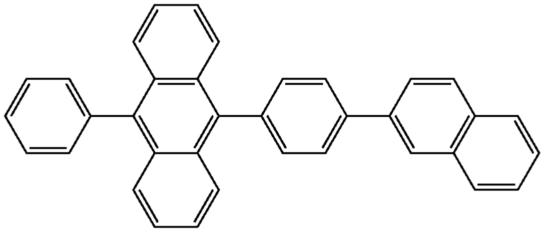
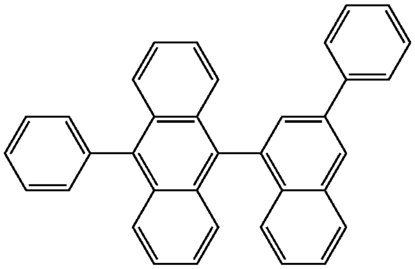
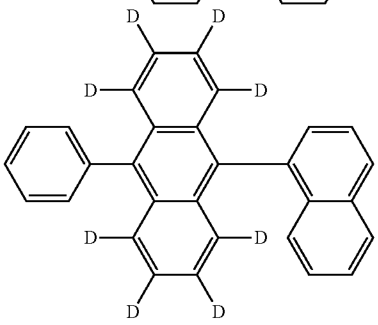
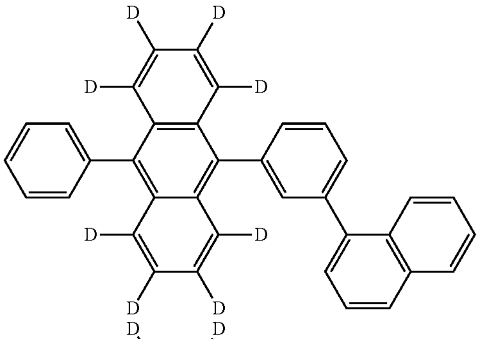
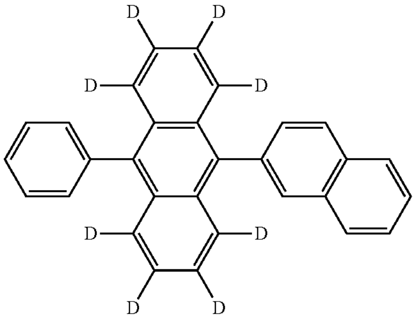

-continued
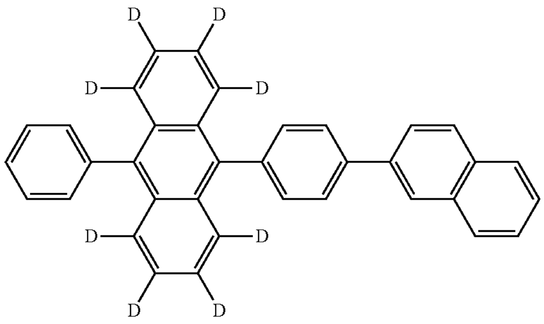
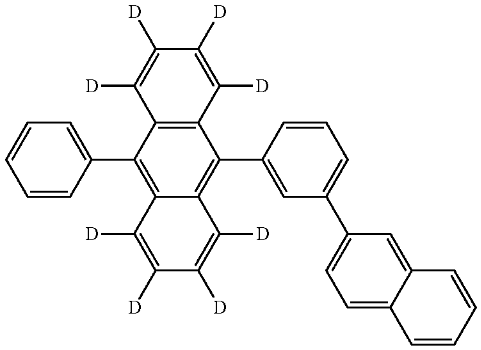
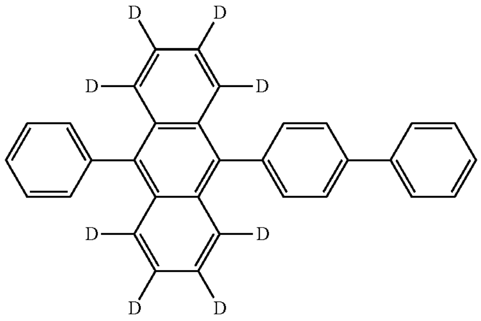
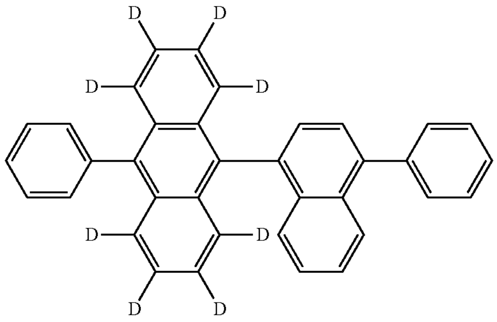
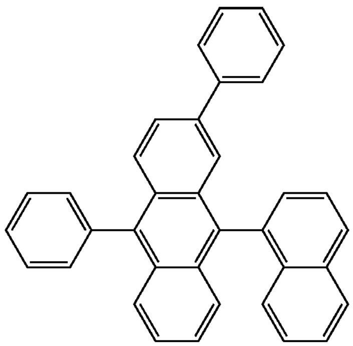
-continued
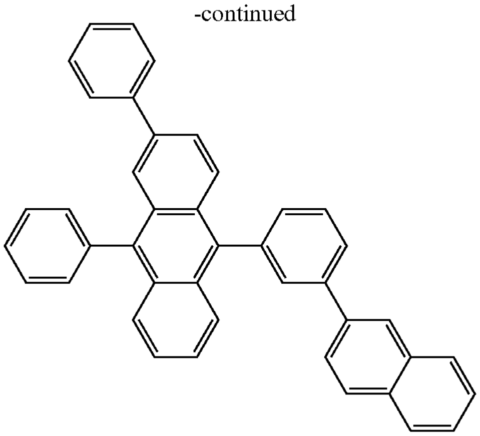
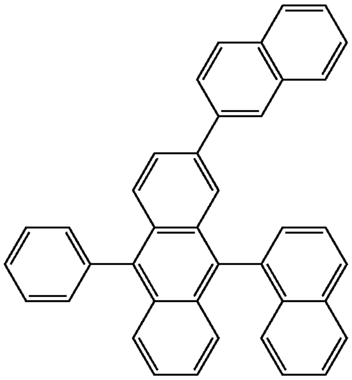
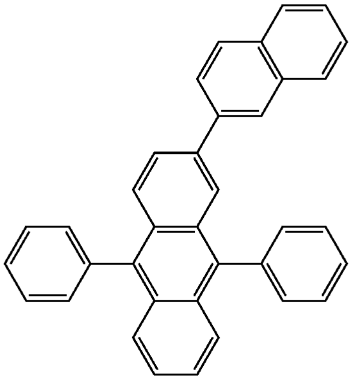
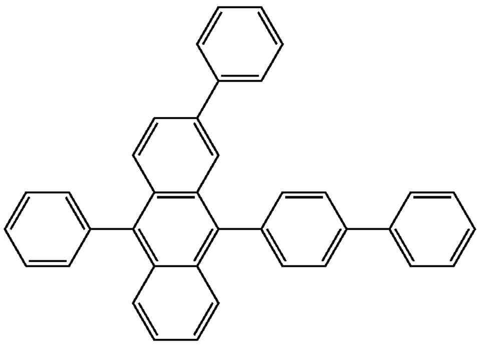

-continued
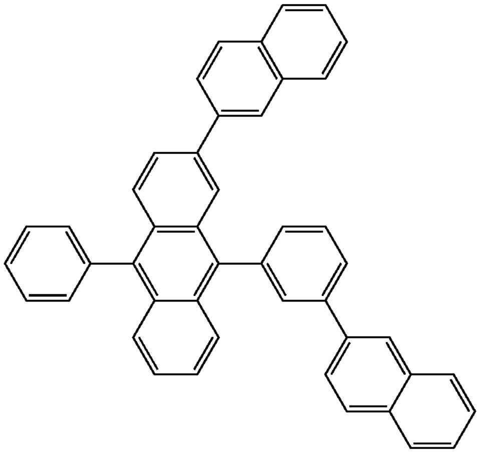
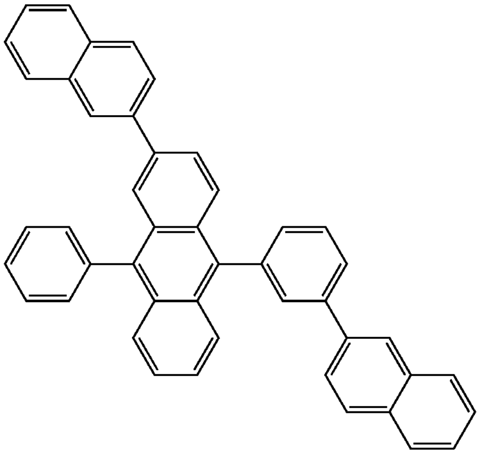
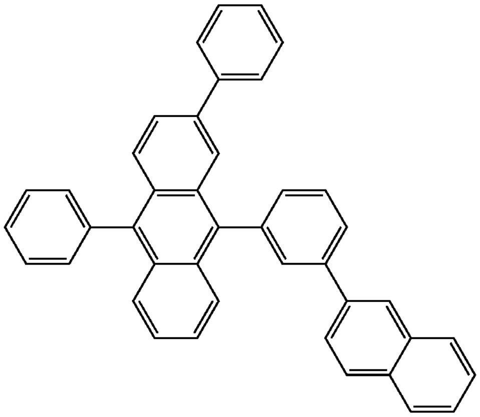
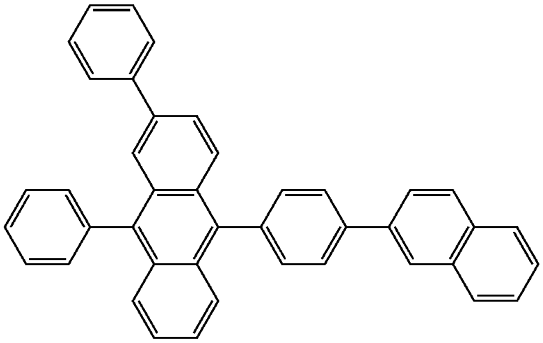
-continued
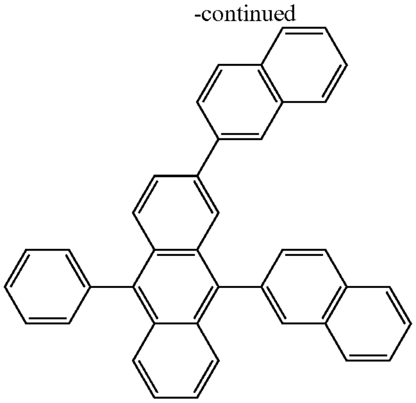
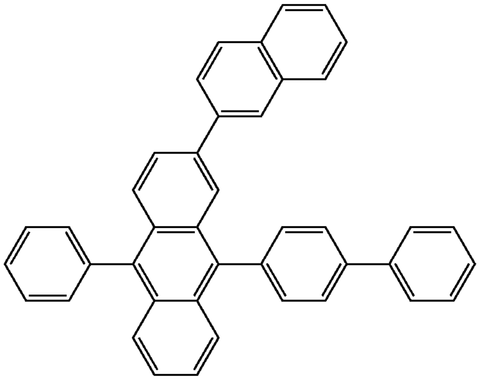
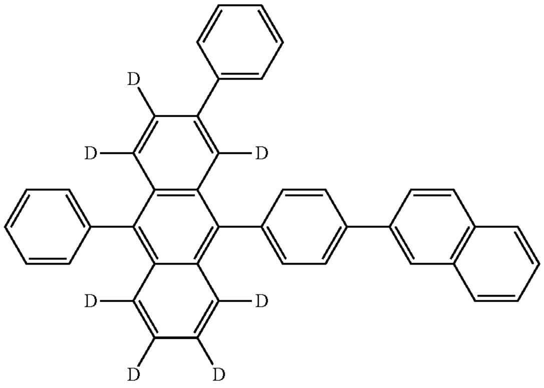
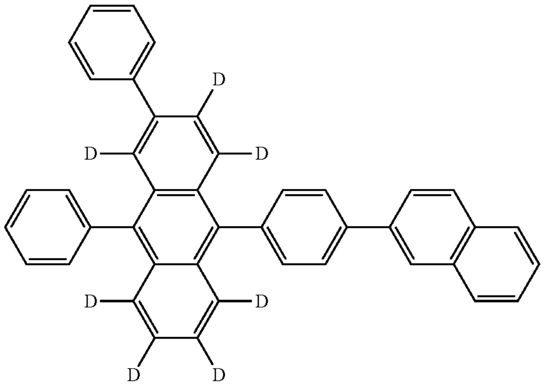

-continued
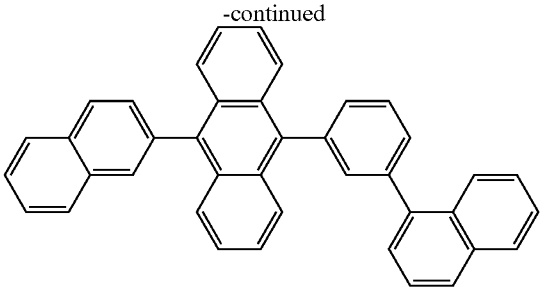
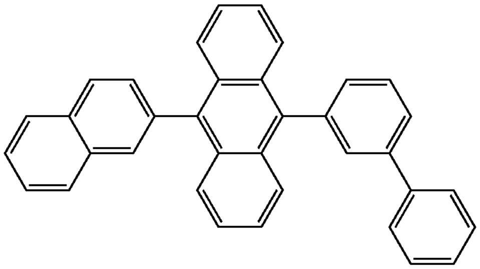
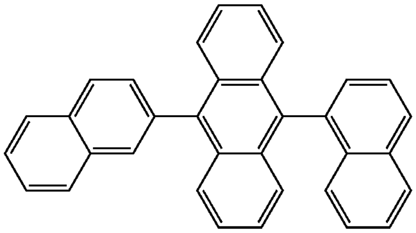
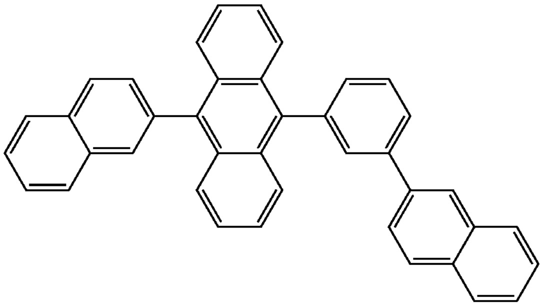
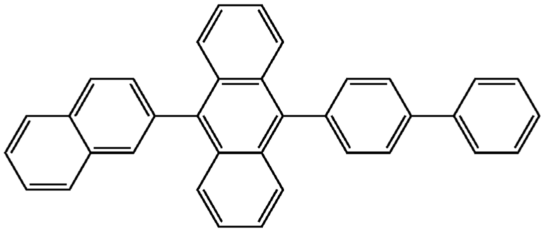
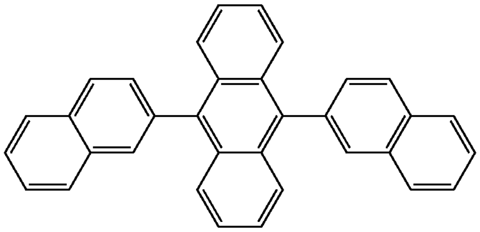
-continued
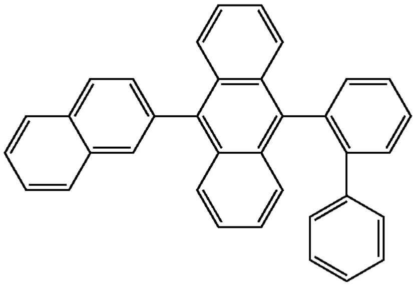
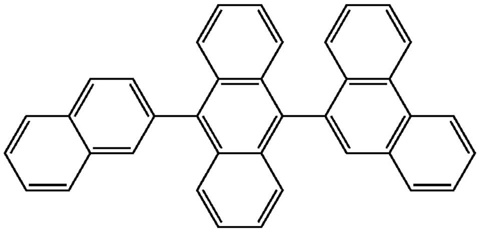
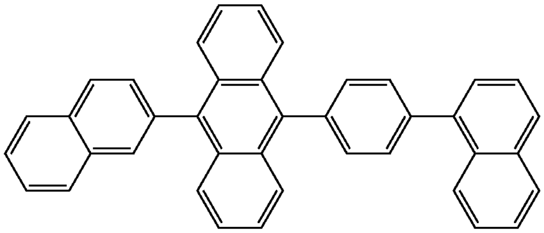
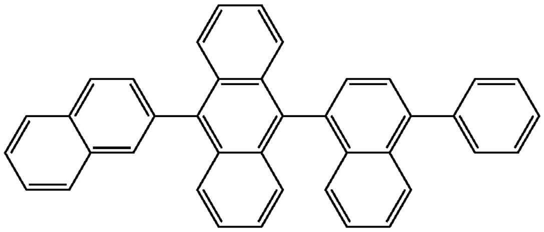
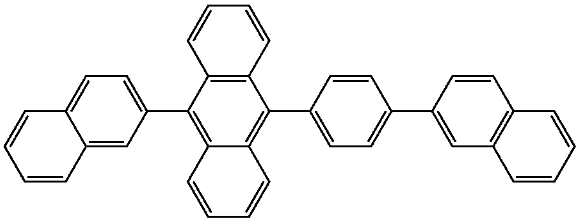
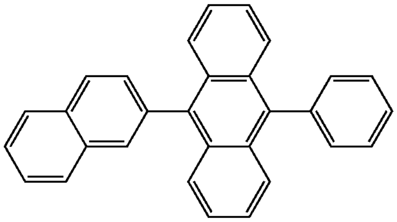
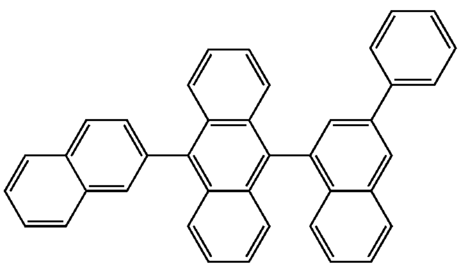

-continued
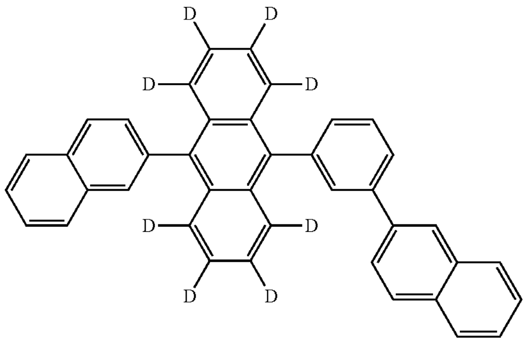
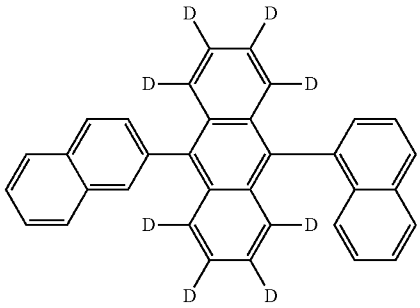
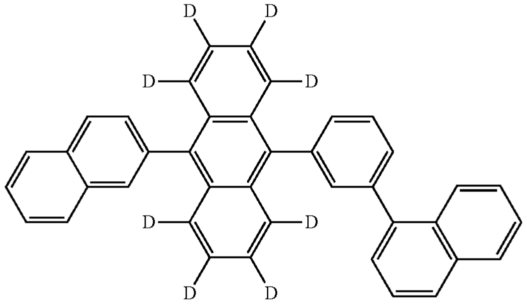
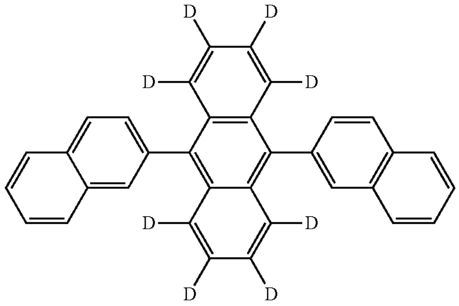
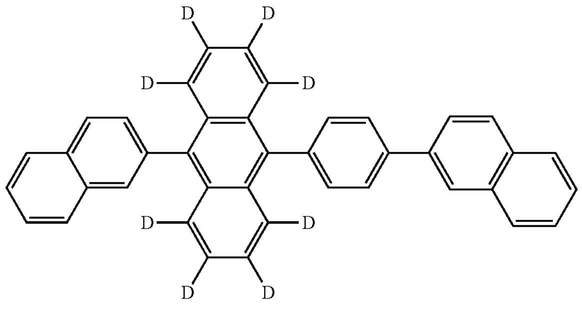
-continued
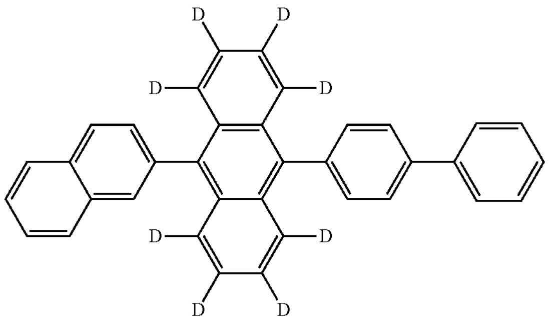
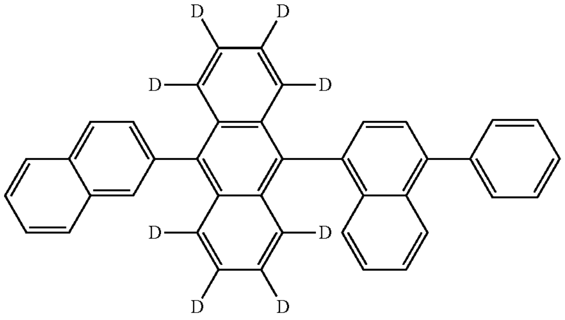
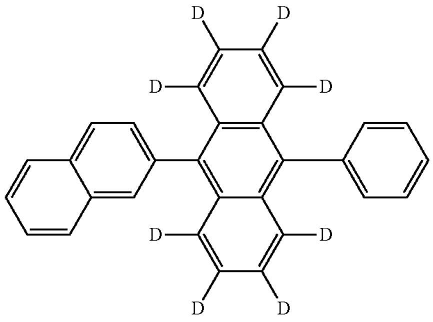
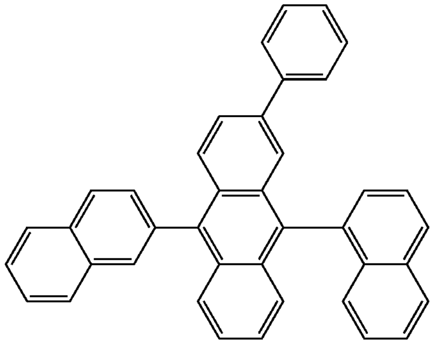
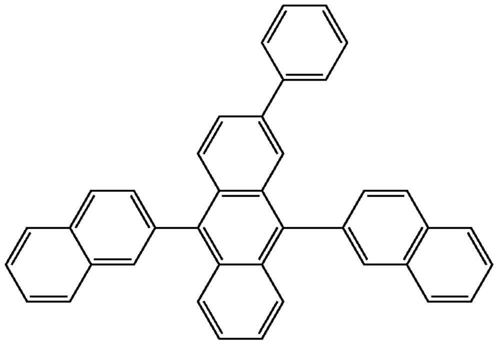

-continued
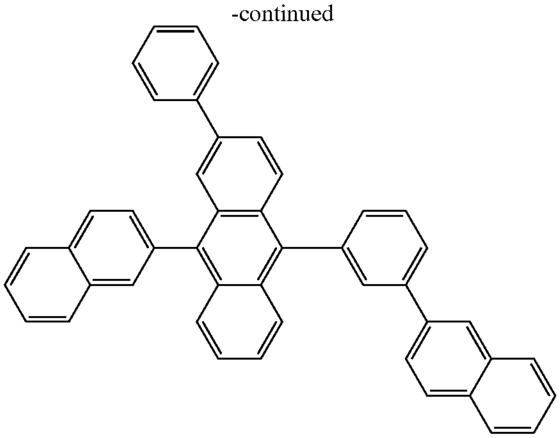
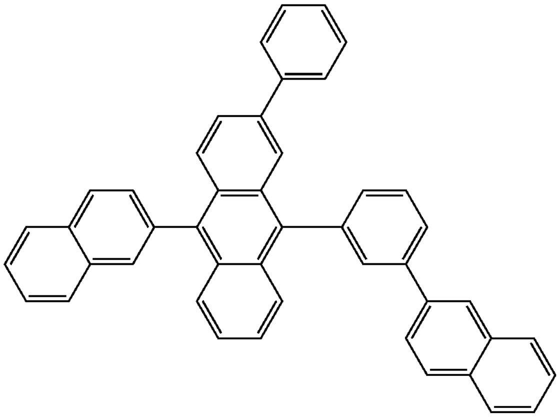
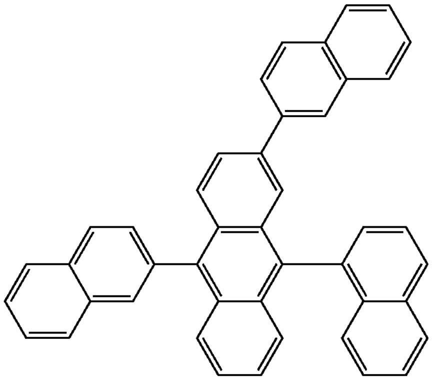
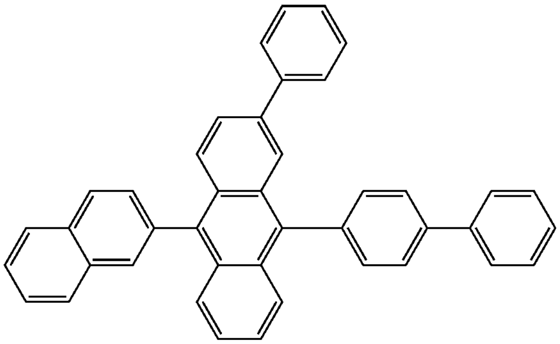
-continued
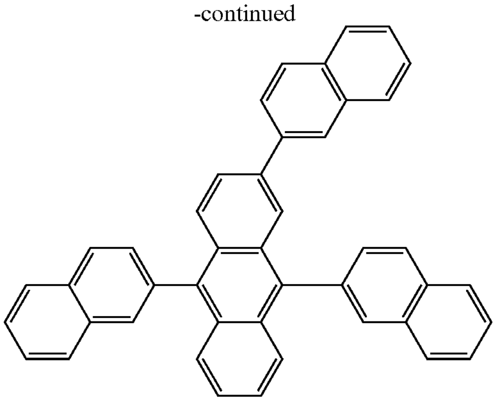
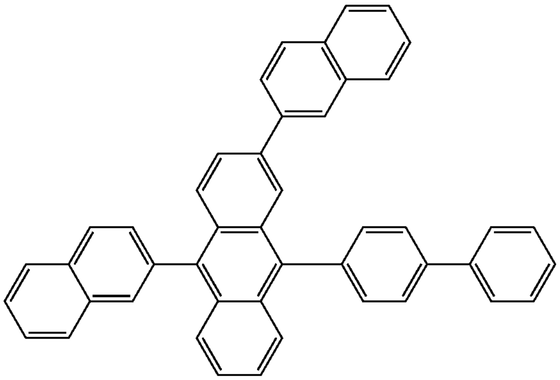
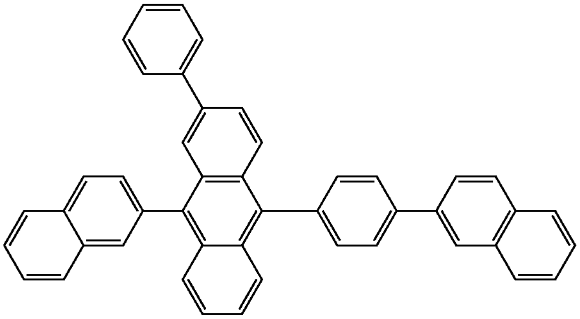
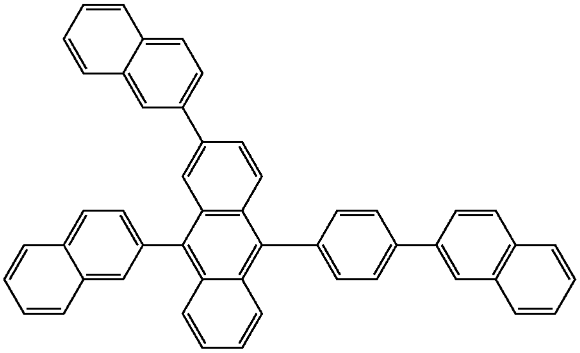

-continued
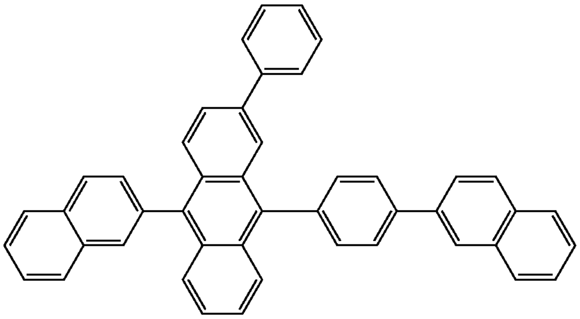
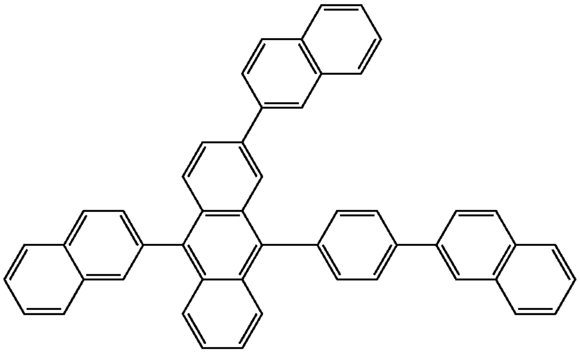
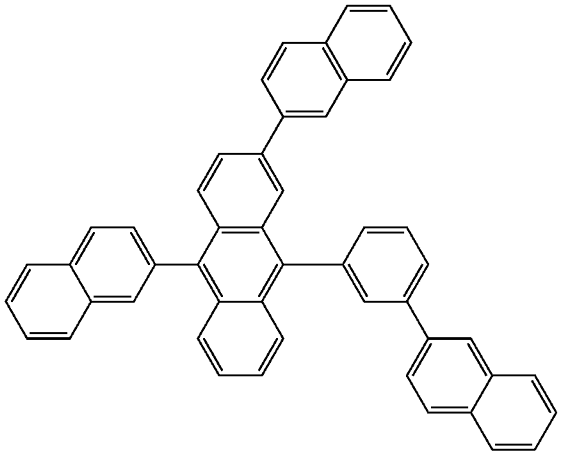
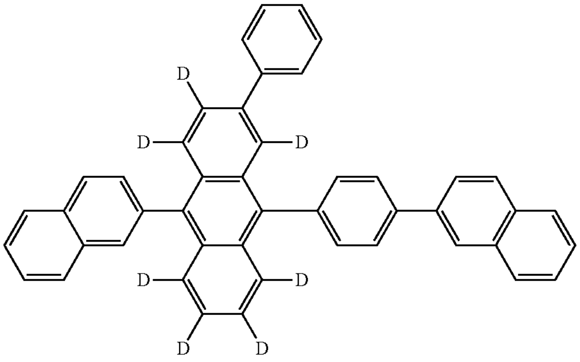
-continued
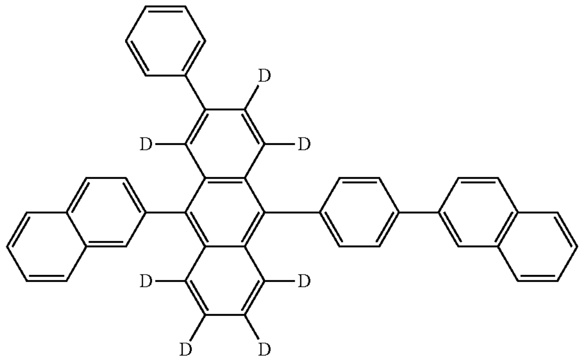
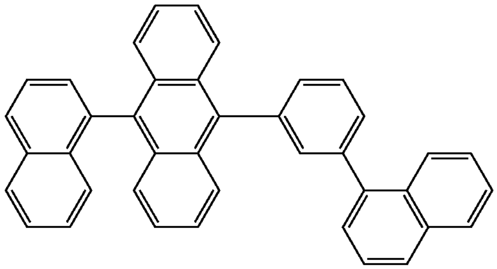
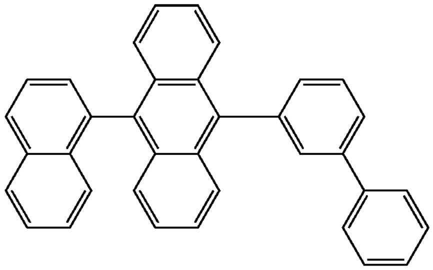
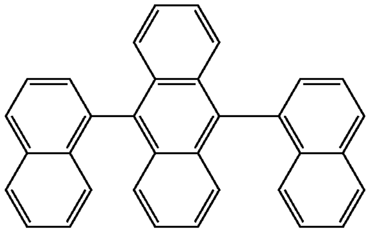
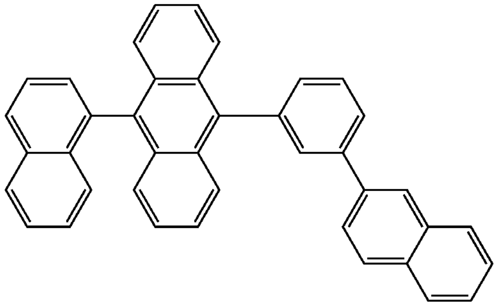
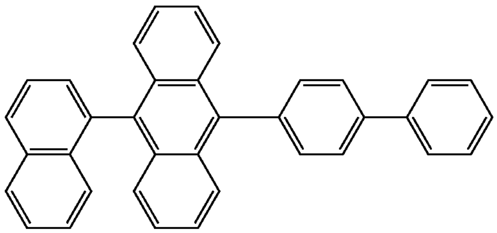

-continued
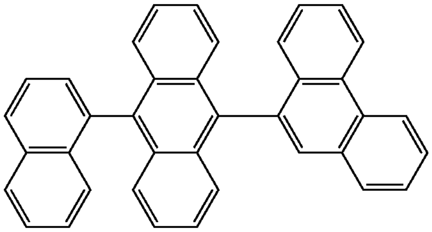
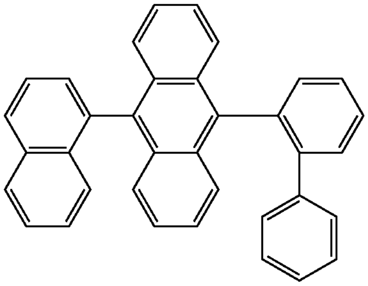
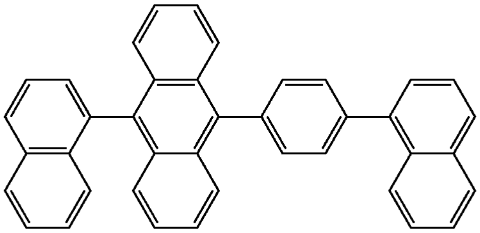
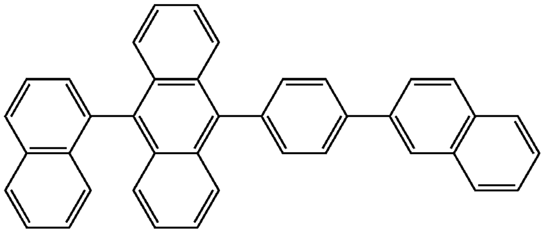
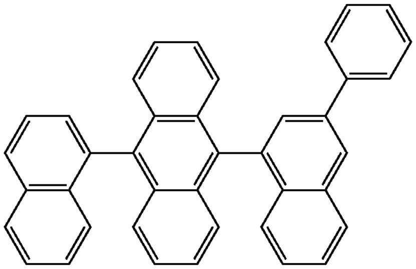
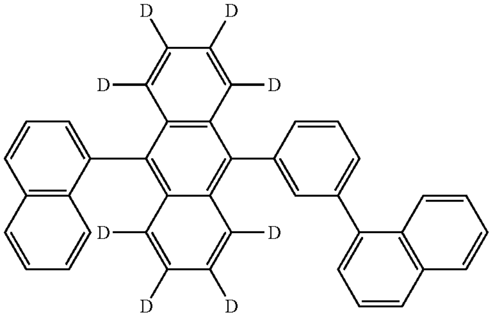
-continued
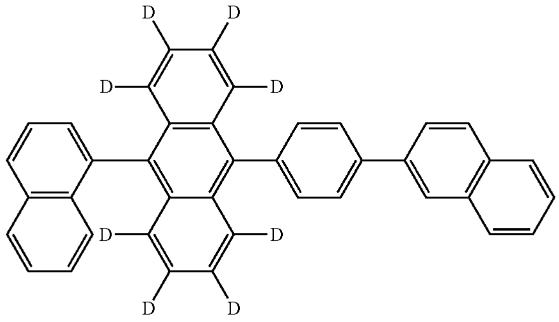
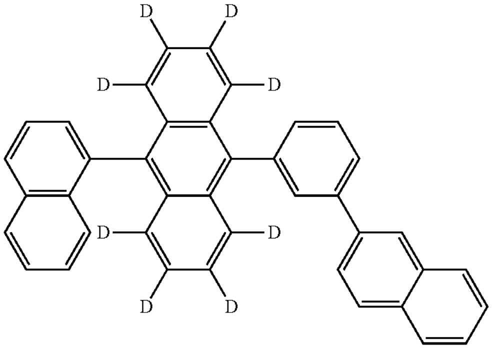
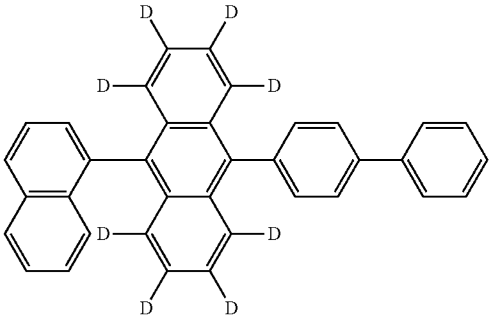
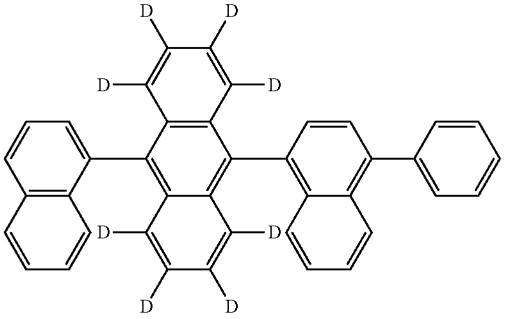
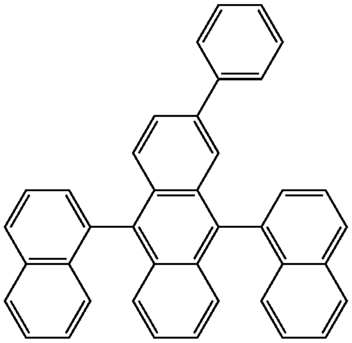

-continued
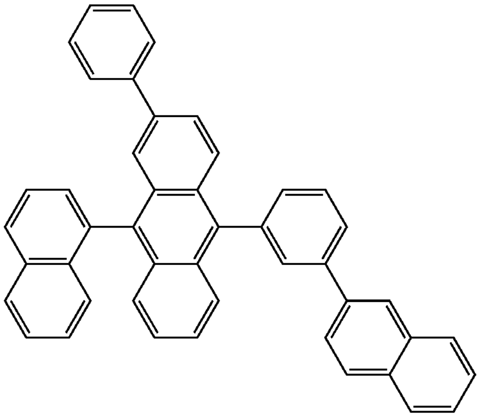
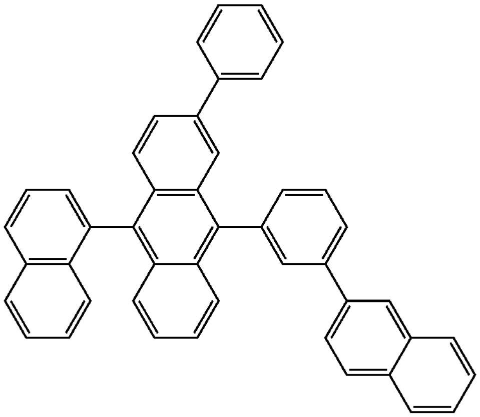
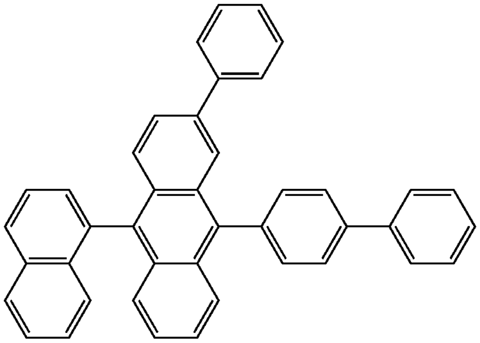
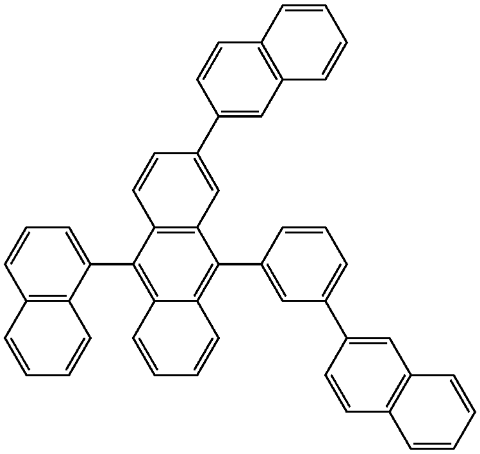
-continued
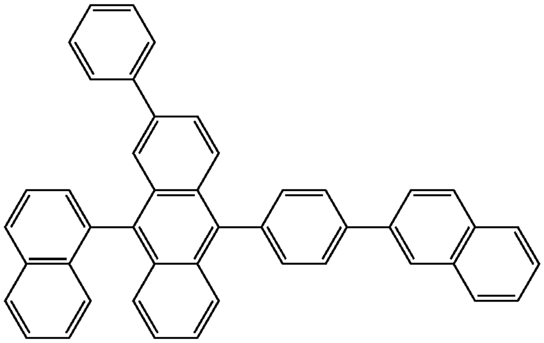
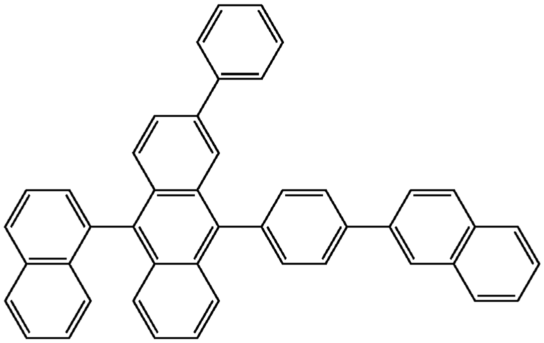
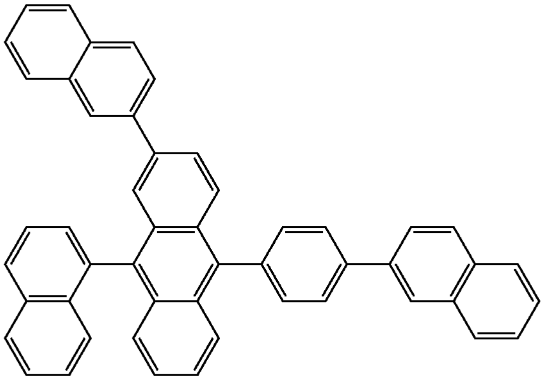
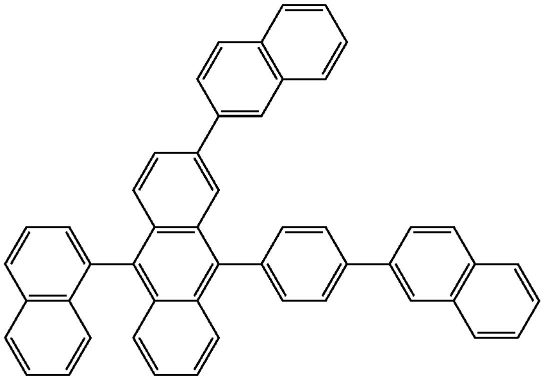

-continued
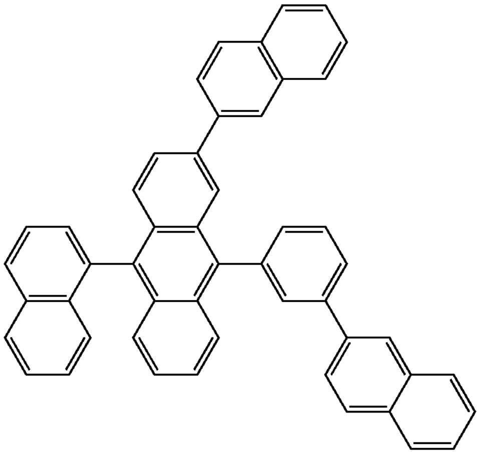
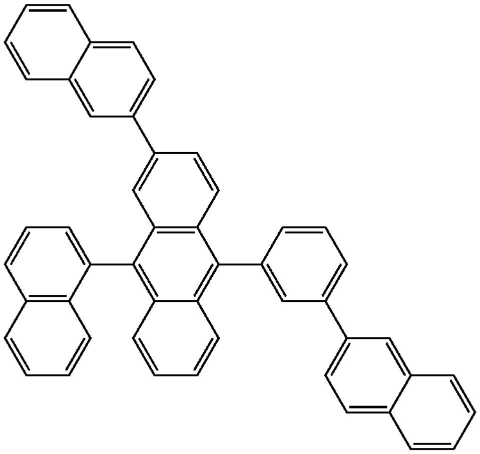
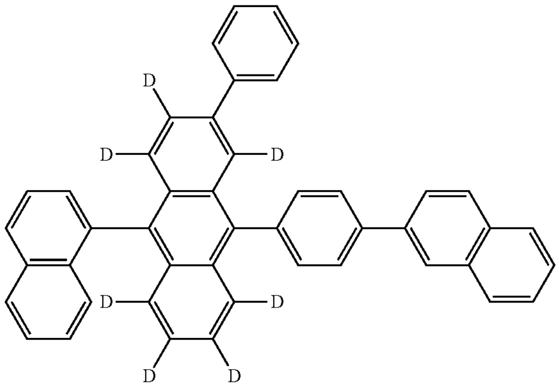
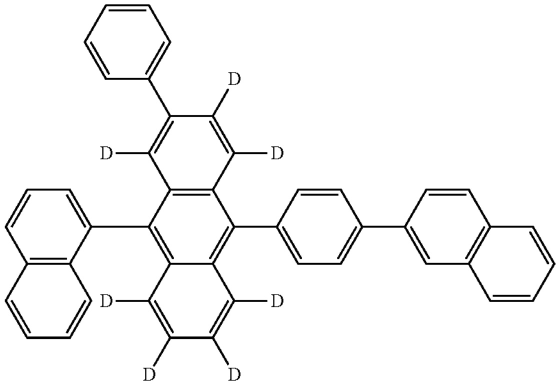
-continued
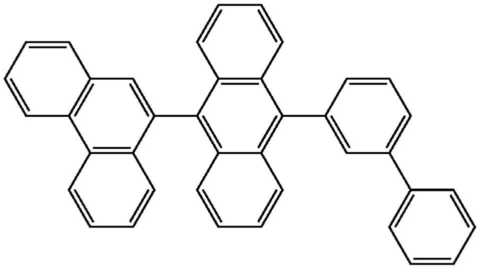
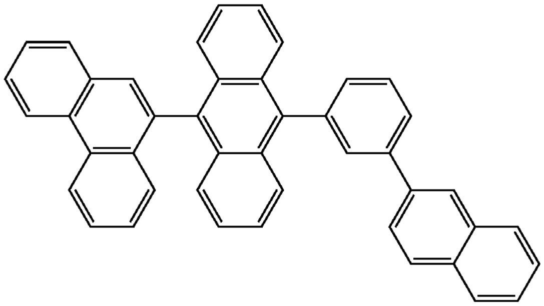
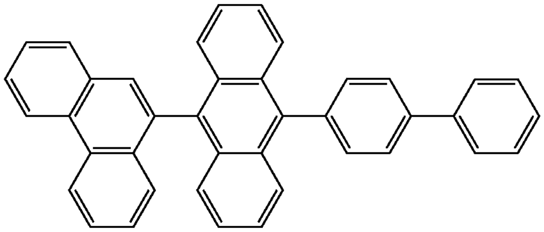
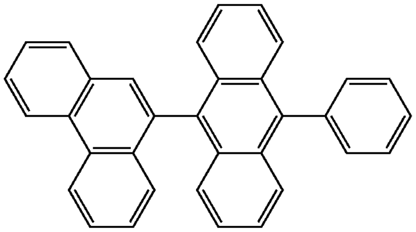
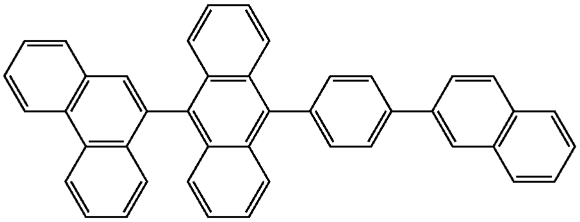
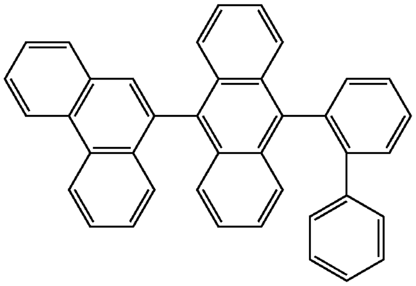

-continued
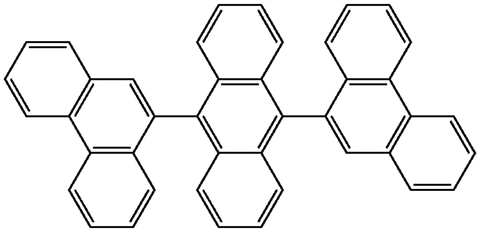
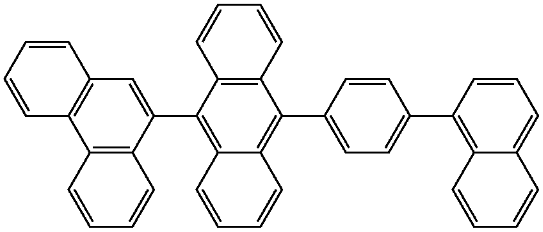
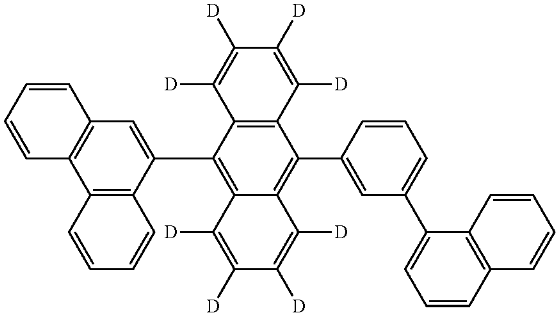
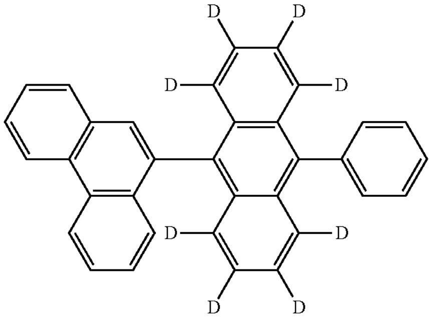
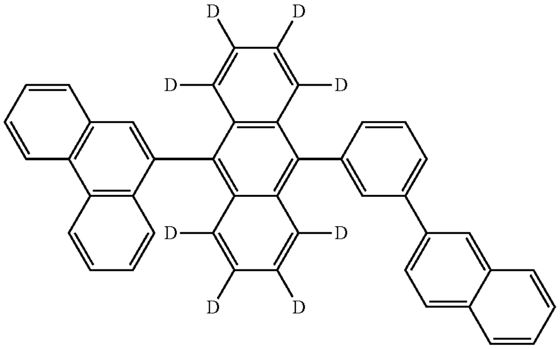
-continued
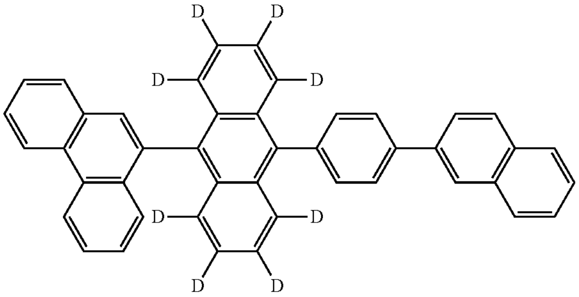
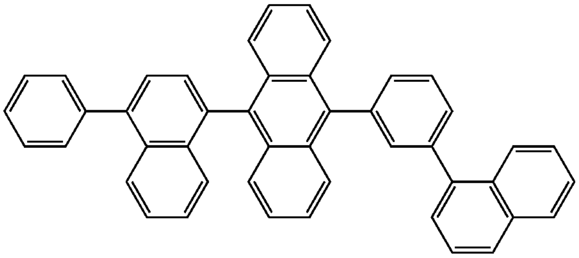
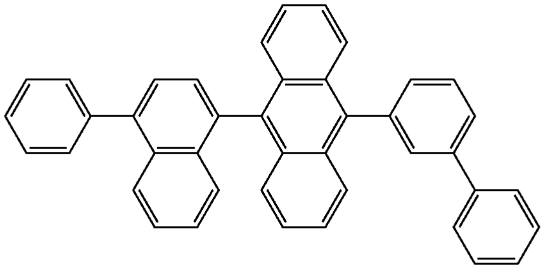
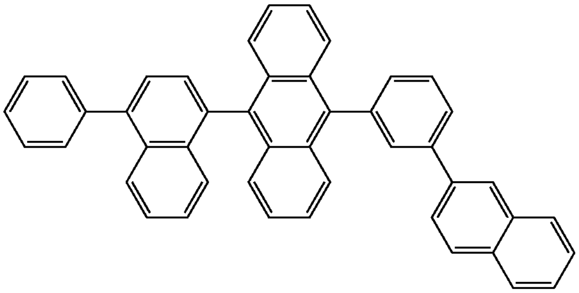
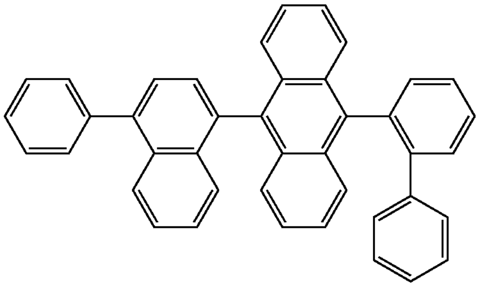
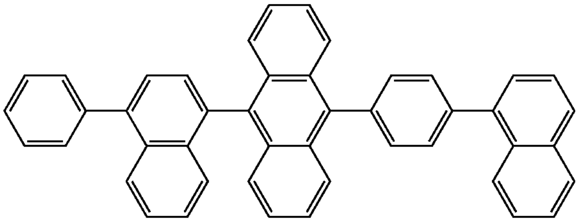

-continued
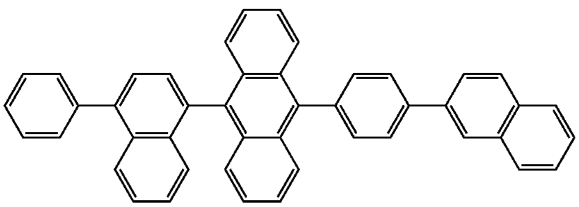
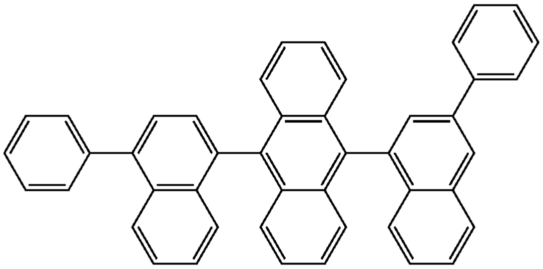
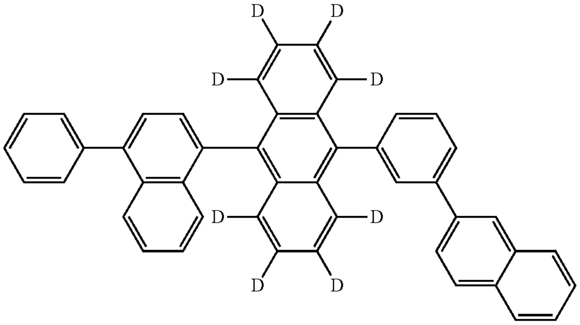
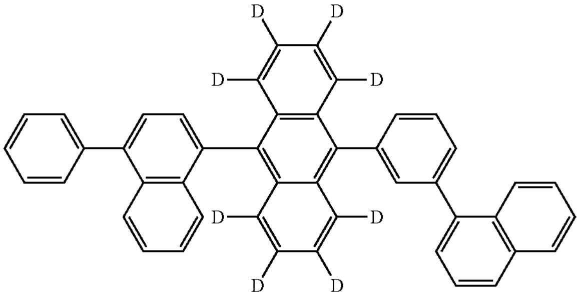
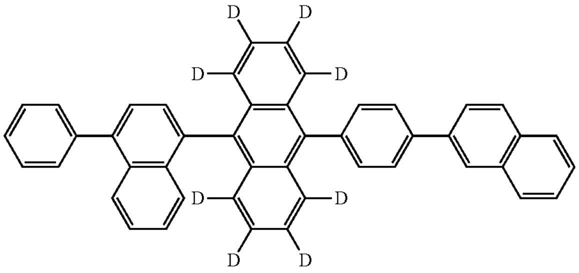
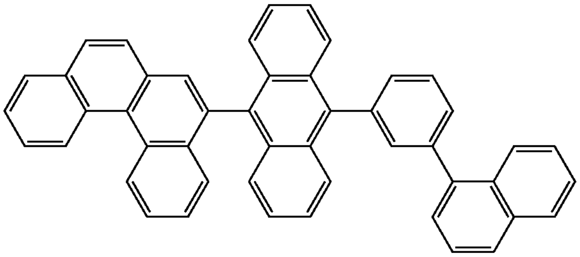
-continued
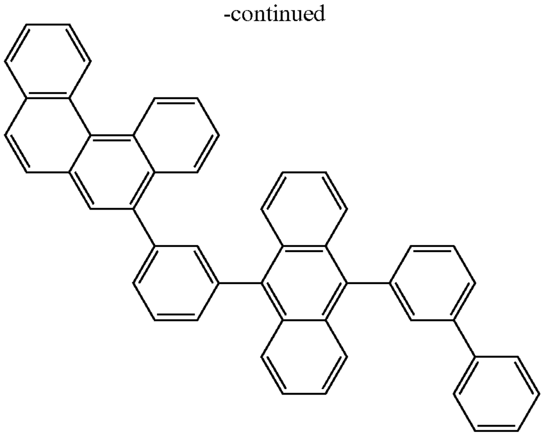
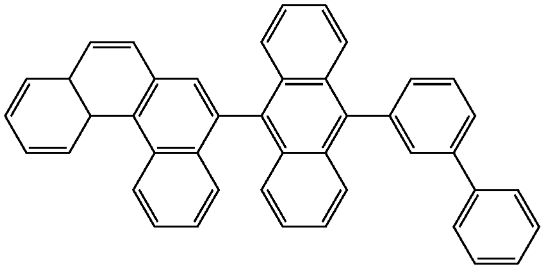
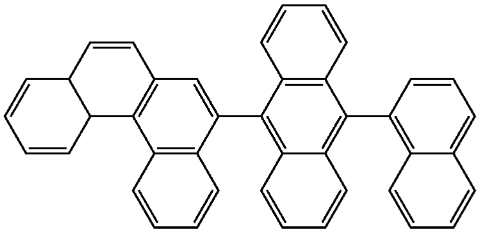
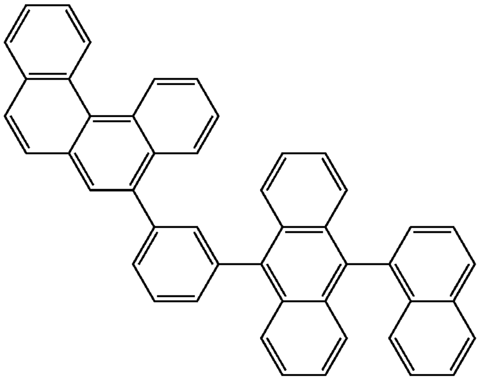
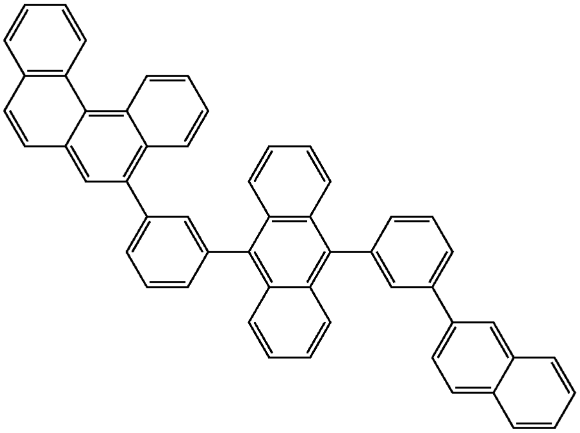

-continued
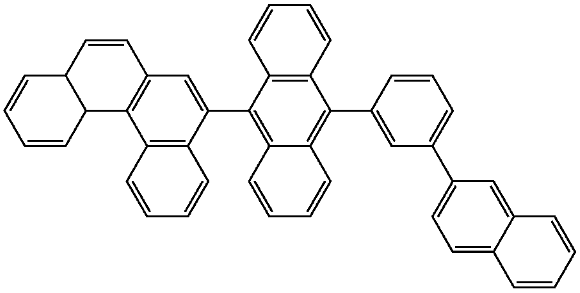
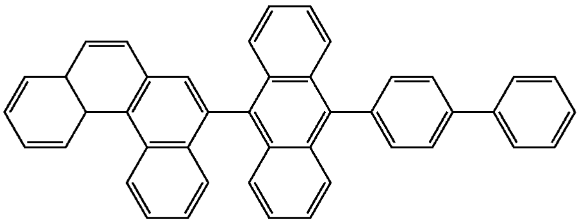
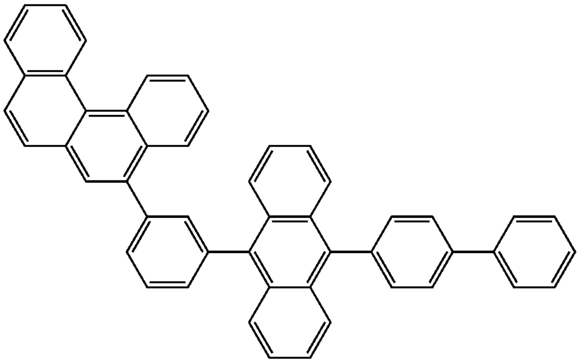
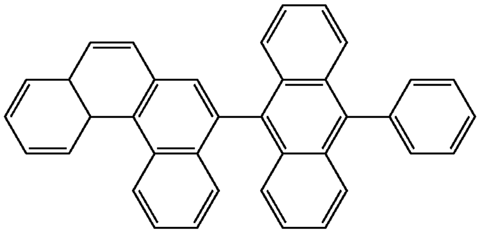
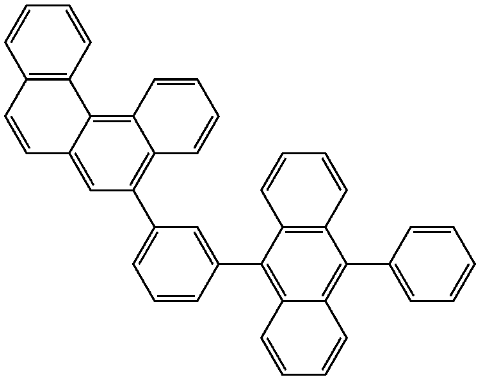
-continued
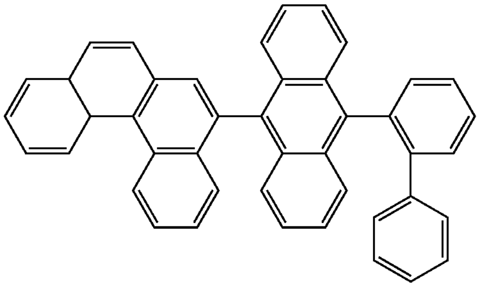
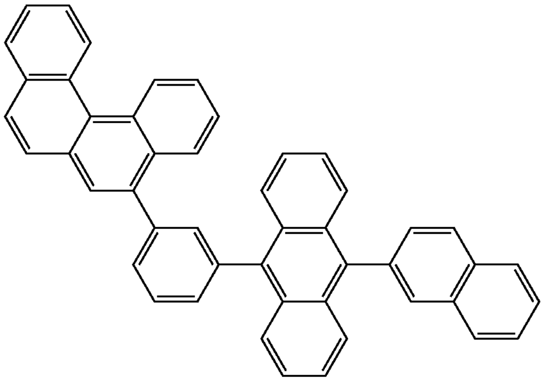
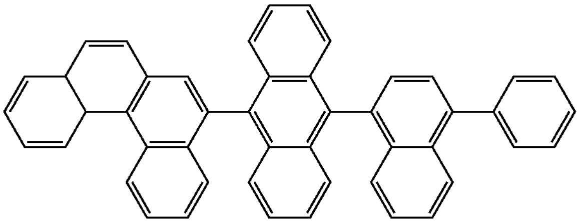
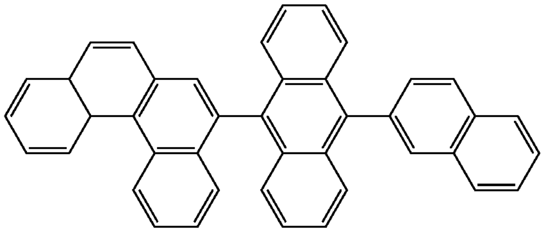
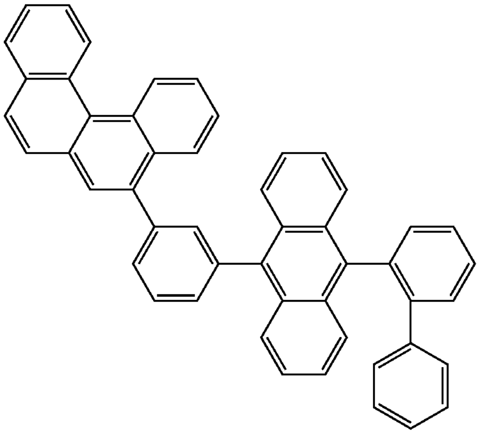

-continued
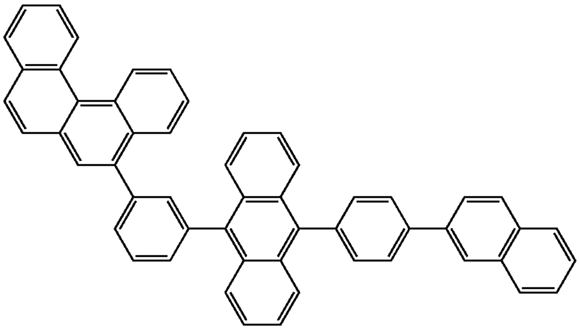
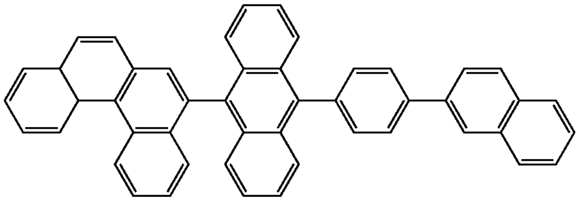
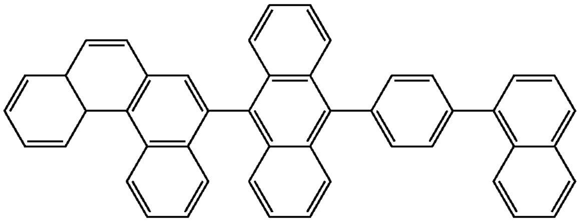
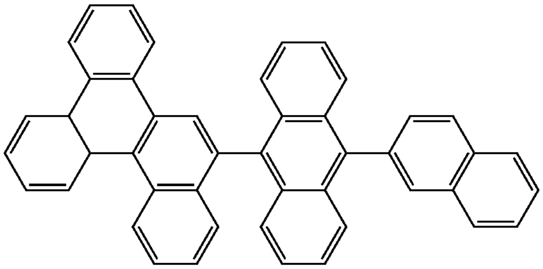
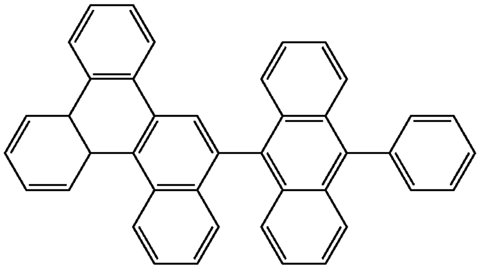
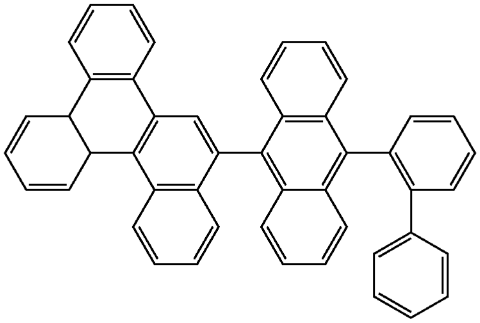
-continued
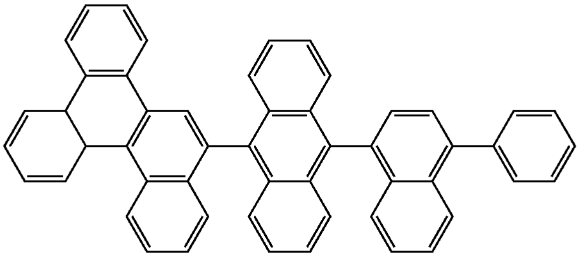
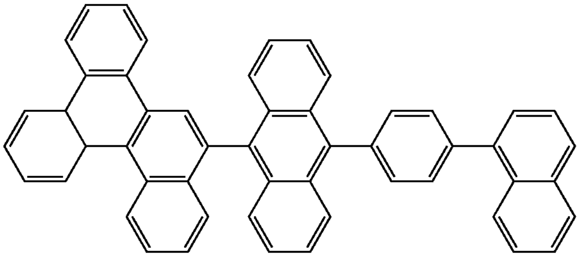
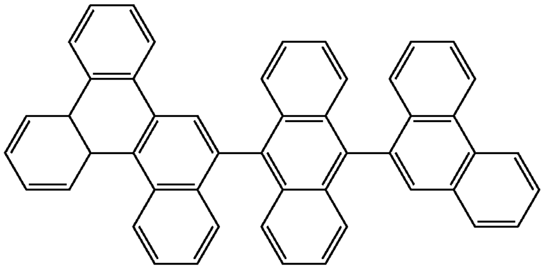
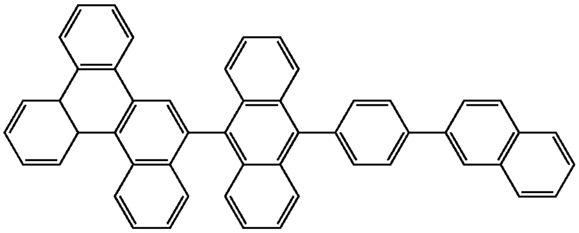
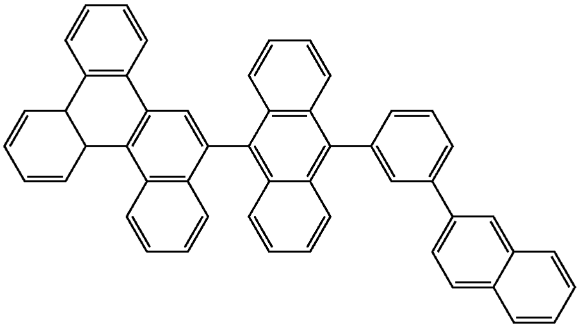
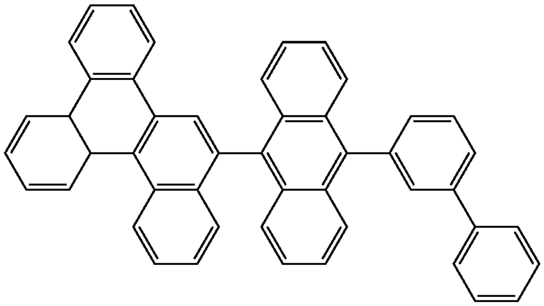

-continued
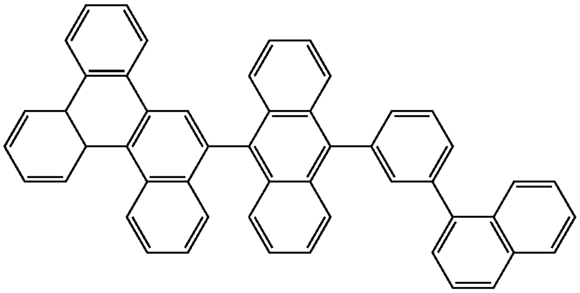
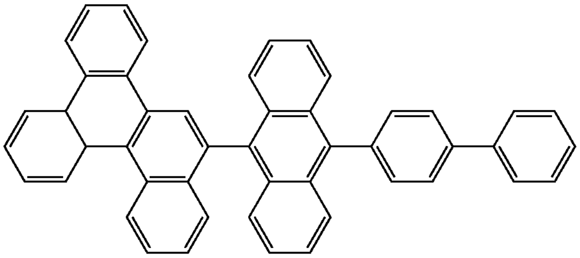
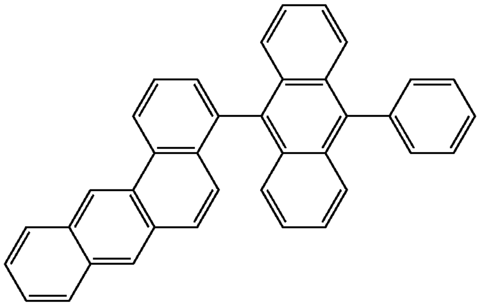
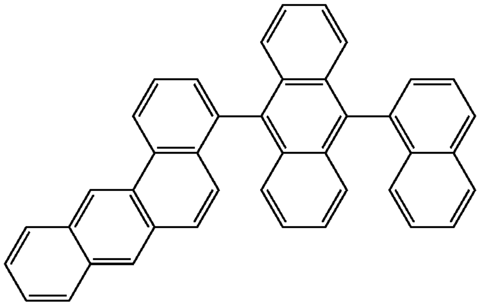
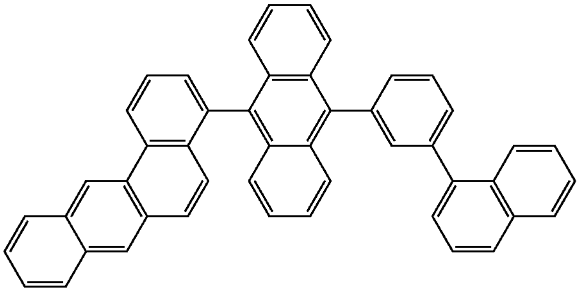
-continued
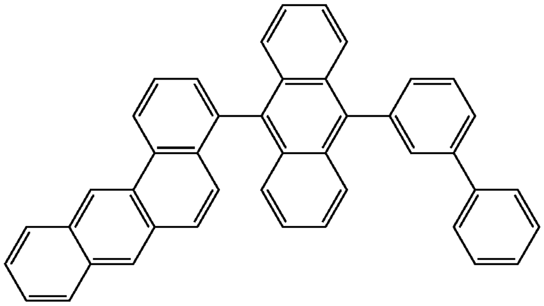
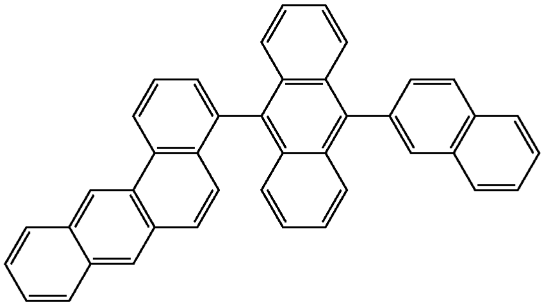
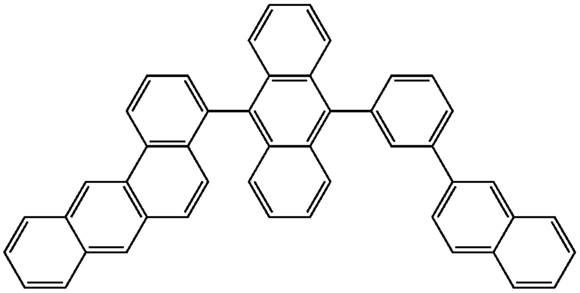
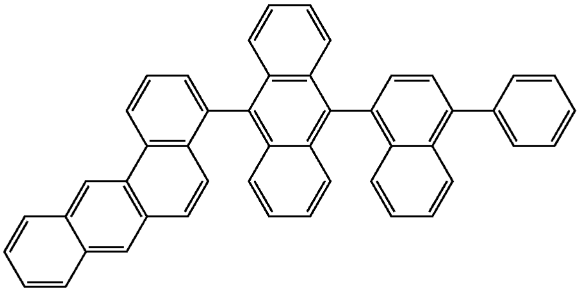
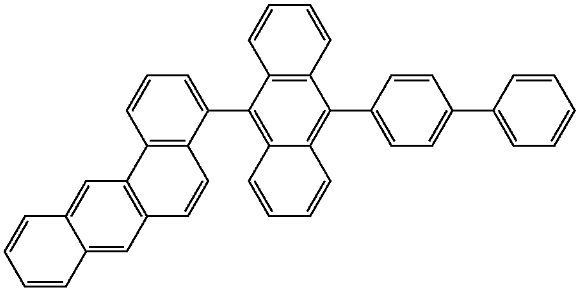

-continued
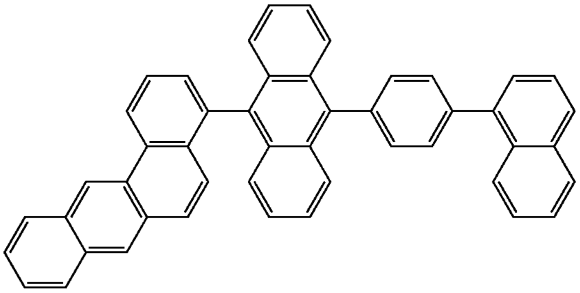
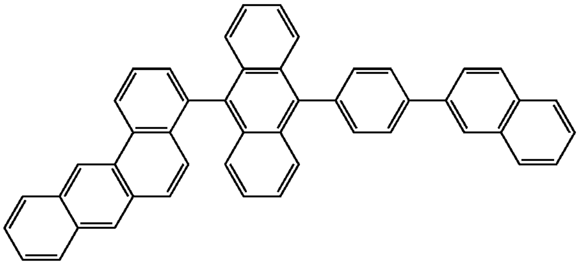
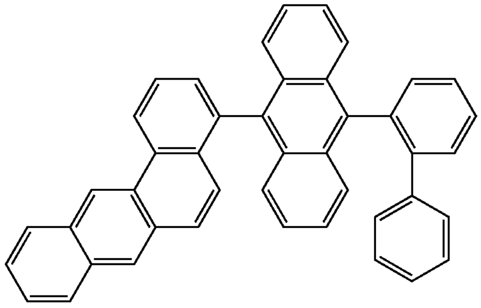
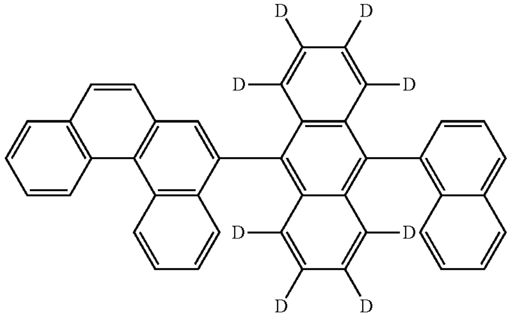
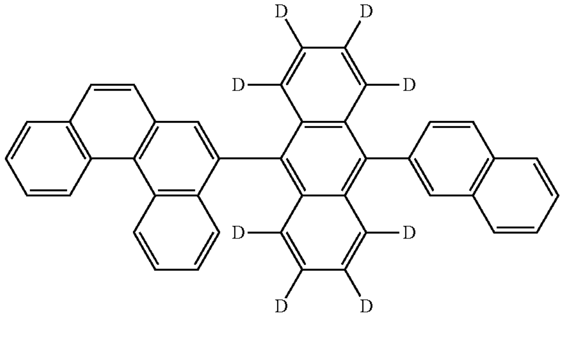
-continued
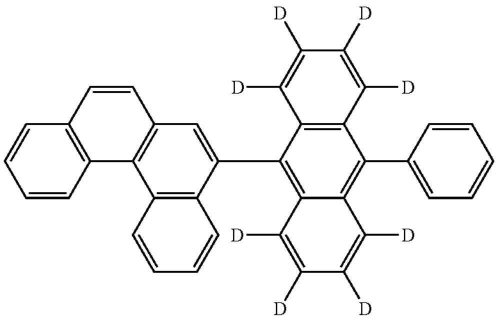
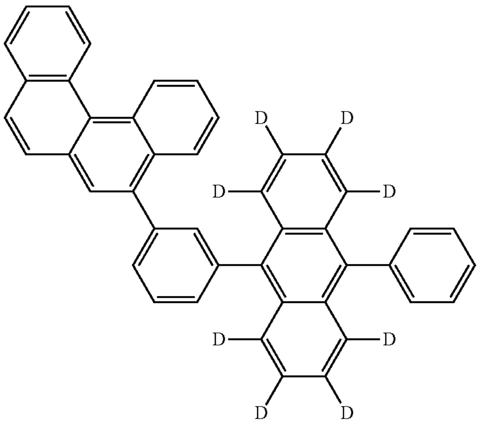
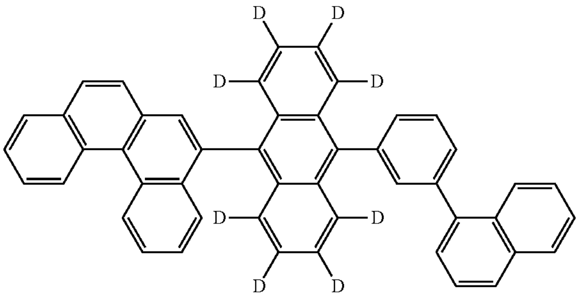
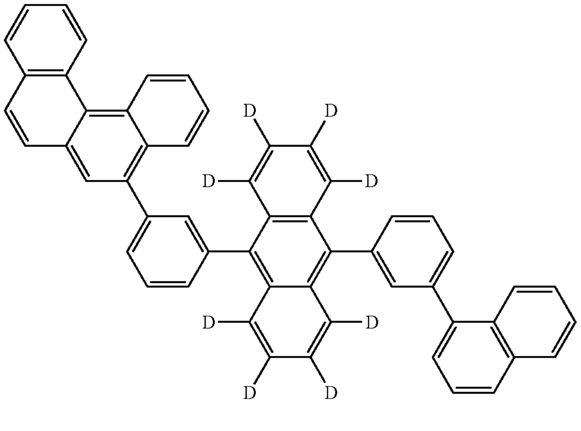

-continued
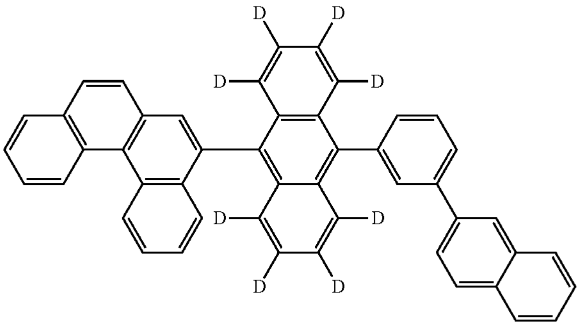
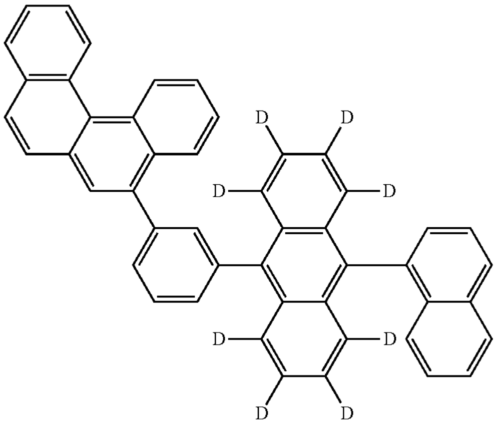
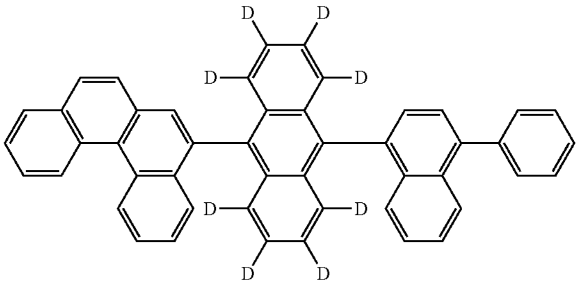
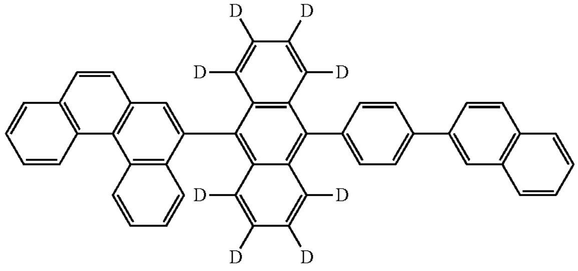
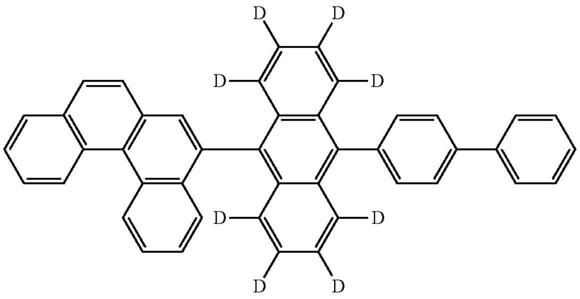
-continued
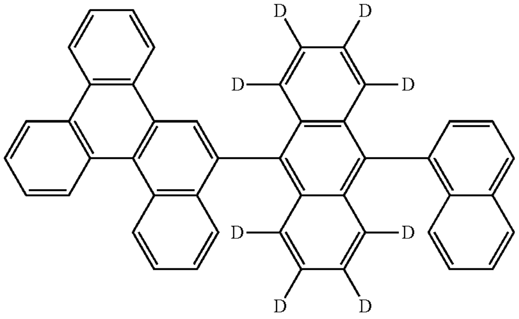
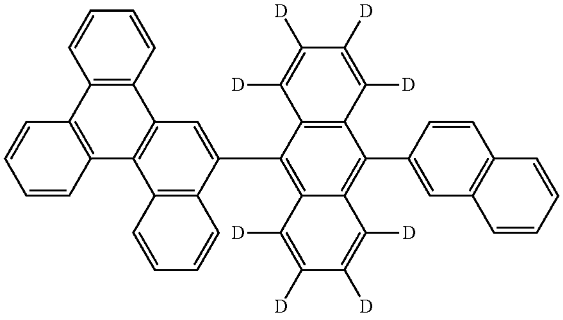
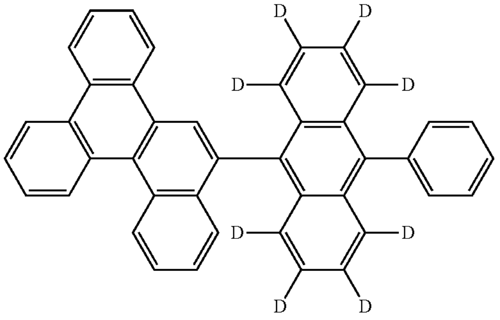
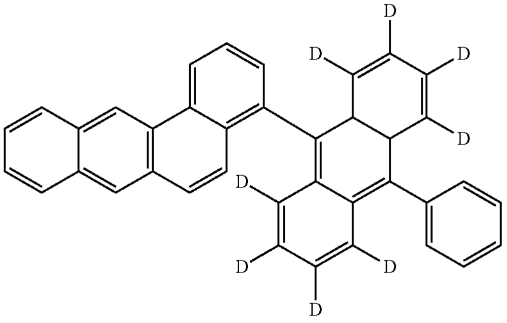
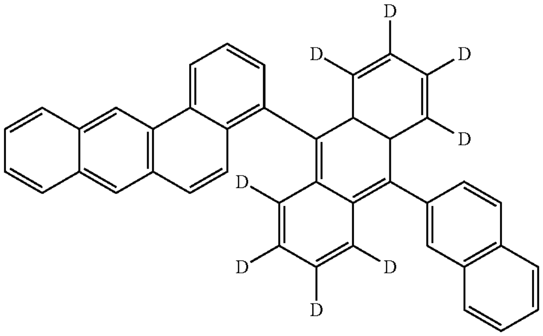

-continued
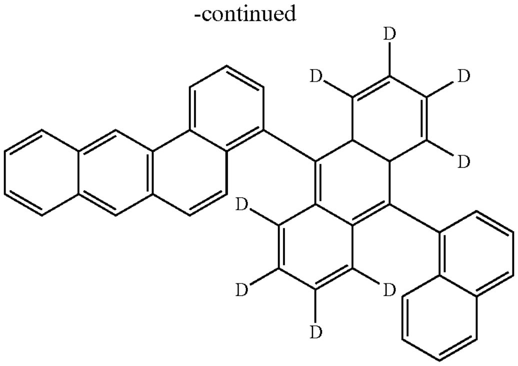
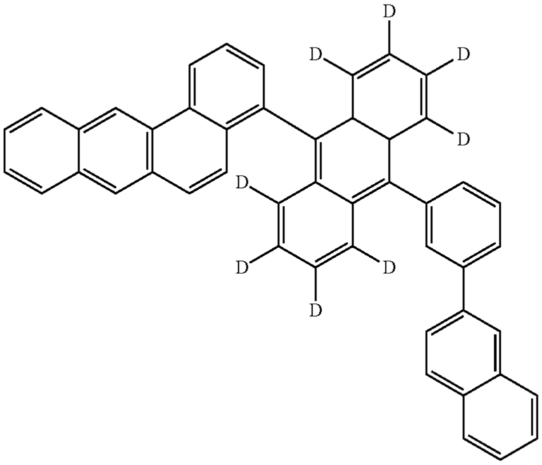
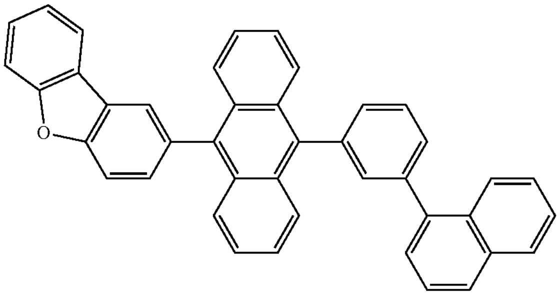
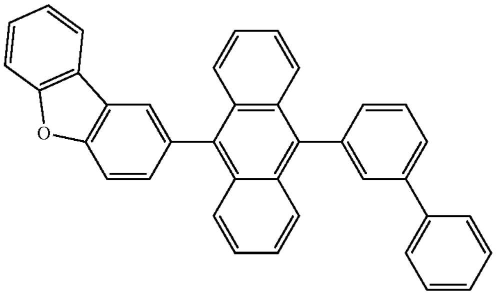
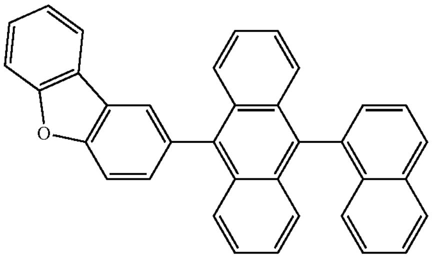
-continued
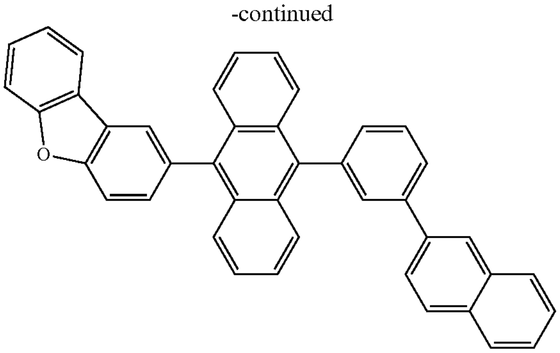
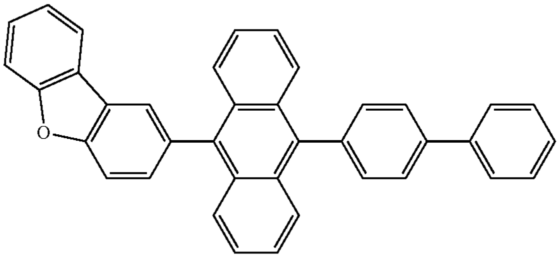
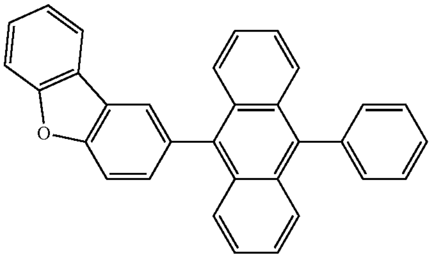
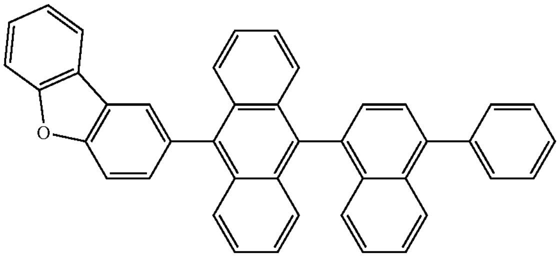
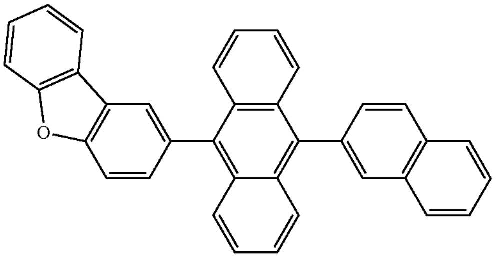
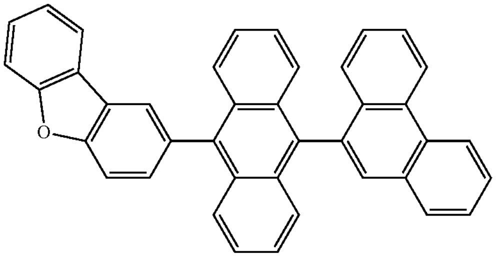

-continued
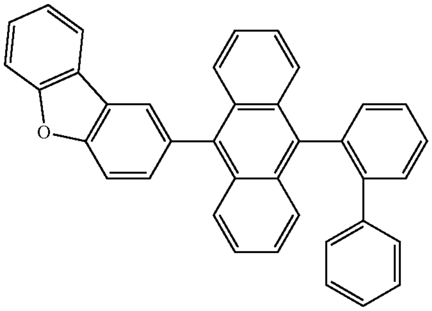
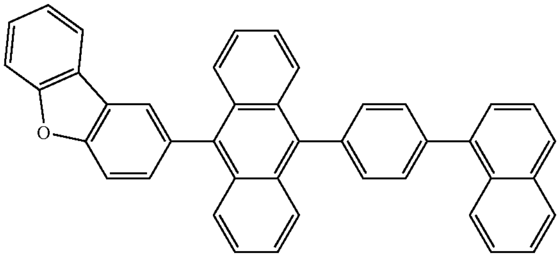
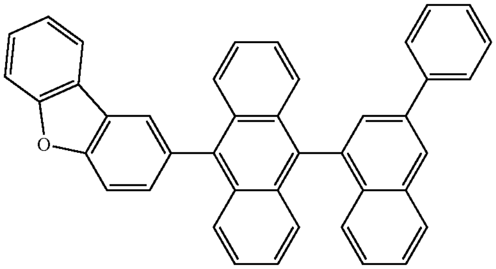
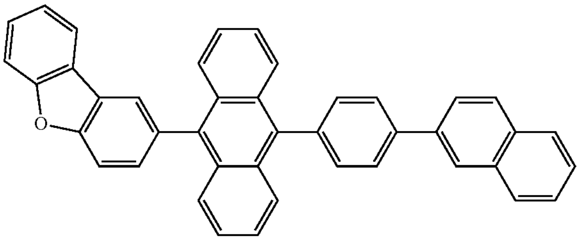
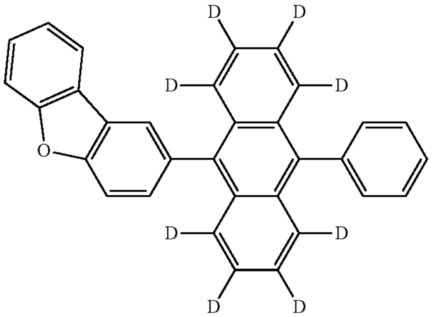
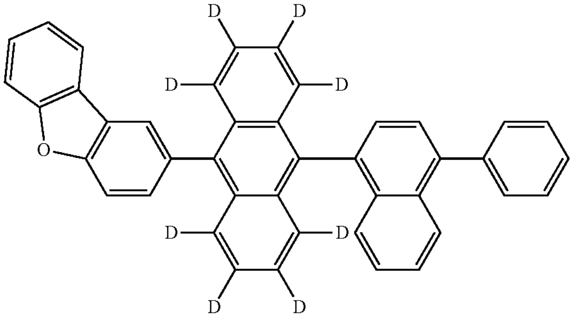
-continued
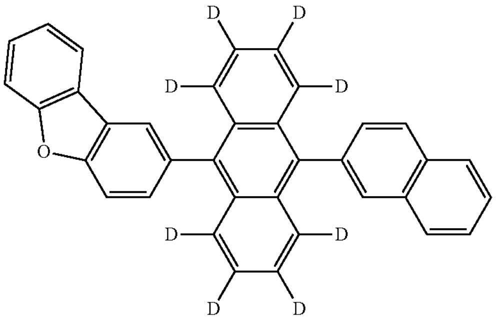
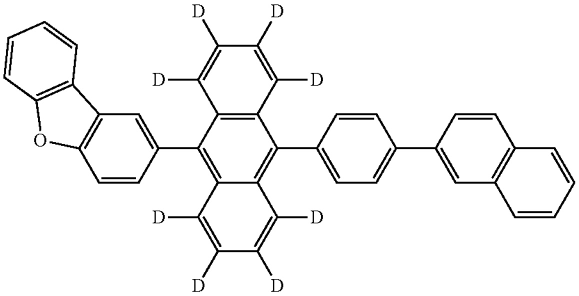
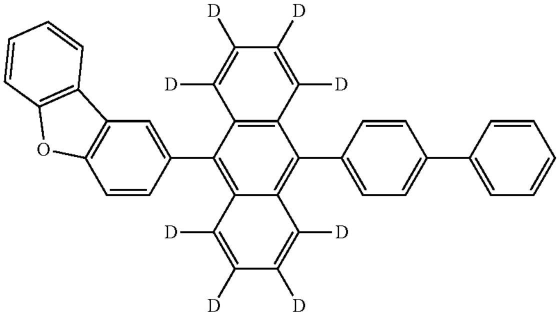
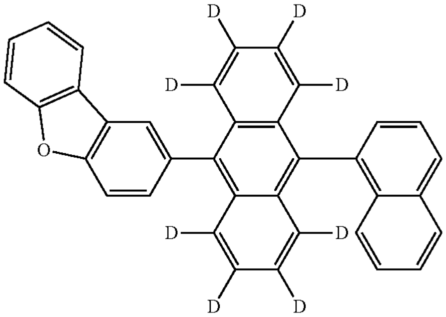
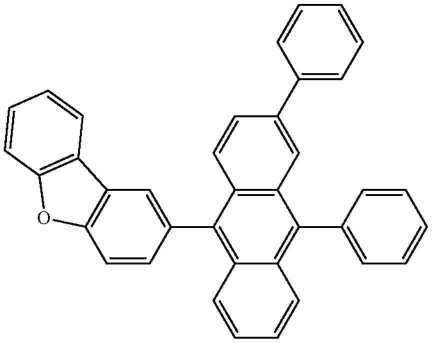

-continued
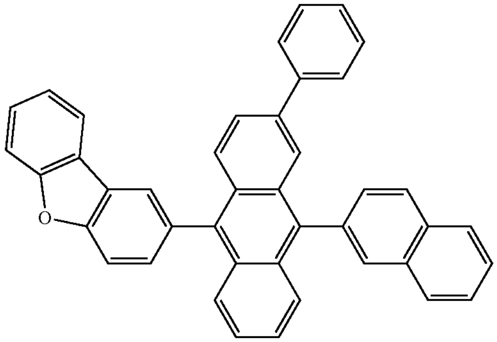
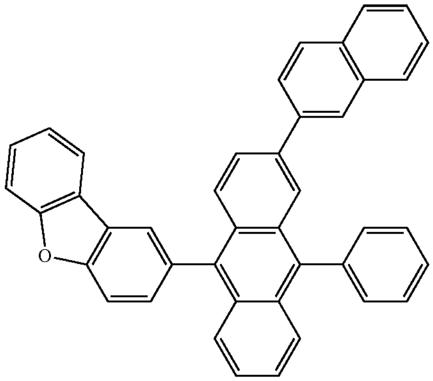
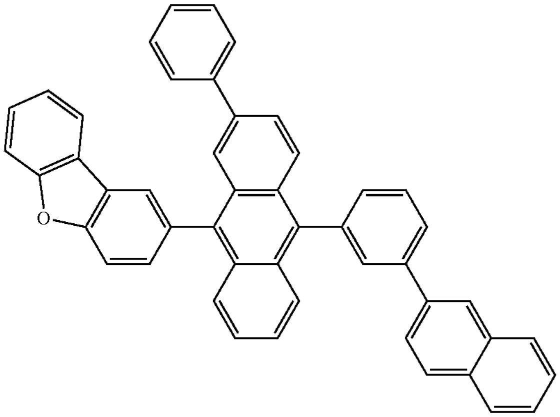
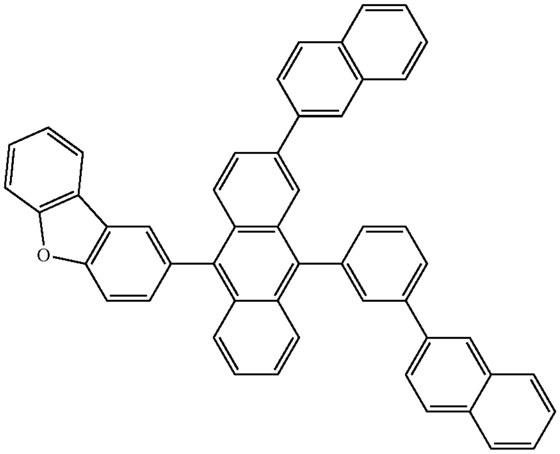
-continued
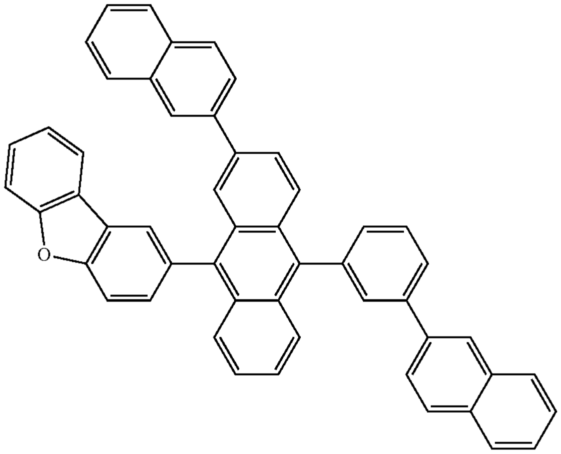
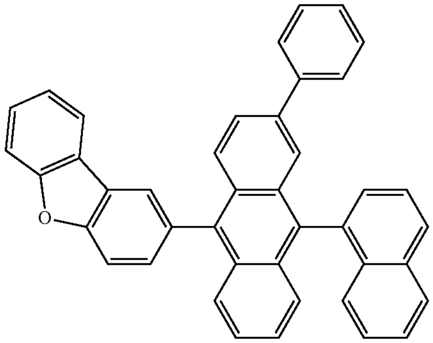
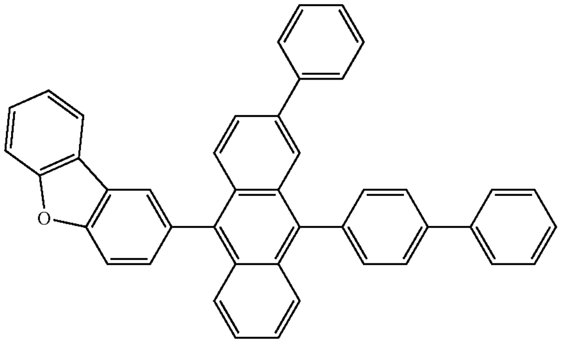
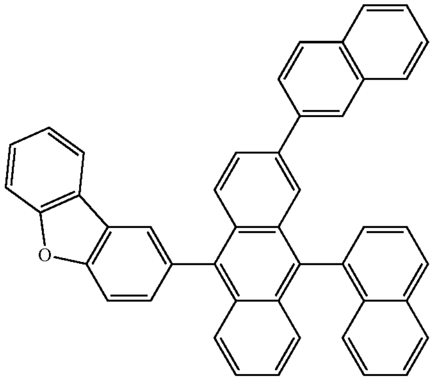

-continued
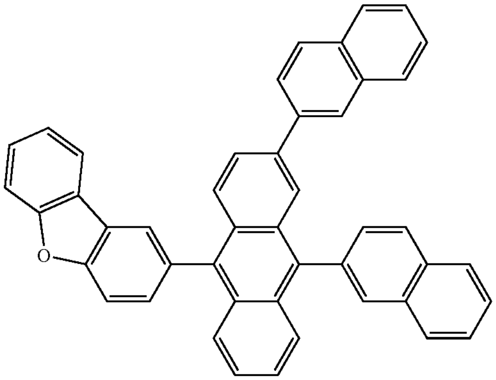
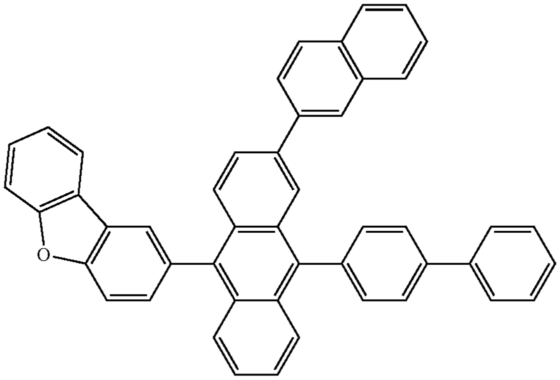
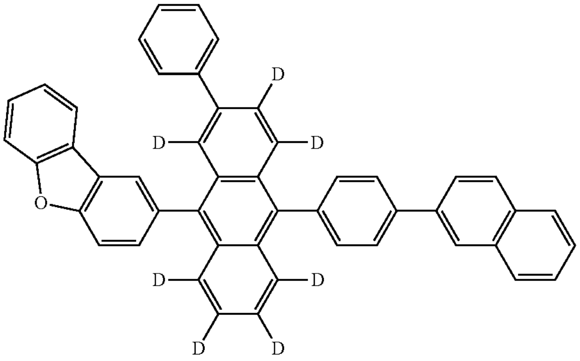
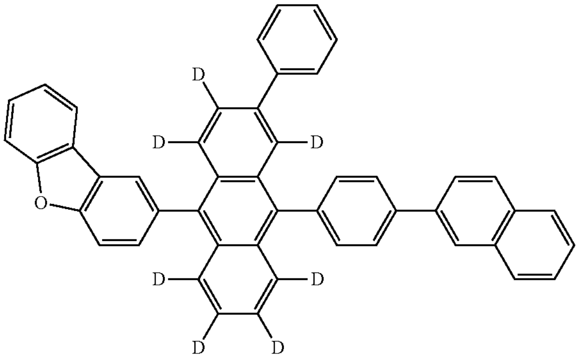
-continued
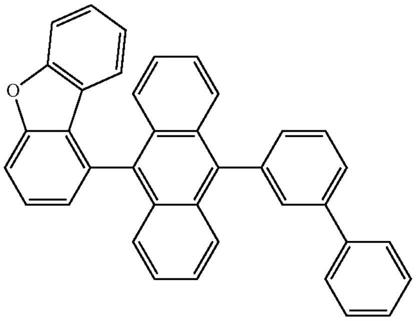
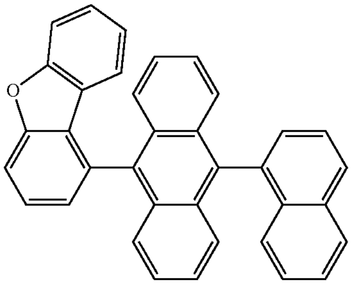
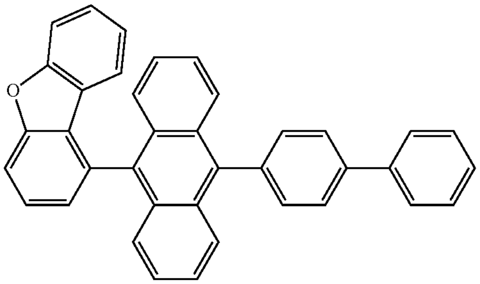
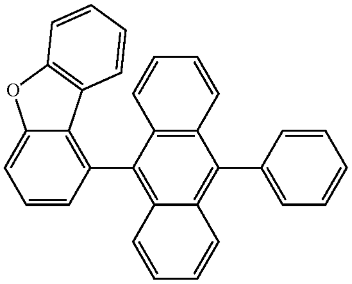
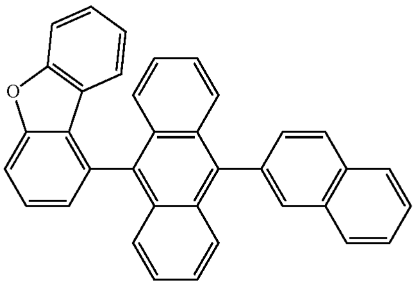

-continued
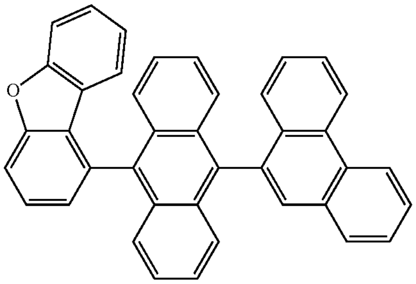
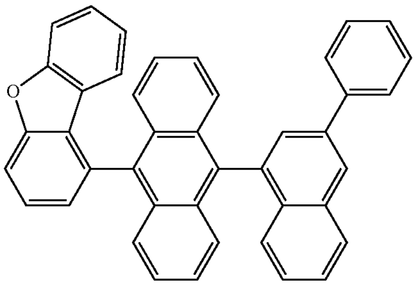
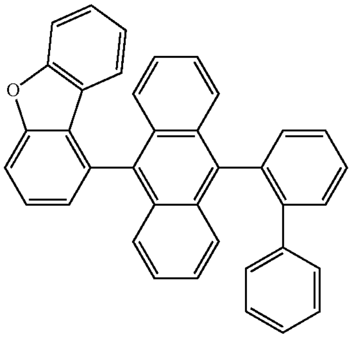
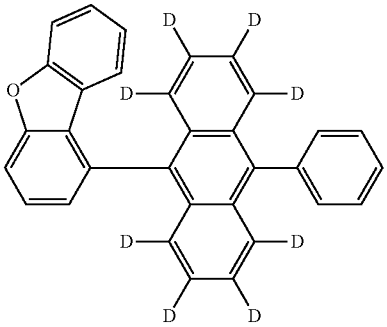
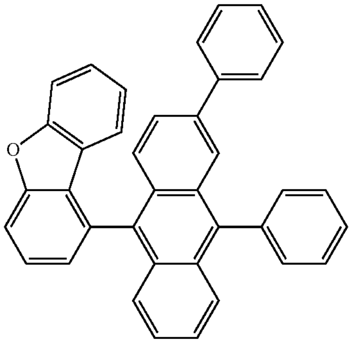
-continued
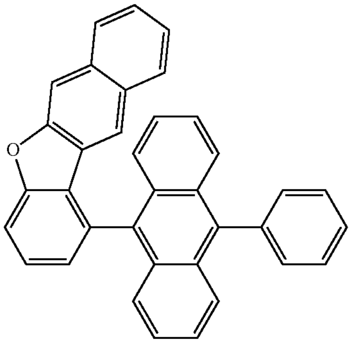
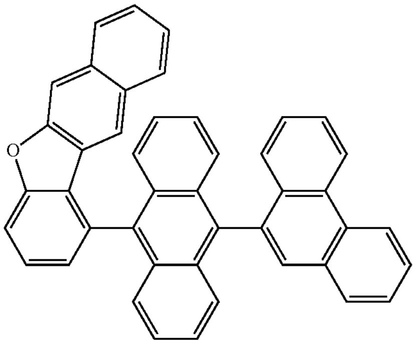
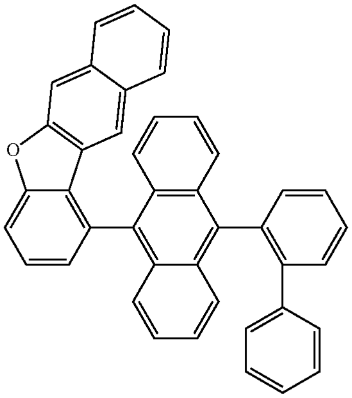
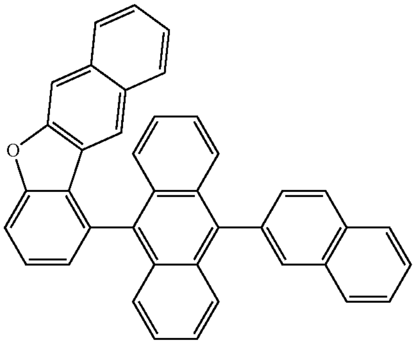

-continued
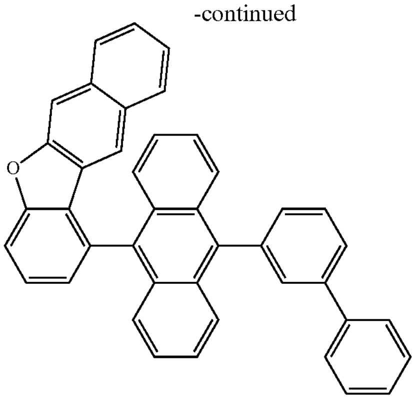
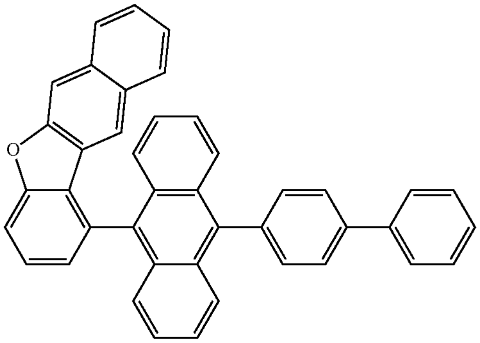
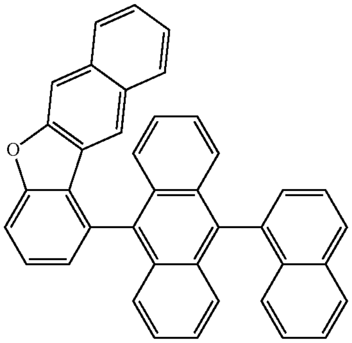
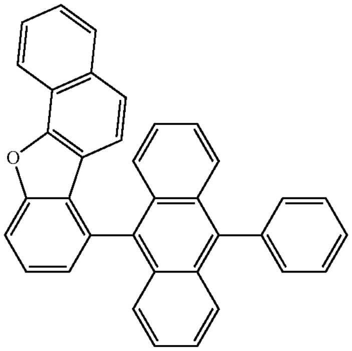
-continued
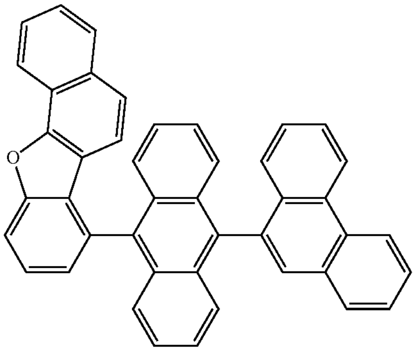
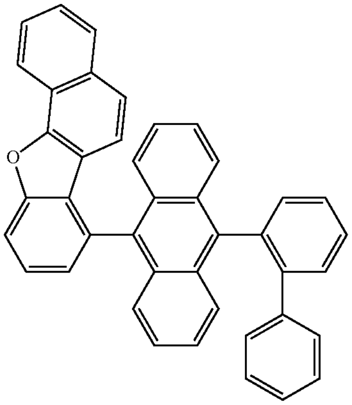
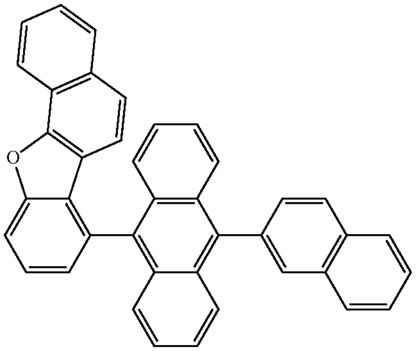
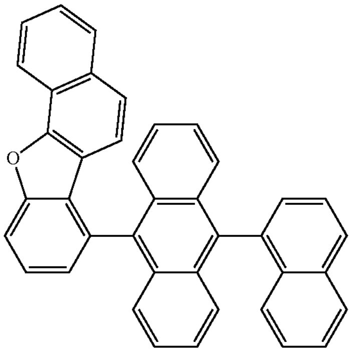

-continued
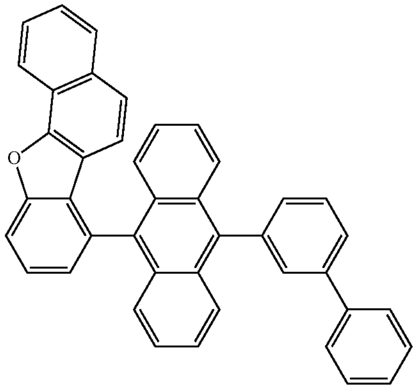
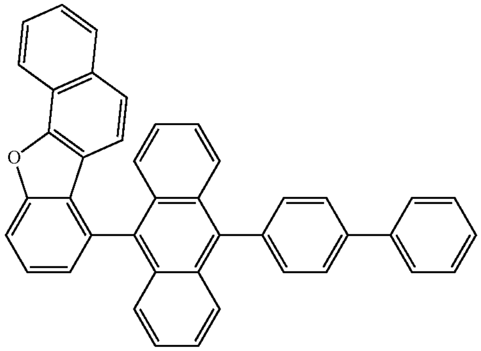
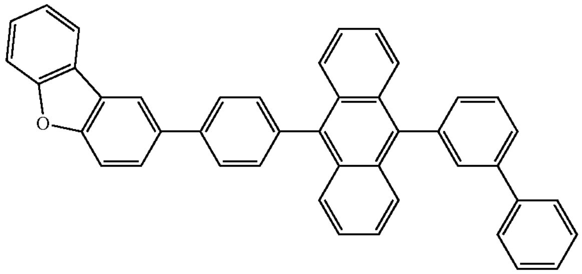
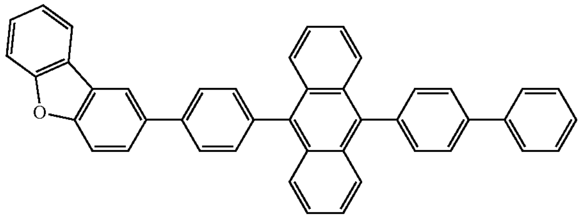
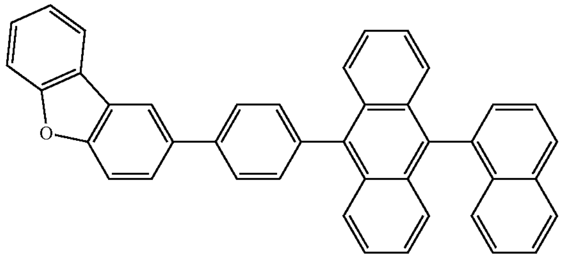
-continued
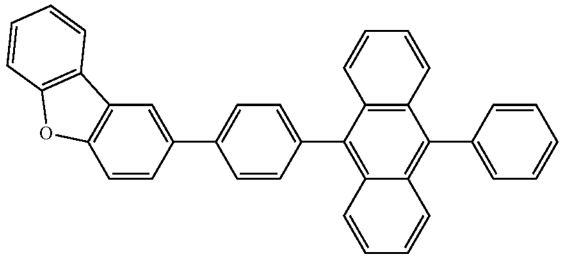
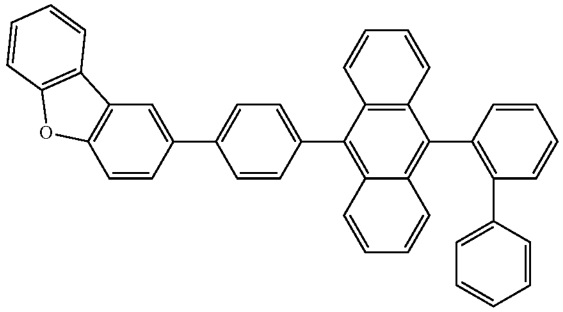
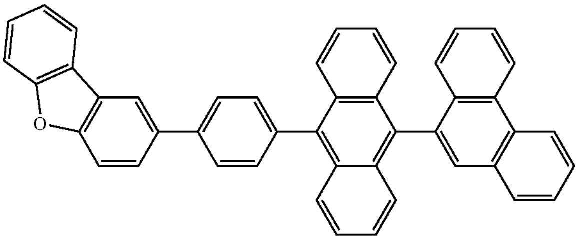
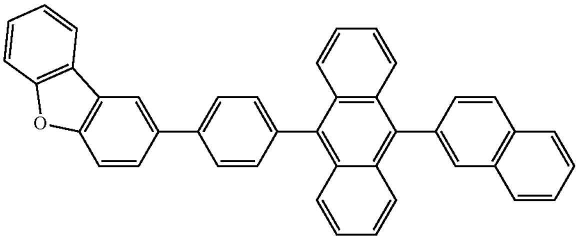
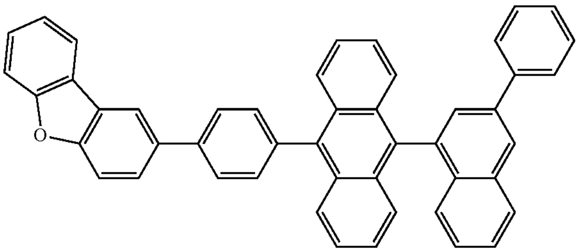
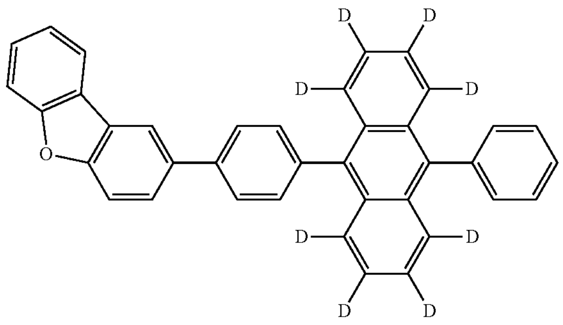

-continued
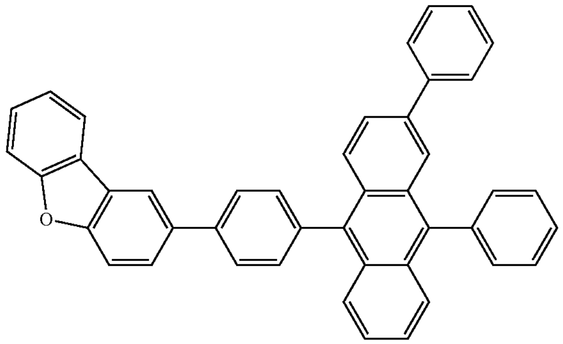
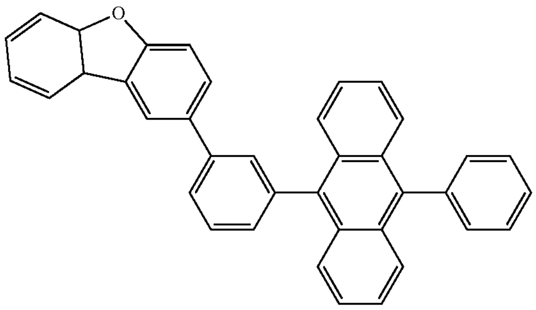
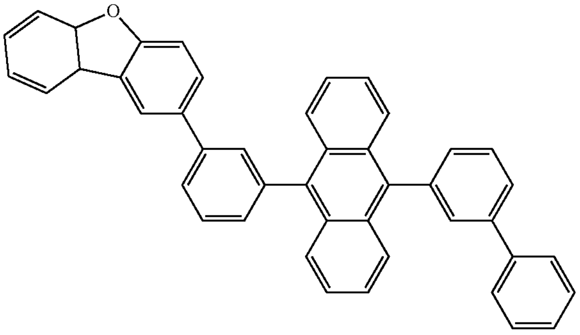
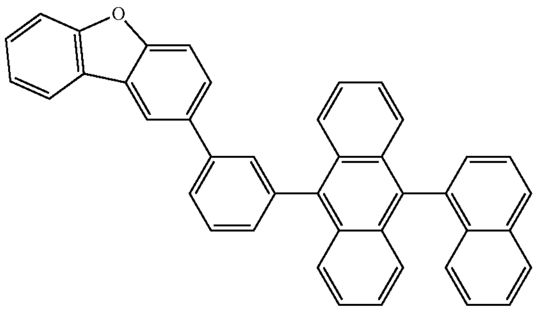
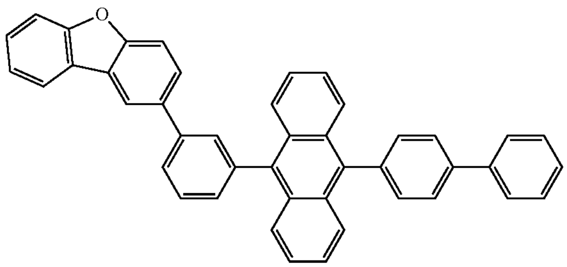
-continued
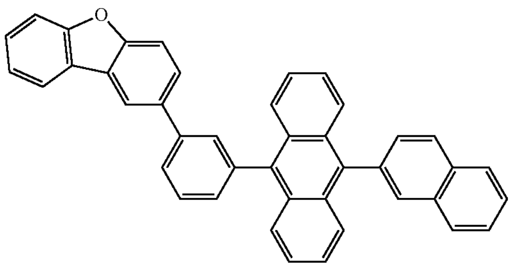
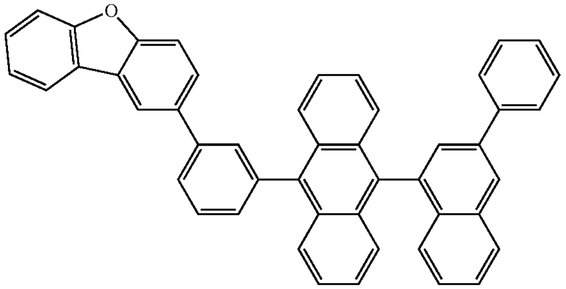
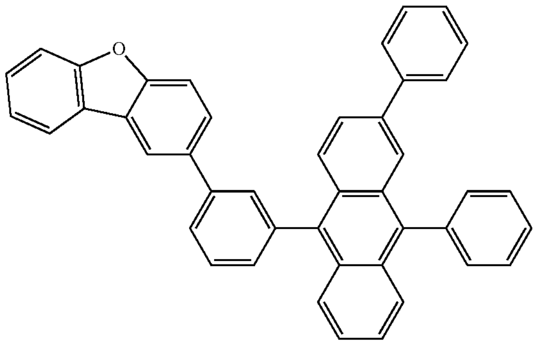
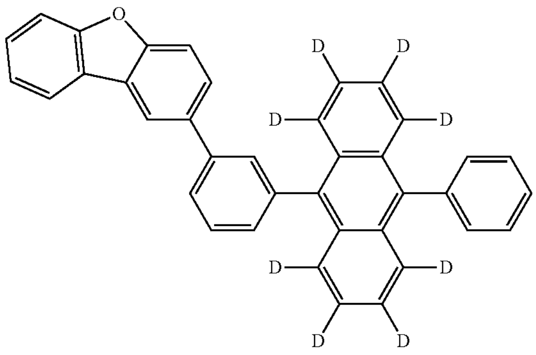 [SMILES: [2H]c1c([2H])c([2H])c2c(-c3cccc(-c4ccc5oc6ccccc6c5c4)c3)c3c([2H])c([2H])c([2H])c([2H])c3c(-c3ccccc3)c2c1[2H]]
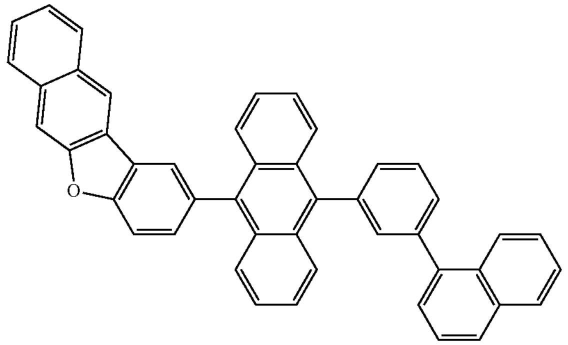

-continued
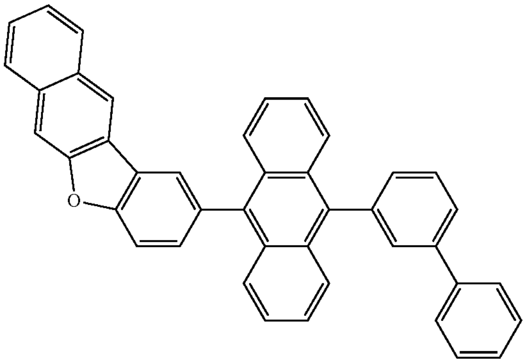
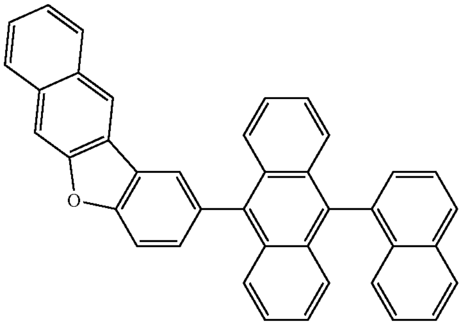
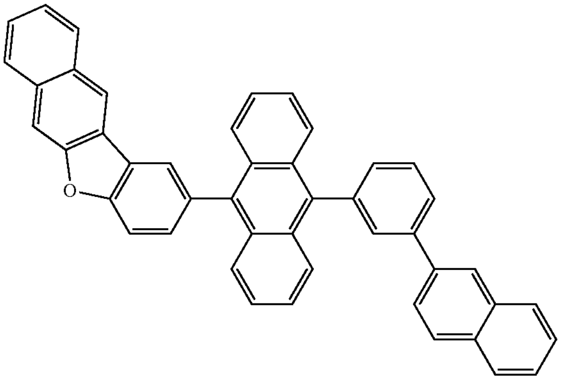
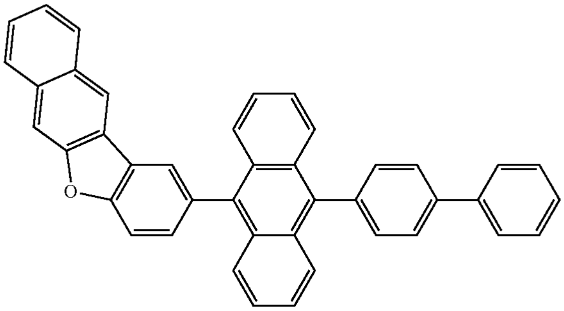
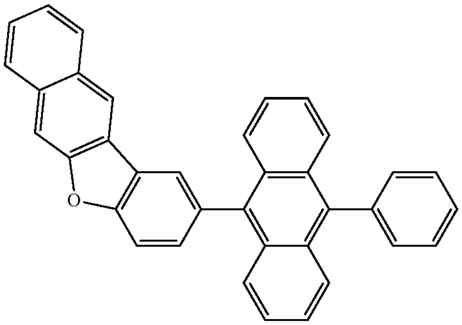
-continued
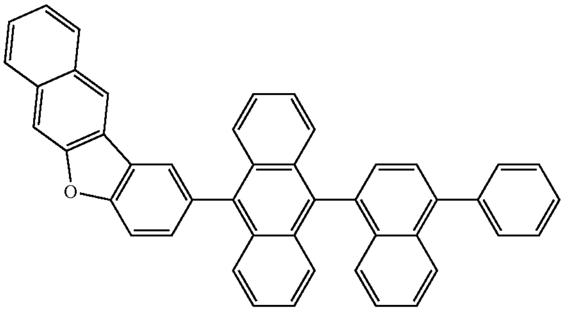
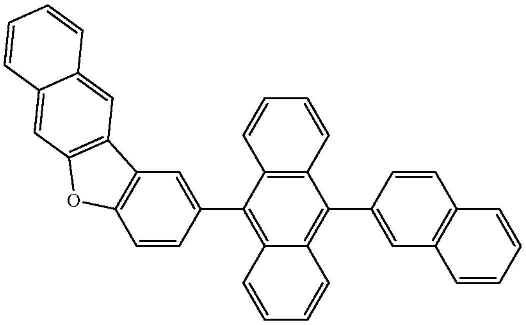
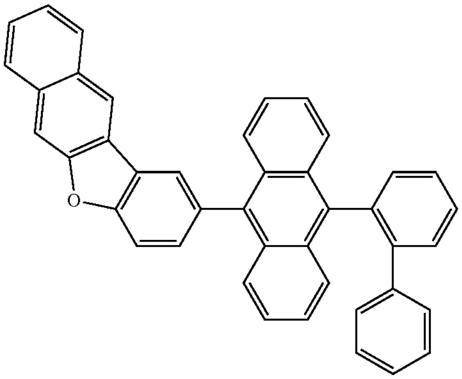
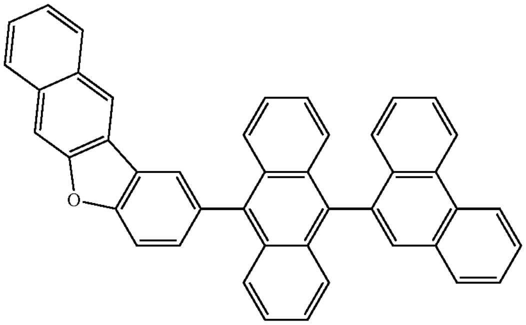
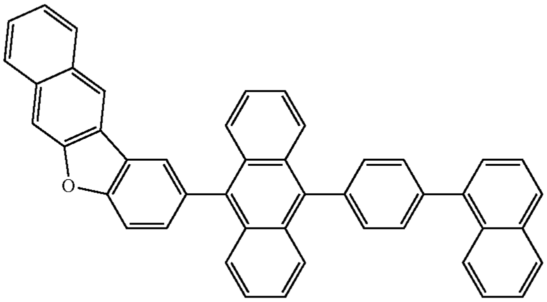

-continued
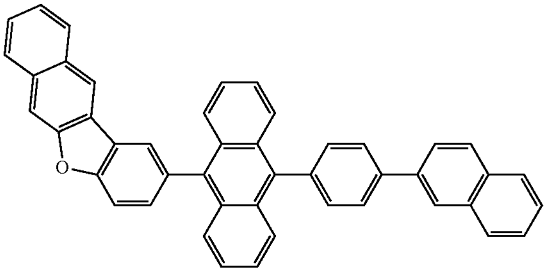
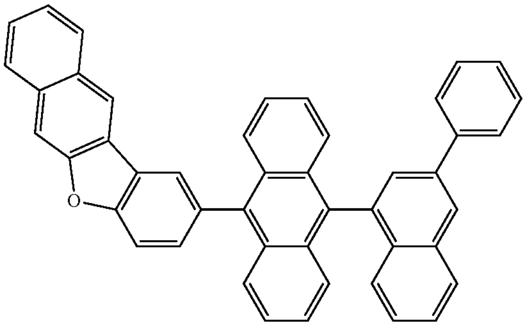
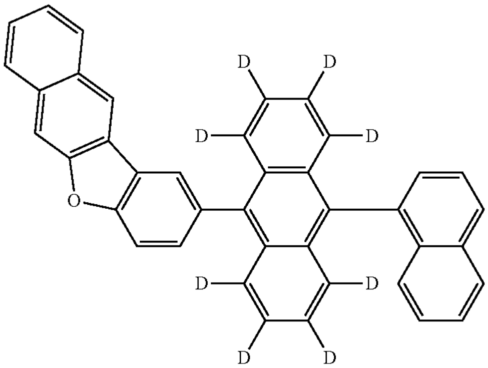
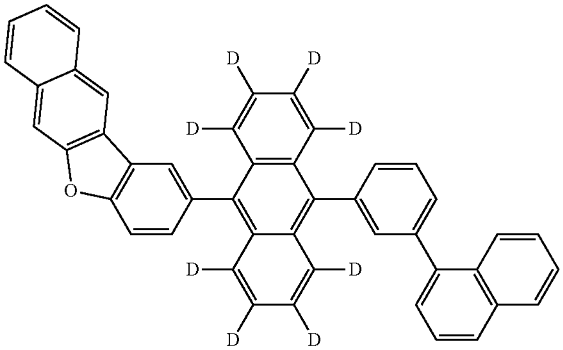
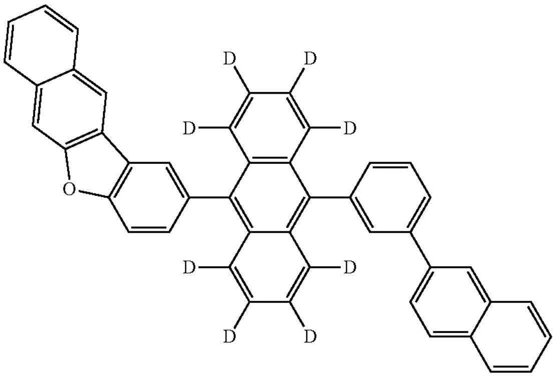
-continued
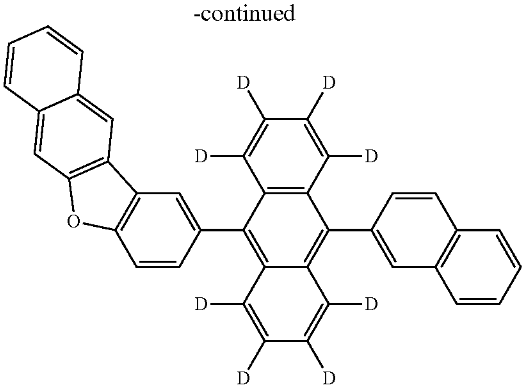
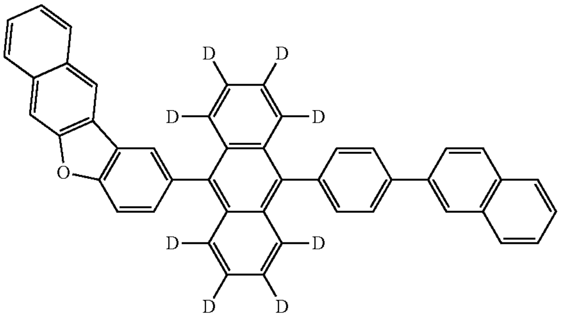
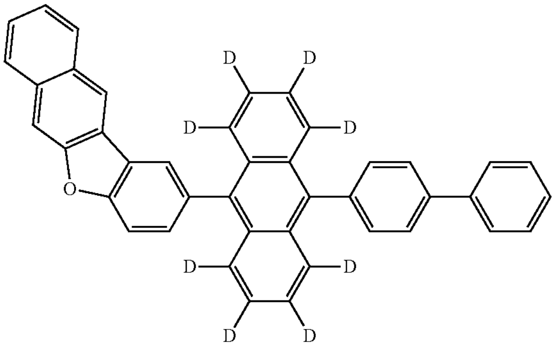
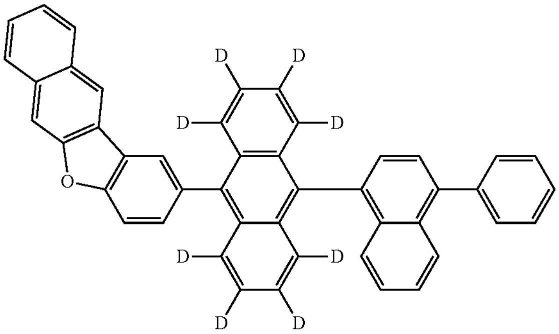
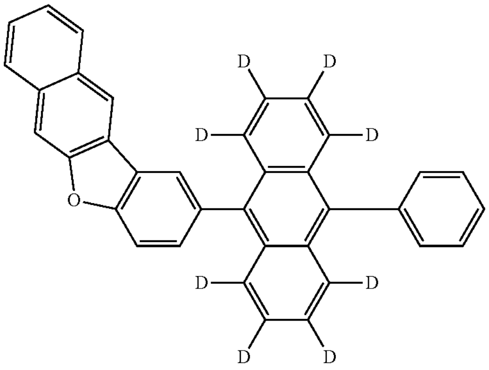

-continued
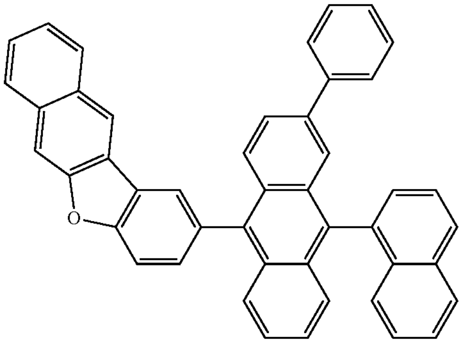
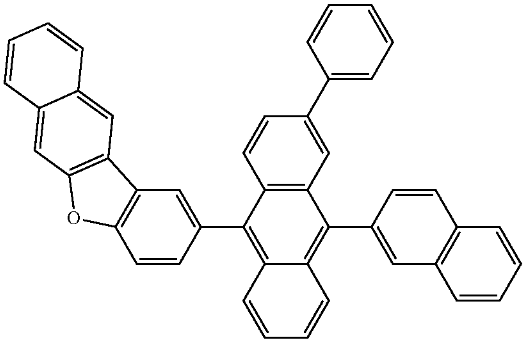
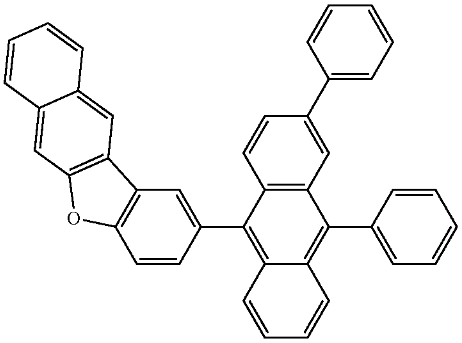
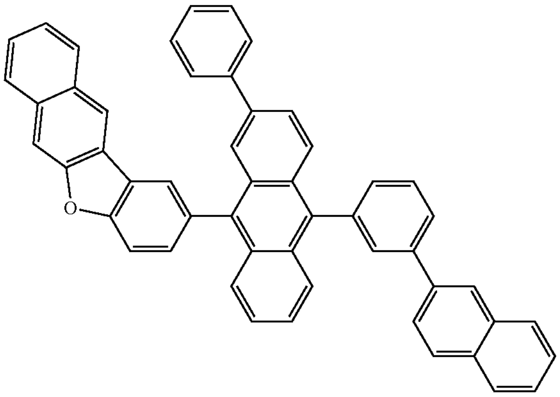
-continued
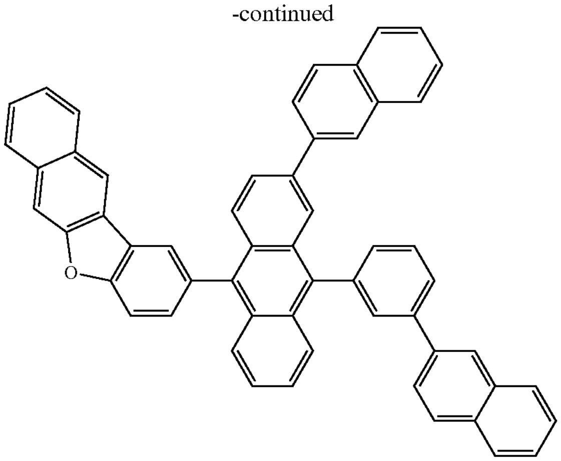
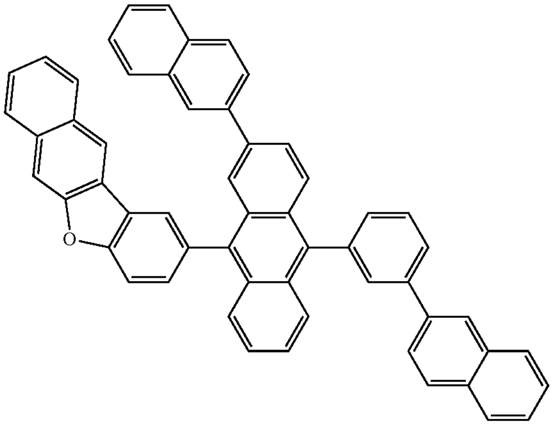
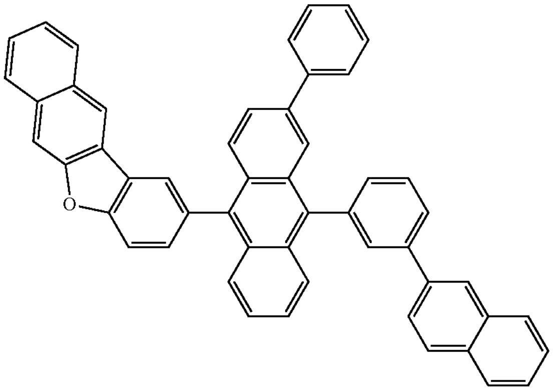
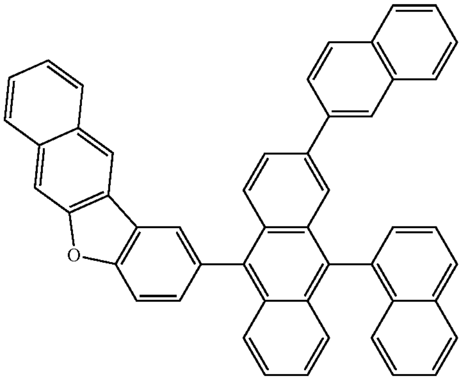

-continued
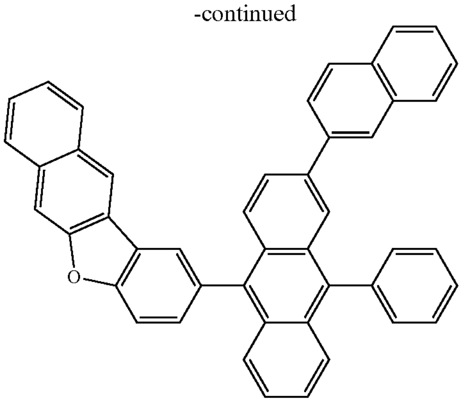
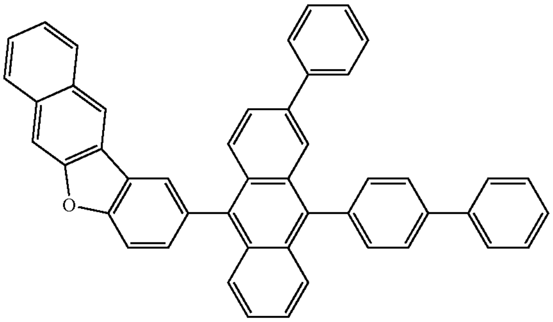
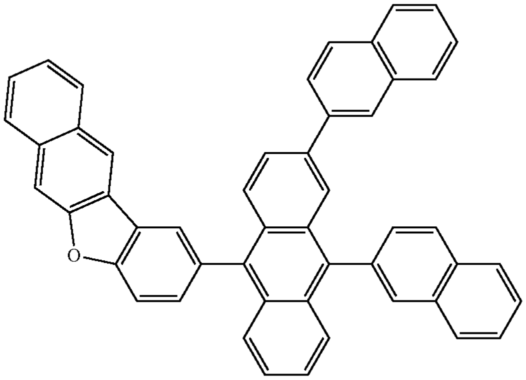
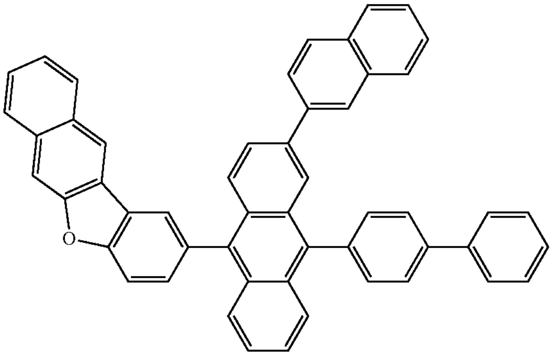
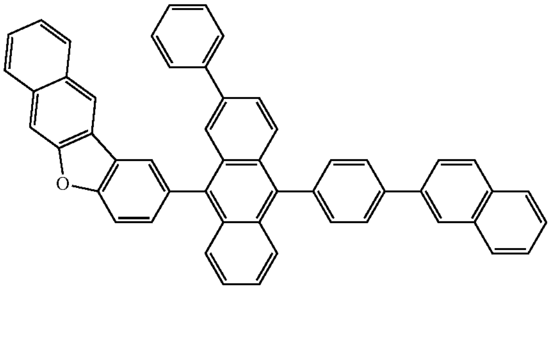
-continued
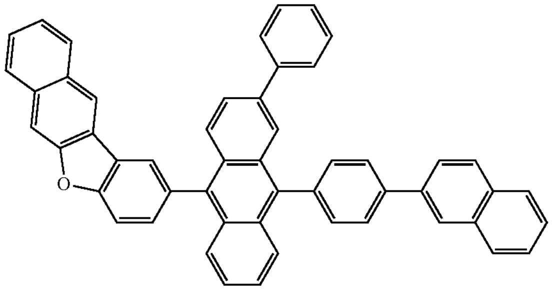
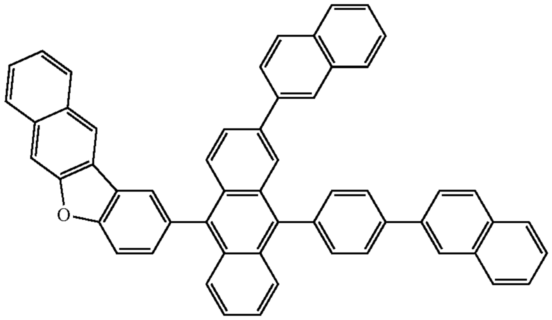
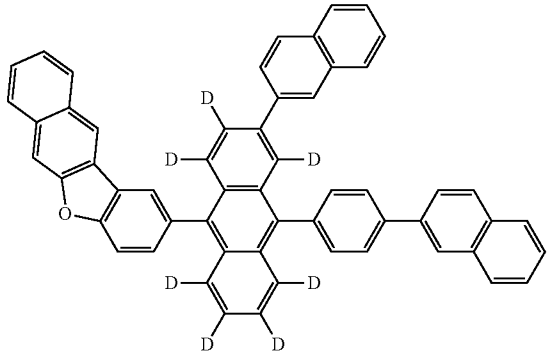
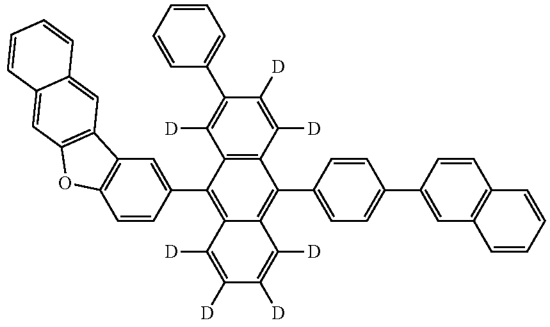
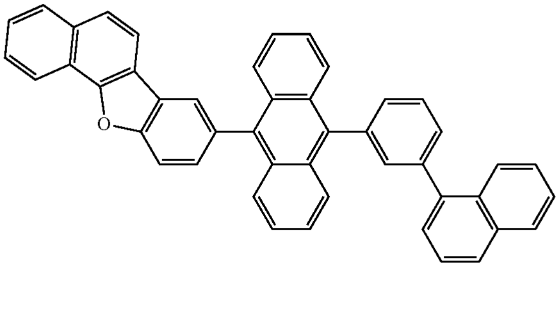

-continued
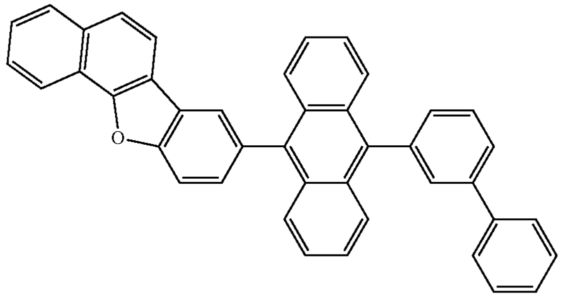
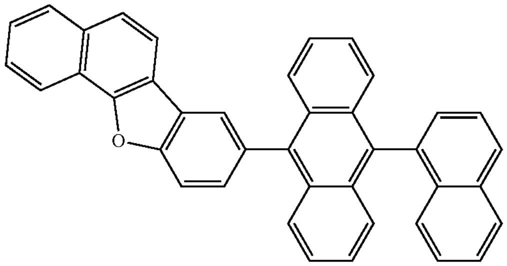
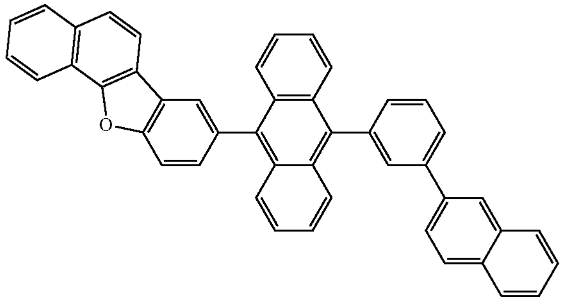
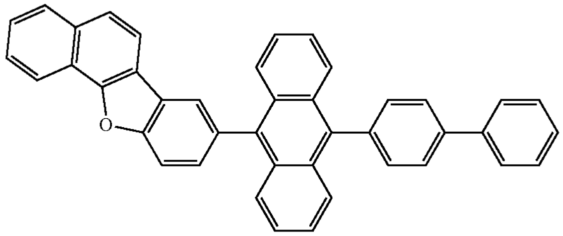
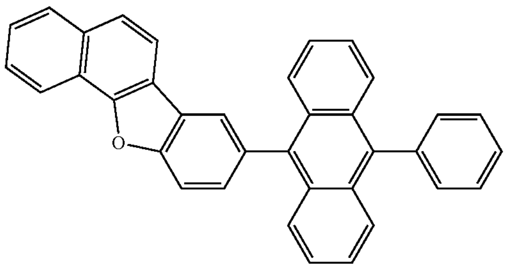
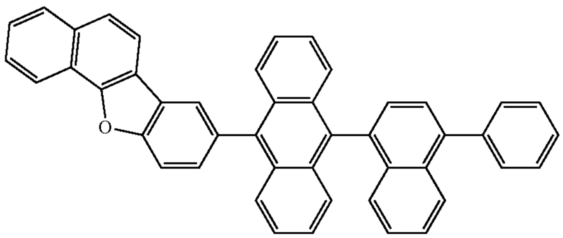
-continued
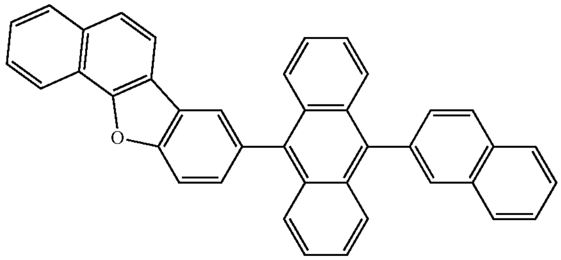
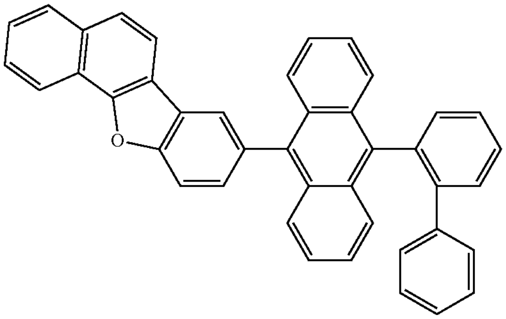
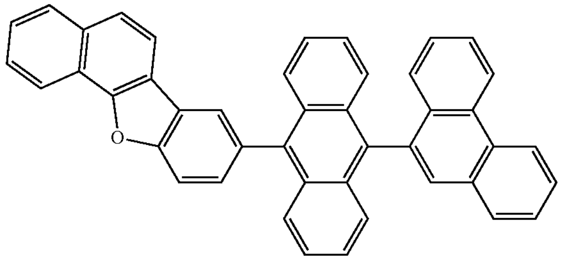
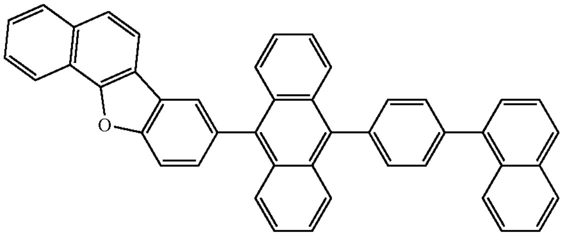
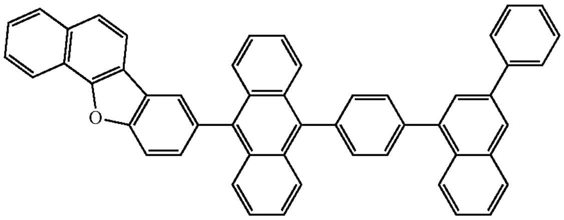
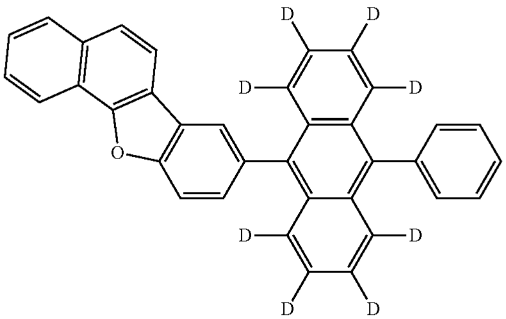

-continued
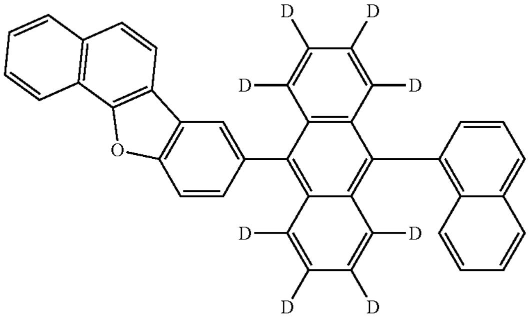
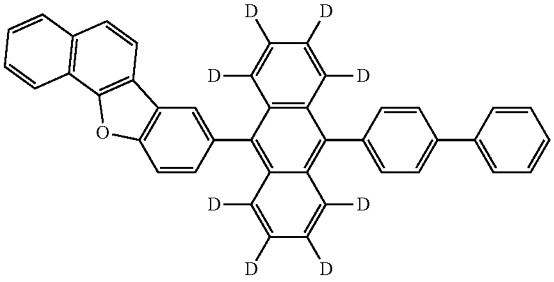
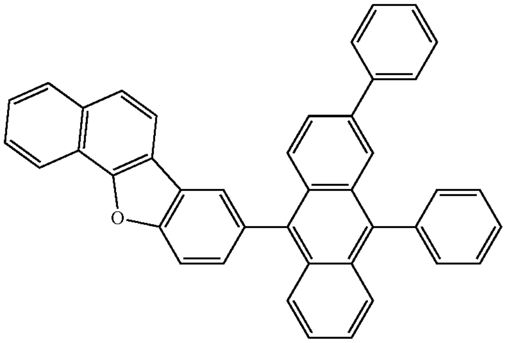
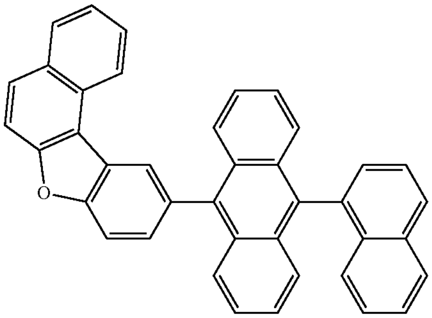
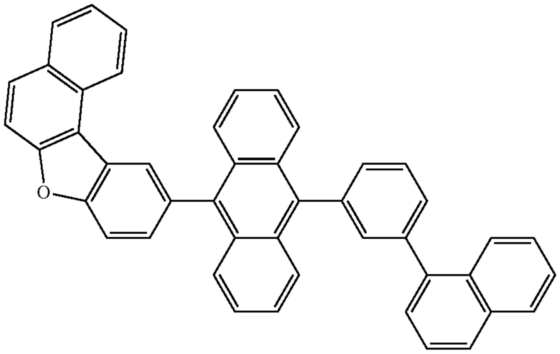
-continued
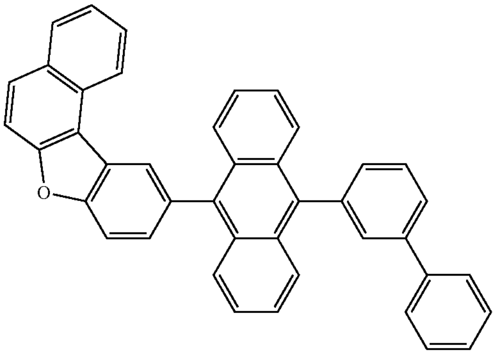
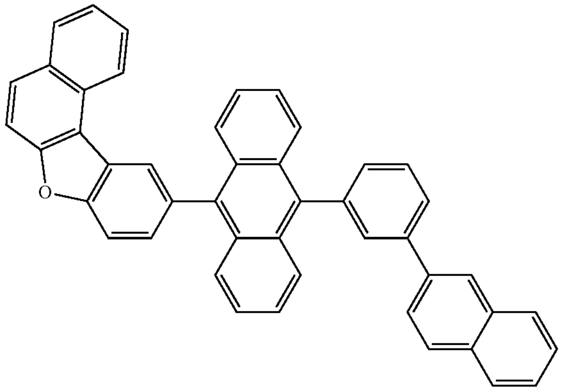
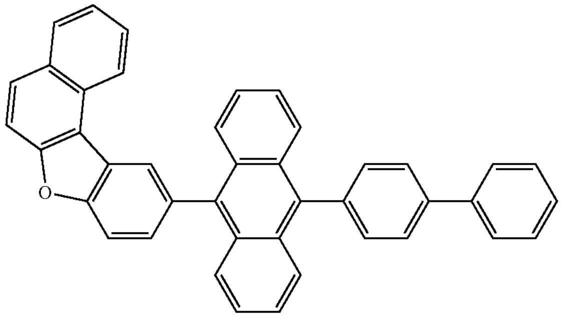
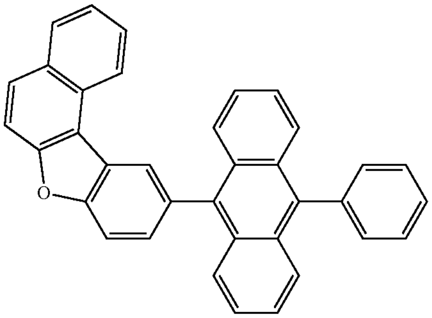
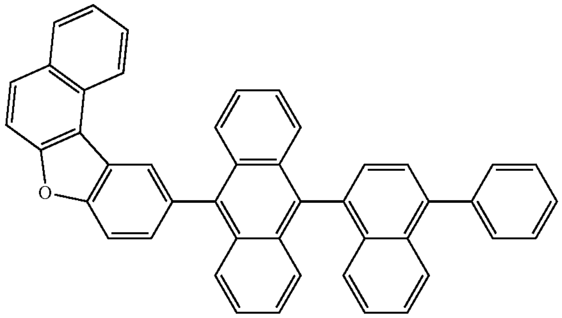

-continued
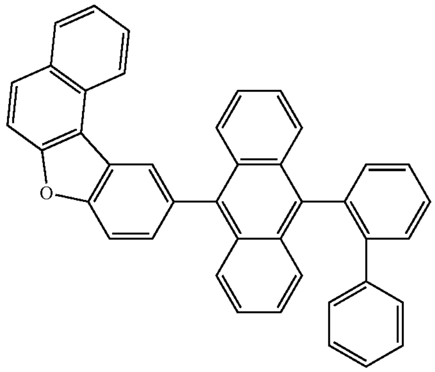
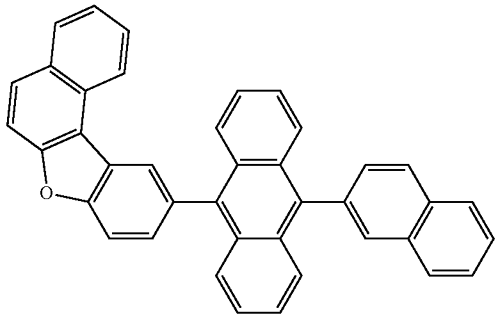
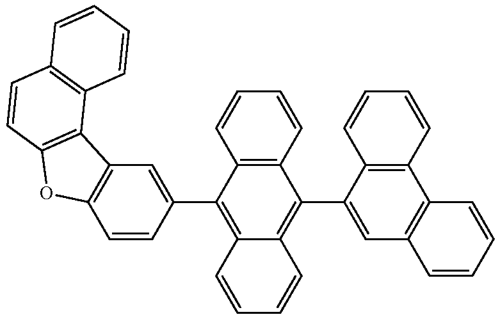
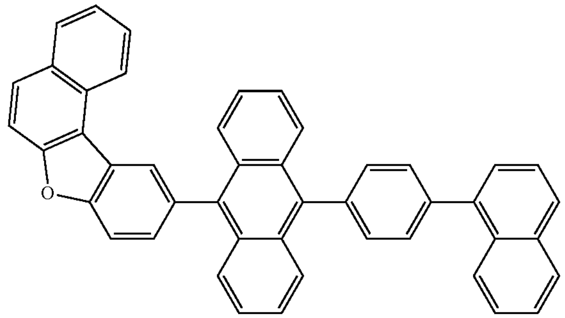
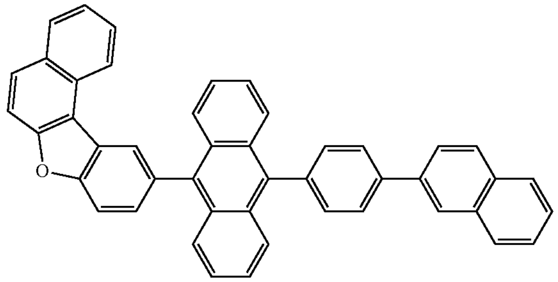
-continued
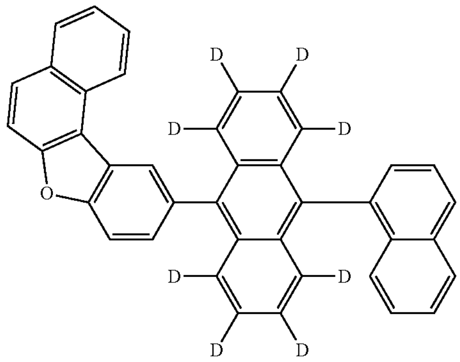
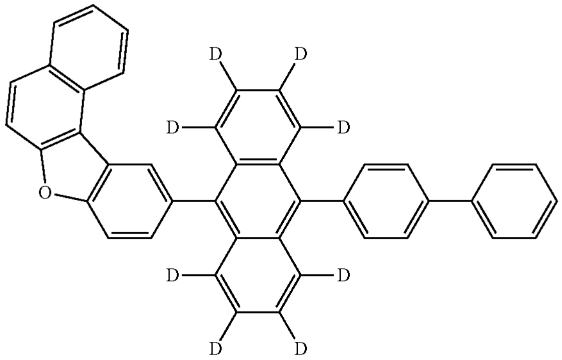
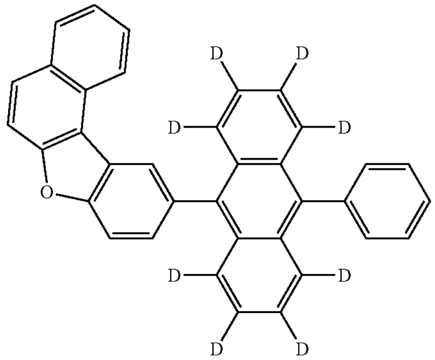
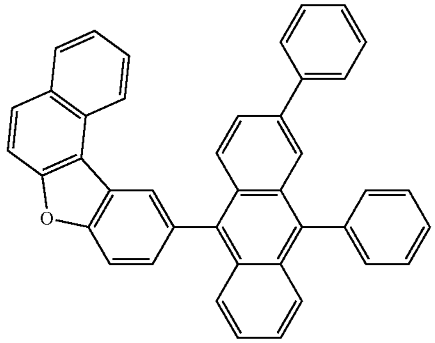
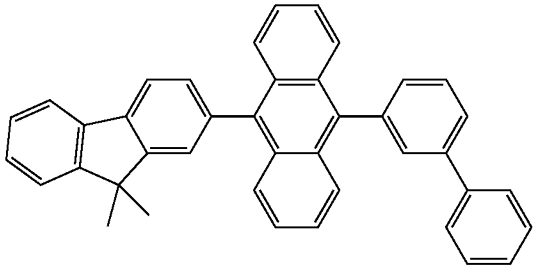

-continued
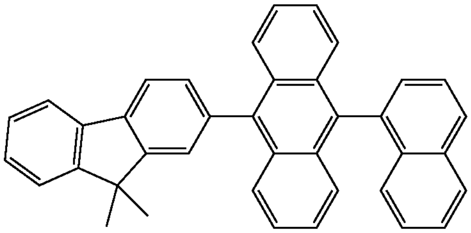
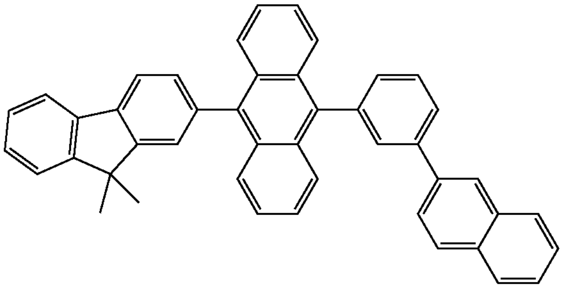
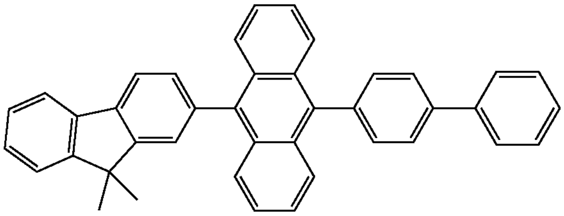
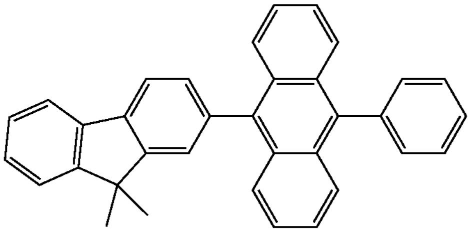
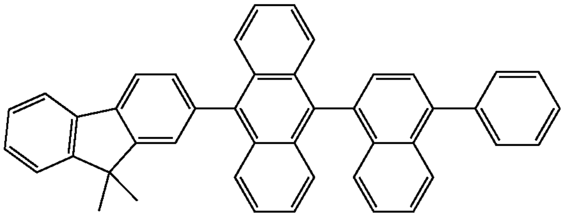
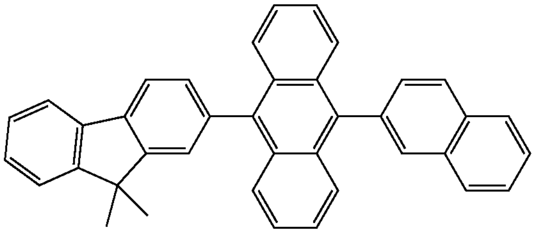
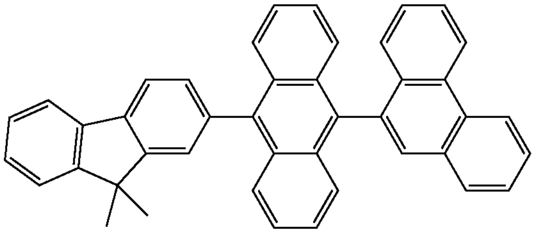
-continued
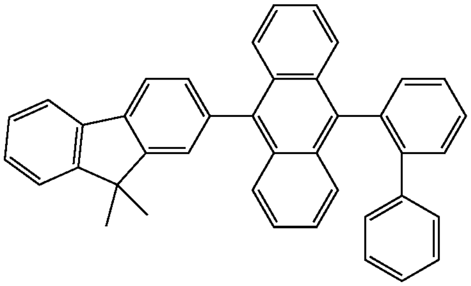
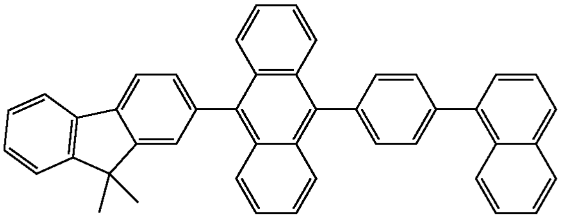
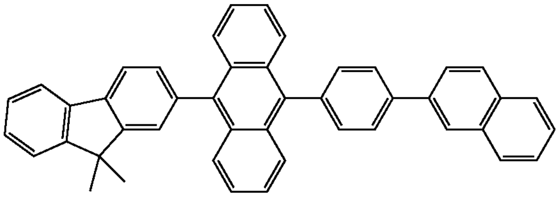
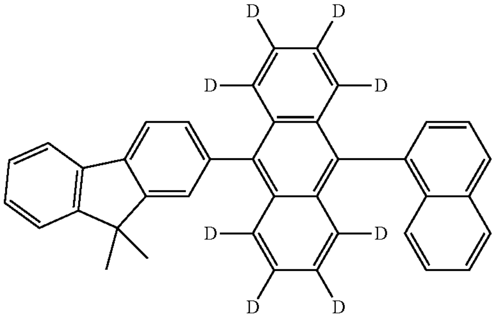
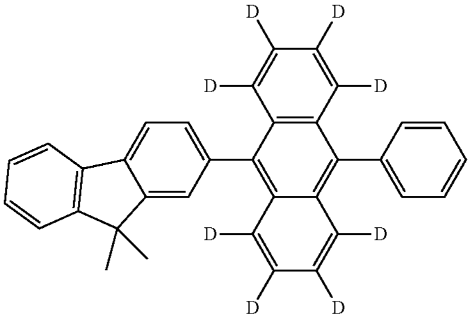
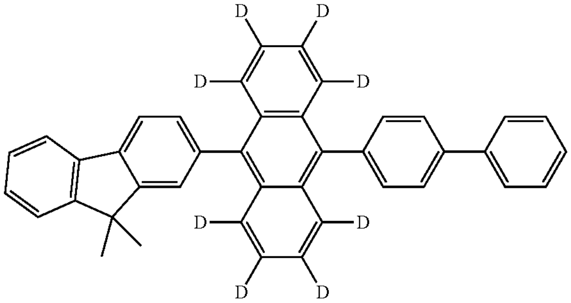

-continued
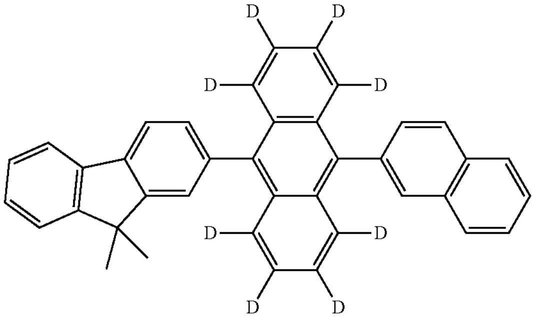
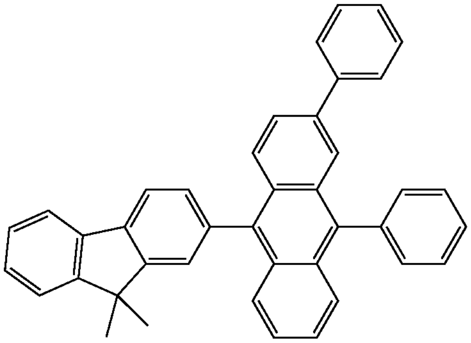
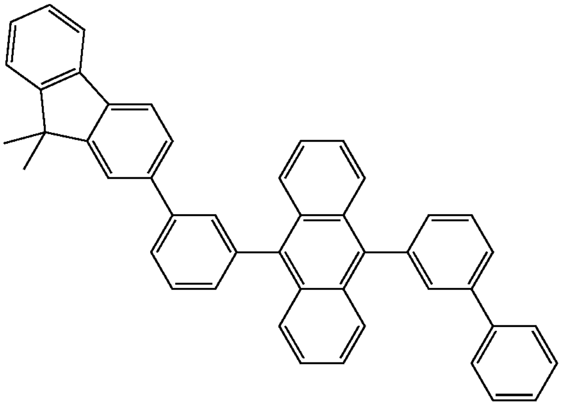
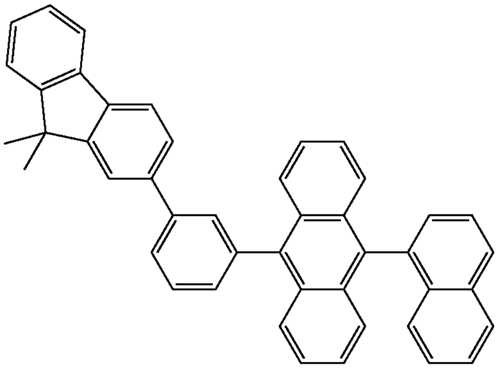
-continued
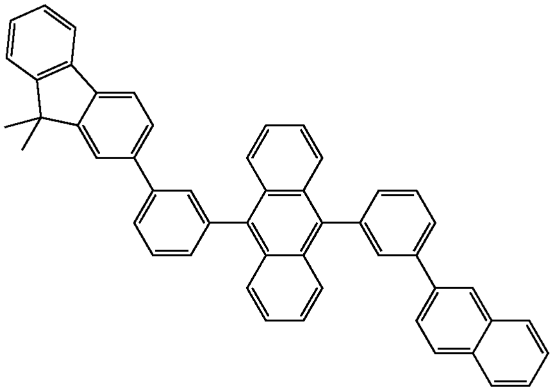
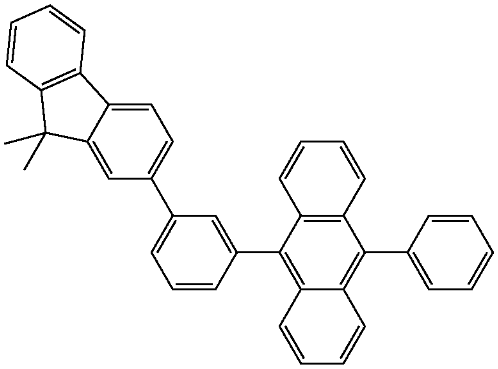
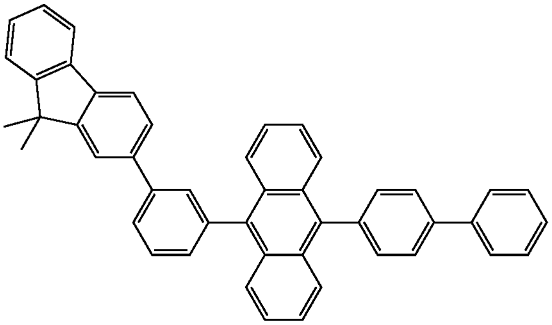
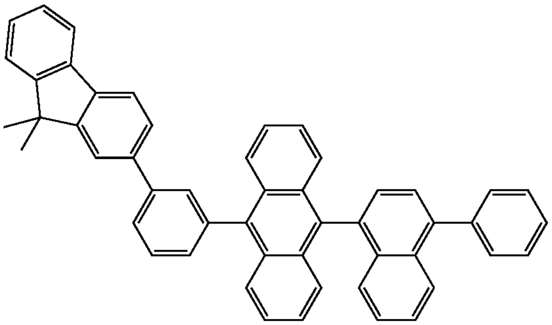

-continued
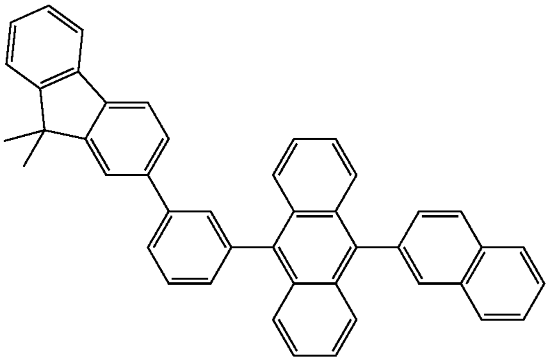
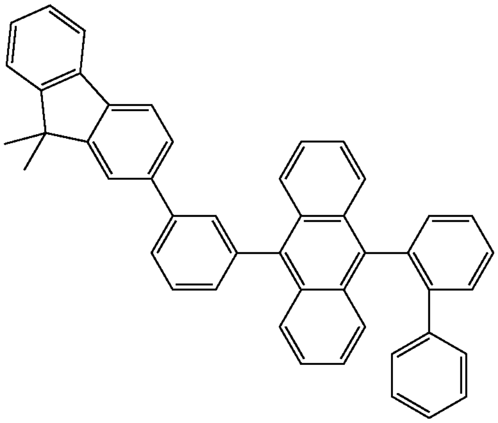
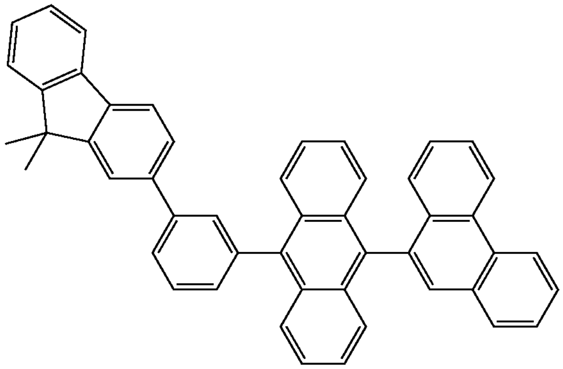
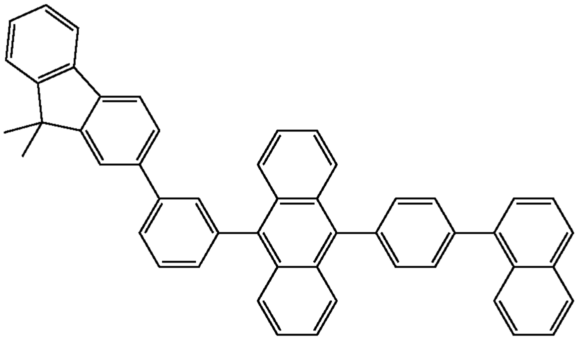
-continued
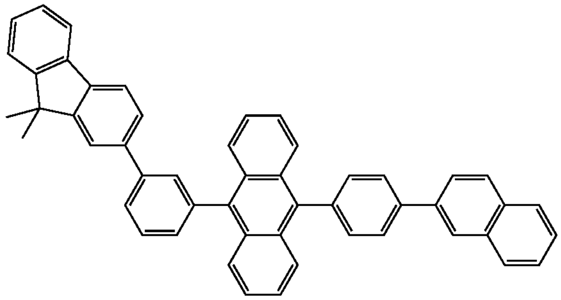
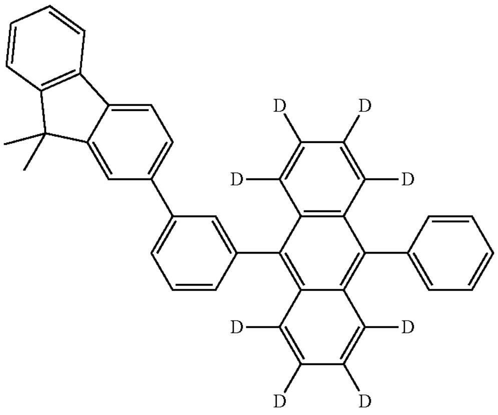
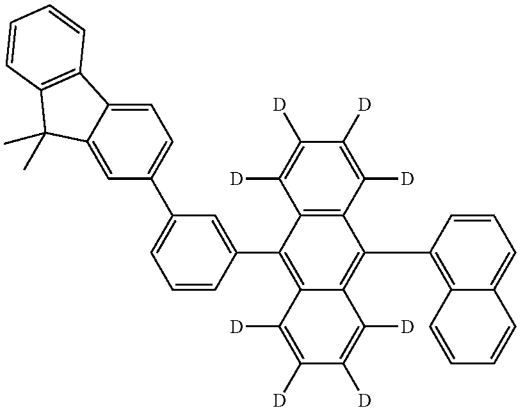
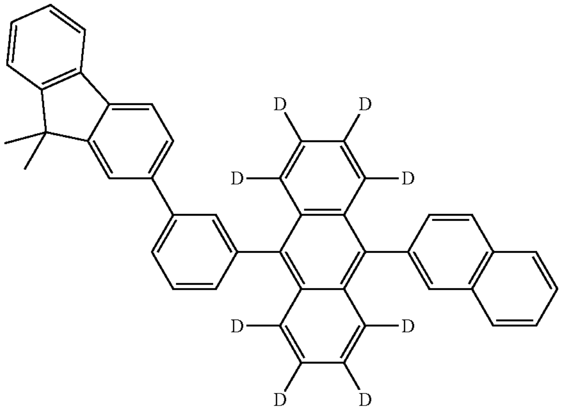

-continued
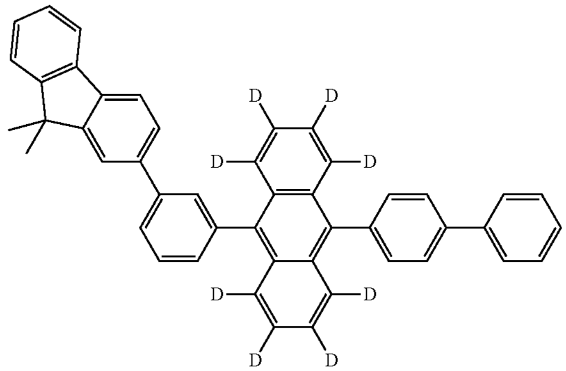
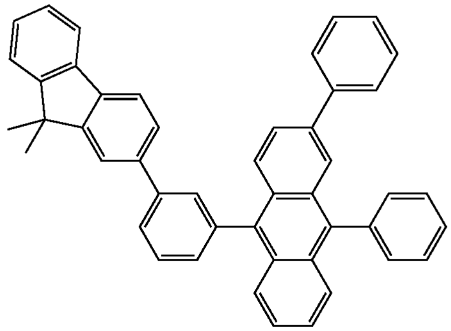
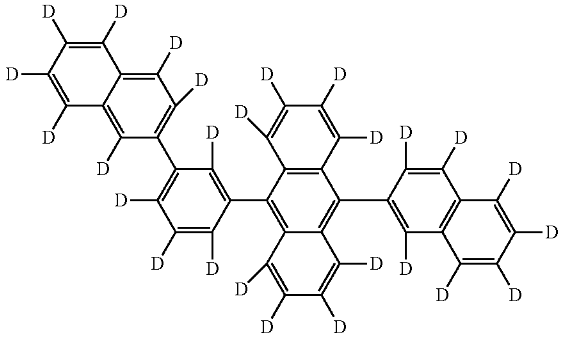
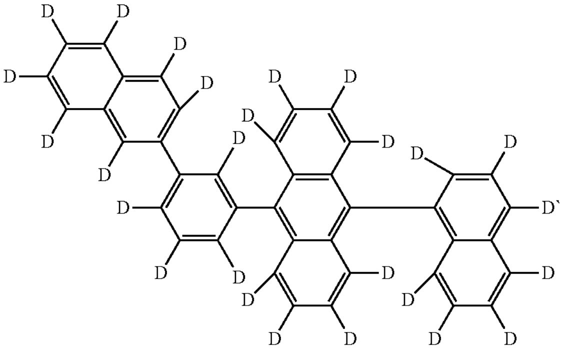
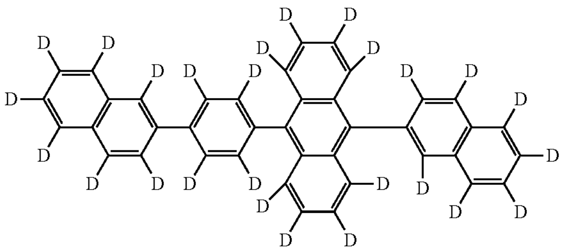
-continued
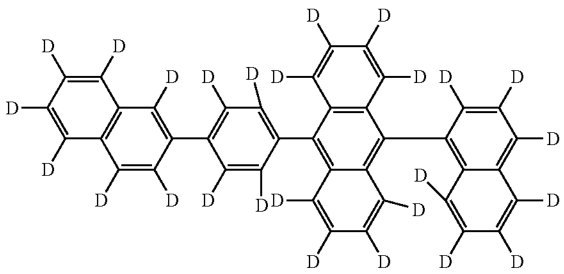
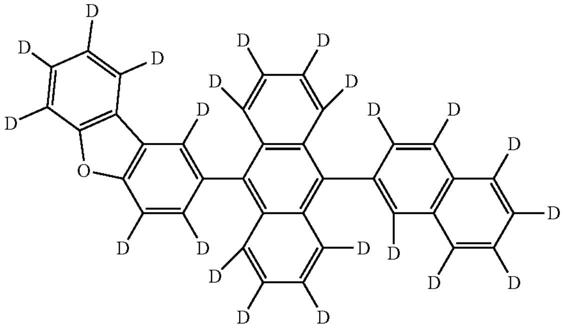
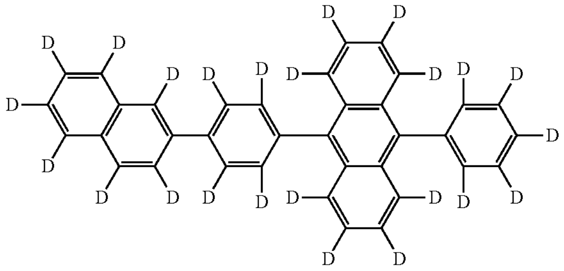
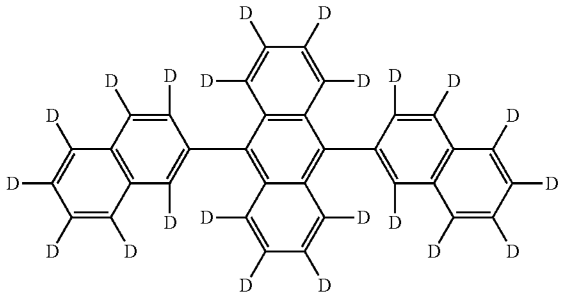
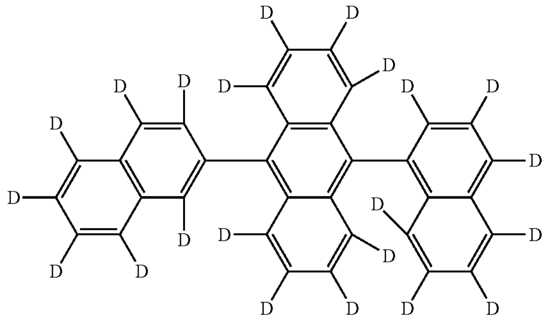

-continued

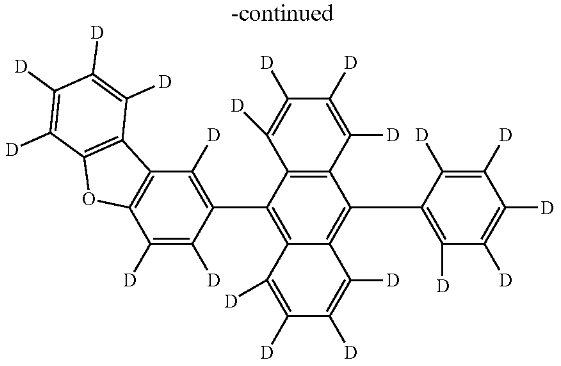

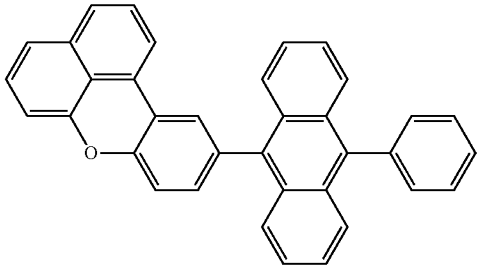

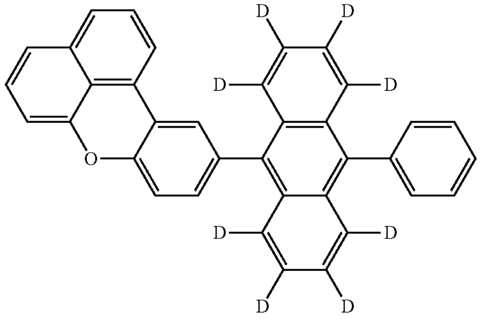

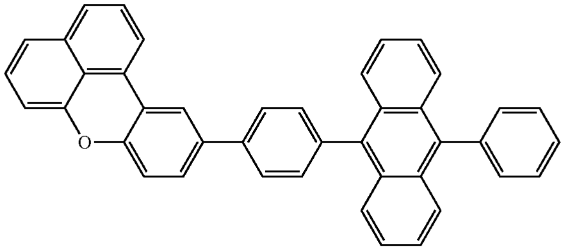

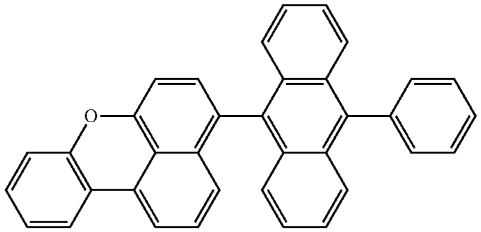

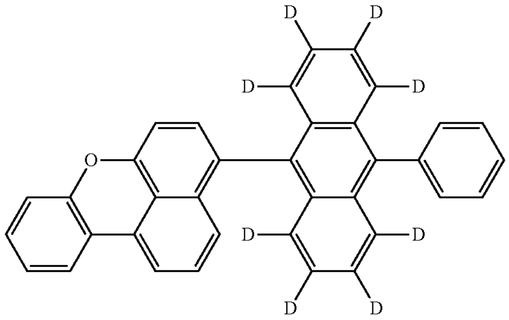

-continued

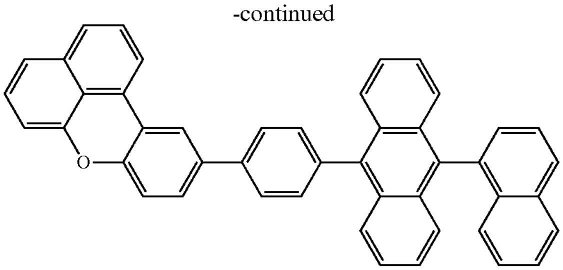

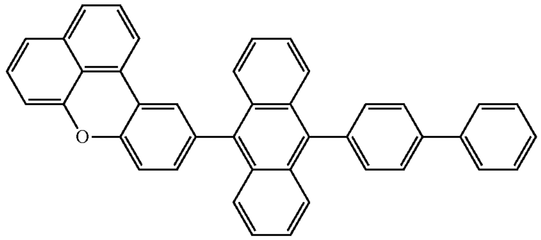

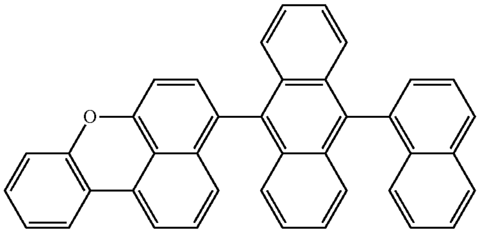

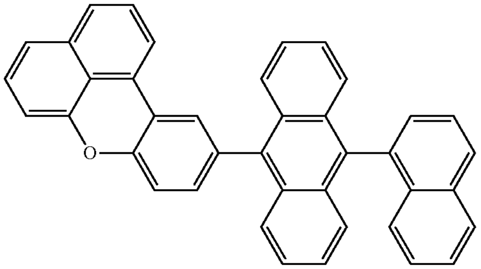

As described above, known materials and device configurations may be applied to the organic EL device according to one embodiment of the invention, as long as the device includes a cathode, an anode, and an emitting layer disposed between the cathode and the anode, and the emitting layer contains the compound represented by the formula (1), and the effect of the invention is not impaired.

The content of the compound represented by the formula (1) in the emitting layer is preferably 1% by mass or more and 20% by mass or less based on the total mass of the emitting layer.

Specific examples of typified device configurations of the organic EL device according to the invention include structures such as (1) an anode/an emitting layer/a cathode, (2) an anode/a hole-injecting layer/an emitting layer/a cathode, (3) an anode/an emitting layer/an electron-injecting-transporting layer/a cathode, (4) an anode/a hole-injecting layer/an emitting layer/an electron-injecting-transporting layer/a cathode, (5) an anode/an organic semiconductor layer/an emitting layer/a cathode, (6) an anode/an organic semiconductor layer/an electron barrier layer/an emitting layer/a cathode, (7) an anode/an organic semiconductor layer/an emitting layer/an adhesion-improving layer/a cathode, (8) an anode/a hole-injecting-transporting layer/an emitting layer/an electron-injecting-transporting layer/a cathode,
(9) an anode/an insulating layer/an emitting layer/an insulating layer/a cathode,
(10) an anode/an inorganic semiconductor layer/an insulating layer/an emitting layer/an insulating layer/a cathode,
(11) an anode/an organic semiconductor layer/an insulating layer/an emitting layer/an insulating layer/a cathode,
(12) an anode/an insulating layer/a hole-injecting-transporting layer/an emitting layer/an insulating layer/a cathode,
(13) an anode/an insulating layer/a hole-injecting-transporting layer/an emitting layer/an electron-injecting-transporting layer/a cathode, and the like.

Among the above-described structures, the configuration of (8) is preferably used, but the device configuration of the organic EL device is not limited to the above configurations.

The "hole-injecting-transporting layer" in this specification means "at least one of the hole-injecting layer and the hole-transporting layer", and the "electron-injecting-transporting layer" in this specification means "at least one of the electron-injecting layer and the electron-transporting layer".

Parts which can be used in the organic EL device according to an aspect of the invention, materials for forming respective layers, other than the above-mentioned compounds, and the like, will be described later.

(Substrate)

A substrate is used as a support of an emitting device. As the substrate, glass, quartz, plastic or the like can be used, for example. Further, a flexible substrate may be used. The "flexible substrate" means a bendable (flexible) substrate, and specific examples thereof include a plastic substrate formed of polycarbonate, polyvinyl chloride, or the like.

(Anode)

For the anode formed on the substrate, metals, alloys, electrically conductive compounds, mixtures thereof, and the like, which have a large work function (specifically 4.0 eV or higher) are preferably used. Specific examples thereof include indium oxide-tin oxide (ITO: Indium Tin Oxide), indium oxide-tin oxide containing silicon or silicon oxide, indium oxide-zinc oxide, tungsten oxide, indium oxide containing zinc oxide, graphene, and the like. In addition thereto, specific examples thereof include gold (Au), platinum (Pt), nitrides of metallic materials (for example, titanium nitride), and the like.

(Hole-Injecting Layer)

The hole-injecting layer is a layer containing a substance having a high hole-injecting property. As such a substance having a high hole-injecting property, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, an aromatic amine compound, or a polymer compound (oligomers, dendrimers, polymers, etc.) can be given.

(Hole-Transporting Layer)

The hole-transporting layer is a layer containing a substance having a high hole-transporting property. For the hole-transporting layer, aromatic amine compounds, carbazole derivatives, anthracene derivatives, and the like can be used. Polymer compounds such as poly(N-vinylcarbazole) (abbreviation: PVK) and poly(4-vinyltriphenylamine) (abbreviation: PVTPA) can also be used. However, a substance other than the above-described substances may be used as long as the substance has a higher hole-transporting property in comparison with an electron-transporting property. It should be noted that the layer containing the substance having a high hole-transporting property may be not only a single layer, but also a stacked layer of two or more layers formed of the above-described substances.

(Guest (Dopant) Material for Emitting Layer)

The emitting layer is a layer containing a substance having a high emitting property, and various materials can be used in addition to the material used in the invention described above (the compound represented by the formula (1)). For example, as the substances having a high emitting property, fluorescent compounds which emit fluorescence or phosphorescent compounds which emit phosphorescence can be used. The fluorescent compound is a compound which can emit from a singlet excited state, and the phosphorescent compound is a compound which can emit from a triplet excited state.

As blue fluorescent emitting materials which can be used for an emitting layer, pyrene derivatives, styrylamine derivatives, chrysene derivatives, fluoranthene derivatives, fluorene derivatives, diamine derivatives, triarylamine derivatives, and the like can be used. As green fluorescent emitting materials which can be used for an emitting layer, aromatic amine derivatives and the like can be used. As red fluorescent emitting materials which can be used for an emitting layer, tetracene derivatives, diamine derivatives and the like can be used.

As blue phosphorescent emitting materials which can be used for an emitting layer, metal complexes such as iridium complexes, osmium complexes, platinum complexes and the like are used. As green phosphorescent emitting materials which can be used for an emitting layer, iridium complexes and the like are used. As red phosphorescent emitting materials which can be used for an emitting layer, metal complexes such as iridium complexes, platinum complexes, terbium complexes, europium complexes and the like are used.

(Host Material for Emitting Layer)

The emitting layer may have a constitution in which the above-described substance having a high emitting property (guest material) is dispersed in another substance (host material). As substances for dispersing the substance having a high emitting property, a variety of substances can be used other than the above-described materials (the compound represented by the formula (10)), and it is preferable to use a substance having a higher lowest unoccupied orbital level (LUMO level) and a lower highest occupied orbital level (HOMO level) than the substance having a high emitting property.

Such substances (host materials) for dispersing the substance having a high emitting property include 1) metal complexes such as aluminum complexes, beryllium complexes, and zinc complexes, 2) heterocyclic compounds such as oxadiazole derivatives, benzimidazole derivatives, and phenanthroline derivatives, 3) fused aromatic compounds such as carbazole derivatives, anthracene derivatives, phenanthrene derivatives, pyrene derivatives, naphthacene derivatives, fluoranthene derivatives, triphenylene derivatives, fluorene derivatives, and chrysene derivatives, 4) aromatic amine compounds such as triarylamine derivatives and fused polycyclic aromatic amine derivatives.

Compounds having a delayed fluorescence (thermally activated delayed fluorescence) can also be used as the host material. It is also preferable that the emitting layer contains the above-described material used in the invention and the host compound having a delayed fluorescence.

(Electron-Transporting Layer)

The electron-transporting layer is a layer containing a substance having a high electron-transporting property. For the electron-transporting layer, 1) metal complexes such as aluminum complexes, beryllium complexes, zinc complexes, and the like; 2) heteroaromatic complexes such as imidazole derivatives, benzimidazole derivatives, azine derivatives, carbazole derivatives, phenanthroline derivatives, and the like; and 3) polymer compounds can be used.

(Electron-Injecting Layer)

The electron-injecting layer is a layer containing a substance having a high electron-injecting property. For the electron-injecting layer, lithium (Li), ytterbium (Yb), lithium fluoride (LiF), cesium fluoride (CsF), calcium fluoride ($CaF_2$), metal complex compounds such as 8-hydroxyquinolinolato-lithium (Liq), alkali metals, alkaline earth metals and compounds thereof such as lithium oxide ($LiO_x$) can be used.

(Cathode)

For the cathode, metals, alloys, electrically conductive compounds, mixtures thereof, and the like having a small work function (specifically, 3.8 eV or lower) are preferably used. Specific examples of such cathode materials include elements belonging to Group 1 or Group 2 of the Periodic Table of the Elements, i.e., alkali metals such as lithium (Li) and cesium (Cs), alkaline earth metals such as magnesium (Mg), calcium (Ca) and strontium (Sr), and alloys containing these metals (e.g., MgAg and AlLi); rare earth metals such as europium (Eu) and ytterbium (Yb), and alloys containing these metals.

In the organic EL device according to an aspect of the invention, the methods for forming the respective layers are not particularly limited. A conventionally-known method for forming each layer by a vacuum deposition process, a spin coating process or the like can be used. Each layer such as the emitting layer can be formed by a known method such as a vacuum deposition process, a molecular beam deposition process (MBE process), or an application process such as a dipping process, a spin coating process, a casting process, a bar coating process or a roll coating process, using a solution prepared by dissolving a material in a solvent.

In the organic EL device according to an aspect of the invention, the thickness of each layer is not particularly limited, but is generally preferable that the thickness be in the range of several nm to 1 μm in order to suppress defects such as pinholes, to suppress applied voltages to be low, and to increase luminous efficiency.

[Electronic Apparatus]

The electronic apparatus according to an aspect of the invention is characterized by equipped with the organic EL device according to an aspect of the invention.

Specific examples of the electronic apparatus include display components such as an organic EL panel module, and the like; display devices for a television, a cellular phone, a personal computer, and the like; and emitting devices such as a light, a vehicular lamp, and the like.

EXAMPLES

Hereinafter, Examples according to the invention will be described. The invention is not limited in any way by these Examples.

<Compounds>

Compounds represented by the formula (1) used in Examples are shown below.

BD-1

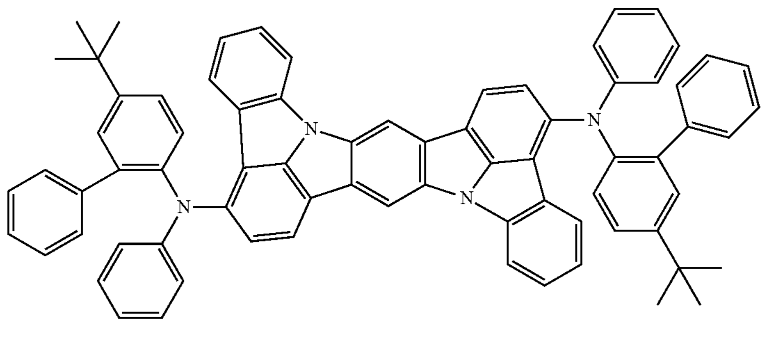

BD-2

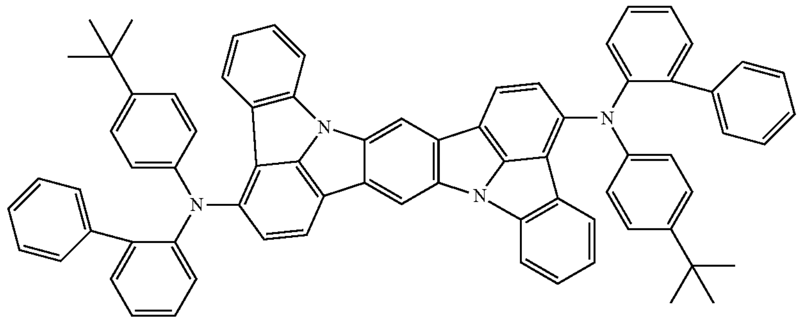

-continued
BD-3
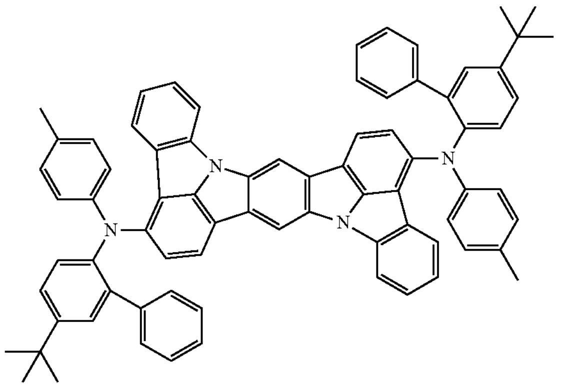
BD-4
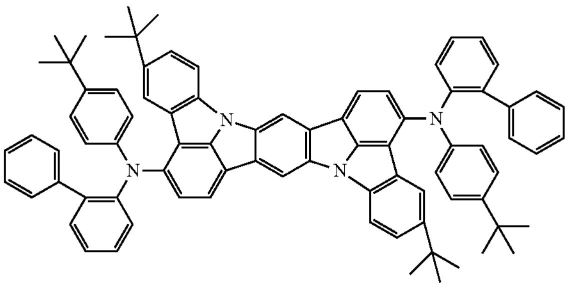
BD-5
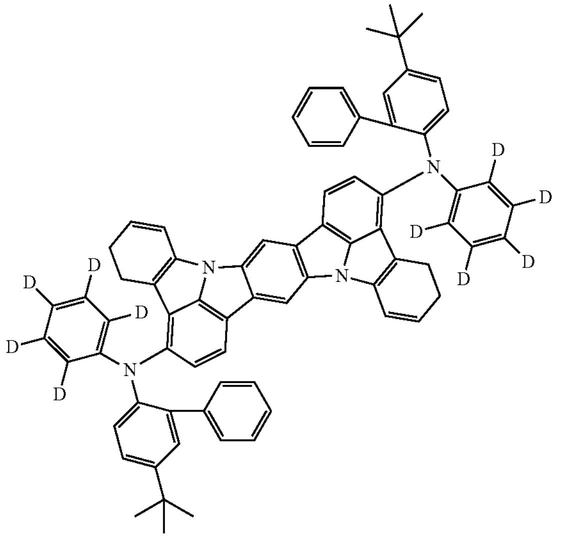
BD-6
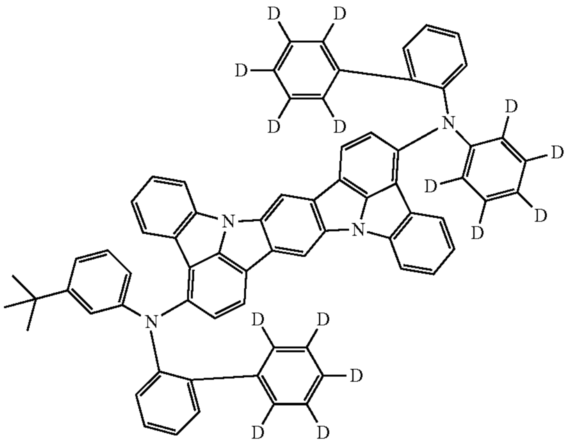
BD-7
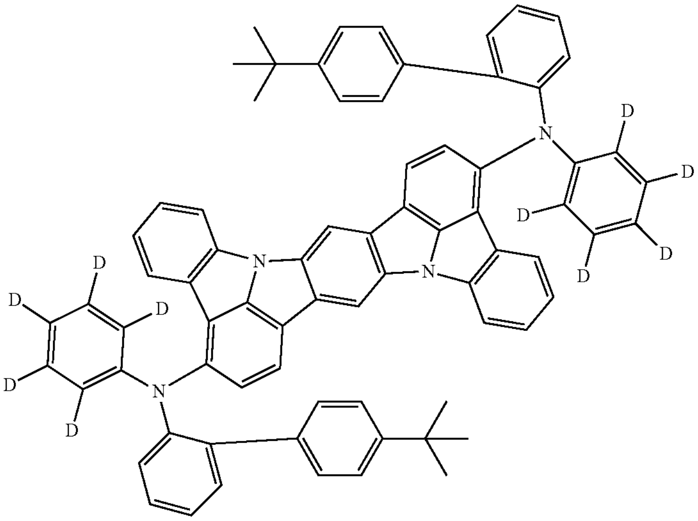
A compound used in Comparative Examples is shown below.

BD-Ref
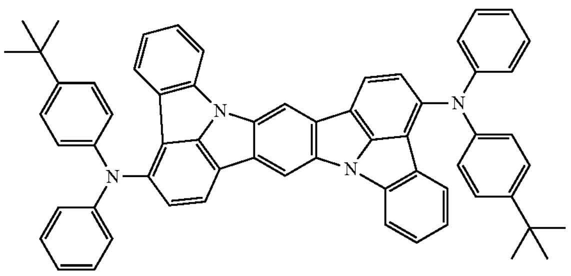
Compounds used in Examples and Comparative Examples are shown below.
HI-1
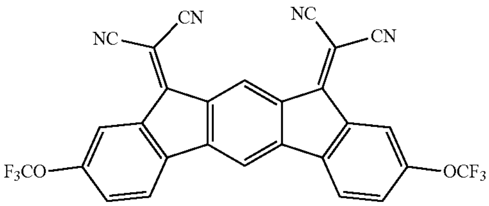
HT-1
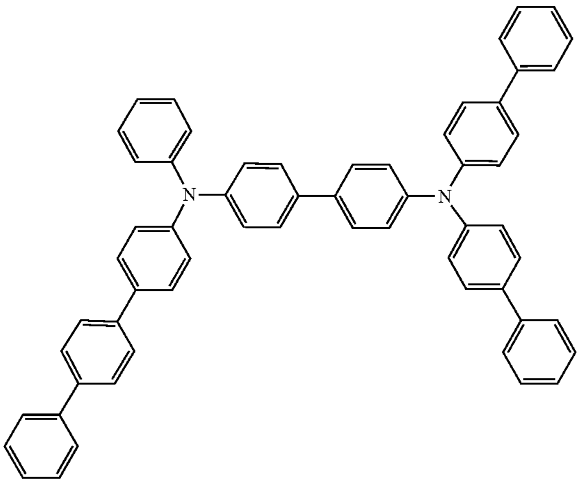
HT-2
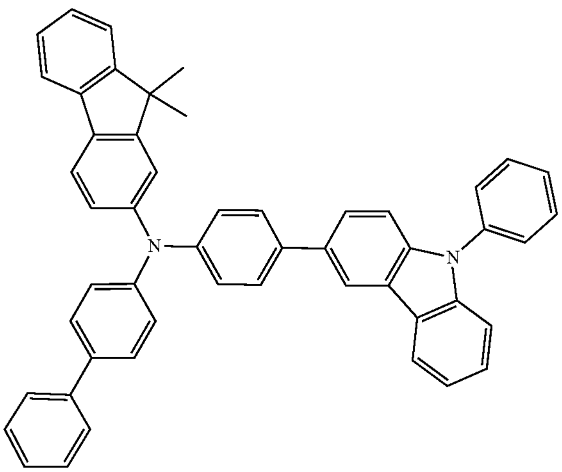
-continued
EBL-1
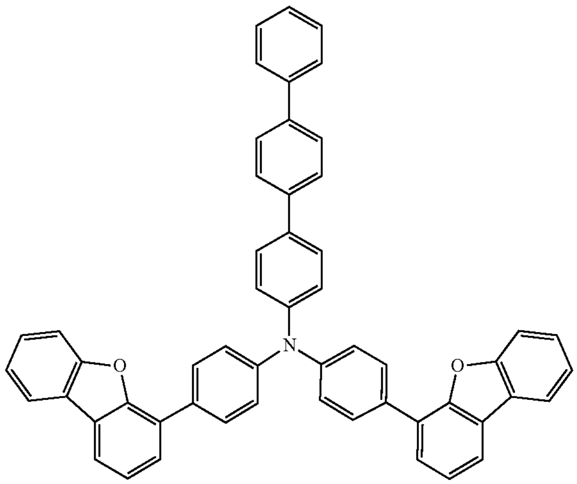
EBL-2
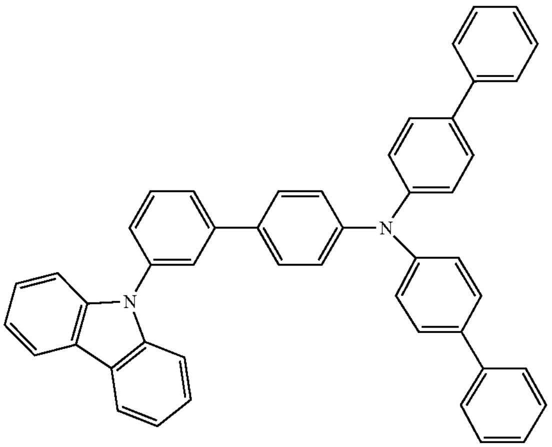
BH-1
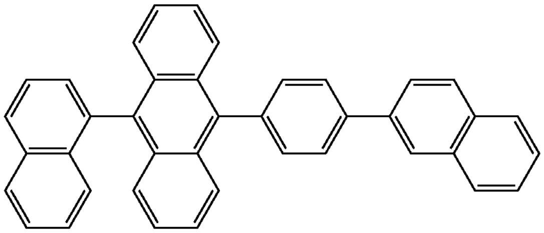
BH-2
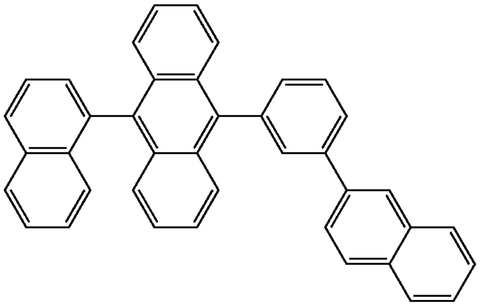

-continued

BH-3

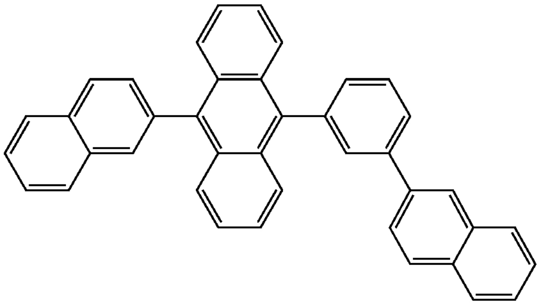

BH-4

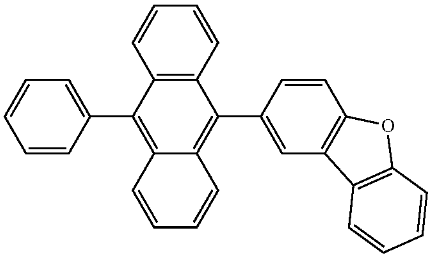

BH-5

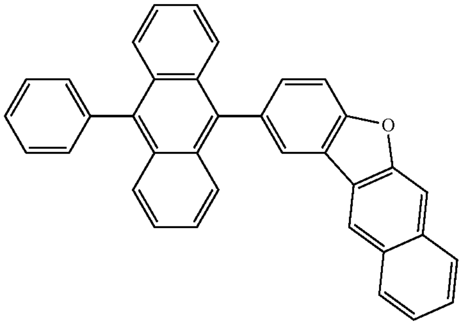

HBL-1

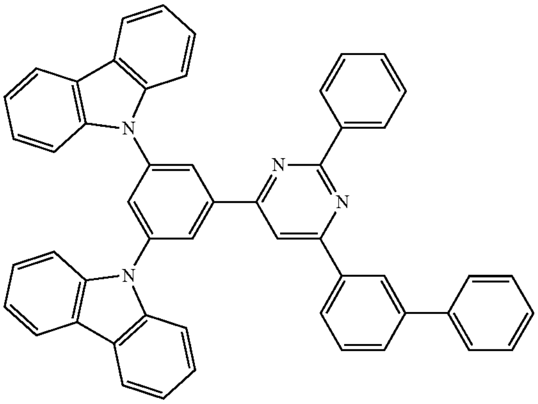

HBL-2

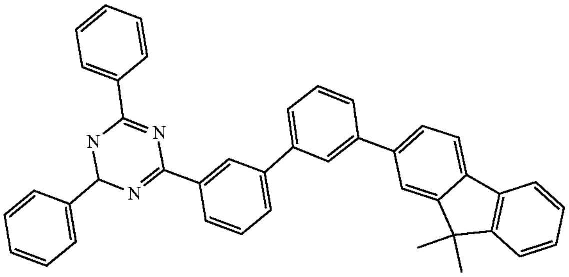

-continued

ET-1

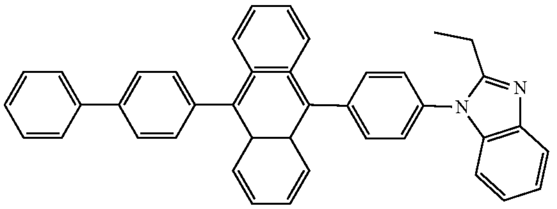

ET-2

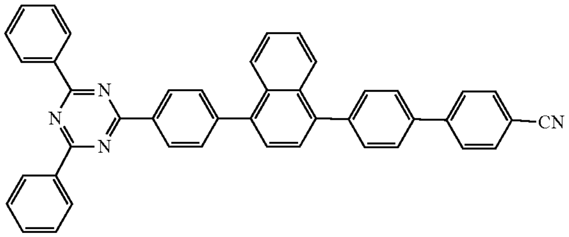

Example 1

<Fabrication of Organic EL Device>

A 25 mm×75 mm×1.1 mm-thick glass substrate with an ITO transparent electrode (anode) (manufactured by GEOMATEC Co., Ltd.) was subjected to ultrasonic cleaning in isopropyl alcohol for 5 minutes, and then subjected to UV-ozone cleaning for 30 minutes. The thickness of the ITO film was 130 nm.

The glass substrate with the transparent electrode after being cleaned was mounted onto a substrate holder in a vacuum vapor deposition apparatus. First, Compound HI-1 was deposited on a surface on the side on which the transparent electrode was formed so as to cover the transparent electrode to form Compound HI-1 film having a thickness of 5 nm. The HI-1 film functions as a hole-injecting layer.

Subsequent to the formation of the HI-1 film, Compound HT-1 was deposited on the HI-1 film to form an HT-1 film having a thickness of 80 nm. The HT-1 film functions as a first hole-transporting layer.

Subsequent to the formation of the HT-1 film, Compound EBL-1 was deposited on the HT-1 film to form an EBL-1 film having a thickness of 10 nm. The EBL-1 film functions as a second hole-transporting layer.

Compound BH-1 (host material) and Compound BD-1 (dopant material) were co-deposited on the EBL-1 film to be 2% in a proportion (weight ratio) of Compound BD-1 to form an emitting layer having a thickness of 25 nm.

Compound HBL-1 was deposited on the emitting layer to form an electron-transporting layer having a thickness of 10 nm. Compound ET-1 as an electron-injecting material was deposited on the electron-transporting layer to form an electron-injecting layer having a thickness of 15 nm. LiF was deposited on the electron-injecting layer to form a LiF film having a thickness of 1 nm. Metal Al was deposited on the LiF film to form a metal cathode having a thickness of 80 nm.

The device configuration of the organic EL device of Example 1 is schematically shown as follows.

ITO(130)/HI-1(5)/HT-1(80)/EBL-1(10)/BH-1:BD-1 (25:2%)/HBL-1(10)/ET-1(15)/LiF(1)/Al(80)

The numerical values in parentheses indicate the film thickness (unit: nm).

<Evaluation of Organic EL Device>

(Device Lifetime)

A voltage was applied to the obtained organic EL device so that the current density became 50 mA/$cm^2$, and the time until the luminance decreases 95% of the initial luminance (LT95 (unit: hours)) was measured. The numerical values in the table are relative values when the LT95 value of Comparative Example 1 described later is set to 100%.

(Luminous Efficiency)

At room temperature, the spectral radiance spectrum when the voltage was applied to the organic EL device so that the current density to be 10 mA/$cm^2$ was measured by a spectroradiance meter CS-2000 (manufactured by Konica Minolta, Inc.). From the obtained spectral radiance spectrum, the current density (cd/A) was calculated. The chromaticity CIE-y was calculated in the same manner. In this Example, the value obtained by dividing the current density by chromaticity is defined as the luminous efficiency obtained by considering the chromaticity. The numerical values in the table are relative values when the luminous efficiency value of Comparative Example described later is set to 100%.

Examples 2 to 7

Organic EL devices were fabricated and evaluated in the same manner as in Example 1, except that the compounds described in Table 1 were used as the dopant material for the emitting layer, respectively. The results are shown in Table 1. In Table 1, "-" indicates that evaluation was not performed. The same applies to Table 2 and subsequent Tables.

Comparative Example 1

An organic EL device was fabricated and evaluated in the same manner as in Example 1, except that the compound described in Table 1 was used as the dopant material for the emitting layer. The results are shown in Table 1.

TABLE 1

| | BH | BD | Luminous efficiency relative value (%) | LT95 relative value (%) |
|---|---|---|---|---|
| Example 1 | BH-1 | BD-1 | 108 | 131 |
| Example 2 | | BD-2 | 106 | 122 |
| Example 3 | | BD-3 | — | 115 |
| Example 4 | | BD-4 | — | 123 |
| Example 5 | | BD-5 | — | 145 |
| Example 6 | | BD-6 | — | 141 |
| Example 7 | | BD-7 | — | 135 |
| Comp. Ex. 1 | | BD-Ref | 100 | 100 |

Example 8

An organic EL device was fabricated and evaluated in the same manner as in Example 1, except that the compound described in Table 2 was used as the host material for the emitting layer. The numerical values in the table are relative values when those values of Comparative Example 2 described later is set to 100%. The results are shown in Table 2.

Examples 9 to 14

Organic EL devices were fabricated and evaluated in the same manner as in Example 8, except that the compounds described in Table 2 were used as the dopant material for the emitting layer, respectively. The results are shown in Table 2.

Comparative Example 2

An organic EL device was fabricated and evaluated in the same manner as in Example 8, except that the compound described in Table 2 was used as the dopant material for the emitting layer. The results are shown in Table 2.

TABLE 2

| | BH | BD | Luminous efficiency relative value (%) | LT95 relative value (%) |
|---|---|---|---|---|
| Example 8 | BH-2 | BD-1 | 107 | 128 |
| Example 9 | | BD-2 | 106 | 119 |
| Example 10 | | BD-3 | — | 113 |
| Example 11 | | BD-4 | — | 125 |
| Example 12 | | BD-5 | — | 136 |
| Example 13 | | BD-6 | — | 127 |
| Example 14 | | BD-7 | — | 130 |
| Comp. Ex. 2 | | BD-Ref | 100 | 100 |

Example 15

An organic EL device was fabricated and evaluated in the same manner as in Example 1, except that the compound described in Table 3 was used as the host material for the emitting layer. The numerical values in the table are relative values when those values of Comparative Example 3 described later is set to 100%. The results are shown in Table 3.

Examples 16 to 21

Organic EL devices were fabricated and evaluated in the same manner as in Example 15, except that the compounds described in Table 3 were used as the dopant material for each of the emitting layer, respectively. The results are shown in Table 3.

Comparative Example 3

An organic EL device was fabricated and evaluated in the same manner as in Example 15, except that the compound described in Table 3 was used as the dopant material for the emitting layer. The results are shown in Table 3.

TABLE 3

| | BH | BD | Luminous efficiency relative value (%) | LT95 relative value (%) |
|---|---|---|---|---|
| Example 15 | BH-3 | BD-1 | 107 | 126 |
| Example 16 | | BD-2 | 106 | 118 |
| Example 17 | | BD-3 | — | 111 |
| Example 18 | | BD-4 | — | 124 |
| Example 19 | | BD-5 | — | 132 |
| Example 20 | | BD-6 | — | 123 |
| Example 21 | | BD-7 | — | 127 |
| Comp. Ex. 3 | | BD-Ref | 100 | 100 |

Example 22

An organic EL device was fabricated in the same manner as in Example 1 except that HT-1 was changed to HT-2, EBL-1 was changed to EBL-2, BH-1 was changed to BH-4, HBL-1 was changed to HBL-2, and ET-1 was changed to ET-2, and the device lifetime was evaluated. The numerical values in the table are relative values when the value of Comparative Example 4 described later is set to 100%. The results are shown in Table 4.

Examples 23 to 28

Organic EL devices were fabricated and evaluated in the same manner as in Example 22, except that the compounds described in Table 4 were used as the dopant material for the emitting layer, respectively. The results are shown in Table 4.

Comparative Example 4

An organic EL device was fabricated and evaluated in the same manner as in Example 22, except that the compound described in Table 4 was used as the dopant material for the emitting layer. The results are shown in Table 4.

TABLE 4

| | BH | BD | LT95 relative value (%) |
|---|---|---|---|
| Example 22 | BH-4 | BD-1 | 127 |
| Example 23 | | BD-2 | 117 |
| Example 24 | | BD-3 | 116 |
| Example 25 | | BD-4 | 121 |
| Example 26 | | BD-5 | 133 |
| Example 27 | | BD-6 | 129 |
| Example 28 | | BD-7 | 130 |
| Comp. Ex. 4 | | BD-Ref | 100 |

Example 29

An organic EL device was fabricated the device lifetime was evaluated in the same manner as in Example 22, except that the compound described in Table 5 was used as the host material for the emitting layer. The numerical values in the table are relative values when the value of Comparative Example 5 described later is set to 100%. The results are shown in Table 5.

Examples 30 to 35

Organic EL devices were fabricated and evaluated in the same manner as in Example 29, except that the compounds described in Table 5 were used as a dopant material of each of the emitting layer. The results are shown in Table 5.

Comparative Example 5

An organic EL device was fabricated and evaluated in the same manner as in Example 29, except that the compound described in Table 5 was used as the dopant material for the emitting layer. The results are shown in Table 5.

TABLE 5

| | BH | BD | LT95 relative value (%) |
|---|---|---|---|
| Example 29 | BH-5 | BD-1 | 123 |
| Example 30 | | BD-2 | 114 |
| Example 31 | | BD-3 | 110 |
| Example 32 | | BD-4 | 117 |
| Example 33 | | BD-5 | 136 |
| Example 34 | | BD-6 | 139 |
| Example 35 | | BD-7 | 125 |
| Comp. Ex. 5 | | BD-Ref | 100 |

From the results of Tables 1 to 5, it can be seen that the organic EL devices using BD-1 to BD-7 have a longer lifetime than the organic EL devices using BD-Ref.

<Synthesis of Compounds>

Synthesis of BD-1

Compound BD-1 was synthesized in accordance with the synthetic route described below.

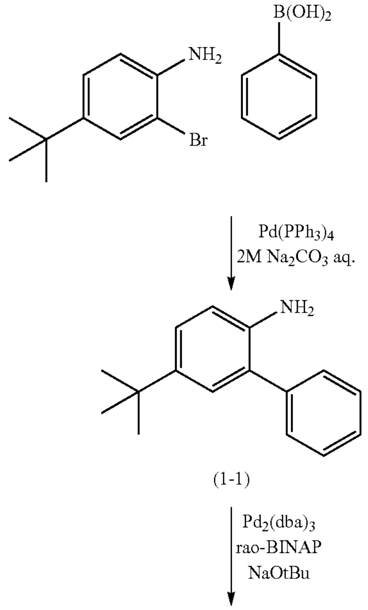

(1-1)

-continued

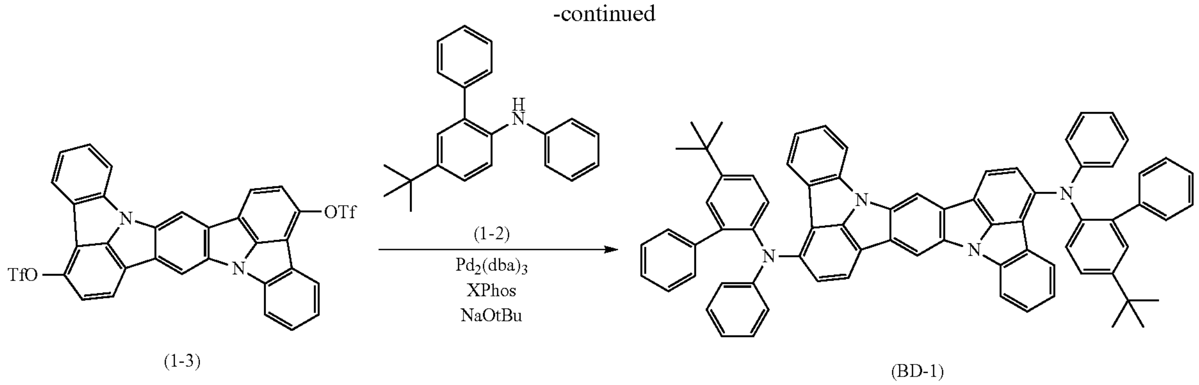

(1-3) (BD-1)

Synthesis of Intermediate 1-1

Under an argon atmosphere, 2-bromo-4-(tertiary-butyl) aniline (5.00 g, 21.9 mmol), phenylboronic acid (5.34 g, 43.8 mmol), tetrakistriphenylphosphine palladium(0) (Pd $(PPh_3)_4$, 0.253 g, 0.219 mmol), 2.7 M $Na_2CO_3$ aqueous solution (20 mL), toluene (20 mL), and ethanol (20 mL)) were mixed, and the mixture was stirred with heat at 80° C. for 6 hours. After completion of the reaction, water and ethyl acetate were added to the reaction mixture, the organic phase was extracted from the reaction mixture. A crude material obtained by distillation of the solvent was purified by column chromatography and recrystallization to obtain a colorless solid (3.20 g, yield: 65%). The obtained solid was identified as a compound 1-1, which was an intended product, based on the results of mass spectrometric analysis being: m/e=225 for a molecular weight of 225.

Synthesis of Intermediate 1-2

Under an argon atmosphere, intermediate 1-1 (3.90 g, 17.3 mmol), bromobenzene (3.26 g, 20.8 mmol), tris(dibenzylideneacetone)dipaladium(0) ($Pd_2(dba)_3$, 0.237 g, 0.259 mmol), rac-2,2'-bis(diphenylphosphino)-1,1'-binaphthyl (rac-BINAP, 0.322 g, 5.17 mmol), NaOt-Bu (2.33 g, 24.2 mmol) were dissolved in toluene (30 mL), and the mixture was stirred with heat at 90° C. for 3 hours. After completion of the reaction, water and ethyl acetate were added to the reaction solution, and the organic phase was extracted. The crude material obtained by distillation of the solvent was purified by column chromatography to obtain an orange oily compound (4.20 g, yield: 81%). The obtained compound was identified as the compound 1-2, which was an intended product, based on the results of mass spectrometric analysis being: m/e=301 for a molecular weight of 301.

Synthesis of BD-1

Under an argon atmosphere, known intermediate 1-3 (synthesized by the methods described in U.S. Pat. No. 10,249,832, 3.33 g, 4.75 mmol), intermediate 1-2 (3.14 g, 10.4 mmol), tris(dibenzylideneacetone)dipaladium(0) ($Pd_2(dba)_3$, 0.218 g, 0.238 mmol), 2-dicyclohexylphosphino-2',4',6'-triisopropylbiphenyl (0.226 g, 0.475 mmol) were dissolved in xylene (240 mL), and 1M solution of lithium bis(trimethylsilyl)amide in tetrahydrofuran (10.9 mL, 10.9 mmol) was added thereto, and the mixture was refluxed at 135° C. for 3 hours. After completion of the reaction, methanol was added to the reaction solution, and the mixture was subjected to filtration. The obtained solid was purified by column chromatography and recrystallization to obtain a yellow solid (3.82 g, yield: 80%). The obtained solid was identified as BD-1, which was an intended product, based on the results of mass spectrometric analysis being: m/e=1002 for a molecular weight of 1002.

Synthesis of BD-2

Compound BD-2 was synthesized in accordance with the synthetic route described below.

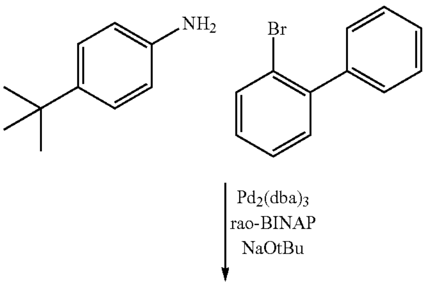

-continued

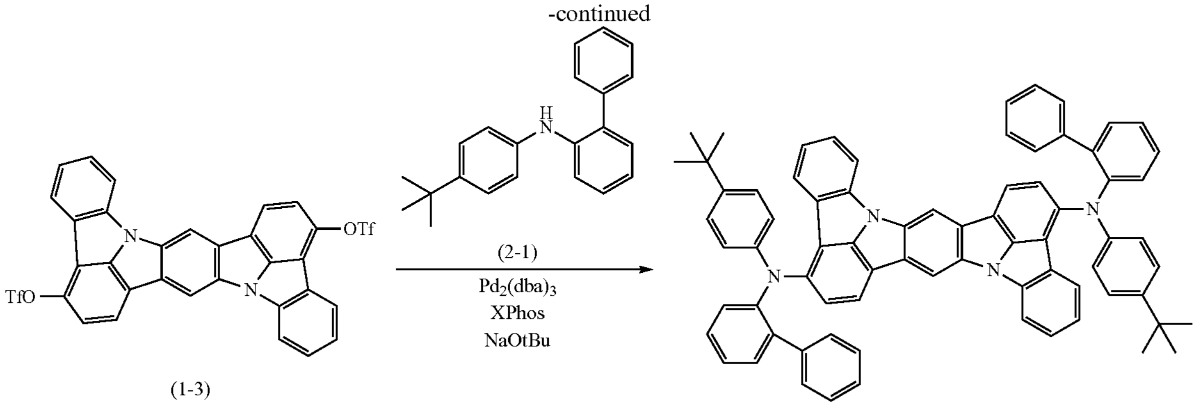

(1-3)

(BD-2)

Synthesis of Intermediate 2-1

Under an argon atmosphere, 2-bromobiphenyl (20.0 g, 86.0 mmol), 4-tertiary-butylaniline (14.1 g, 94.0 mmol), tris(dibenzylideneacetone)dipaladium(0) ($Pd_2(dba)_3$, 1.18 g, 1.29 mmol), rac-2,2'-bis(diphenylphosphino)-1,1'-binaphthyl (rac-BINAP, 1.60 g, 2.57 mmol), and NaOt-Bu (11.5 g, 120 mmol) were dissolved in toluene (500 mL) and the mixture was stirred at 90° C. for 5 hours. Water and ethyl acetate were added thereto, and the organic phase was extracted. The crude material obtained by distillation of the solvent was purified by column chromatography to obtain an orange oily compound (21.5 g, yield: 83%). The obtained compound was identified as Compound 2-1, which was an intended product, based on the results of mass spectrometric analysis being: m/e=301 for a molecular weight of 301.

Synthesis of BD-2

Under an argon atmosphere, known intermediate 1-2 (synthesized by the methods described in U.S. Pat. No. 10,249,832, 1.48 g, 2.11 mmol), intermediate 2-1 (1.34 mg, 4.44 mmol), tris(dibenzylideneacetone)dipaladium(0) ($Pd_2(dba)_3$, 97 mg, 0.106 mmol), and 2-dicyclohexylphosphino-2',4',6'-triisopropylbiphenyl (101 mg, 0.211 mmol) were dissolved in xylene (120 mL), and 1M solution of lithium bis(trimethylsilyl)amide in tetrahydrofuran (4.9 mL, 4.9 mmol) was added thereto, and the mixture was refluxed for 5 hours. After completion of the reaction, methanol was added to the reaction solution, and the mixture was subjected to filtration. The obtained solid was purified by column chromatography to obtain a yellow solid (1.20 mg, yield: 57%). The obtained solid was identified as BD-2, which was an intended product, based on the results of mass spectrometric analysis being: m/e=1002 for a molecular weight of 1002.

Synthesis of BD-3

Compound BD-3 was synthesized in accordance with the synthetic route described below.

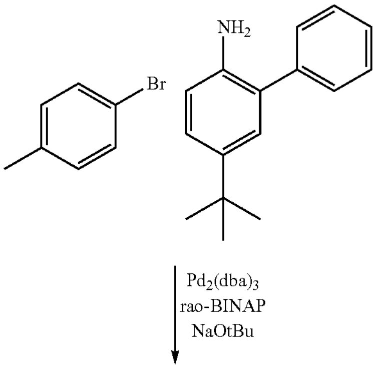

-continued

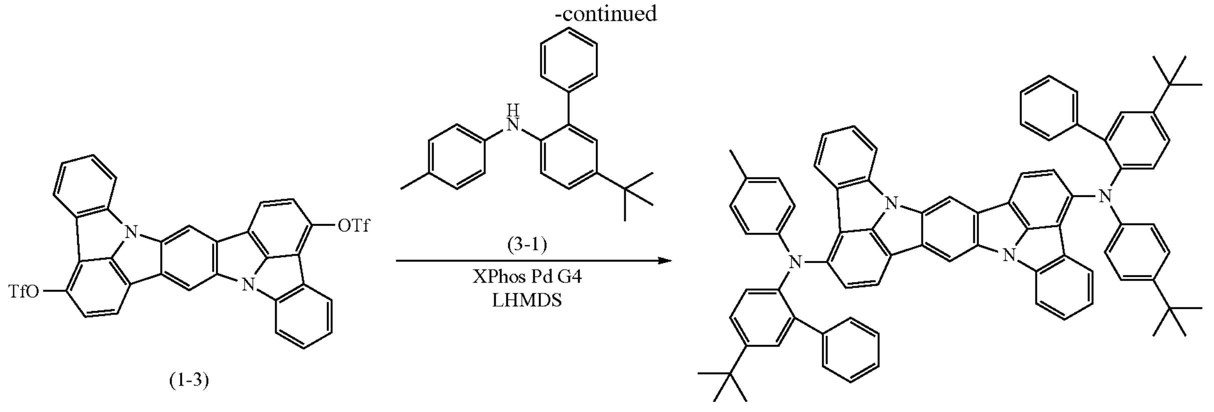

(1-3)

(BD-3)

Synthesis of Intermediate 3-1

Under an argon atmosphere, p-bromotoluene (3.00 g, 17.5 mmol), 4-tertiary-butyl phenylaniline (4.35 g, 19.3 mmol), tris(dibenzylideneacetone)dipalladium(0) ($Pd_2(dba)_3$, 0.241 g, 0.263 mmol), rac-2,2'-bis(diphenylphosphino)-1,1'-binaphthyl (BINAP, 0.328 g, 0.526 mmol), and NaOt-Bu (2.36 g, 24.6 mmol) were dissolved in toluene (900 mL), and the solution was stirred with heat at 90° C. for 5 hours. Water and ethyl acetate were added thereto, the organic layer was extracted. The crude material obtained by distillation of the solvent was purified by column chromatography to obtain a white solid compound (4.6 g, yield: 83%). The obtained compound was identified as intermediate 3-1, which was an intended product, based on the results of mass spectrometric analysis being: m/e=315 for a molecular weight of 315.

Synthesis of BD-3

Under an argon atmosphere, intermediate 1-3 (3.03 g, 4.33 mmol), intermediate 3-1 (2.87 g, 9.09 mmol), and XPhosPdG4 (186 mg, 0.217 mmol) were dissolved in xylene (100 mL), and 1M solution of lithium bis(trimethylsilyl) amide in tetrahydrofuran (9.96 mL, 9.96 mmol) was added thereto, and the mixture was refluxed for 5 hours. After completion of the reaction, methanol was added to the reaction solution, the mixture was subjected to filtration. The obtained solid was purified by column chromatography to obtain a yellow solid (3.71 g, yield: 83%). The obtained solid was identified as BD-3, which was an intended product, based on the results of mass spectrometric analysis being: m/e=1031 for a molecular weight of 1031.

Synthesis of BD-4

Compound BD-4 was synthesized in accordance with the synthetic route described below.

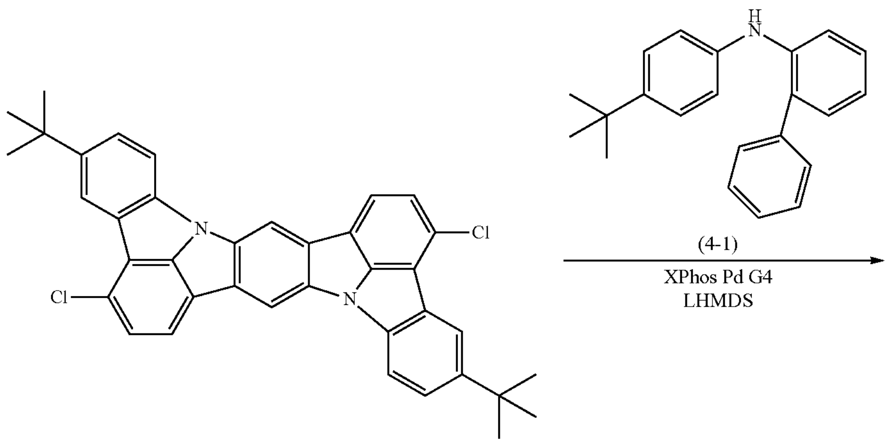

(1-4)

-continued

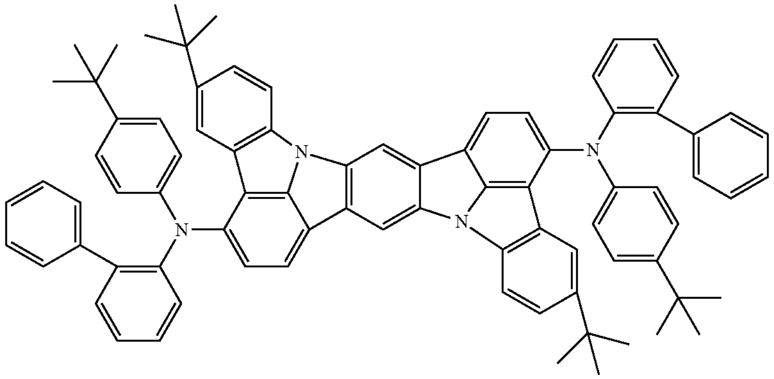

(BD-4)

Under an argon atmosphere, known intermediate 1-4 (0.600 g, 1.03 mmol), intermediate 4-1 (0.679 g, 2.25 mmol), and XPhosPdG4 (44 mg, 0.051 mmol) were dissolved in xylene (50 mL), and 1M solution of lithium bis(trimethylsilyl)amide in tetrahydrofuran (2.46 mL, 2.46 mmol) was added thereto, and the mixture was refluxed for 5 hours. After completion of the reaction, methanol was added to the reaction solution, the mixture was subjected to filtration, The obtained solid was purified by column chromatography to obtain a yellow solid (595 mg, yield: 52%). The obtained solid was identified as BD-4, which was an intended product, based on the results of mass spectrometric analysis being: m/e=1115 for a molecular weight of 1115.

Synthesis of BD-5

Compound BD-5 was synthesized in accordance with the synthetic route described below.

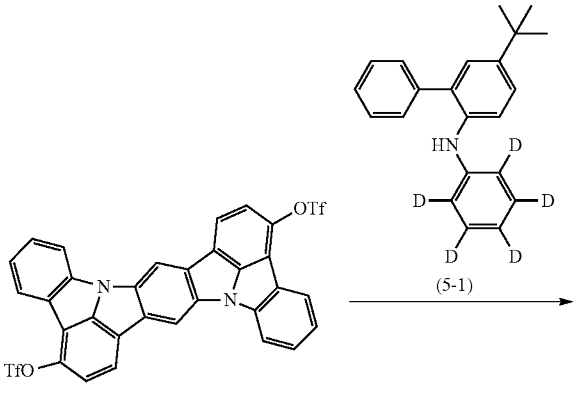

-continued

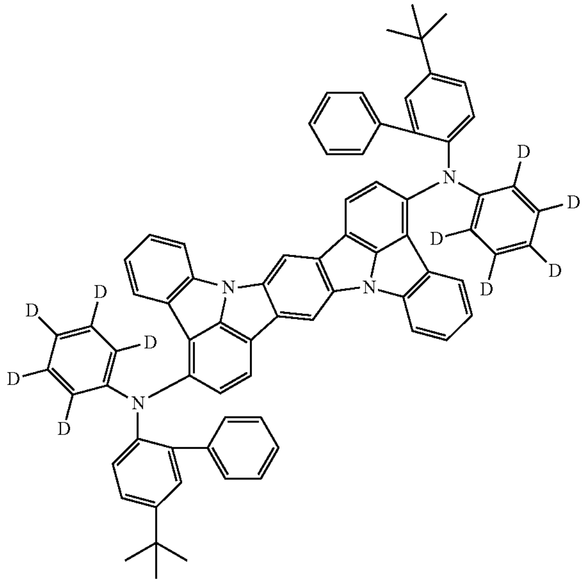

(BD-5)

Synthesis was carried out in the same manner as in Synthesis of Compound BD-1, except that the corresponding secondary amine intermediate 5-1 was used in place of intermediate 3-1 as a reaction raw material. The molecular weight of BD-5 was 1013, and the result of mass spectrum analysis of the resulting compound was: m/z (ratio of mass to charge)=1013. Based on this result, the resulting compound was identified as Compound BD-5.

Synthesis of BD-6

Compound BD-6 was synthesized in accordance with the synthetic route described below.

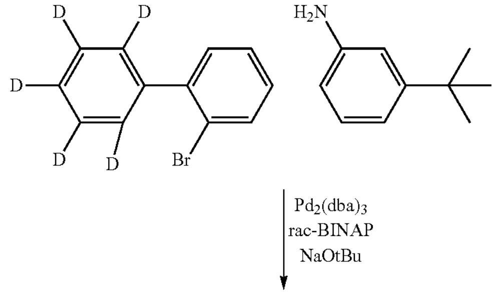

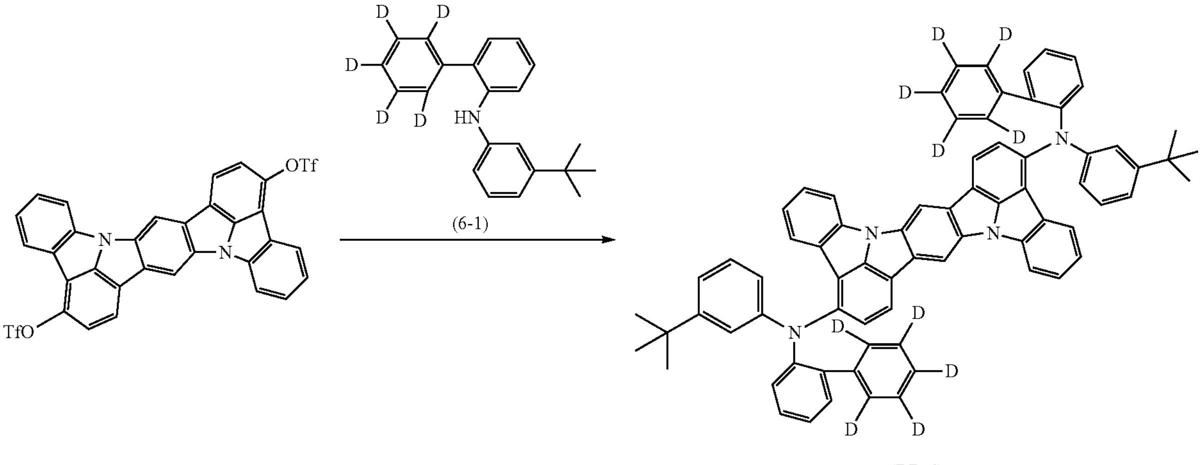

(BD-6)

Synthesis of Intermediate 6-1

Intermediate 6-1 was synthesized in the same manner as in intermediate 3-1 using 2'-bromo-1,1'-biphenyl-2,3,4,5,6-d5 and m-tertiarybutylaniline as reaction raw materials.

Synthesis of BD-6

Synthesis was carried out in the same manner as in Synthesis of Compound BD-1, except that the corresponding secondary amine intermediate 6-1 was used in place of intermediate 3-1 as a reaction raw material. The molecular weight of BD-6 was 1013, and the result of mass spectrum analysis of the resulting compound was: m/z (ratio of mass to charge)=1013. Based on this result, the resulting compound was identified as Compound BD-6.

Synthesis of BD-7

Compound BD-7 was synthesized in accordance with the synthetic route described below.

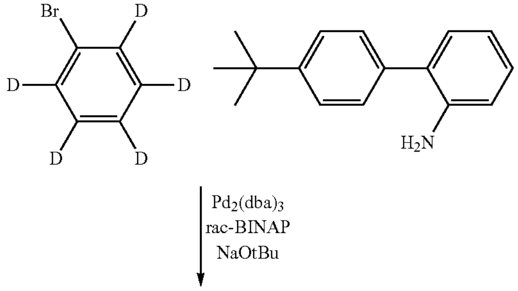

-continued

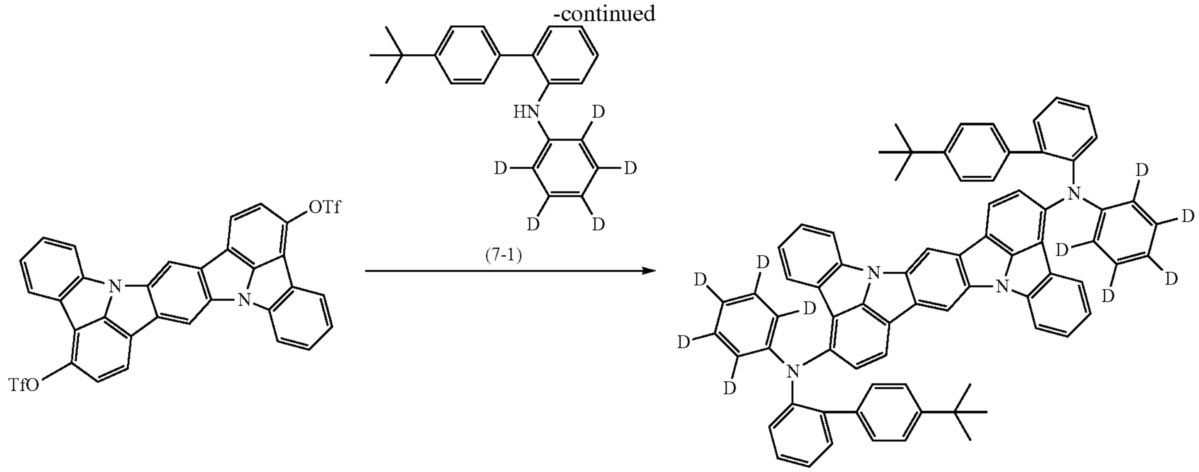

(BD-7)

Synthesis of Intermediate 7-1

Intermediate 7-1 was synthesized in the same manner as in intermediate 3-1 using bromobenzene-d5 and 2-(4-tertiarybutylphenyl)aniline as reaction raw materials.

Synthesis of Compound BD-7

Synthesis was carried out in the same manner as in Synthesis of Compound BD-1, except that the corresponding secondary amine intermediate 7-1 was used in place of intermediate 3-1 as a reaction raw material. The molecular weight of BD-7 was 1013, and the result of mass spectrum analysis of the resulting compound was: m/z (ratio of mass to charge)=1013. Based on this result, the resulting compound was identified as Compound BD-7.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The invention claimed is:

1. A compound represented by the following formula (1):

(1)

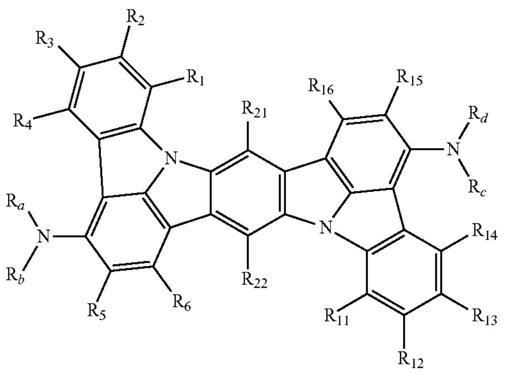

wherein in the formula (1), $R_a$ to $R_d$ are independently a substituted or unsubstituted aryl group including 6 to 50 ring carbon atoms, and at least one of $R_a$ to $R_d$ is a substituted or unsubstituted biphenyl-2-yl group;

at least one of $R_a$ to $R_d$ has a substituent A; the substituent A is one or more selected from the group consisting of a substituted or unsubstituted alkyl group including 1 to 50 carbon atoms, a substituted or unsubstituted cycloalkyl group including 3 to 50 ring carbon atoms, and —$Si(R_{31})(R_{32})(R_{33})$;

one or more sets of adjacent two or more of $R_1$ to $R_6$ and $R_{11}$ to $R_{16}$ form a substituted or unsubstituted, saturated or unsaturated ring, or do not form the substituted or unsubstituted, saturated or unsaturated ring;

$R_{21}$ and $R_{22}$, and $R_1$ to $R_6$ and $R_{11}$ to $R_{16}$ which do not form the substituted or unsubstituted, saturated or unsaturated ring are independently a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —$Si(R_{31})(R_{32})(R_{33})$, —$C(=O)R_{34}$, —$COOR_{35}$, —$N(R_{36})(R_{37})$, a halogen atom, a cyano group, a nitro group, a substituted or unsubstituted aryl group including 6 to 50 ring carbon atoms, or a substituted or unsubstituted monovalent heterocyclic group including 5 to 50 ring atoms;

$R_{31}$ to $R_{37}$ are independently a hydrogen atom, a substituted or unsubstituted alkyl group including 1 to 50 carbon atoms, a substituted or unsubstituted cycloalkyl group including 3 to 50 ring carbon atoms, a substituted or unsubstituted aryl group including 6 to 50 ring carbon atoms, or a substituted or unsubstituted monovalent heterocyclic group including 5 to 50 ring atoms;

when a plurality of each of $R_{31}$ to $R_{37}$ is present, the plurality of each of $R_{31}$ to $R_{37}$ may be the same as or different from each other.

2. The compound according to claim 1, wherein at least two of $R_a$ to $R_d$ are substituted or unsubstituted biphenyl-2-yl groups.

3. The compound according to claim 1, wherein at least one of $R_a$ and $R_b$ is a substituted or unsubstituted biphenyl-2-yl group, and at least one of $R_c$ and $R_d$ is a substituted or unsubstituted biphenyl-2-yl group.

4. The compound according to claim 1, wherein the substituent A is one or more selected from the group consisting of a substituted or unsubstituted alkyl group including 1 to 20 carbon atoms, a substituted or unsubstituted cycloalkyl group including 3 to 20 ring carbon atoms, and —$Si(R_{31})(R_{32})(R_{33})$.

5. The compound according to claim 1, wherein the substituent A is a substituted or unsubstituted alkyl group including 1 to 20 carbon atoms.

6. The compound according to claim 1, wherein the compound is represented by the following formula (1-1):

(1-1)

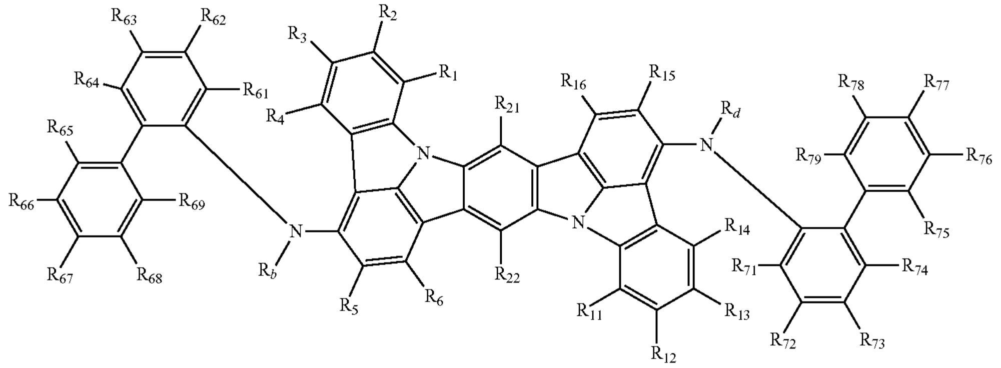

wherein in the formula (1-1), $R_1$ to $R_6$, $R_{11}$ to $R_{16}$, $R_{21}$, $R_{22}$, $R_b$, and $R_d$ are as defined in the formula (1);

$R_{61}$ to $R_{69}$ and $R_{71}$ to $R_{79}$ are independently a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —$Si(R_{31})(R_{32})(R_{33})$, —C(=O) $R_{34}$, —$COOR_{35}$, —$N(R_{36})(R_{37})$, a halogen atom, a cyano group, a nitro group, a substituted or unsubstituted aryl group including 6 to 50 ring carbon atoms, or a substituted or unsubstituted monovalent heterocyclic group including 5 to 50 ring atoms;

$R_{31}$ to $R_{37}$ are as defined in the formula (1);

at least one of $R_{61}$ to $R_{69}$, $R_{71}$ to $R_{79}$, the substituent by which $R_b$ is substituted, and the substituent by which $R_d$ is substituted is the substituent A.

7. The compound according to claim 1, wherein $R_b$ and $R_d$ are substituted or unsubstituted aryl groups including 6 to 30 ring carbon atoms.

8. The compound according to claim 1, wherein the compound is represented by the following formula (1-2):

(1-2)

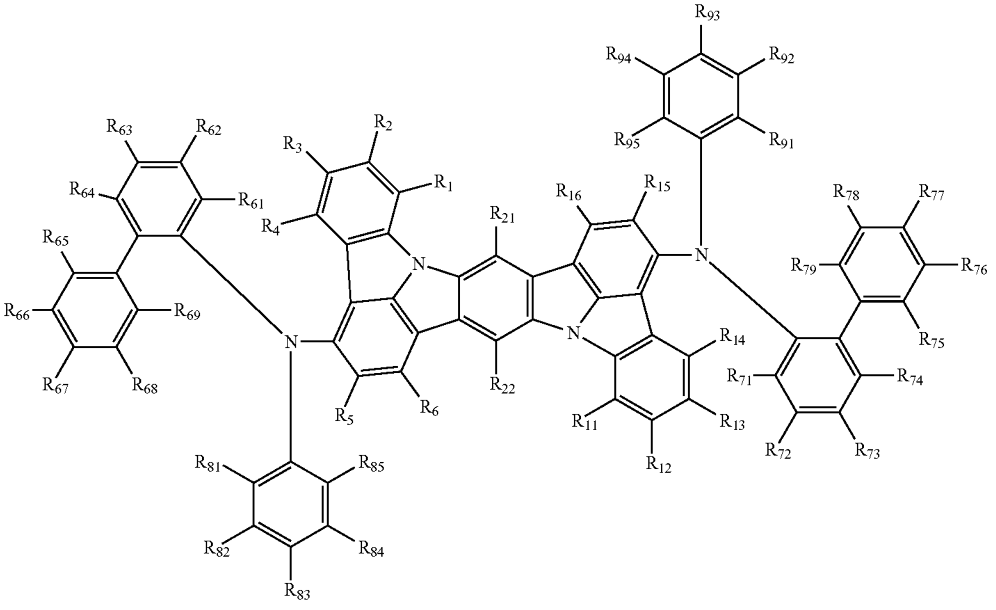

wherein in the formula (1-2), $R_1$ to $R_6$, $R_{11}$ to $R_{16}$, $R_{21}$, and $R_{22}$ are as defined in the formula (1);

$R_{61}$ to $R_{69}$, $R_{71}$ to $R_{79}$, $R_{81}$ to $R_{85}$, and $R_{91}$ to $R_{95}$ are independently a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —$Si(R_{31})(R_{32})(R_{33})$, —$C(=O)R_{34}$, —$COOR_{35}$, —$N(R_{36})(R_{37})$, a halogen atom, a cyano group, a nitro group, a substituted or unsubstituted aryl group including 6 to 50 ring carbon atoms, or a substituted or unsubstituted monovalent heterocyclic group including 5 to 50 ring atoms;

$R_{31}$ to $R_{37}$ are as defined in the formula (1);

at least one of $R_{61}$ to $R_{69}$, $R_{71}$ to $R_{79}$, $R_{81}$ to $R_{85}$, and $R_{91}$ to $R_{95}$ is the substituent A.

9. The compound according to claim 8, wherein at least one of $R_{61}$ to $R_{69}$ and $R_{71}$ to $R_{79}$ is the substituent A.

10. The compound according to claim 8, wherein at least one of $R_{61}$ to $R_{69}$ and at least one of $R_{71}$ to $R_{79}$ are independently the substituent A.

11. The compound according to claim 1, wherein $R_1$ to $R_6$, $R_{11}$ to $R_{16}$, $R_{21}$, and $R_{22}$ are hydrogen atoms.

12. The compound according to claim 1, wherein the compound is represented by the following formula (1-3):

(1-3)

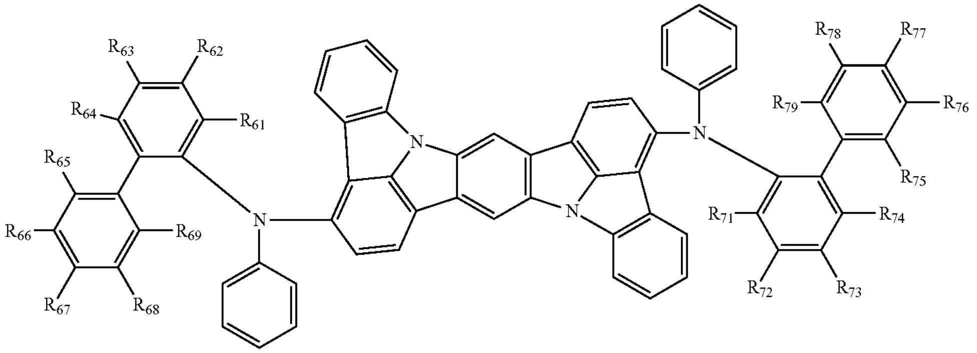

wherein in the formula (1-3), $R_{61}$ to $R_{69}$ and $R_{71}$ to $R_{79}$ are independently a hydrogen atom, a substituted or unsubstituted alkyl group including 1 to 50 carbon atoms, a substituted or unsubstituted haloalkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, a substituted or unsubstituted alkoxy group including 1 to 50 carbon atoms, a substituted or unsubstituted alkylthio group including 1 to 50 carbon atoms, a substituted or unsubstituted aryloxy group including 6 to 50 ring carbon atoms, a substituted or unsubstituted arylthio group including 6 to 50 ring carbon atoms, a substituted or unsubstituted aralkyl group including 7 to 50 carbon atoms, —$Si(R_{31})(R_{32})(R_{33})$, —C(=O) $R_{34}$, —$COOR_{35}$, —$N(R_{36})(R_{37})$, a halogen atom, a cyano group, a nitro group, a substituted or unsubstituted aryl group including 6 to 50 ring carbon atoms, or a substituted or unsubstituted monovalent heterocyclic group including 5 to 50 ring atoms;

$R_{31}$ to $R_{37}$ are as defined in the formula (1);

at least one of $R_{61}$ to $R_{69}$ and $R_{71}$ to $R_{79}$ is the substituent A.

13. The compound according to claim 1, wherein the substituent in the case of the "substituted or unsubstituted" is selected from the group consisting of an alkyl group including 1 to 50 carbon atoms, a haloalkyl group including 1 to 50 carbon atoms, an alkenyl group including 2 to 50 carbon atoms, an alkynyl group including 2 to 50 carbon atoms, a cycloalkyl group including 3 to 50 carbon atoms, an alkoxy group including 1 to 50 carbon atoms, an alkylthio group including 1 to 50 carbon atoms, an aryloxy group including 6 to 50 ring carbon atoms, an arylthio group including 6 to 50 ring carbon atoms, an aralkyl group including 7 to 50 carbon atoms, —$Si(R_{41})(R_{42})(R_{43})$, —C(=O) $R_{44}$, —$COOR_{45}$, —$S(=O)_2R_{46}$, —$P(=O)(R_{47})(R_{48})$, —$Ge(R_{49})(R_{50})(R_{51})$, —$N(R_{52})(R_{53})$ (where $R_{41}$ to $R_{53}$ are independently a hydrogen atom, an alkyl group including 1 to 50 carbon atoms, an aryl group including 6 to 50 carbon atoms, or a monovalent heterocyclic group including 5 to 50 ring atoms; and when two or more of each of $R_{41}$ to $R_{53}$ are present, the two or more of each of $R_{41}$ to $R_{53}$ may be the same as or different from each other), a hydroxy group, a halogen atom, a cyano group, a nitro group, an aryl group including 6 to 50 ring carbon atoms, and a monovalent heterocyclic group including 5 to 50 ring atoms.

14. A material for an organic electroluminescence device, comprising the compound according to claim 1.

15. An organic electroluminescence device comprising:

a cathode;

an anode; and at least one organic layer disposed between the cathode and the anode, wherein at least one of the at least one organic layer comprises the compound according to claim 1.

16. The organic electroluminescence device according to claim 15, wherein at least one of the at least one organic layer comprises a second compound which is not the same as the compound.

17. The organic electroluminescence device according to claim 16, wherein the second compound is a heterocyclic compound or a fused aromatic compound.

18. The organic electroluminescence device according to claim 16, wherein the second compound is an anthracene derivative.

19. The organic electroluminescence device according to claim 16, wherein the second compound is a compound represented by the following formula (20):

(20)

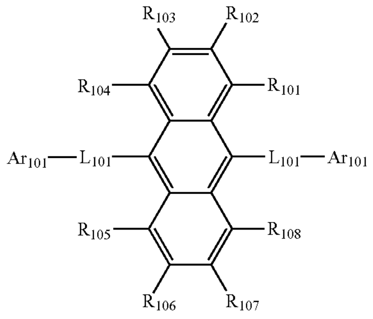

one or more sets of adjacent two or more of $R_{101}$ to $R_{108}$ form a substituted or unsubstituted, saturated or unsaturated ring, or do not form the substituted or unsubstituted, saturated or unsaturated ring;

$R_{101}$ to $R_{108}$ which do not form the substituted or unsubstituted, saturated or unsaturated ring are independently a group represented by a hydrogen atom, or a substituent R;

$L_{101}$ is a single bond, a substituted or unsubstituted arylene group including 6 to 50 ring carbon atoms, or a substituted or unsubstituted divalent heterocyclic group including 5 to 50 ring atoms;

$Ar_{101}$ is a substituted or unsubstituted aryl group including 6 to 50 ring carbon atoms, or a substituted or unsubstituted monovalent heterocyclic group including 5 to 50 ring atoms;

the substituent R is a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, —$Si(R_{901})(R_{902})(R_{903})$,

—O—$(R_{904})$,

—S—$(R_{905})$,

—$N(R_{906})(R_{907})$, a halogen atom, a cyano group, a nitro group, a substituted or unsubstituted aryl group including 6 to 50 ring carbon atoms, or a substituted or unsubstituted monovalent heterocyclic group including 5 to 50 ring atoms;

the two $Ar_{101}$'s may be the same as or different from each other;

the two $L_{101}$'s may be the same as or different from each other;

when two or more of the substituent R's are present, the two or more of the substituent R's may be the same as or different from each other;

$R_{901}$ to $R_{907}$ are independently
a hydrogen atom,
a substituted or unsubstituted alkyl group including 1 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted monovalent heterocyclic group including 5 to 50 ring atoms; and
when two or more of each of $R_{901}$ to $R_{907}$ are present, the two or more of each of $R_{901}$ to $R_{907}$ are the same as or different from each other.

20. An organic electroluminescence device according to claim 15, wherein at least one of the at least one organic layer is an emitting layer.

21. The organic electroluminescence device according to claim 20, comprising a hole-transporting layer disposed between the anode and the emitting layer.

22. The organic electroluminescence device of claim 20, comprising an electron-transporting layer disposed between the cathode and the emitting layer.

23. The organic electroluminescence device according to claim 20, wherein the emitting layer comprises the compound represented by the formula (20).

24. The organic electroluminescence device according to claim 20, wherein the emitting layer further comprises a delayed fluorescent host compound.

25. An electronic apparatus equipped with the organic electroluminescence device according to claim 15.

* * * * *